United States Patent
Shi et al.

(10) Patent No.: US 11,685,782 B2
(45) Date of Patent: Jun. 27, 2023

(54) METHODS OF TREATING CANCER USING LSD1 INHIBITORS IN COMBINATION WITH IMMUNOTHERAPY

(71) Applicants: Children's Medical Center Corporation, Boston, MA (US); President & Fellows of Harvard College, Cambridge, MA (US)

(72) Inventors: Yang Shi, Newton, MA (US); Wanqiang Sheng, Allston, MA (US); Arlene H. Sharpe, Brookline, MA (US); Martin W. LaFleur, Boston, MA (US)

(73) Assignees: Children's Medical Center Corporation, Boston, MA (US); President & Fellows of Harvard College, Cambridge, MA (US)

( * ) Notice: Subject to any disclaimer, the term of this patent is extended or adjusted under 35 U.S.C. 154(b) by 329 days.

(21) Appl. No.: 16/758,474

(22) PCT Filed: Oct. 23, 2018

(86) PCT No.: PCT/US2018/057058
§ 371 (c)(1),
(2) Date: Apr. 23, 2020

(87) PCT Pub. No.: WO2019/083971
PCT Pub. Date: May 2, 2019

(65) Prior Publication Data
US 2020/0255527 A1    Aug. 13, 2020

Related U.S. Application Data

(60) Provisional application No. 62/688,002, filed on Jun. 21, 2018, provisional application No. 62/576,001, filed on Oct. 23, 2017.

(51) Int. Cl.
*C07K 16/28* (2006.01)
*A61P 35/00* (2006.01)
(Continued)

(52) U.S. Cl.
CPC .......... *C07K 16/2818* (2013.01); *A61P 35/00* (2018.01); *C07K 16/2827* (2013.01); *C12N 15/1137* (2013.01); *A61K 2039/505* (2013.01)

(58) Field of Classification Search
CPC ............ C07K 16/2818; C07K 16/2827; C07K 2317/76; A61P 35/00; C12N 15/1137;
(Continued)

(56) References Cited

U.S. PATENT DOCUMENTS 8,617,546 B2   12/2013   Kang et al.
9,084,776 B2   7/2015    Korman et al.
(Continued)

FOREIGN PATENT DOCUMENTS

CN           107523569 A  * 12/2017  ......... A61K 31/7105
WO    WO-2007084865 A2 *  7/2007   ......... C12N 15/1138
(Continued)

OTHER PUBLICATIONS

Barrero, M.J. (2017) Epigenetic Strategies to Boost Cancer Immunotherapies Int. J. Mol. Sci 18(1108); 1-12 (Published May 23, 2017) (Year: 2017).*
(Continued)

*Primary Examiner* — Joanne Hama
*Assistant Examiner* — Audrey L Buttice
(74) *Attorney, Agent, or Firm* — Fish & Richardson P.C.

(57) ABSTRACT

Provided herein are methods of treating cancer using LSD1 inhibitors in combination with immunotherapy.

21 Claims, 62 Drawing Sheets
Specification includes a Sequence Listing.

(51) Int. Cl.
C12N 15/113 (2010.01)
A61K 39/00 (2006.01)

(58) Field of Classification Search
CPC ............ C12N 9/0004; A61K 2039/505; A61K 38/2013; A61K 38/212; A61K 31/445; A61K 31/713; A61K 45/06
See application file for complete search history.

(56) References Cited

U.S. PATENT DOCUMENTS

| | | | |
|---|---|---|---|
| 9,102,727 | B2 | 8/2015 | Freeman et al. |
| 9,346,840 | B2 | 5/2016 | Johnson et al. |
| 9,457,080 | B2 | 10/2016 | Freeman et al. |
| 9,492,540 | B2 | 11/2016 | Korman et al. |
| 9,493,442 | B2 | 11/2016 | Wu et al. |
| 9,624,298 | B2 | 4/2017 | Nastri et al. |
| 9,771,425 | B2 | 9/2017 | Wang et al. |
| 9,789,183 | B1 | 10/2017 | Wang et al. |
| 9,914,783 | B1 | 3/2018 | Afar et al. |
| 11,168,326 | B2 * | 11/2021 | Thanos .................... A61P 35/00 |
| 2010/0086550 | A1 | 4/2010 | Kang et al. |
| 2013/0035377 | A1 | 2/2013 | Minucci et al. |
| 2013/0210888 | A1 | 8/2013 | Shi et al. |
| 2015/0225401 | A1 | 8/2015 | Wu et al. |
| 2016/0009711 | A1 | 1/2016 | Wu et al. |
| 2016/0115455 | A1 | 4/2016 | Mikkelsen et al. |
| 2016/0362489 | A1 | 12/2016 | Yang |
| 2017/0000885 | A1 | 1/2017 | Rhee et al. |
| 2017/0044101 | A1 | 2/2017 | Pan et al. |
| 2017/0129857 | A1 | 5/2017 | Vaisburg et al. |
| 2017/0183308 | A1 | 6/2017 | Marx et al. |
| 2017/0209432 | A1 | 7/2017 | Fyfe et al. |
| 2017/0240635 | A1 | 8/2017 | Wang et al. |
| 2017/0281566 | A1 | 10/2017 | Ciceri et al. |
| 2017/0281567 | A1 | 10/2017 | Demario et al. |
| 2017/0283397 | A1 | 10/2017 | Vankayalapati et al. |
| 2017/0319690 | A1 | 11/2017 | Wang et al. |
| 2018/0030137 | A1 | 2/2018 | Van Eenennaam et al. |
| 2018/0079814 | A1 | 3/2018 | Higgs et al. |

FOREIGN PATENT DOCUMENTS

| | | | |
|---|---|---|---|
| WO | WO 2010/040112 | | 4/2010 |
| WO | WO 2016/007736 | | 1/2016 |
| WO | WO 2016/161282 | | 10/2016 |
| WO | WO-2017114497 | A1 * | 7/2017 ............. A61K 35/17 |
| WO | WO 2017/190009 | | 11/2017 |

OTHER PUBLICATIONS

ChemIDplus datasheet for Durvalumab, CAS# 1428935-60-7; accessed Jun. 1, 2022 (Year: 2022).*
ChemIDplus datasheet for Atezolizumab, CAS# 1380723-44-3; accessed Jun. 1, 2022 (Year: 2022).*
ChemIDplus datasheet for Avelumab, CAS# 1537032-82-8; accessed Jun. 1, 2022 (Year: 2022).*
Bhinder, B., et al (2013) An arrayed Genome-Scale Lentiviral-Enabled Short Hairpin RNA Screen Identifies Lethal and Rescuer Gene Candidates Assay and Drug Development Technologies 11(3); 173-190 (Year: 2013).*
Wang, X., et al (2013) A simple and robust vector-based shRNA expression system used for RNA Interference PLOS One 8(2) e56110, 1-8 (Year: 2013).*
Bally, A.P.R., et al (2016) Genetic and Epigenetic Regulation of PD-1 Expression The Journal of Immunology 196; 2431-2437 (Year: 2016).*
Dunn, J., and S. Rao (2017) Epigenetics and immunotherapy: The current state of play Molecular Immunology 87; 227-239 (Year: 2017).*
Althoff et al., "MiR-137 functions as a tumor suppressor in neuroblastoma by downregulating KDM1A," Int. J. Cancer, 2013, 133(5):1064-1074.
Altschul et al., "Basic local alignment search tool," Journal of Molecular Biology, Oct. 5, 1990, 215(3):403-10.
Carthew et al., "Origins and mechanisms of miRNAs and siRNAs," Cell, Feb. 20, 2009, 136(4):642-55.
Chen et al., "Combination of 4-1BB agonist and PD-1 antagonist promotes antitumor effector/memory CD8 T cells in a poorly immunogenic tumor model," Cancer Immunology Research, Feb. 1, 2015, 3(2):149-60.
Chen et al., "Regulation and function of the cGAS-STING pathway of cytosolic DNA sensing," Nature Immunology, Oct. 2016, 17(10):1142-9.
Chiappinelli et al., "Inhibiting DNA methylation causes an interferon response in cancer via dsRNA including endogenous retroviruses," Cell, Aug. 27, 2015, 162(5):974-86.
Fritz et al., "Efficient storage of high throughput DNA sequencing data using reference-based compression," Genome Research, May 1, 2011, 21(5):734-40.
Fu et al., "Advances toward LSD1 inhibitors for cancer therapy," Future Medicinal Chemistry, Jul. 2017, 9(11):1227-42.
GenBank Accession No. NM_005018.2, "Homo sapiens programmed cell death 1 (PDCD1), mRNA," Oct. 15, 2017, 4 pages.
GenBank Accession No. NM_01009999.2, "Homo sapiens lysine demethylase 1A (KDM1A), transcript variant 1, mRNA," Oct. 16, 2017, 4 pages.
GenBank Accession No. NM_014143.3, "Homo sapiens CD274 molecule (CD274), transcript variant 1, mRNA," dated Sep. 25, 2017, 4 pages.
Ghoneim et al., "De novo epigenetic programs inhibit PD-1 blockade-mediated T cell rejuvenation," Cell, Jun. 29, 2017, 170(1):142-57.
Harris et al., "The histone demethylase KDM1A sustains the oncogenic potential of MLL-AF9 leukemia stem cells," Cancer Cell, Apr. 17, 2012, 21(4):473-87.
Heinz et al., "Simple combinations of lineage-determining transcription factors prime cis-regulatory elements required for macrophage and B cell identities," Molecular Cell, May 28, 2010, 38(4):576-89.
Herbst et al., "Predictive correlates of response to the anti-PD-L1 antibody MPDL3280A in cancer patients," Nature, Nov. 2014, 515(7528):563-7.
Hornung et al., "5'-Triphosphate RNA is the ligand for RIG-I," Science, Nov. 10, 2006, 314(5801):994-7.
Juneja et al., "PD-L1 on tumor cells is sufficient for immune evasion in immunogenic tumors and inhibits CD8 T cell cytotoxicity," Journal of Experimental Medicine, Apr. 3, 2017, 214(4):895-904.
Kassiotis et al., "Immune responses to endogenous retroelements: taking the bad with the good," Nature Reviews Immunology, Apr. 2016, 16(4):207-19.
Kato et al., "Differential roles of MDA5 and RIG-I helicases in the recognition of RNA viruses," Nature, May 2006, 441(7089):101-5.
Kato et al., "Length-dependent recognition of double-stranded ribonucleic acids by retinoic acid-inducible gene-I and melanoma differentiation-associated gene 5," The Journal of Experimental Medicine, Jul. 7, 2008, 205(7):1601-10.
Kim et al., "Mammaglobin-A is a target for breast cancer vaccination," Oncoimmunology, Feb. 1, 2016, 5(2):e1069940, 4 pages.
Kleffel et al., "Melanoma cell-intrinsic PD-1 receptor functions promote tumor growth," Cell, Sep. 10, 2015, 162(6):1242-56.
Kübler et al., "Self-adjuvanted mRNA vaccination in advanced prostate cancer patients: a first-in-man phase I/IIa study," Journal for Immunotherapy of Cancer, Dec. 2015, 3(1):1-4.
Leung et al., "Silencing of endogenous retroviruses: when and why do histone marks predominate?," Trends in Biochemical Sciences, Apr. 1, 2012, 37(4):127-33.
Li et al., "Exploring single-sample SNP and INDEL calling with whole-genome de novo assembly," Bioinformatics, Jul. 15, 2012, 28(14):1838-44.
Liu et al., "Structural basis of toll-like receptor 3 signaling with double-stranded RNA," Science, Apr. 18, 2008, 320(5874):379-81.
Macfarlan et al., "Endogenous retroviruses and neighboring genes are coordinately repressed by LSD1/KDM1A," Genes & Development, Mar. 15, 2011, 25(6):594-607.

(56) References Cited

OTHER PUBLICATIONS

McCarthy et al., "Differential expression analysis of multifactor RNA-Seq experiments with respect to biological variation," Nucleic Acids Research, May 1, 2012, 40(10):4288-97.

Mohammad et al., "A DNA hypomethylation signature predicts antitumor activity of LSD1 inhibitors in SCLC," Cancer Cell, Jul. 13, 2015, 28(1):57-69.

Okamura et al., "Endogenous small interfering RNAs in animals," Nature Reviews Molecular Cell Biology, Sep. 2008, 9(9):673-8.

Ott et al., "An immunogenic personal neoantigen vaccine for patients with melanoma," Nature, Jul. 2017, 547(7662):217-21.

Parker et al., "Antitumour actions of interferons: implications for cancer therapy," Nature Reviews Cancer, Mar. 2016, 16(3):131.

PCT International Preliminary Report on Patentability in PCT Appln. No. PCT/US2018/057058, dated Apr. 28, 2020, 9 pages.

PCT International Search Report and Written Opinion in PCT Appln. No. PCT/US2018/057058, dated Jan. 2, 2019, 13 pages.

Pichlmair et al., "RIG-I-mediated antiviral responses to single-stranded RNA bearing 5'-phosphates," Science, Nov. 10, 2006, 314(5801):997-1001.

Pohl et al., "bwtool: a tool for bigWig files," Bioinformatics, Jun. 1, 2014, 30(11):1618-9.

Qi et al., "Prolyl 4-hydroxylation regulates Argonaute 2 stability," Nature, Sep. 2008, 455(7211):421-4.

Rausch et al., "mRNA vaccine CV9103 and CV9104 for the treatment of prostate cancer," Human Vaccines & Immunotherapeutics, Nov. 2, 2014, 10(11):3146-52.

Reimand et al., "g: Profiler—a web server for functional interpretation of gene lists (2016 update)," Nucleic Acids Research, Jul. 8, 2016, 44(W1):W83-9.

Rooney et al., "Molecular and genetic properties of tumors associated with local immune cytolytic activity," Cell, Jan. 15, 2015, 160(1-2):48-61.

Roulois et al., "DNA-demethylating agents target colorectal cancer cells by inducing viral mimicry by endogenous transcripts," Cell, Aug. 27, 2015, 162(5):961-73.

Sahin et al., "Personalized RNA mutanome vaccines mobilize poly-specific therapeutic immunity against cancer," Nature, Jul. 2017, 547(7662):222-6.

Sharma et al., "Immune checkpoint targeting in cancer therapy: toward combination strategies with curative potential," Cell, Apr. 9, 2015, 161(2):205-14.

Sharma et al., "Primary, adaptive, and acquired resistance to cancer immunotherapy," Cell, Feb. 9, 2017, 168(4):707-23.

Sharpe et al., "The diverse functions of the PD1 inhibitory pathway," Nature Reviews Immunology, Mar. 2018, 18(3):153.

Song et al., "The functions and regulation of the PTEN tumour suppressor," Nature Reviews Molecular Cell biology, May 2012, 13(5):283-96.

Takeuchi et al., "Pattern recognition receptors and inflammation," Cell, Mar. 19, 2010, 140(6):805-20.

Tam et al., "Pseudogene-derived small interfering RNAs regulate gene expression in mouse oocytes," Nature, May 2008, 453(7194):534-8.

Tumeh et al., "PD-1 blockade induces responses by inhibiting adaptive immune resistance," Nature, Nov. 2014, 515(7528):568-71.

Watanabe et al., "Endogenous siRNAs from naturally formed dsRNAs regulate transcripts in mouse oocytes," Nature, May 2008, 453(7194):539-43.

White et al., "Human nuclear Dicer restricts the deleterious accumulation of endogenous double-stranded RNA," Nature structural & Molecular Biology, Jun. 2014, 21(6):552-9.

Wiesen et al., "Dicer is regulated by cellular stresses and interferons," Molecular Immunology, Mar. 1, 2009, 46(6):1222-8.

Yu et al., "clusterProfiler: an R package for comparing biological themes among gene clusters," Omics: A Journal of Integrative Biology, May 1, 2012, 16(5):284-7.

Zhang et al., "Model-based analysis of ChIP-Seq (MACS)," Genome Biology, Nov. 2008, 9(9):1-9.

Zhang et al., "Pluripotent stem cell protein Sox2 confers sensitivity to LSD1 inhibition in cancer cells," Cell Reports, Oct. 31, 2013, 5(2):445-57.

Zhang et al., "PowerBLAST: a new network BLAST application for interactive or automated sequence analysis and annotation," Genome Research, Jun. 1, 1997, 7(6):649-56.

\* cited by examiner

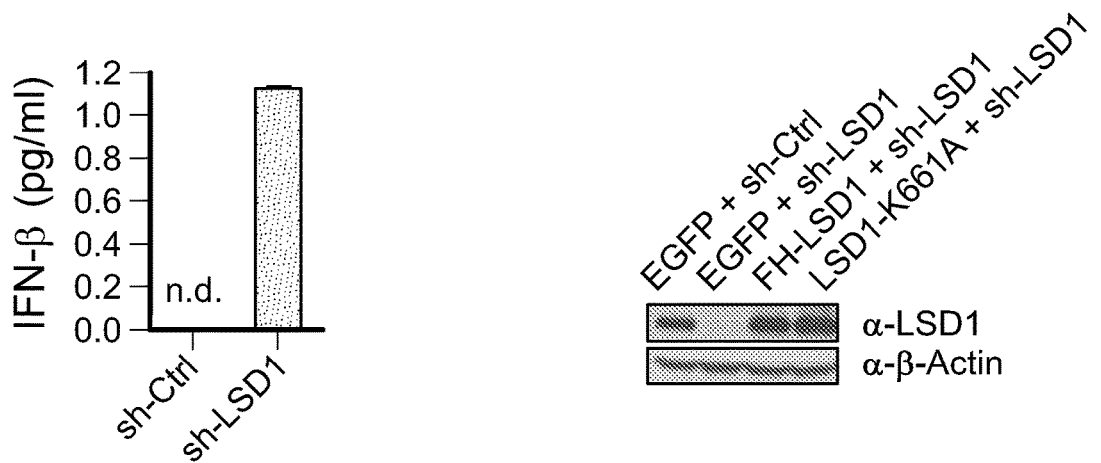
FIG. 1D
FIG. 1E
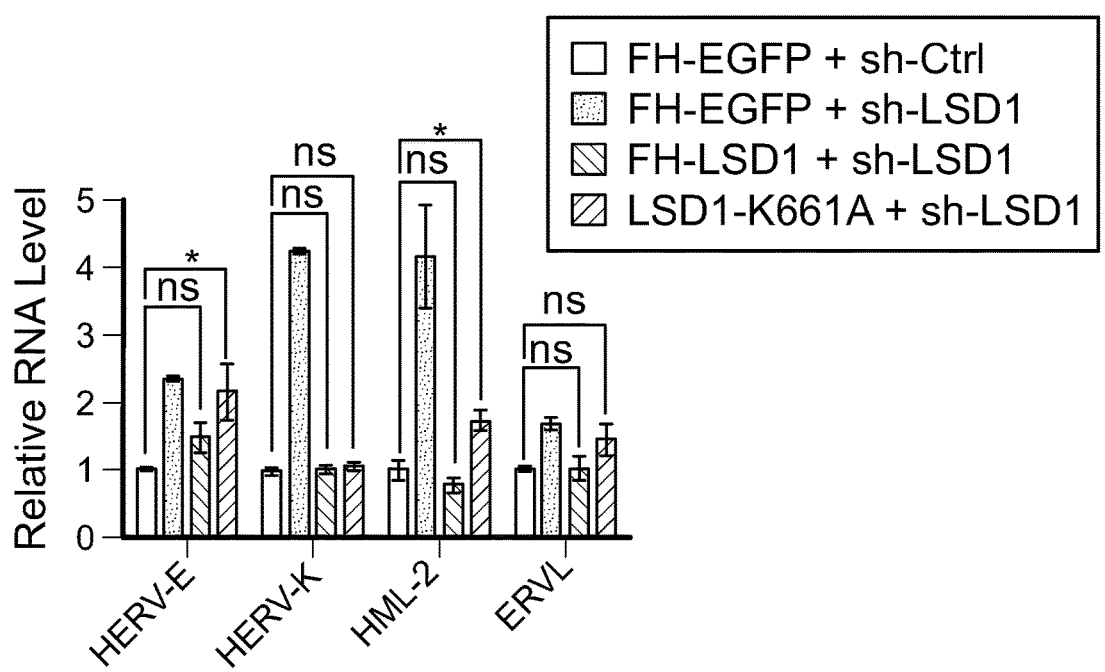
FIG. 1F

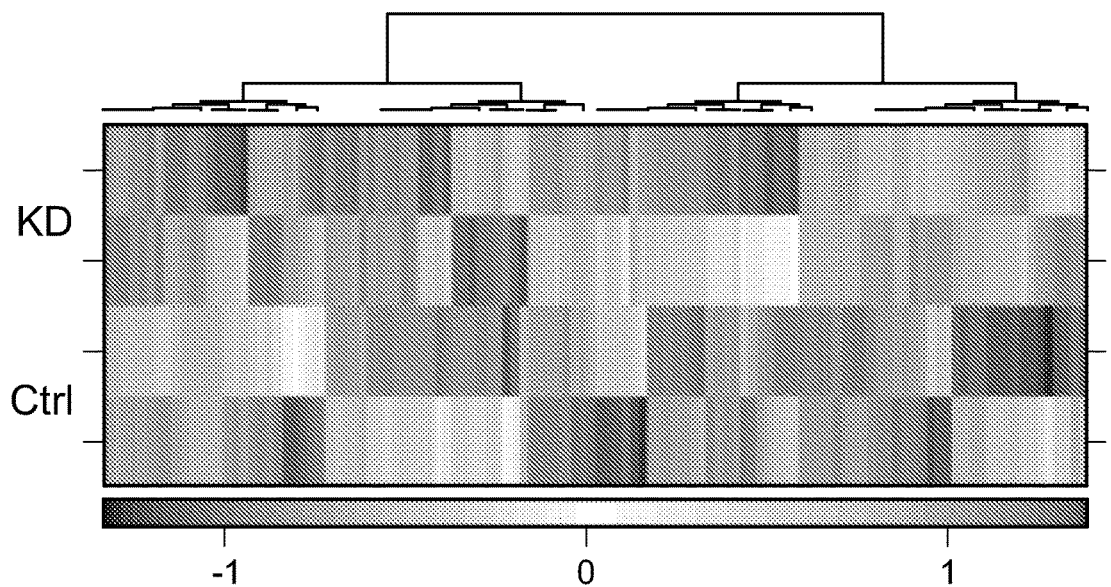
FIG. 2E
Sense Stranded ERVs
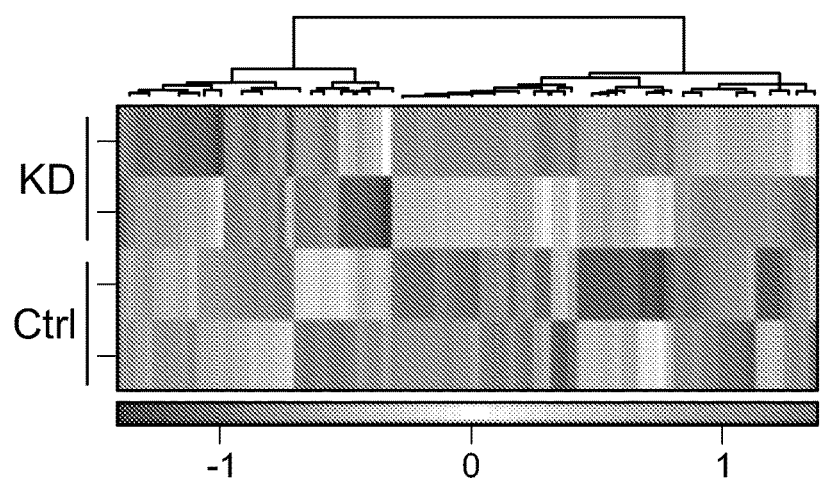
Anti-sense Stranded ERVs
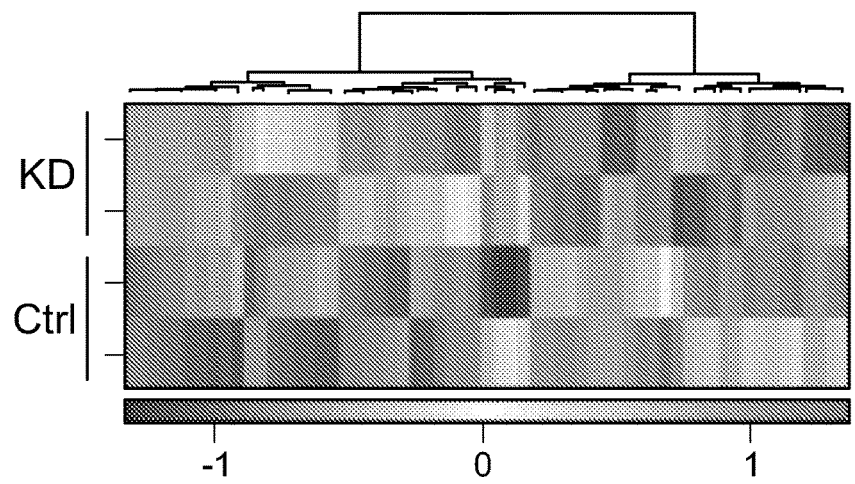
FIG. 2F

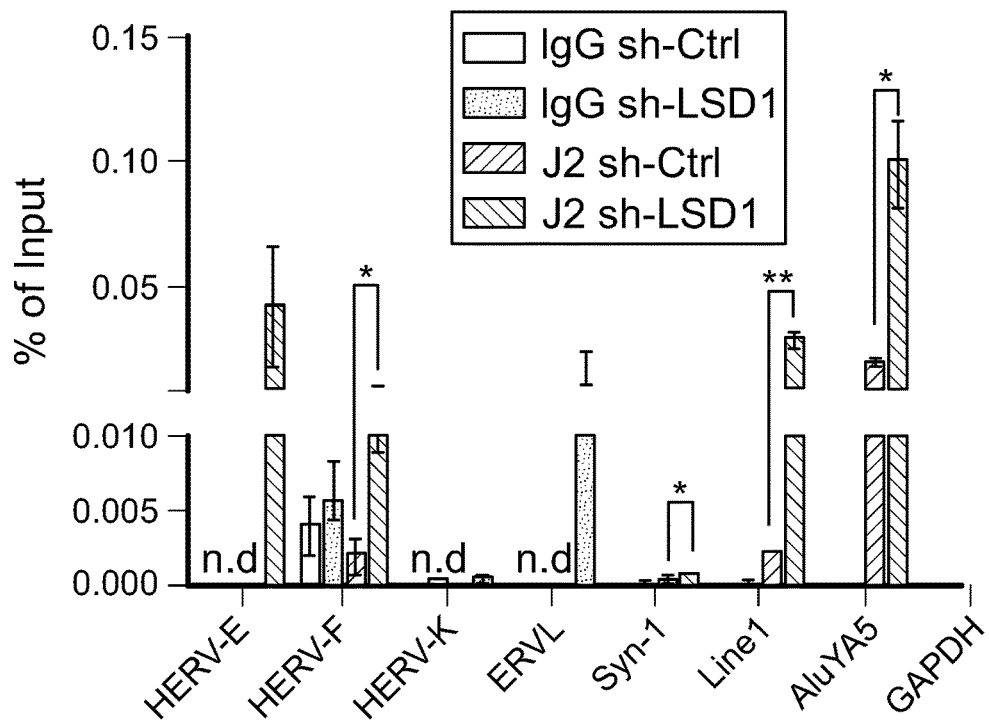
FIG. 2O
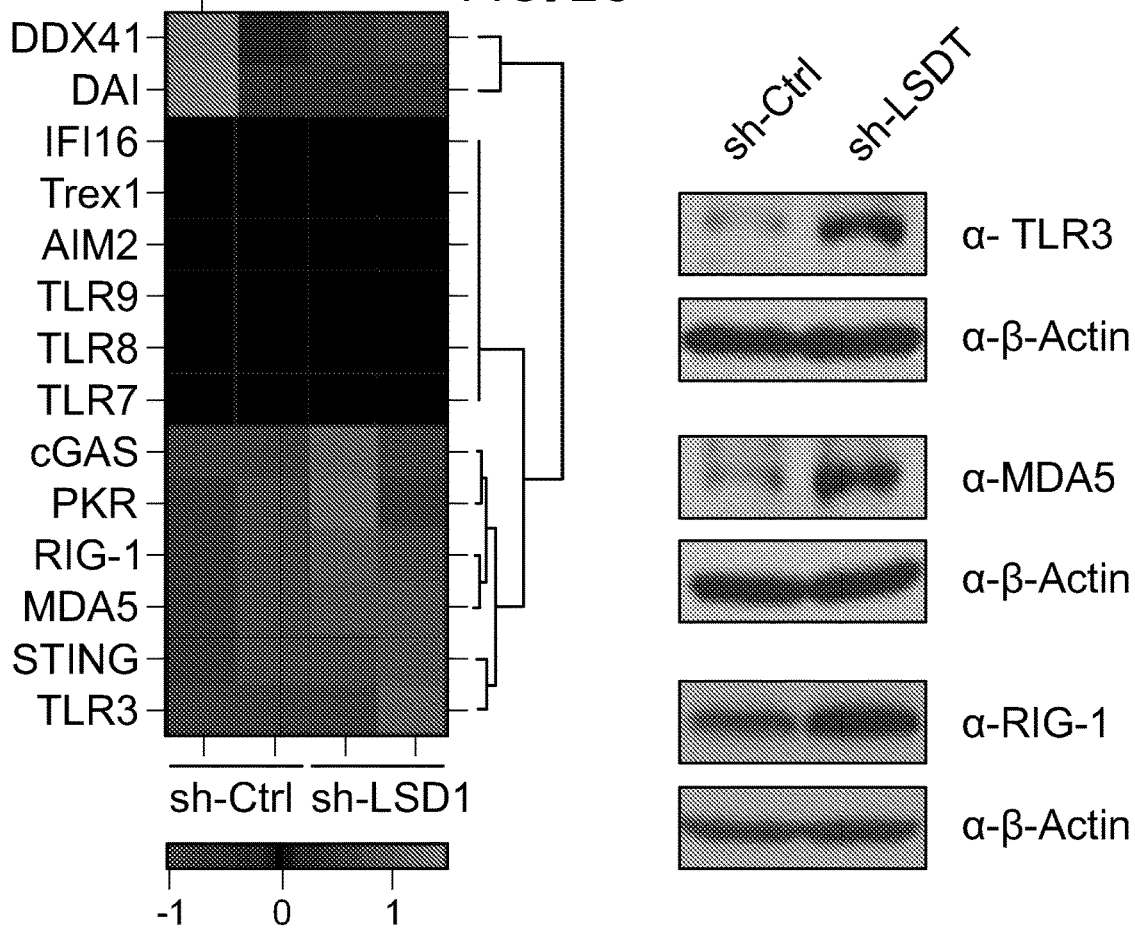
FIG. 2P
FIG. 2Q

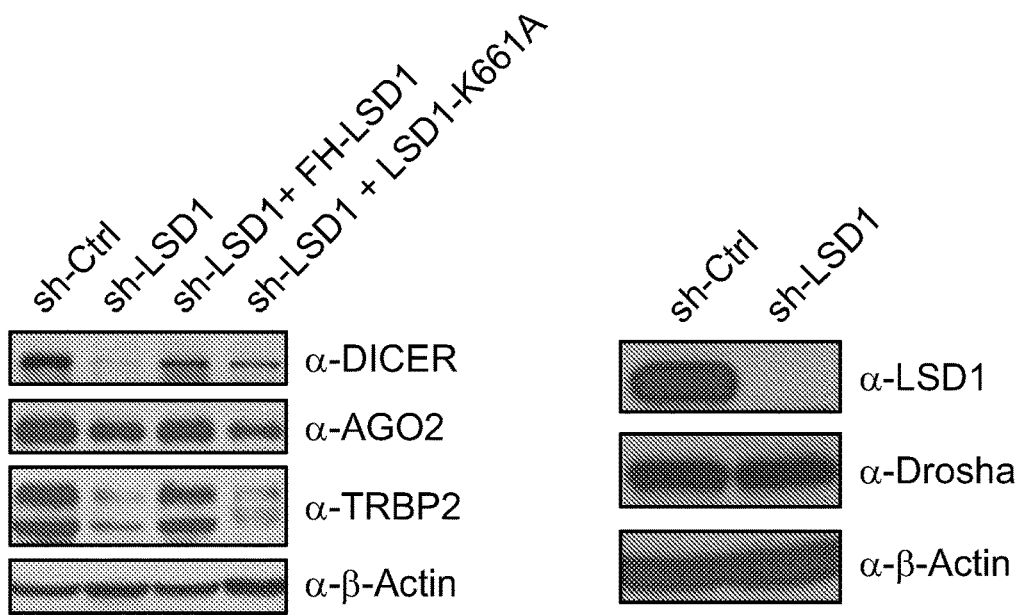
FIG. 4A
FIG. 4B
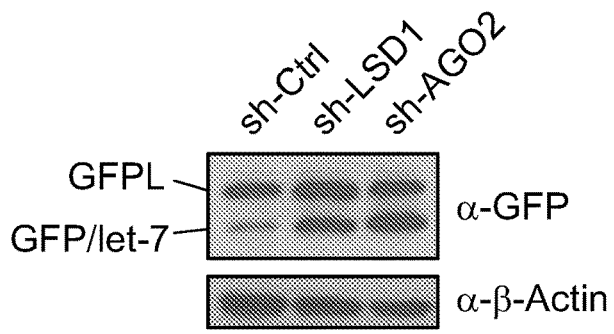
FIG. 4C
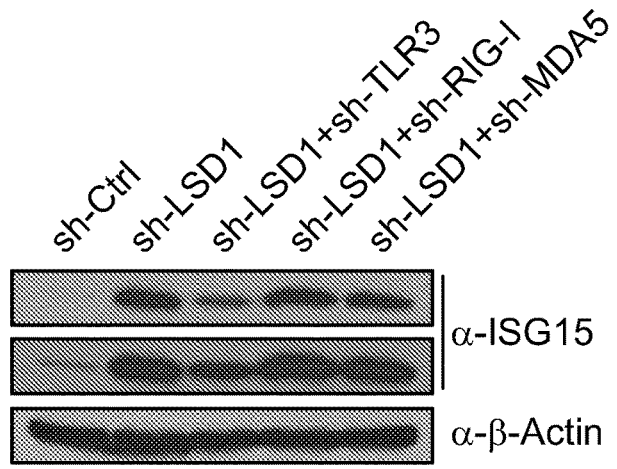
FIG. 4D

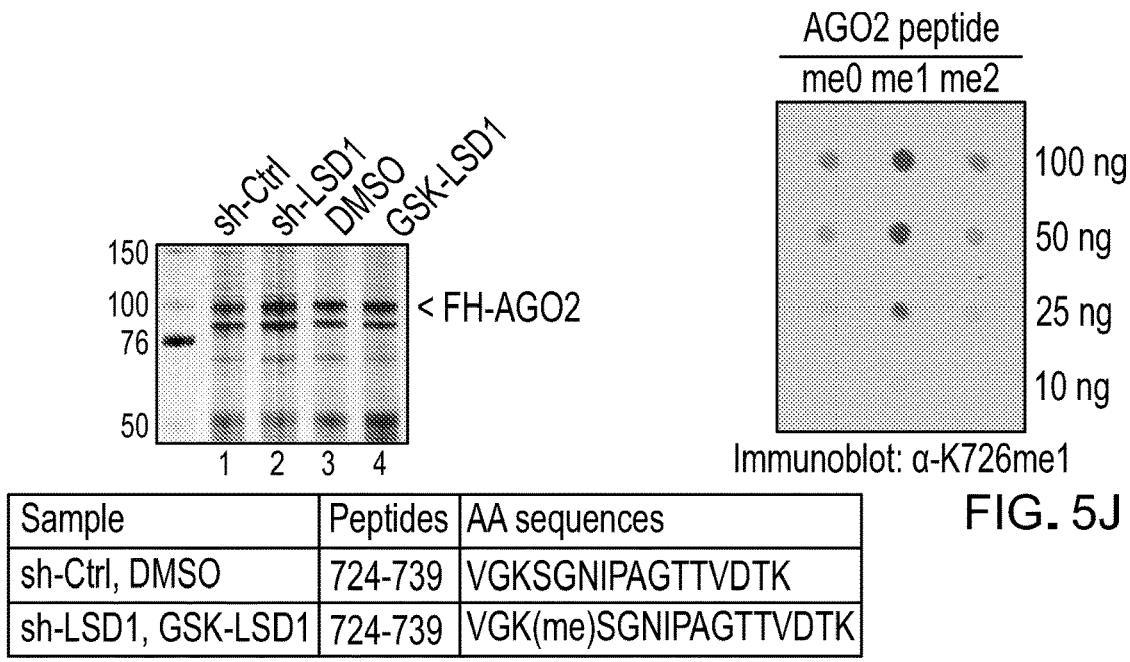
FIG. 5I
FIG. 5J
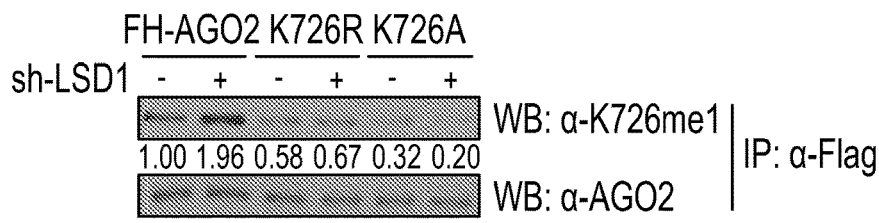
FIG. 5K
FIG. 5L
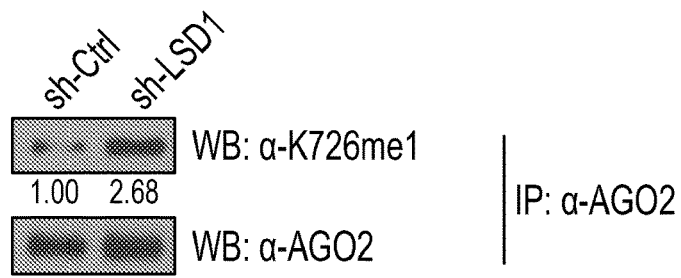
FIG. 5M

B16 CRIPSR-LSD1, clone gRNA4-7
Target    CACTITCATITICITCCICACGIGCOGCOTTGA
Reference CACTITCATITICITCCICACGIGCOGC-TTGA

B16 CRIPSR-LSD1, clone gRNA5-4
Target    TCCTGAGAGGTCATTCOG-CA7GGGGAAGTCGG
Reference TCCTGAGAGGTCAITCOGTCA7GGGGAAGTCGG

B16 CRIPSR-MDA5, clone gRNA4-16
Target    CA7G-TGCCIGAATGCCTGOCCATGITGCIGIT     One Allele
Reference CA7GGTGCCIGAATGCCTGOCCATGITGCIGIT
Target    CA7GG-GCCIGAATCCCTGCCCATGITGCIGIT     The Other Allele
Reference CA7GGIGCCIGAATCCCTGCCCATGITGCTGIT

B16 CRIPSR-LSD1/MDA5, clone gRNA4-19
Target    CA7G-TGCCIGAA7CCCTGCCATGI7GCTGIT      One Allele
Reference CA7GGTGCCIGAA7CCC7GCCCATGI7GCTGIT
Target    CA7GG--CCIGAA7CCCTGCCCATGI7GCIGIT     The Other Allele
Reference CA7GGTGCCIGAA7CCCTGCCCATGI7GCIGIT

B16 CRIPSR-IFNAR1, clone gRNA1-10
Target    ACCC----TCAATCCCCACTCTGACCTI7ICAC     One Allele
Reference ACGGAGAGTCAATCCCCACTCTGACCTI7ICAC
Target    AOGGAAGAGICAA7GGGCAGTGIGACCI7ITCA     The Other Allele
Reference AOGG-AGAGICAA7GGGCAGTGIGACCI7ITCA

B16 CRIPSR-LSD1/IFNAR1, clone gRNA1-16
Target    ACG--GAGTCAATGGGCAGTGTGACC7I7ICAG
Reference ACGGAGAGTCAATGGGCAGTGTGACC7I7ICAG

B16 CRIPSR-IFN-β, clone gRNA3-14
Target    GGGCGGACTICAAGA7CC-7ATGGAGATGACGG
Reference GGGCGGACTICAAGA7CCC7ATGGAGATGACGG

B16 CRIPSR-LSD1/IFN-β, clone gRNA3-16
Target    GGGCGGACT7CAAGATCC-TATGGAGA7GACGG
Reference GGGCGGACT7CAAGATCCCTATGGAGA7GACGG

B16 CRIPSR-LSD1/TLR3, clone gRNA6-7
Target    ACTI7CAACAAAGGGAGTAT-----------CT
Reference ACTI7CAACAAAGGGAGTAT7TGGCACAGTTCT

FIG. 6L

LLC CRIPSR-LSD1, clone gRNA5-A29

Target     AACAGGCTGCTTCCTGAGAGGTCATTCGG-CAT
           |||||||||||||||||||||||||||| |||
Reference  AACAGGCTGCTTCCTGAGAGGTCATTCGGTCAT

LLC CRIPSR-LSD1, clone gRNA5-B30

Target     AACAGGCTGCTTCCTGAGA--------GGTCAT
           |||||||||||||||||||        ||||||
Reference  AACAGGCTGCTTCCTGAGAGGTCATTCGGTCAT

FIG. 7A

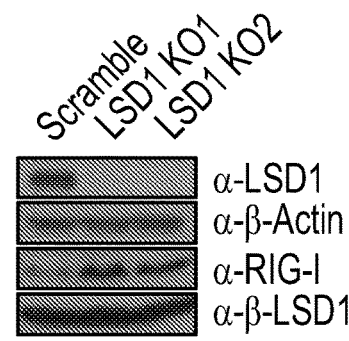

FIG. 7B

D4m CRIPSR-LSD1, clone gRNA5-B37

Target     AACAGGCTGCTTCCTGAGAGGTCATTC--TCAT
           ||||||||||||||||||||||||||  ||||
Reference  AACAGGCTGCTTCCTGAGAGGTCATTCGGTCAT

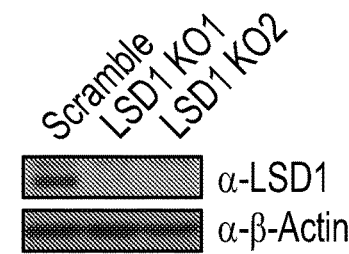

FIG. 7D

D4m CRIPSR-LSD1, clone gRNA3-8

Target     AATATTCATCTTCTGAG-GGTTGGCCAAGCTTT
           |||||||||||||||||  |||||||||||||| one allele
Reference  AATATTCATCTTCTGAGAGGTTGGCCAAGCTTT Target     AATATTCATCTTC--------TGGCCAAGCTTT
           |||||||||||||        |||||||||||| the other allele
Reference  AATATTCATCTTCTGAGAGGTTGGCCAAGCTTT

FIG. 7C gRNA4 clone #   5  7  9 10 12

 α-LSD1

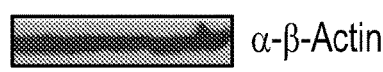 α-β-Actin gRNA clone #   1  2  4  7  8

 α-LSD1

 α-β-Actin mAb against truncated recombinant LSD1

FIG. 7E gRNA3 g4 g5 g6
clone #  C 1 7 8 9 7 1 4 5

 α-LSD1

 α-β-Actin rAb against aa800-C terminus

FIG. 7F

Scramble

LSD1 KO

MDA5 KO

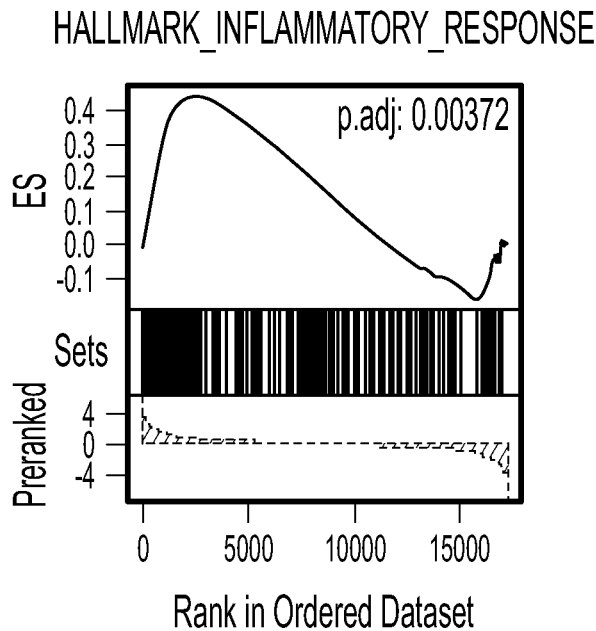
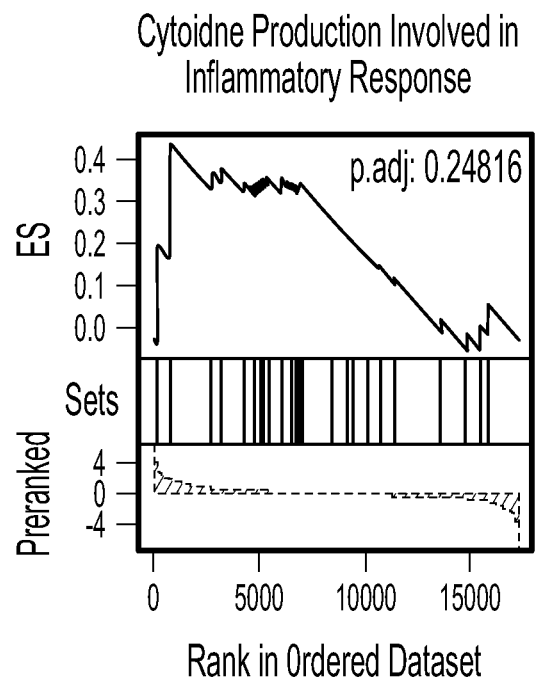
FIG. 10K
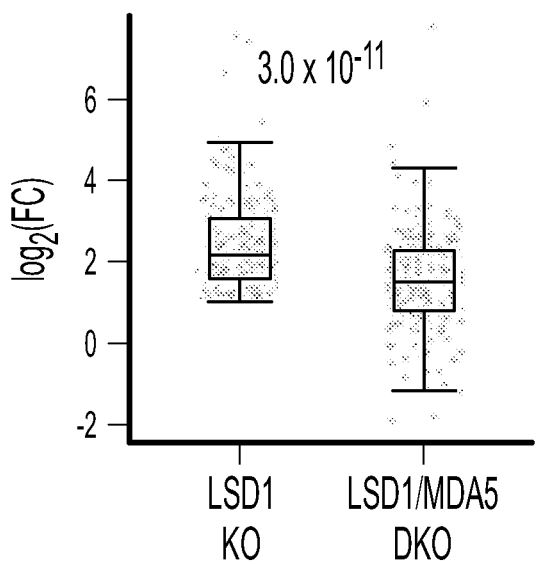
FIG. 10L
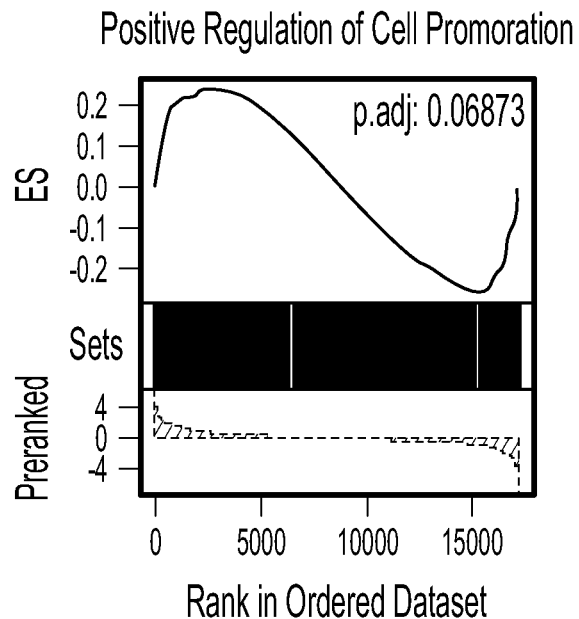
FIG. 10M

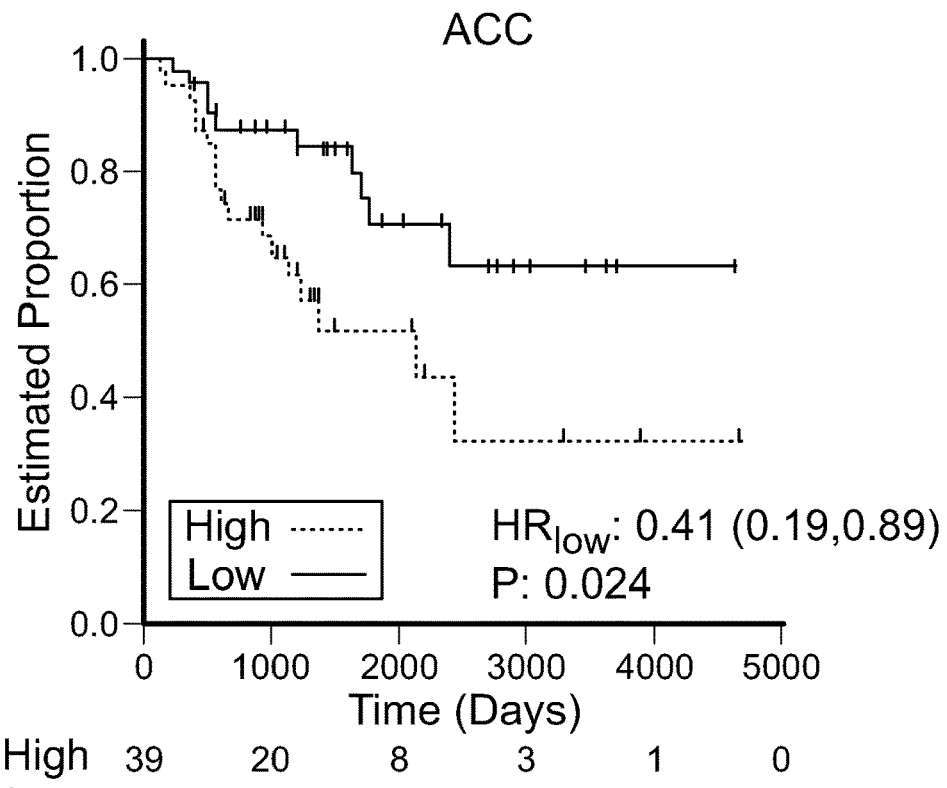
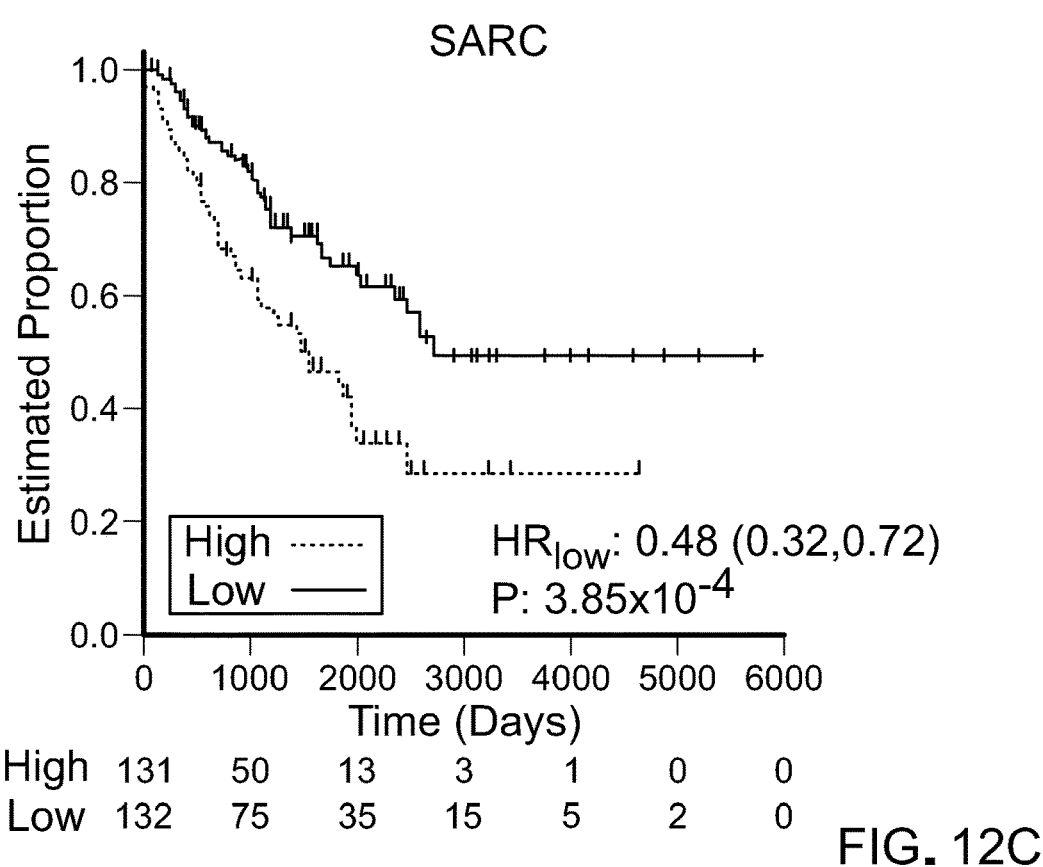
FIG. 12C

SEQUENCE LISTING

```
<160> NUMBER OF SEQ ID NOS: 157

<210> SEQ ID NO 1
<211> LENGTH: 2631
<212> TYPE: DNA
<213> ORGANISM: Homo sapiens

<400> SEQUENCE: 1
atgttatctg ggaagaaggc ggcagccgcg gcggcggcgg ctgcagcggc agcaaccggg      60
acggaggctg gccctgggac agcaggcggc tccgagaacg ggtctgaggt ggccgcgcag     120
cccgcgggcc tgtcgggccc agccgaggtc gggccggggg cggtggggga gcgcacaccc     180
cgcaagaaag agcctccgcg ggcctcgccc ccgggggcc tggcggaacc gccggggtcc      240
gcagggcctc aggccggccc tactgtcgtg cctgggtctg cgaccccat ggaaactgga      300 atagcagaga ctccggaggg gcgtcggacc agccggcgca agcgggcgaa ggtagagtac     360
agagagatgg atgaaagctt ggccaacctc tcagaagatg agtattattc agaagaagag     420
agaaatgcca aagcagagaa ggaaaagaag cttcccccac caccccctca agccccacct     480
gaggaagaaa atgaaagtga gcctgaagaa ccatcggggc aagcaggagg acttcaagac     540
gacagttctg gagggtatgg agacggccaa gcatcaggtg tggagggcgc agctttccag     600
agccgacttc ctcatgaccg gatgacttct caagaagcag cctgttttcc agatattatc     660
agtggaccac aacagaccca gaaggttttt cttttcatta gaaaccgcac actgcagttg     720
tggttggata atccaaagat tcagctgaca tttgaggcta ctctccaaca attagaagca     780
ccttataaca gtgatactgt gcttgtccac cgagttcaca gttatttaga gcgtcatggt     840
cttatcaact tcggcatcta taagaggata aaacccctac caactaaaaa gacaggaaag     900
gtaattatta taggctctgg ggtctcaggc ttggcagcag ctcgacagtt acaaagtttt     960
ggaatggatg tcacactttt ggaagccagg gatcgtgtgg gtggacgagt tgccacattt    1020
cgcaaaggaa actatgtagc tgatcttgga gccatggtgg taacaggtct tggagggaat    1080
cctatggctg tggtcagcaa acaagtaaat atggaactgc caagatcaa gcaaaaatgc    1140 ccactttatg aagccaacgg acaagctgac actgtcaagg ttcctaaaga gaaagatgaa    1200
atggtagagc aagagtttaa ccggttgcta gaagctacat cttaccttag tcatcaacta    1260
gacttcaatg tcctcaataa taagcctgtg tcccttggcc aggcattgga agttgtcatt    1320
cagttacaag agaagcatgt caaagatgag cagattgaac attggaagaa gatagtgaaa    1380
actcaggaag aattgaaaga acttcttaat aagatggtaa atttgaaaga gaaattaaa    1440 gaactccatc agcaatacaa agaagcatct gaagtaaagc cacccagaga tattactgcc    1500
```

```
gagttcttag tgaaaagcaa acacagggat ctgaccgccc tatgcaagga atatgatgaa    1560
ttagctgaaa cacaaggaaa gctagaagaa aaacttcagg agttggaagc gaatccccca    1620
agtgatgtat atctctcatc aagagacaga caaatacttg attggcattt tgcaaatctt    1680
gaatttgcta atgccacacc tctctcaact ctctcccttta agcactggga tcaggatgat    1740
gactttgagt tcactggcag ccacctgaca gtaaggaatg ctactcgtg tgtgcctgtg     1800 gctttagcag aaggcctaga cattaaactg aatacagcag tgcgacaggt tcgctacacg    1860
gcttcaggat gtgaagtgat agctgtgaat acccgctcca cgagtcaaac ctttattat     1920 aaatgcgacg cagttctctg tacccttccc ctgggtgtgc tgaagcagca gccaccagcc    1980
gttcagtttg tgccacctct ccctgagtgg aaaacatctg cagtccaaag gatgggattt    2040
ggcaacctta acaaggtggt gttgtgtttt gatcgggtgt tctgggatcc aagtgtcaat    2100
ttgttcgggc atgttggcag tacgactgcc agcaggggtg agctcttcct cttctggaac    2160
ctctataaag ctccaatact gttggcacta gtggcaggag aagctgctgg tatcatggaa    2220
aacataagtg acgatgtgat tgttggccga tgcctggcca ttctcaaagg gattttggt    2280 agcagtgcag tacctcagcc caaagaaact gtggtgtctc gttggcgtgc tgatccctgg    2340
gctcggggct cttattccta tgttgctgca ggatcatctg gaaatgacta tgatttaatg    2400
gctcagccaa tcactcctgg cccctcgatt ccaggtgccc cacagccgat tccacgactc    2460
ttctttgcgg gagaacatac gatccgtaac tacccagcca cagtgcatgg tgctctgctg    2520
agtgggctgc gagaagcggg aagaattgca gaccagtttt tgggggccat gtatacgctg    2580
cctcgccagg ccacaccagg tgttcctgca cagcagtccc aagcatgtg a              2631

<210> SEQ ID NO 2
<211> LENGTH: 58
<212> TYPE: DNA
<213> ORGANISM: Artificial Sequence
<220> FEATURE:
<223> OTHER INFORMATION: shRNA targeting human LSD1

<400> SEQUENCE: 2
ccgggcctag acattaaact gaatactcga gtattcagtt taatgtctag gcttttttg     58

<210> SEQ ID NO 3
<211> LENGTH: 867
<212> TYPE: DNA
<213> ORGANISM: Homo sapiens

<400> SEQUENCE: 3
atgcagatcc cacaggcgcc ctggccagtc gtctgggcgg tgctacaact gggctggcgg    60
ccaggatggt tcttagactc cccagacagg ccctggaacc ccccaccttt ctccccagcc    120
ctgctcgtgg tgaccgaagg ggacaacgcc accttcacct gcagcttctc caacacatcg    180
gagagcttcg tgctaaactg gtaccgcatg agccccagca accagacgga caagctggcc    240
gccttccccg aggaccgcag ccagcccggc caggactgcc gcttccgtgt cacacaactg    300
cccaacgggc gtgacttcca catgagcgtg gtcagggccc ggcgcaatga cagcggcacc    360
tacctctgtg gggccatctc cctggcccc aaggcgcaga tcaaagagag cctgcgggca    420
gagctcaggg tgacagagag aagggcagaa gtgcccacag cccaccccag ccctcacccc    480
aggccagccg ccagttccaa accctggtgg ttggtgtcg tgggcggcct gctgggcagc    540
ctggtgctgc tagtctgggt cctggccgtc atctgctcc gggccgcacg agggacaata    600
```

```
ggagccaggc gcaccggcca gcccctgaag gaggacccct cagccgtgcc tgtgttctct    660
gtggactatg gggagctgga tttccagtgg cgagagaaga ccccggagcc ccccgtgccc    720
tgtgtccctg agcagacgga gtatgccacc attgtctttc ctagcggaat gggcacctca    780
tcccccgccc gcaggggctc agctgacggc cctcggagtg cccagccact gaggcctgag    840
gatggacact gctcttggcc cctctga                                        867
```

```
<210> SEQ ID NO 4
<211> LENGTH: 58
<212> TYPE: DNA
<213> ORGANISM: Artificial Sequence
<220> FEATURE:
<223> OTHER INFORMATION: shRNA targeting human PD-1

<400> SEQUENCE: 4
ccggcattgt ctttcctagc ggaatctcga gattccgcta ggaaagacaa tgttttg       58
```

```
<210> SEQ ID NO 5
<211> LENGTH: 873
<212> TYPE: DNA
<213> ORGANISM: Homo sapiens

<400> SEQUENCE: 5
atgaggatat ttgctgtctt tatattcatg acctactggc atttgctgaa cgcatttact     60
gtcacggttc ccaaggacct atatgtggta gagtatggta gcaatatgac aattgaatgc    120
aaattcccag tagaaaaaca attagacctg gctgcactaa ttgtctattg ggaaatggag    180
gataagaaca ttattcaatt tgtgcatgga gaggaagacc tgaaggttca gcatagtagc    240
tacagacaga gggcccggct gttgaaggac cagctctccc tgggaaatgc tgcacttcag    300
atcacagatg tgaaattgca ggatgcaggg gtgtaccgct gcatgatcag ctatggtggt    360
gccgactaca agcgaattac tgtgaaagtc aatgccccat acaacaaaat caaccaaaga    420
attttggttg tggatccagt cacctctgaa catgaactga catgtcaggc tgagggctac    480
cccaaggccg aagtcatctg acaagcagt gaccatcaag tcctgagtgg taagaccacc    540
accaccaatt ccaagagaga ggagaagctt tcaatgtga ccagcacact gagaatcaac    600
acaacaacta atgagatttt ctactgcact tttaggagat tagatcctga ggaaaaccat    660
acagctgaat tggtcatccc agaactacct ctggcacatc ctccaaatga aaggactcac    720
ttggtaattc tgggagccat cttattatgc cttggtgtag cactgacatt catcttccgt    780
ttaagaaaag ggagaatgat ggatgtgaaa aatgtggca tccaagatac aaactcaaag    840
aagcaaagtg atacacattt ggaggagacg taa                                 873
```

```
<210> SEQ ID NO 6
<211> LENGTH: 58
<212> TYPE: DNA
<213> ORGANISM: Artificial Sequence
<220> FEATURE:
<223> OTHER INFORMATION: ShRNA targeting human PD-L1

<400> SEQUENCE: 6
ccggctgaca ttcatcttcc gtttactcga gtaaacggaa gatgaatgtc agttttg       58
```

```
<210> SEQ ID NO 7
<211> LENGTH: 22
<212> TYPE: DNA
<213> ORGANISM: Artificial Sequence
<220> FEATURE:
<223> OTHER INFORMATION: ShRNA targeting human PD-L1
```

```
<400> SEQUENCE: 7
gcaagctgac cctgaagttc at                                          22

<210> SEQ ID NO 8
<211> LENGTH: 21
<212> TYPE: DNA
<213> ORGANISM: Artificial Sequence
<220> FEATURE:
<223> OTHER INFORMATION: GCAAGCTGACCCTGAAGTTCAT

<400> SEQUENCE: 8
cctaaggtta agtcgccctc g                                           21

<210> SEQ ID NO 9
<211> LENGTH: 21
<212> TYPE: DNA
<213> ORGANISM: Artificial Sequence
<220> FEATURE:
<223> OTHER INFORMATION: Scrambled shRNA sequence

<400> SEQUENCE: 9
gcctagacat taaactgaat a                                           21

<210> SEQ ID NO 10
<211> LENGTH: 19
<212> TYPE: DNA
<213> ORGANISM: Artificial Sequence
<220> FEATURE:
<223> OTHER INFORMATION: shRNA targeting human TLR3

<400> SEQUENCE: 10
ccttacacat actcaacct                                              19

<210> SEQ ID NO 11
<211> LENGTH: 21
<212> TYPE: DNA
<213> ORGANISM: Artificial Sequence
<220> FEATURE:
<223> OTHER INFORMATION: shRNA targeting human MDA5

<400> SEQUENCE: 11
ccaacaaaga agcagtgtat a                                           21

<210> SEQ ID NO 12
<211> LENGTH: 19
<212> TYPE: DNA
<213> ORGANISM: Artificial Sequence
<220> FEATURE:
<223> OTHER INFORMATION: shRNA targeting human RIG-I

<400> SEQUENCE: 12
aattcatcag agatagtca                                              19

<210> SEQ ID NO 13
<211> LENGTH: 19
<212> TYPE: DNA
<213> ORGANISM: Artificial Sequence
<220> FEATURE:
<223> OTHER INFORMATION: shRNA targeting human MAVS

<400> SEQUENCE: 13
gcatctcttc aataccctt                                              19

<210> SEQ ID NO 14
```

```
<211> LENGTH: 19
<212> TYPE: DNA
<213> ORGANISM: Artificial Sequence
<220> FEATURE:
<223> OTHER INFORMATION: shRNA targeting human MAVS

<400> SEQUENCE: 14
ggagagaatt cagagcaag                                                   19

<210> SEQ ID NO 15
<211> LENGTH: 21
<212> TYPE: DNA
<213> ORGANISM: Artificial Sequence
<220> FEATURE:
<223> OTHER INFORMATION: shRNA targeting human cGAS

<400> SEQUENCE: 15
atctattctc tagcaactta a                                                21

<210> SEQ ID NO 16
<211> LENGTH: 19
<212> TYPE: DNA
<213> ORGANISM: Artificial Sequence
<220> FEATURE:
<223> OTHER INFORMATION: shRNA targeting human STING

<400> SEQUENCE: 16
gcatggtcat attacatcg                                                   19

<210> SEQ ID NO 17
<211> LENGTH: 21
<212> TYPE: DNA
<213> ORGANISM: Artificial Sequence
<220> FEATURE:
<223> OTHER INFORMATION: shRNA targeting human AGO2

<400> SEQUENCE: 17
gcacagccag taatcgagtt t                                                21

<210> SEQ ID NO 18
<211> LENGTH: 21
<212> TYPE: DNA
<213> ORGANISM: Artificial Sequence
<220> FEATURE:
<223> OTHER INFORMATION: shRNA 1 targeting human DICER

<400> SEQUENCE: 18
aagaatcagc ctcgcaacaa a                                                21

<210> SEQ ID NO 19
<211> LENGTH: 19
<212> TYPE: DNA
<213> ORGANISM: Artificial Sequence
<220> FEATURE:
<223> OTHER INFORMATION: shRNA 4 targeting human DICER

<400> SEQUENCE: 19
tctattagca ccttgatgt                                                   19

<210> SEQ ID NO 20
<211> LENGTH: 19
<212> TYPE: DNA
<213> ORGANISM: Artificial Sequence
<220> FEATURE:
<223> OTHER INFORMATION: shRNA 1 targeting human TRBP2

<400> SEQUENCE: 20
```

-continued gctgcctagt atagagcaa                                                19

<210> SEQ ID NO 21
<211> LENGTH: 19
<212> TYPE: DNA
<213> ORGANISM: Artificial Sequence
<220> FEATURE:
<223> OTHER INFORMATION: shRNA 2 targeting human TRBP2

<400> SEQUENCE: 21
tctacgaaat tcagtagga                                                19

<210> SEQ ID NO 22
<211> LENGTH: 19
<212> TYPE: DNA
<213> ORGANISM: Artificial Sequence
<220> FEATURE:
<223> OTHER INFORMATION: shRNA 4 targeting human TRBP2

<400> SEQUENCE: 22
ggattctcta cgaaattca                                                19

<210> SEQ ID NO 23
<211> LENGTH: 19
<212> TYPE: DNA
<213> ORGANISM: Artificial Sequence
<220> FEATURE:
<223> OTHER INFORMATION: shRNA 1 targeting mouse LSD1

<400> SEQUENCE: 23
cacaaggaaa gctagaaga                                                19

<210> SEQ ID NO 24
<211> LENGTH: 21
<212> TYPE: DNA
<213> ORGANISM: Artificial Sequence
<220> FEATURE:
<223> OTHER INFORMATION: shRNA 2 targeting mouse LSD1

<400> SEQUENCE: 24
ggatgggatt tggcaacctt a                                             21

<210> SEQ ID NO 25
<211> LENGTH: 21
<212> TYPE: DNA
<213> ORGANISM: Artificial Sequence
<220> FEATURE:
<223> OTHER INFORMATION: shRNA 3 targeting mouse LSD1

<400> SEQUENCE: 25
aactccatgt catcagctac t                                             21

<210> SEQ ID NO 26
<211> LENGTH: 21
<212> TYPE: DNA
<213> ORGANISM: Artificial Sequence
<220> FEATURE:
<223> OTHER INFORMATION: shRNA 4 targeting mouse LSD1

<400> SEQUENCE: 26
cggcatctac aagaggataa a                                             21

<210> SEQ ID NO 27
<211> LENGTH: 20
<212> TYPE: DNA

-continued

<213> ORGANISM: Mus musculus

<400> SEQUENCE: 27
atattcatct tctgagaggt                                           20

<210> SEQ ID NO 28
<211> LENGTH: 20
<212> TYPE: DNA
<213> ORGANISM: Mus musculus

<400> SEQUENCE: 28
tcttcctcag gtggggcttg                                           20

<210> SEQ ID NO 29
<211> LENGTH: 20
<212> TYPE: DNA
<213> ORGANISM: Mus musculus

<400> SEQUENCE: 29
cctgagaggt cattcggtca                                           20

<210> SEQ ID NO 30
<211> LENGTH: 20
<212> TYPE: DNA
<213> ORGANISM: Mus musculus

<400> SEQUENCE: 30
ccatgaccga atgacctctc                                           20

<210> SEQ ID NO 31
<211> LENGTH: 20
<212> TYPE: DNA
<213> ORGANISM: Mus musculus

<400> SEQUENCE: 31
ggcagggatt caggcaccat                                           20

<210> SEQ ID NO 32
<211> LENGTH: 20
<212> TYPE: DNA
<213> ORGANISM: Artificial Sequence
<220> FEATURE:
<223> OTHER INFORMATION: Forward primer sequence for human GAPDH

<400> SEQUENCE: 32
aacgggaagc ttgtcatcaa                                           20

<210> SEQ ID NO 33
<211> LENGTH: 20
<212> TYPE: DNA
<213> ORGANISM: Artificial Sequence
<220> FEATURE:
<223> OTHER INFORMATION: Reverse primer sequence for human GAPDH

<400> SEQUENCE: 33
tggactccac gacgtactca                                           20

<210> SEQ ID NO 34
<211> LENGTH: 21
<212> TYPE: DNA
<213> ORGANISM: Artificial Sequence
<220> FEATURE:
<223> OTHER INFORMATION: Forward primer sequence for human LSD1

<400> SEQUENCE: 34

```
gtggacgagt tgccacattt c                                              21

<210> SEQ ID NO 35
<211> LENGTH: 21
<212> TYPE: DNA
<213> ORGANISM: Artificial Sequence
<220> FEATURE:
<223> OTHER INFORMATION: Reverse primer sequence for human LSD1

<400> SEQUENCE: 35
tgaccacagc cataggattc c                                              21

<210> SEQ ID NO 36
<211> LENGTH: 20
<212> TYPE: DNA
<213> ORGANISM: Artificial Sequence
<220> FEATURE:
<223> OTHER INFORMATION: Forward primer sequence for human HERV-E

<400> SEQUENCE: 36
ggtgtcacta ctcaatacac                                                20

<210> SEQ ID NO 37
<211> LENGTH: 17
<212> TYPE: DNA
<213> ORGANISM: Artificial Sequence
<220> FEATURE:
<223> OTHER INFORMATION: Reverse primer sequence for human HERV-E

<400> SEQUENCE: 37
gcagcctagg tctctgg                                                   17

<210> SEQ ID NO 38
<211> LENGTH: 19
<212> TYPE: DNA
<213> ORGANISM: Artificial Sequence
<220> FEATURE:
<223> OTHER INFORMATION: Forward primer sequence for human HERV-F

<400> SEQUENCE: 38
cctccagtca caacaactc                                                 19

<210> SEQ ID NO 39
<211> LENGTH: 19
<212> TYPE: DNA
<213> ORGANISM: Artificial Sequence
<220> FEATURE:
<223> OTHER INFORMATION: Reverse primer sequence for human HERV-F

<400> SEQUENCE: 39
tattgaagaa ggcggctgg                                                 19

<210> SEQ ID NO 40
<211> LENGTH: 22
<212> TYPE: DNA
<213> ORGANISM: Artificial Sequence
<220> FEATURE:
<223> OTHER INFORMATION: Forward primer sequence for human HERV-K

<400> SEQUENCE: 40
attggcaaca ccgtattctg ct                                             22

<210> SEQ ID NO 41
<211> LENGTH: 23
<212> TYPE: DNA
```

```
<213> ORGANISM: Artificial Sequence
<220> FEATURE:
<223> OTHER INFORMATION: Reverse primer sequence for human HERV-K

<400> SEQUENCE: 41
cagtcaaaat atggacggat ggt                                          23

<210> SEQ ID NO 42
<211> LENGTH: 18
<212> TYPE: DNA
<213> ORGANISM: Artificial Sequence
<220> FEATURE:
<223> OTHER INFORMATION: Forward primer sequence for human HML-2

<400> SEQUENCE: 42
aaagaaccag ccaccagg                                                18

<210> SEQ ID NO 43
<211> LENGTH: 21
<212> TYPE: DNA
<213> ORGANISM: Artificial Sequence
<220> FEATURE:
<223> OTHER INFORMATION: Reverse primer sequence for human HML-2

<400> SEQUENCE: 43
cagtctgaaa acttttctct a                                            21

<210> SEQ ID NO 44
<211> LENGTH: 20
<212> TYPE: DNA
<213> ORGANISM: Artificial Sequence
<220> FEATURE:
<223> OTHER INFORMATION: Forward primer sequence for human ERVL

<400> SEQUENCE: 44
atatcctgcc tggatggggt                                              20

<210> SEQ ID NO 45
<211> LENGTH: 22
<212> TYPE: DNA
<213> ORGANISM: Artificial Sequence
<220> FEATURE:
<223> OTHER INFORMATION: Reverse primer sequence for human ERVL

<400> SEQUENCE: 45
gagcttctta gtcctcctgt gt                                           22

<210> SEQ ID NO 46
<211> LENGTH: 19
<212> TYPE: DNA
<213> ORGANISM: Artificial Sequence
<220> FEATURE:
<223> OTHER INFORMATION: Forward primer sequence for human Line 1

<400> SEQUENCE: 46
gccaagatgg ccgaatagg                                               19

<210> SEQ ID NO 47
<211> LENGTH: 22
<212> TYPE: DNA
<213> ORGANISM: Artificial Sequence
<220> FEATURE:
<223> OTHER INFORMATION: Reverse primer sequence for human Line 1

<400> SEQUENCE: 47
tggcactccc tagtgagatg aa                                           22
```

<210> SEQ ID NO 48
<211> LENGTH: 22
<212> TYPE: DNA
<213> ORGANISM: Artificial Sequence
<220> FEATURE:
<223> OTHER INFORMATION: Forward primer sequence for human AluYA5

<400> SEQUENCE: 48
accatcccgg ctaaaacggt ga                                          22

<210> SEQ ID NO 49
<211> LENGTH: 17
<212> TYPE: DNA
<213> ORGANISM: Artificial Sequence
<220> FEATURE:
<223> OTHER INFORMATION: Reverse primer sequence for human AluYA5

<400> SEQUENCE: 49
gcgatctcgg ctcactg                                                17

<210> SEQ ID NO 50
<211> LENGTH: 23
<212> TYPE: DNA
<213> ORGANISM: Artificial Sequence
<220> FEATURE:
<223> OTHER INFORMATION: Forward primer sequence for human IFN alpha

<400> SEQUENCE: 50
aatgacagaa ttcatgaaag cgt                                         23

<210> SEQ ID NO 51
<211> LENGTH: 18
<212> TYPE: DNA
<213> ORGANISM: Artificial Sequence
<220> FEATURE:
<223> OTHER INFORMATION: Reverse primer sequence for human IFN alpha

<400> SEQUENCE: 51
ggaggttgtc agagcaga                                               18

<210> SEQ ID NO 52
<211> LENGTH: 21
<212> TYPE: DNA
<213> ORGANISM: Artificial Sequence
<220> FEATURE:
<223> OTHER INFORMATION: Forward primer sequence for human IFN beta

<400> SEQUENCE: 52
gccatcagtc acttaaacag c                                           21

<210> SEQ ID NO 53
<211> LENGTH: 22
<212> TYPE: DNA
<213> ORGANISM: Artificial Sequence
<220> FEATURE:
<223> OTHER INFORMATION: Reverse primer sequence for human IFN beta

<400> SEQUENCE: 53
gaaactgaag atctcctagc ct                                          22

<210> SEQ ID NO 54
<211> LENGTH: 17
<212> TYPE: DNA
<213> ORGANISM: Artificial Sequence
<220> FEATURE:

```
<223> OTHER INFORMATION: Forward primer sequence for human IL-28a/b

<400> SEQUENCE: 54
tccagtcacg gtcagca                                                    17

<210> SEQ ID NO 55
<211> LENGTH: 21
<212> TYPE: DNA
<213> ORGANISM: Artificial Sequence
<220> FEATURE:
<223> OTHER INFORMATION: Reverse primer sequence for human IL-28a/b

<400> SEQUENCE: 55
cagcctcaga gtgtttcttc t                                               21

<210> SEQ ID NO 56
<211> LENGTH: 20
<212> TYPE: DNA
<213> ORGANISM: Artificial Sequence
<220> FEATURE:
<223> OTHER INFORMATION: Forward primer sequence for human OASL

<400> SEQUENCE: 56
gcagaaattt ccaggaccac                                                 20

<210> SEQ ID NO 57
<211> LENGTH: 19
<212> TYPE: DNA
<213> ORGANISM: Artificial Sequence
<220> FEATURE:
<223> OTHER INFORMATION: Reverse primer for sequence human OASL

<400> SEQUENCE: 57
cccatcacgg tcaccattg                                                  19

<210> SEQ ID NO 58
<211> LENGTH: 17
<212> TYPE: DNA
<213> ORGANISM: Artificial Sequence
<220> FEATURE:
<223> OTHER INFORMATION: Forward primer sequence for human ISG15

<400> SEQUENCE: 58
ccttcagctc tgacacc                                                    17

<210> SEQ ID NO 59
<211> LENGTH: 22
<212> TYPE: DNA
<213> ORGANISM: Artificial Sequence
<220> FEATURE:
<223> OTHER INFORMATION: Reverse primer sequence for human ISG15

<400> SEQUENCE: 59
cgaactcatc tttgccagta ca                                              22

<210> SEQ ID NO 60
<211> LENGTH: 21
<212> TYPE: DNA
<213> ORGANISM: Artificial Sequence
<220> FEATURE:
<223> OTHER INFORMATION: Forward primer sequence for human TLR3

<400> SEQUENCE: 60
tggttgggcc acctagaagt a                                               21
```

```
<210> SEQ ID NO 61
<211> LENGTH: 19
<212> TYPE: DNA
<213> ORGANISM: Artificial Sequence
<220> FEATURE:
<223> OTHER INFORMATION: Reverse primer sequence for human TLR3

<400> SEQUENCE: 61
tctccattcc tggcctgtg                                              19

<210> SEQ ID NO 62
<211> LENGTH: 21
<212> TYPE: DNA
<213> ORGANISM: Artificial Sequence
<220> FEATURE:
<223> OTHER INFORMATION: Forward primer sequence for human MDA5

<400> SEQUENCE: 62
cacttccttc tgccaaactt g                                           21

<210> SEQ ID NO 63
<211> LENGTH: 22
<212> TYPE: DNA
<213> ORGANISM: Artificial Sequence
<220> FEATURE:
<223> OTHER INFORMATION: Reverse primer sequence for human MDA5

<400> SEQUENCE: 63
gagcaacttc tttcaaccac ag                                          22

<210> SEQ ID NO 64
<211> LENGTH: 23
<212> TYPE: DNA
<213> ORGANISM: Artificial Sequence
<220> FEATURE:
<223> OTHER INFORMATION: Forward primer sequence for human RIG-I

<400> SEQUENCE: 64
ccagcattac tagtcagaag gaa                                         23

<210> SEQ ID NO 65
<211> LENGTH: 21
<212> TYPE: DNA
<213> ORGANISM: Artificial Sequence
<220> FEATURE:
<223> OTHER INFORMATION: Reverse primer sequence for human RIG-I

<400> SEQUENCE: 65
cacagtgcaa tcttgtcatc c                                           21

<210> SEQ ID NO 66
<211> LENGTH: 20
<212> TYPE: DNA
<213> ORGANISM: Artificial Sequence
<220> FEATURE:
<223> OTHER INFORMATION: Forward primer sequence for human MAVS

<400> SEQUENCE: 66
aggagacaga tggagacaca                                             20

<210> SEQ ID NO 67
<211> LENGTH: 18
<212> TYPE: DNA
<213> ORGANISM: Artificial Sequence
<220> FEATURE:
<223> OTHER INFORMATION: Reverse primer sequence for human MAVS
```

```
<400> SEQUENCE: 67
cagaactggg cagtaccc                                              18

<210> SEQ ID NO 68
<211> LENGTH: 23
<212> TYPE: DNA
<213> ORGANISM: Artificial Sequence
<220> FEATURE:
<223> OTHER INFORMATION: Forward primer sequence for human cGAS

<400> SEQUENCE: 68
taaccctggc tttggaatca aaa                                        23

<210> SEQ ID NO 69
<211> LENGTH: 23
<212> TYPE: DNA
<213> ORGANISM: Artificial Sequence
<220> FEATURE:
<223> OTHER INFORMATION: Reverse primer sequence for human cGAS

<400> SEQUENCE: 69
tgggtacaag gtaaaatggc ttt                                        23

<210> SEQ ID NO 70
<211> LENGTH: 22
<212> TYPE: DNA
<213> ORGANISM: Artificial Sequence
<220> FEATURE:
<223> OTHER INFORMATION: Forward primer sequence for human STING

<400> SEQUENCE: 70
agcattacaa caacctgcta cg                                         22

<210> SEQ ID NO 71
<211> LENGTH: 21
<212> TYPE: DNA
<213> ORGANISM: Artificial Sequence
<220> FEATURE:
<223> OTHER INFORMATION: Reverse primer sequence for human STING

<400> SEQUENCE: 71
gttggggtca gccatactca g                                          21

<210> SEQ ID NO 72
<211> LENGTH: 20
<212> TYPE: DNA
<213> ORGANISM: Artificial Sequence
<220> FEATURE:
<223> OTHER INFORMATION: Forward primer sequence for human AGO2

<400> SEQUENCE: 72
ccggccttct ctctggaaaa                                            20

<210> SEQ ID NO 73
<211> LENGTH: 21
<212> TYPE: DNA
<213> ORGANISM: Artificial Sequence
<220> FEATURE:
<223> OTHER INFORMATION: Reverse primer sequence for human AGO2

<400> SEQUENCE: 73
gccttgtaaa acgctgttgc t                                          21

<210> SEQ ID NO 74
<211> LENGTH: 21
```

```
<212> TYPE: DNA
<213> ORGANISM: Artificial Sequence
<220> FEATURE:
<223> OTHER INFORMATION: Forward primer sequence for mouse LSD1

<400> SEQUENCE: 74
gtggtgttat gctttgaccg t                                         21

<210> SEQ ID NO 75
<211> LENGTH: 22
<212> TYPE: DNA
<213> ORGANISM: Artificial Sequence
<220> FEATURE:
<223> OTHER INFORMATION: Reverse primer sequence for mouse LSD1

<400> SEQUENCE: 75
gctgccaaaa atccctttga ga                                        22

<210> SEQ ID NO 76
<211> LENGTH: 22
<212> TYPE: DNA
<213> ORGANISM: Artificial Sequence
<220> FEATURE:
<223> OTHER INFORMATION: Forward primer sequence for mouse ERV-L

<400> SEQUENCE: 76
tttctcaagg cccaccaata gt                                        22

<210> SEQ ID NO 77
<211> LENGTH: 25
<212> TYPE: DNA
<213> ORGANISM: Artificial Sequence
<220> FEATURE:
<223> OTHER INFORMATION: Reverse primer sequence for mouse ERV-L

<400> SEQUENCE: 77 gacaccttttt ttaactatgc gagct                                    25

<210> SEQ ID NO 78
<211> LENGTH: 24
<212> TYPE: DNA
<213> ORGANISM: Artificial Sequence
<220> FEATURE:
<223> OTHER INFORMATION: Forward primer sequence for mouse MusD

<400> SEQUENCE: 78
gattggtgga agtttagcta gcat                                      24

<210> SEQ ID NO 79
<211> LENGTH: 25
<212> TYPE: DNA
<213> ORGANISM: Artificial Sequence
<220> FEATURE:
<223> OTHER INFORMATION: Reverse primer sequence for mouse MusD

<400> SEQUENCE: 79
tagcattctc ataagccaat tgcat                                     25

<210> SEQ ID NO 80
<211> LENGTH: 24
<212> TYPE: DNA
<213> ORGANISM: Artificial Sequence
<220> FEATURE:
<223> OTHER INFORMATION: Forward primer sequence for mouse IAP Pol

<400> SEQUENCE: 80
```
cttgccctta aaggtctaaa agca                                            24

<210> SEQ ID NO 81
<211> LENGTH: 29
<212> TYPE: DNA
<213> ORGANISM: Artificial Sequence
<220> FEATURE:
<223> OTHER INFORMATION: Reverse primer sequence for mouse IAP Pol

<400> SEQUENCE: 81
gcggtataag gtacaattaa aagatatgg                                       29

<210> SEQ ID NO 82
<211> LENGTH: 20
<212> TYPE: DNA
<213> ORGANISM: Artificial Sequence
<220> FEATURE:
<223> OTHER INFORMATION: Forward primer sequence for mouse Line 1

<400> SEQUENCE: 82
tttgggacac aatgaaagca                                                 20

<210> SEQ ID NO 83
<211> LENGTH: 20
<212> TYPE: DNA
<213> ORGANISM: Artificial Sequence
<220> FEATURE:
<223> OTHER INFORMATION: Reverse primer sequence for mouse Line 1

<400> SEQUENCE: 83
ctgccgtcta ctcctcttgg                                                 20

<210> SEQ ID NO 84
<211> LENGTH: 18
<212> TYPE: DNA
<213> ORGANISM: Artificial Sequence
<220> FEATURE:
<223> OTHER INFORMATION: Forward primer sequence for mouse IFN alpha

<400> SEQUENCE: 84
cggtgctgag ctactggc                                                   18

<210> SEQ ID NO 85
<211> LENGTH: 21
<212> TYPE: DNA
<213> ORGANISM: Artificial Sequence
<220> FEATURE:
<223> OTHER INFORMATION: Reverse primer sequence for mouse IFN alpha

<400> SEQUENCE: 85
tttgtaccag gagtgtcaag g                                               21

<210> SEQ ID NO 86
<211> LENGTH: 21
<212> TYPE: DNA
<213> ORGANISM: Artificial Sequence
<220> FEATURE:
<223> OTHER INFORMATION: Forward primer sequence for mouse IFN beta

<400> SEQUENCE: 86
ggtggaatga gactattgtt g                                               21

<210> SEQ ID NO 87
<211> LENGTH: 17
<212> TYPE: DNA
<213> ORGANISM: Artificial Sequence

```
<220> FEATURE:
<223> OTHER INFORMATION: Reverse primer sequence for mouse IFN beta

<400> SEQUENCE: 87
aggacatctc ccacgtc                                                17

<210> SEQ ID NO 88
<211> LENGTH: 19
<212> TYPE: DNA
<213> ORGANISM: Artificial Sequence
<220> FEATURE:
<223> OTHER INFORMATION: Forward primer sequence for mouse IL-28b

<400> SEQUENCE: 88
agctgcaggt ccaagagcg                                              19

<210> SEQ ID NO 89
<211> LENGTH: 21
<212> TYPE: DNA
<213> ORGANISM: Artificial Sequence
<220> FEATURE:
<223> OTHER INFORMATION: Reverse primer sequence for mouse IL-28b

<400> SEQUENCE: 89
ggtggtcagg gctgagtcat t                                           21

<210> SEQ ID NO 90
<211> LENGTH: 21
<212> TYPE: DNA
<213> ORGANISM: Artificial Sequence
<220> FEATURE:
<223> OTHER INFORMATION: Forward primer sequence for mouse ISG15

<400> SEQUENCE: 90
ggtgtccgtg actaactcca t                                           21

<210> SEQ ID NO 91
<211> LENGTH: 21
<212> TYPE: DNA
<213> ORGANISM: Artificial Sequence
<220> FEATURE:
<223> OTHER INFORMATION: Reverse primer sequence for mouse ISG15

<400> SEQUENCE: 91 tggaagggt aagaccgtcc t                                            21

<210> SEQ ID NO 92
<211> LENGTH: 19
<212> TYPE: DNA
<213> ORGANISM: Artificial Sequence
<220> FEATURE:
<223> OTHER INFORMATION: Forward primer sequence for mouse OASL

<400> SEQUENCE: 92
caggagctgt acggcttcc                                              19

<210> SEQ ID NO 93
<211> LENGTH: 23
<212> TYPE: DNA
<213> ORGANISM: Artificial Sequence
<220> FEATURE:
<223> OTHER INFORMATION: Reverse primer sequence for mouse OASL

<400> SEQUENCE: 93
cctaccttga gtaccttgag cac                                         23
```

<210> SEQ ID NO 94
<211> LENGTH: 23
<212> TYPE: DNA
<213> ORGANISM: Artificial Sequence
<220> FEATURE:
<223> OTHER INFORMATION: Forward primer sequence for mouse TLR3

<400> SEQUENCE: 94
gtgagataca acgtagctga ctg                                           23

<210> SEQ ID NO 95
<211> LENGTH: 22
<212> TYPE: DNA
<213> ORGANISM: Artificial Sequence
<220> FEATURE:
<223> OTHER INFORMATION: Reverse primer sequence for mouse TLR3

<400> SEQUENCE: 95
tcctgcatcc aagatagcaa gt                                            22

<210> SEQ ID NO 96
<211> LENGTH: 22
<212> TYPE: DNA
<213> ORGANISM: Artificial Sequence
<220> FEATURE:
<223> OTHER INFORMATION: Forward primer sequence for mouse RIG-I

<400> SEQUENCE: 96
aagagccaga gtgtcagaat ct                                            22

<210> SEQ ID NO 97
<211> LENGTH: 23
<212> TYPE: DNA
<213> ORGANISM: Artificial Sequence
<220> FEATURE:
<223> OTHER INFORMATION: Reverse primer for sequence mouse RIG-I

<400> SEQUENCE: 97
agctccagtt ggtaatttct tgg                                           23

<210> SEQ ID NO 98
<211> LENGTH: 20
<212> TYPE: DNA
<213> ORGANISM: Artificial Sequence
<220> FEATURE:
<223> OTHER INFORMATION: Forward primer sequence for mouse beta actin

<400> SEQUENCE: 98
ggctgtattc ccctccatcg                                               20

<210> SEQ ID NO 99
<211> LENGTH: 22
<212> TYPE: DNA
<213> ORGANISM: Artificial Sequence
<220> FEATURE:
<223> OTHER INFORMATION: Reverse primer sequence for mouse beta actin

<400> SEQUENCE: 99
ccagttggta acaatgccat gt                                            22

<210> SEQ ID NO 100
<211> LENGTH: 23
<212> TYPE: DNA
<213> ORGANISM: Artificial Sequence
<220> FEATURE:
<223> OTHER INFORMATION: Forward primer sequence for mouse GAPDH

```
<400> SEQUENCE: 100
tgacctcaac tacatggtct aca                                           23

<210> SEQ ID NO 101
<211> LENGTH: 19
<212> TYPE: DNA
<213> ORGANISM: Artificial Sequence
<220> FEATURE:
<223> OTHER INFORMATION: Reverse primer sequence for mouse GAPDH

<400> SEQUENCE: 101
cttcccattc tcggccttg                                                19

<210> SEQ ID NO 102
<211> LENGTH: 21
<212> TYPE: DNA
<213> ORGANISM: Artificial Sequence
<220> FEATURE:
<223> OTHER INFORMATION: Forward primer sequence for GFP-com

<400> SEQUENCE: 102
gaacggcatc aaggtgaact t                                             21

<210> SEQ ID NO 103
<211> LENGTH: 27
<212> TYPE: DNA
<213> ORGANISM: Artificial Sequence
<220> FEATURE:
<223> OTHER INFORMATION: Reverse primer sequence for GFPL

<400> SEQUENCE: 103
tagcgtaatc tggaacatcg tatgggt                                       27

<210> SEQ ID NO 104
<211> LENGTH: 31
<212> TYPE: DNA
<213> ORGANISM: Artificial Sequence
<220> FEATURE:
<223> OTHER INFORMATION: Reverse primer sequence for GFP-let7

<400> SEQUENCE: 104
gacgacctcg agtgaggtag taggttgtat a                                  31

<210> SEQ ID NO 105
<211> LENGTH: 23
<212> TYPE: DNA
<213> ORGANISM: Artificial Sequence
<220> FEATURE:
<223> OTHER INFORMATION: Non-human Tag

<400> SEQUENCE: 105
gcacacgacg acagacgacg cac                                           23

<210> SEQ ID NO 106
<211> LENGTH: 52
<212> TYPE: DNA
<213> ORGANISM: Homo sapiens

<400> SEQUENCE: 106
gcacacgacg acagacgacg cacccagagt caggtgtcac tactcaatac ac           52

<210> SEQ ID NO 107
<211> LENGTH: 54
<212> TYPE: DNA
```

<213> ORGANISM: Homo sapiens

<400> SEQUENCE: 107
gcacacgacg acagacgacg cactactgga gcaacacgca gcctaggtct ctgg    54

<210> SEQ ID NO 108
<211> LENGTH: 20
<212> TYPE: DNA
<213> ORGANISM: Homo sapiens

<400> SEQUENCE: 108
ggtgtcacta ctcaatacac    20

<210> SEQ ID NO 109
<211> LENGTH: 17
<212> TYPE: DNA
<213> ORGANISM: Homo sapiens

<400> SEQUENCE: 109
gcagcctagg tctctgg    17

<210> SEQ ID NO 110
<211> LENGTH: 51
<212> TYPE: DNA
<213> ORGANISM: Homo sapiens

<400> SEQUENCE: 110
gcacacgacg acagacgacg cacgggaaga atgtgtggcc aatagtgcgg t    51

<210> SEQ ID NO 111
<211> LENGTH: 54
<212> TYPE: DNA
<213> ORGANISM: Homo sapiens

<400> SEQUENCE: 111
gcacacgacg acagacgacg cacggtagag attcctttt ctccccattc ccag    54

<210> SEQ ID NO 112
<211> LENGTH: 19
<212> TYPE: DNA
<213> ORGANISM: Homo sapiens

<400> SEQUENCE: 112
gtgtggccaa tagtgcggt    19

<210> SEQ ID NO 113
<211> LENGTH: 24
<212> TYPE: DNA
<213> ORGANISM: Homo sapiens

<400> SEQUENCE: 113 attcctttt ctccccattc ccag    24

<210> SEQ ID NO 114
<211> LENGTH: 48
<212> TYPE: DNA
<213> ORGANISM: Homo sapiens

<400> SEQUENCE: 114
gcacacgacg acagacgacg cacatggagc ccaagatgca gtccaaga    48

<210> SEQ ID NO 115
<211> LENGTH: 52

```
<212> TYPE: DNA
<213> ORGANISM: Homo sapiens

<400> SEQUENCE: 115
gcacacgacg acagacgacg cacctaactg cttcctgctg aattggggcg ta      52

<210> SEQ ID NO 116
<211> LENGTH: 18
<212> TYPE: DNA
<213> ORGANISM: Homo sapiens

<400> SEQUENCE: 116
atggagccca agatgcag                                             18

<210> SEQ ID NO 117
<211> LENGTH: 30
<212> TYPE: DNA
<213> ORGANISM: Homo sapiens

<400> SEQUENCE: 117
ctaactgctt cctgctgaat tggggcgtag                                30

<210> SEQ ID NO 118
<211> LENGTH: 50
<212> TYPE: DNA
<213> ORGANISM: Homo sapiens

<400> SEQUENCE: 118
gcacacgacg acagacgacg cacgctcgtc gtcgacaacg gctccggcat          50

<210> SEQ ID NO 119
<211> LENGTH: 48
<212> TYPE: DNA
<213> ORGANISM: Homo sapiens

<400> SEQUENCE: 119
gcacacgacg acagacgacg caccaaacat gatctgggtc atcttctc            48

<210> SEQ ID NO 120
<211> LENGTH: 26
<212> TYPE: DNA
<213> ORGANISM: Homo sapiens

<400> SEQUENCE: 120
gctcgtcgtc gacaacggct ccggca                                    26

<210> SEQ ID NO 121
<211> LENGTH: 25
<212> TYPE: DNA
<213> ORGANISM: Homo sapiens

<400> SEQUENCE: 121
caaacatgat ctgggtcatc ttctc                                     25

<210> SEQ ID NO 122
<211> LENGTH: 33
<212> TYPE: DNA
<213> ORGANISM: Artificial Sequence
<220> FEATURE:
<223> OTHER INFORMATION: CRISPR guide sequence LSD1, clone gRNA4-7

<400> SEQUENCE: 122
cactttcatt ttcttcctca ggtgggggct tga                            33
```

<210> SEQ ID NO 123
<211> LENGTH: 32
<212> TYPE: DNA
<213> ORGANISM: Mus musculus

<400> SEQUENCE: 123
cactttcatt ttcttcctca ggtggggctt ga                          32

<210> SEQ ID NO 124
<211> LENGTH: 32
<212> TYPE: DNA
<213> ORGANISM: Artificial Sequence
<220> FEATURE:
<223> OTHER INFORMATION: CRISPR guide sequence LSD1, clone gRNA5-4

<400> SEQUENCE: 124
tcctgagagg tcattcggca tggggaagtc gg                          32

<210> SEQ ID NO 125
<211> LENGTH: 33
<212> TYPE: DNA
<213> ORGANISM: Mus musculus

<400> SEQUENCE: 125
tcctgagagg tcattcggtc atggggaagt cgg                         33

<210> SEQ ID NO 126
<211> LENGTH: 32
<212> TYPE: DNA
<213> ORGANISM: Artificial Sequence
<220> FEATURE:
<223> OTHER INFORMATION: CRISPR guide sequence MDA5, clone gRNA4-16

<400> SEQUENCE: 126
catgtgcctg aatccctgcc catgttgctg tt                          32

<210> SEQ ID NO 127
<211> LENGTH: 33
<212> TYPE: DNA
<213> ORGANISM: Mus musculus

<400> SEQUENCE: 127
catggtgcct gaatccctgc ccatgttgct gtt                         33

<210> SEQ ID NO 128
<211> LENGTH: 32
<212> TYPE: DNA
<213> ORGANISM: Artificial Sequence
<220> FEATURE:
<223> OTHER INFORMATION: CRISPR guide sequence MDA5, clone gRNA4-16

<400> SEQUENCE: 128
catgggcctg aatccctgcc catgttgctg tt                          32

<210> SEQ ID NO 129
<211> LENGTH: 33
<212> TYPE: DNA
<213> ORGANISM: Mus musculus

<400> SEQUENCE: 129
catggtgcct gaatccctgc ccatgttgct gtt                         33

<210> SEQ ID NO 130
<211> LENGTH: 32

```
<212> TYPE: DNA
<213> ORGANISM: Artificial Sequence
<220> FEATURE:
<223> OTHER INFORMATION: CRISPR guide sequence LSD1/MDA5, clone gRNA4-19

<400> SEQUENCE: 130
catgtgcctg aatccctgcc catgttgctg tt                                    32

<210> SEQ ID NO 131
<211> LENGTH: 33
<212> TYPE: DNA
<213> ORGANISM: Mus musculus

<400> SEQUENCE: 131
catggtgcct gaatccctgc ccatgttgct gtt                                   33

<210> SEQ ID NO 132
<211> LENGTH: 31
<212> TYPE: DNA
<213> ORGANISM: Artificial Sequence
<220> FEATURE:
<223> OTHER INFORMATION: CRISPR guide sequence LSD1/MDA5, clone gRNA4-19

<400> SEQUENCE: 132
catggcctga atccctgccc atgttgctgt t                                     31

<210> SEQ ID NO 133
<211> LENGTH: 33
<212> TYPE: DNA
<213> ORGANISM: Mus musculus

<400> SEQUENCE: 133
catggtgcct gaatccctgc ccatgttgct gtt                                   33

<210> SEQ ID NO 134
<211> LENGTH: 29
<212> TYPE: DNA
<213> ORGANISM: Artificial Sequence
<220> FEATURE:
<223> OTHER INFORMATION: CRISPR guide sequence IFNAR1, clone gRNA1-10

<400> SEQUENCE: 134
acggtcaatg ggcagtgtga ccttttcag                                        29

<210> SEQ ID NO 135
<211> LENGTH: 33
<212> TYPE: DNA
<213> ORGANISM: Mus musculus

<400> SEQUENCE: 135
acggagagtc aatgggcagt gtgacctttt cag                                   33

<210> SEQ ID NO 136
<211> LENGTH: 33
<212> TYPE: DNA
<213> ORGANISM: Artificial Sequence
<220> FEATURE:
<223> OTHER INFORMATION: CRISPR guide sequence IFNAR1, clone gRNA1-10

<400> SEQUENCE: 136
acggaagagt caatgggcag tgtgaccttt tca                                   33

<210> SEQ ID NO 137
<211> LENGTH: 32
<212> TYPE: DNA
```

```
<213> ORGANISM: Mus musculus

<400> SEQUENCE: 137
acggagagtc aatgggcagt gtgaccttt ca                                    32

<210> SEQ ID NO 138
<211> LENGTH: 31
<212> TYPE: DNA
<213> ORGANISM: Artificial Sequence
<220> FEATURE:
<223> OTHER INFORMATION: CRISPR guide sequence LSD1/IFNAR1, clone
      gRNA1-16

<400> SEQUENCE: 138
acggagtcaa tgggcagtgt gaccttttca g                                    31

<210> SEQ ID NO 139
<211> LENGTH: 33
<212> TYPE: DNA
<213> ORGANISM: Mus musculus

<400> SEQUENCE: 139
acggagagtc aatgggcagt gtgaccttt cag                                   33

<210> SEQ ID NO 140
<211> LENGTH: 32
<212> TYPE: DNA
<213> ORGANISM: Artificial Sequence
<220> FEATURE:
<223> OTHER INFORMATION: CRISPR guide sequence IFN-beta, clone gRNA3-14

<400> SEQUENCE: 140
gggcggactt caagatccta tggagatgac gg                                   32

<210> SEQ ID NO 141
<211> LENGTH: 33
<212> TYPE: DNA
<213> ORGANISM: Mus musculus

<400> SEQUENCE: 141
gggcggactt caagatccct atggagatga cgg                                  33

<210> SEQ ID NO 142
<211> LENGTH: 32
<212> TYPE: DNA
<213> ORGANISM: Artificial Sequence
<220> FEATURE:
<223> OTHER INFORMATION: CRISPR guide sequence LSD1/IFN-beta, clone
      gRNA3-16

<400> SEQUENCE: 142
gggcggactt caagatccta tggagatgac gg                                   32

<210> SEQ ID NO 143
<211> LENGTH: 33
<212> TYPE: DNA
<213> ORGANISM: Mus musculus

<400> SEQUENCE: 143
gggcggactt caagatccct atggagatga cgg                                  33

<210> SEQ ID NO 144
<211> LENGTH: 22
<212> TYPE: DNA
<213> ORGANISM: Artificial Sequence
```

```
<220> FEATURE:
<223> OTHER INFORMATION: CRISPR guide sequence LSD1/TRL3, clone gRNA6-7

<400> SEQUENCE: 144
actttcaaca aagggagtat ct                                              22

<210> SEQ ID NO 145
<211> LENGTH: 33
<212> TYPE: DNA
<213> ORGANISM: Mus musculus

<400> SEQUENCE: 145
actttcaaca aagggagtat ttggcacagt tct                                  33

<210> SEQ ID NO 146
<211> LENGTH: 32
<212> TYPE: DNA
<213> ORGANISM: Artificial Sequence
<220> FEATURE:
<223> OTHER INFORMATION: CRISPR guide sequence LSD1, clone gRNA5-A29

<400> SEQUENCE: 146
aacaggctgc ttcctgagag gtcattcggc at                                   32

<210> SEQ ID NO 147
<211> LENGTH: 33
<212> TYPE: DNA
<213> ORGANISM: Mus musculus

<400> SEQUENCE: 147
aacaggctgc ttcctgagag gtcattcggt cat                                  33

<210> SEQ ID NO 148
<211> LENGTH: 25
<212> TYPE: DNA
<213> ORGANISM: Artificial Sequence
<220> FEATURE:
<223> OTHER INFORMATION: CRISPR guide sequence LSD1, clone gRNA5-B30

<400> SEQUENCE: 148
aacaggctgc ttcctgagag gtcat                                           25

<210> SEQ ID NO 149
<211> LENGTH: 33
<212> TYPE: DNA
<213> ORGANISM: Mus musculus

<400> SEQUENCE: 149
aacaggctgc ttcctgagag gtcattcggt cat                                  33

<210> SEQ ID NO 150
<211> LENGTH: 31
<212> TYPE: DNA
<213> ORGANISM: Artificial Sequence
<220> FEATURE:
<223> OTHER INFORMATION: CRISPR guide sequence LSD1, clone gRNA5-B37

<400> SEQUENCE: 150
aacaggctgc ttcctgagag gtcattctca t                                    31

<210> SEQ ID NO 151
<211> LENGTH: 33
<212> TYPE: DNA
<213> ORGANISM: Mus musculus
```

```
<400> SEQUENCE: 151
aacaggctgc ttcctgagag gtcattcggt cat                                   33

<210> SEQ ID NO 152
<211> LENGTH: 32
<212> TYPE: DNA
<213> ORGANISM: Artificial Sequence
<220> FEATURE:
<223> OTHER INFORMATION: CRISPR guide sequence LSD1, clone gRNA3-8

<400> SEQUENCE: 152
aatattcatc ttctgagggt tggccaagct tt                                    32

<210> SEQ ID NO 153
<211> LENGTH: 33
<212> TYPE: DNA
<213> ORGANISM: Mus musculus

<400> SEQUENCE: 153
aatattcatc ttctgagagg ttggccaagc ttt                                   33

<210> SEQ ID NO 154
<211> LENGTH: 25
<212> TYPE: DNA
<213> ORGANISM: Artificial Sequence
<220> FEATURE:
<223> OTHER INFORMATION: CRISPR guide sequence LSD1, clone gRNA3-8

<400> SEQUENCE: 154
aatattcatc ttctggccaa gcttt                                            25

<210> SEQ ID NO 155
<211> LENGTH: 33
<212> TYPE: DNA
<213> ORGANISM: Mus musculus

<400> SEQUENCE: 155
aatattcatc ttctgagagg ttggccaagc ttt                                   33

<210> SEQ ID NO 156
<211> LENGTH: 16
<212> TYPE: PRT
<213> ORGANISM: Homo sapiens

<400> SEQUENCE: 156

Val Gly Lys Ser Gly Asn Ile Pro Ala Gly Thr Thr Val Asp Thr Lys
1               5                   10                  15

<210> SEQ ID NO 157
<211> LENGTH: 16
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: METHYLATION

<400> SEQUENCE: 157

Val Gly Lys Ser Gly Asn Ile Pro Ala Gly Thr Thr Val Asp Thr Lys
1               5                   10                  15
```

METHODS OF TREATING CANCER USING LSD1 INHIBITORS IN COMBINATION WITH IMMUNOTHERAPY

CROSS-REFERENCE TO RELATED APPLICATIONS

This application is a 371 U.S. National Phase Application of PCT/US2018/057058, filed on Oct. 23, 2018, which claims priority to U.S. Provisional Patent Application Ser. No. 62/576,001, filed Oct. 23, 2017, and U.S. Provisional Patent Application Ser. No. 62/688,002, filed Jun. 21, 2018; the entire contents of each of which are herein incorporated by reference.

STATEMENT AS TO FEDERALLY SPONSORED RESEARCH

This invention was made with Government support under Grant Nos. CA118487 and CA210104, awarded by the National Institutes of Health. The Government has certain rights in the invention.

SEQUENCE LISTING

This instant application contains a Sequence Listing which has been submitted electronically in ASCII format and is hereby incorporated by reference in its entirety. Said ASCII copy, created on Oct. 19, 2018, is named Sequence Listing.txt and is 35.7 kilobytes in size.

TECHNICAL FIELD

The present invention relates to the treatment of cancer.

BACKGROUND

Chromatin modifications play a broad and general role in regulating gene expression, and when they go awry, can lead to diseases. Consistent with this notion, recent cancer genome sequencing efforts have identified mutations in chromatin regulators, and in the case of hematopoietic cancers, chromatin regulators are one of the most frequently mutated groups of genes.

SUMMARY

Without wishing to be bound by theory, the present results provide evidence that the histone H3K4 demethylase, lysine-specific demethylase 1A (LSD1, also known as KDM1A) plays a critical role in suppressing endogenous double stranded RNA (dsRNA) levels and interferon responses in tumor cells, by regulating transcription of endogenous retroviral elements (ERVs) and dsRNA turnover mediated by the RNA-inducing silencing complex (RISC). dsRNA stress can lead to increased T cell infiltration and an enhanced anti-tumor T cell immunity to transplanted tumors cells lacking LSD1, as these tumors showed significant growth disadvantage only in the immunocompetent mice. Furthermore, depletion of LSD1 rendered programmed cell death 1 (PD-1) blockade-refractory B16 tumors significantly responsive to anti-PD-1 therapy. Collectively, LSD1 was identified as a critical regulator of anti-tumor immunity, thereby suggesting that manipulating LSD1 can lead to a significant relief of tumor burden in vivo, especially in combination with anti-PD-1 therapy. These findings may have important implications for harnessing chromatin and epigenetic regulators for onco-immunotherapy. In some embodiments, the immunotherapy is an antibody therapy (e.g., a monoclonal antibody, a conjugated antibody).

Provided herein are methods of treating cancer in a patient that include: administering to a patient in need of cancer treatment therapeutically effective amounts of a lysine-specific demethylase 1A (LSD1) inhibitor and at least one of a programmed-cell death 1 (PD-1) inhibitor and a programmed-cell death ligand 1 (PD-L1) inhibitor, to thereby treat cancer in the patient.

Also provided herein are methods of treating cancer in a patient that include: administering to a patient in need of cancer treatment therapeutically effective amounts of a lysine-specific demethylase 1A (LSD1) inhibitor and at least one immunotherapy, to thereby treat cancer in the patient.

In some embodiments of any of the methods described herein, the method further includes identifying the patient as having cancer prior to administering.

In some embodiments, the method includes administering a LSD1 inhibitor and a PD-1 inhibitor.

In some embodiments, the method includes administering a LSD1 inhibitor, a PD-1 inhibitor, and a PD-L1 inhibitor.

In some embodiments, the method includes administering a LSD1 inhibitor and a PD-L1 inhibitor.

In some embodiments, the at least one immunotherapy is selected from the group consisting of: an antibody, an adoptive cellular therapy, an antibody-drug conjugate, a toxin, a cytokine therapy, a cancer vaccine, a checkpoint inhibitor. In some embodiments, the method includes the checkpoint inhibitor is a CTLA-4 inhibitor, a PD-1 inhibitor, a PD-L1 inhibitor, a PD-L2 inhibitor, an OX40 (TNFRSF4) inhibitor, a TIM3 (T Cell Immunoglobulin Mucin 3) inhibitor, or a LAG3 (Lymphocyte Activating 3) inhibitor. In some embodiments, the PD-1 inhibitors blocks the interaction of PD-1 with its ligands (e.g., PD-L1 or PD-L1).

In some embodiments of any of the methods described herein, the LSD1 inhibitor is selected from the group consisting of: a small molecule, an antibody, and an inhibitory nucleic acid. In some embodiments wherein the LSD1 inhibitor is an inhibitory nucleic acid, the inhibitory nucleic acid is a small interfering RNA or a short hairpin RNA. In some embodiments wherein the inhibitory nucleic acid is a short hairpin RNA, the short hairpin RNA includes SEQ ID NO: 2.

In some embodiments of any of the methods described herein, the LSD1 inhibitor is a small molecule selected from the group consisting of: tranylcypromine, RN 1 dihydrochloride, GSK-LSD1, GSK2879552, ORY1001, GSK690, namoline, Cpd 2d, S2101, OG-L002, SP2509, CBB2007 and IMG-7289.

In some embodiments of any of the methods described herein, the PD-1 inhibitor is selected from the group consisting of: a small molecule, an antibody, and an inhibitory nucleic acid.

In some embodiments wherein the PD-1 inhibitor is an inhibitory nucleic acid, the inhibitory nucleic acid is a small interfering RNA or a short hairpin RNA. In some embodiments wherein the inhibitory nucleic acid is a short hairpin RNA, the short hairpin RNA includes e.g., SEQ ID NO: 4.

In some embodiments wherein the PD-1 inhibitor is an antibody, the antibody is nivolumab or pembrolizumab.

In some embodiments of any of the methods described herein, the PD-L1 inhibitor is selected from the group consisting of: a small molecule, an antibody, and an inhibitory nucleic acid.

In some embodiments wherein the PD-L1 inhibitor is an inhibitory nucleic acid, the inhibitory nucleic acid is a small interfering RNA or a short hairpin RNA. In some embodiments wherein the inhibitory nucleic acid is a short hairpin RNA, the short hairpin RNA includes e.g., SEQ ID NO: 6.

In some embodiments of any of the methods described herein, the PD-L1 inhibitor is an antibody selected from the group consisting of: durvalumab, atezolizumab and avelumab.

In some embodiments of any of the methods described herein, the cancer is a primary tumor.

In some embodiments of any of the methods described herein, the cancer is a metastatic tumor.

In some embodiments of any of the methods described herein, the cancer is selected from the group consisting of: melanoma, acute myeloid leukemia (AML), squamous cell carcinoma, renal cell carcinoma, non-small cell lung cancer (NSCLC), small cell lung cancer (SCLC), gastric cancer, bladder cancer, kidney cancer, head and neck cancer, Ewing sarcoma, Hodgkin's lymphoma, Merkel cell carcinoma, breast cancer and prostate cancer.

In some embodiments of any of the methods described herein, the cancer is a non-T-cell-infiltrating cancer.

In some embodiments of any of the methods described herein, the cancer is a PD-1 and/or PD-L1 refractory cancer.

In some embodiments of any of the methods described herein, the cancer is a PD-1 and/or PD-L1 resistant cancer.

In some embodiments of any of the methods described herein, the patient has previously received cancer treatment.

In some embodiments of any of the methods described herein, administering occurs at least once a week.

In some embodiments of any of the methods described herein, administering is via intravenous, subcutaneous, intraperitoneal, rectal, and/or oral administration.

In some embodiments of any of the methods described herein, the LSD1 inhibitor and the at least one PD-1 inhibitor or PD-L1 inhibitor are administered simultaneously to the patient.

In some embodiments of any of the methods described herein, the LSD1 inhibitor is administered to the patient prior to administration of the PD-1 inhibitor or PD-L1 inhibitor.

In some embodiments of any of the methods described herein, the administration of the LSD1 inhibitor is stopped before the administration of the PD-1 inhibitor or the PD-L1 inhibitor.

In some embodiments of any of the methods described herein, the method further includes administering a chemotherapeutic agent.

In some embodiments of any of the methods described herein, treating includes reducing the volume of primary tumor in the patient.

In some embodiments of any of the methods described herein, treating includes delaying cancer progression in the patient.

In some embodiments of any of the methods described herein, treating includes modifying the tumor microenvironment of a cancer in the patient.

In some embodiments of any of the methods described herein, treating includes sensitizing a cancer to a checkpoint inhibitor therapy.

In some embodiments of any of the methods described herein, treating includes decreasing the risk of developing at least one metastatic tumor in the patient.

In some embodiments of any of the methods described herein, treating includes decreasing the rate of and/or delaying tumor growth at a metastatic site.

In some embodiments of any of the methods described herein, treating includes decreasing tumor cell migration.

In some embodiments of any of the methods described herein, treating includes decreasing tumor cell invasion.

In some embodiments of any of the methods described herein, treating includes decreasing the rate of tumor growth in the patient.

In some embodiments of any of the methods described herein, treating includes eliciting tumor-intrinsic double-stranded RNA stress in a cancer cell in the patient.

The present specification also provides compositions that are useful in the methods described herein, e.g., combined compositions that include a lysine-specific demethylase 1A (LSD1) inhibitor and at least one immunotherapy, e.g., at least one programmed-cell death 1 (PD-1) inhibitor and/or at least one programmed-cell death ligand 1 (PD-L1) inhibitor.

Also provided herein are methods of treating cancer in a patient that include: administering to a patient in need of cancer treatment therapeutically effective amounts of a lysine-specific demethylase 1A (LSD1) inhibitor and at least one immunotherapy, to thereby treat cancer in the patient.

The term "treat" or "treatment" is used herein to denote delaying the onset of, inhibiting, alleviating the effects of, or prolonging the life of a patient suffering from, a condition, e.g., cancer. The terms "effective amount" and "amount effective to treat," as used herein, refer to an amount or concentration of a composition or treatment described herein, e.g., an LSD1 inhibitor, utilized for a period of time (including acute or chronic administration and periodic or continuous administration) that is effective within the context of its administration for causing an intended effect or physiological outcome. For example, effective amounts of a LSD1 inhibitor and an immunotherapy (e.g., any immunotherapy described herein) for use in the present disclosure include, for example, amounts that inhibit the growth of cancer, e.g., tumors and/or tumor cells, improve delay tumor growth, improve survival for a patient suffering from or at risk for cancer, and improve the outcome of other cancer treatments. As another example, effective amounts of a LSD1 inhibitor and an immunotherapy (e.g., any immunotherapy described herein) can include amounts that advantageously affect a tumor microenvironment.

The term "patient" or "subject" is used throughout the specification to describe an animal, human or non-human, to whom treatment according to the methods of the present disclosure is provided. Veterinary applications are clearly anticipated by the present disclosure. The term includes but is not limited to birds, reptiles, amphibians, and mammals, e.g., humans, other primates, pigs, rodents such as mice and rats, rabbits, guinea pigs, hamsters, cows, horses, cats, dogs, sheep and goats. Preferred subjects are humans, farm animals, and domestic pets such as cats and dogs.

Compositions and treatments described herein can be used to treat cellular proliferative and/or differentiation disorders. Examples of cellular proliferative and/or differentiation disorders include cancer, e.g., carcinoma, sarcoma, metastatic disorders and hematopoietic neoplastic disorders, e.g., leukemias.

The term "cancer" refers to cells having the capacity for autonomous growth. Examples of such cells include cells having an abnormal state or condition characterized by rapidly proliferating cell growth. The term is meant to include cancerous growths, e.g., tumors; oncogenic processes, metastatic tissues, and malignantly transformed cells, tissues, or organs, irrespective of histopathologic type or stage of invasiveness. Also included are malignancies of the various organ systems, such as respiratory, cardiovascular, renal, reproductive, hematological, neurological, hepatic, gastrointestinal, and endocrine systems; as well as adenocarcinomas, which include malignancies such as most colon cancers, renal-cell carcinoma, prostate cancer and/or testicular tumors, non-small cell carcinoma of the lung, cancer of the small intestine, and cancer of the esophagus. Cancer that is "naturally arising" includes any cancer that is not experimentally induced by implantation of cancer cells into a subject, and includes, for example, spontaneously arising cancer, cancer caused by exposure of a patient to a carcinogen(s), cancer resulting from insertion of a transgenic oncogene or knockout of a tumor suppressor gene, and cancer caused by infections, e.g., viral infections. The term "carcinoma" is art recognized and refers to malignancies of epithelial or endocrine tissues. The term also includes carcinosarcomas, which include malignant tumors composed of carcinomatous and sarcomatous tissues. An "adenocarcinoma" refers to a carcinoma derived from glandular tissue or in which the tumor cells form recognizable glandular structures.

The term "sarcoma" is art recognized and refers to malignant tumors of mesenchymal derivation. The term "hematopoietic neoplastic disorders" includes diseases involving hyperplastic/neoplastic cells of hematopoietic origin. A hematopoietic neoplastic disorder can arise from myeloid, lymphoid or erythroid lineages, or precursor cells thereof.

A metastatic tumor can arise from a multitude of primary tumor types, including but not limited to those of prostate, colon, lung, breast, bone, and liver origin. Metastases develop, e.g., when tumor cells shed from a primary tumor adhere to vascular endothelium, penetrate into surrounding tissues, and grow to form independent tumors at sites separate from a primary tumor.

The term "PD-1 or PD-L1 refractory cancer" refers to a cancer characterized by resistance to PD-1 inhibitor or PD-L1 inhibitor treatment. In some embodiments, the cancer is characterized by a population of cells (e.g., cancer cells or immune cells such as T cells) that have a reduced level of PD-1 or PD-L1 on the surface, or a reduced expression of PD-1 or PD-L1 (e.g., as compared to non-cancer cells, as compared to cells obtained from subjects without PD-1 or PD-L1 refractory cancer, or as compared to a reference level or value), and/or a genetic lesion in a PD-1 or PD-L1 gene. The terms "a reduced level" or "a decreased level" is a reduction or decrease of PD-1 or PD-L1 of at least a 1% (e.g., at least 2%, at least 4%, at least 6%, at least 8%, at least 10%, at least 12%, at least 14%, at least 16%, at least 18%, at least 20%, at least 22%, at least 24%, at least 26%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%) reduction as compared to a reference level or value.

The term "non-T-cell-infiltrating tumor" means a tumor that lacks T cells within its tumor microenvironment. In some embodiments, a non-T-cell-infiltrating tumor is characterized by a population of cancer cells that have down-regulated genes associated with T cell recognition, a reduced expression of polypeptides associated with T cell recognition on its cell surface (e.g., a T-cell receptor), and/or T cell dysfunction.

The term "population" when used before a noun means two or more of the specific noun. For example, the phrase "a population of cancer cells" means "two or more cancer cells." Non-limiting examples of cancer cells are described herein.

A "chemotherapeutic agent" refers to a chemical compound useful in the treatment of a cancer. Chemotherapeutic agents include, e.g., "anti-hormonal agents" or "endocrine therapeutics" which act to regulate, reduce, block, or inhibit the effects of hormones that can promote the growth of cancer. Additional classes, subclasses, and examples of chemotherapeutic agents are known in the art.

Individuals considered at risk for developing cancer may benefit from the present disclosure, e.g., because prophylactic treatment can begin before there is any evidence and/or diagnosis of the disorder. Individuals "at risk" include, e.g., individuals exposed to carcinogens, e.g., by consumption (e.g., by inhalation and/or ingestion), at levels that have been shown statistically to promote cancer in susceptible individuals. Also included are individuals at risk due to exposure to ultraviolet radiation, or their environment, occupation, and/or heredity, as well as those who show signs of a precancerous condition such as polyps. Similarly, individuals in very early stages of cancer or development of metastases (i.e., only one or a few aberrant cells are present in the individual's body or at a particular site in an individual's tissue) may benefit from such prophylactic treatment.

Skilled practitioners will appreciate that a patient can be diagnosed, e.g., by a medical professional, e.g., a physician or nurse (or veterinarian, as appropriate for the patient being diagnosed), as suffering from or at risk for a condition described herein, e.g., cancer, using any method known in the art, e.g., by assessing a patient's medical history, performing diagnostic tests, and/or by employing imaging techniques.

Skilled practitioners will also appreciate that treatment need not be administered to a patient by the same individual who diagnosed the patient (or the same individual who prescribed the treatment for the patient). Treatment can be administered (and/or administration can be supervised), e.g., by the diagnosing and/or prescribing individual, and/or any other individual, including the patient her/himself (e.g., where the patient is capable of self-administration).

Also contemplated by the present disclosure is administration of a LSD1 inhibitor and an immunotherapy (e.g., any immunotherapy described herein) to a patient in conjunction with at least one other treatment, e.g., chemotherapy, radiation therapy, gene therapy, and/or surgery, to treat conditions and disorders described herein (e.g., cancer). Alternatively or in addition, treatments described herein can be administered in combination with chemotherapy. Chemotherapy can involve administration of any of the following classes of compounds: alkylating agents, antimetabolites, e.g., folate antagonists, purine antagonists and/or pyrimidine antagonists; spindle poisons, e.g., vincas (e.g., paclitaxel) and podophillotoxins; antibiotics, e.g., doxorubicin, bleomycin and/or mitomycin; nitrosoureas; inorganic ions, e.g., cisplatin; biologic response modifiers, e.g., tumor necrosis factor-α (TNF-α) and interferon; enzymes, e.g., asparaginase; protein toxins conjugated to targeting moieties; antisense molecules; and hormones, e.g, tomoxifen, leuprolide, flutamide, and megestrol. Alternatively or in addition, treatments described herein can be administered in combination with radiation therapy, e.g., using γ-radiation, neutron beams, electron beams, and/or radioactive isotopes. Alternatively or in addition, treatments described herein can be administered to patients in combination with immunotherapies other than administering a PD-1 inhibitor, a PD-L1 inhibitor or a CTLA-4 inhibitor, e.g., administering specific effector cells, tumor antigens, and/or antitumor antibodies. Alternatively or in addition, treatments described herein can be administered to patients in combination with gene therapy, e.g., the administration of DNA encoding tumor antigens and/or cytokines. Methods for treating cancer, e.g., surgery, chemotherapy, immunotherapy, and radiotherapy, are more fully described in *The Merck Manual of Diagnosis and Therapy*, 17th Edition, Section 11, Chapters 143 and 144, the contents of which are expressly incorporated herein by reference in their entirety.

Unless otherwise defined, all technical and scientific terms used herein have the same meaning as commonly understood by one of ordinary skill in the art to which this disclosure belongs. Methods and materials are described herein for use in the present disclosure; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the disclosure will be apparent from the following detailed description and figures, and from the claims.

BRIEF DESCRIPTION OF DRAWINGS

FIG. 1D is a bar graph showing IFN-β secretion (pg/mL) in LSD1 knockdown (KD) MCF-7 cells detected by ELISA (n=3). Error bars represent standard deviation (SD) between triplicates in one of two experiments. n.d., not detected.

FIG. 1E is a picture of immunoblots showing LSD1 KD MCF-7 cells that were transduced with either wild type (WT) LSD1 or catalytically inactive LSD1 that harbors a K661A mutation (LSD1-K661A). Actin was used as a control for protein level.

FIG. 1F is a bar graph showing RT-qPCR analysis of selected ERVs (HERV-E, HERV-F, HERV-K, HML-2, and ERVL) in MCF-7 cells transduced with shRNA against scramble (sh-C) or LSD1 (sh-LSD1). RT-qPCR was performed in duplicates and repeated two to three times. Error bars represent SEM from two experiments. $*p<0.05$, $**p<0.01$, ns, not significant, as determined by unpaired t-test.

FIG. 2E is a heatmap for differential transcript expression of repetitive elements between LSD1 KD and WT control.

FIG. 2F is heatmaps showing differential expression of sense or antisense transcripts of ERVs between LSD1 KD and WT control.

FIG. 2O is a bar graph showing RT-qPCR analysis of selected retrotransposon transcripts (HERV-E, HERV-F, HERV-K, ERVL, Syn-1, Line1, AluYA5) and GAPDH captured by a dsRNA-specific antibody (J2) pulldown assay in MCF-7 cells with sh-C or sh-LSD1. Error bars represent SD between duplicates. $*p<0.05$, $p<0.01$, $*p<0.001$, ns, not significant, as determined by unpaired t-test.

FIG. 2P is a heatmap showing the expression nucleic acid receptors in control and LSD1 KD MCF-7 cells as determined by RNA-seq.

FIG. 2Q is a representative immunoblot of TLR3, MDA5 and RIG-I in control and LSD1 KD cells.

FIG. 4A is a picture of immunoblots showing shRNA-mediated knockdown of LSD1 in MCF-7 cells (sh-LSD1), rescue with WT LSD1 or catalytically inactive LSD1-K661A. Actin was used as a control for protein level. The protein expression of core components (DICER, AGO2 and TRBP2) of the RISC complex was measured by immunoblot.

FIG. 4B is a picture of immunoblots showing protein expression of LSD1 and Drosha in MCF-7 cells transduced with control shRNA (sh-C) or LSD1 shRNA (sh-LSD1). Actin was used as a control for protein level.

FIG. 4C is a picture of immunoblots showing GFP and GFPL protein expression in U2OS cells expressing dual reporters GFPL/GFP-let-7 and transduced with shRNA against scramble, LSD1 or AGO2. Actin was used as a control for protein level.

FIG. 4D is a picture of immunoblots showing ISG15 protein expression in MCF-7+sh-C cells, MCF-7+sh-LSD1 cells, MCF-7+sh-LSD1+sh-TLR3 cells, MCF-7+sh-LSD1+sh-RIG-I cells, and MCF-7+sh-LSD1+sh-MDA5 cells. Actin was used as a control for protein level.

FIG. 5I is a picture of immunoblots showing purified FH-AGO2 from MCF-7 cells treated by LSD1 KD or GSK-LSD1 as determined by mass spectrometry for the identification of lysine methylation. sh-Ctrl (VGKSGNI-PAGTTVDTK; SEQ ID NO: 156) and sh-LSD1, GSK-LSD1(VGK(me)SGNIPAGTTVDTK; SEQ ID NO: 157).

FIG. 5J is a dot plot detecting the reactivity of K726me1-specific antibody against un-, mono- or di-methylated AGO2 peptides.

FIG. 5K is a picture of immunoblots showing ectopically expressed wild type FH-AGO2, FH-AGO2-K726R and FH-AGO2-K726A in MCF-7 cells treated with LSD1 KD co-immunoprecipitated by α-Flag and immunoblotted with mono-methyl AGO2 specific antibody.

FIG. 5L is a picture of immunoblots showing ectopically expressed wild type FH-AGO2, FH-AGO2-K726R and FH-AGO2-K726A in MCF-7 cells treated with GSK-LSD1 co-immunoprecipitated by α-HA and immunoblotted with mono-methyl AGO2 specific antibody.

FIG. 5M is a picture of immunoblots showing K726me1 on endogenous AGO2 in control or LSD1 KD MCF-7 cells.

FIG. 6L is a representative image of sequencing results of genomic Lsd1, Mda5, Ifnar1, Ifnb and Tlr3 exons targeted by gRNAs in corresponding B16 clones and in alignment with reference sequences. From top to bottom: B16 CRISPR-LSD1, clone gRNA4-A7 (SEQ ID NO: 122), reference (SEQ ID NO: 123); B16 CRISPR-LSD1, clone gRNA5-4 (SEQ ID NO: 124), reference (SEQ ID NO: 125); B16 CRISPR-MDA5, clone gRNA4-16 (SEQ ID NO: 126), reference (SEQ ID NO: 127); B16 CRISPR-MDA5, clone gRN4-16 (SEQ ID NO: 128), reference (SEQ ID NO: 129); B16 CRISPR-LSD1/MDA5, clone gRNA4-19 (SEQ ID NO: 130), reference (SEQ ID NO: 131); B16 CRISPR-LSD1/MDA5, clone gRNA4-19 (SEQ ID NO: 132), reference (SEQ ID NO: 133); B16 CRISPR-IFNAR1, clone gRNA1-10 (SEQ ID NO: 134), reference (SEQ ID NO: 135); B16 CRISPR-IFNAR1, clone gRNA1-10 (SEQ ID NO: 136), reference (SEQ ID NO: 137); B16 CRISPR-LSD1/IFNAR1, clone gRNA1-16 (SEQ ID NO: 138), reference (SEQ ID NO: 139); B16 CRISPR-IFNβ, clone gRNA3-14 (SEQ ID NO: 140), reference (SEQ ID NO: 141); B16 CRISPR-LSD1/IFNβ, clone gRNA3-16 (SEQ ID NO: 142), reference (SEQ ID NO: 143); B16 CRISPR-LSD1/TLR3, clone gRNA6-7 (SEQ ID NO: 144), reference (SEQ ID NO: 145).

FIG. 7A is a representative image of sequencing results of genomic Lsd1 exon targeted by gRNA5 in corresponding LLC clones and in alignment with reference sequences. From top to bottom: LLC CRISPR-LSD1, clone gRNA5-A29 (SEQ ID NO: 146), reference (SEQ ID NO: 147); LLC CRISPR-LSD1, clone gRNA5-B30 (SEQ ID NO: 148), reference (SEQ ID NO: 149).

FIG. 7B is a picture of immunoblots of LSD1 in CRISPR/Cas9-modified LLC clones.

FIG. 7C is a representative image of sequencing results of genomic Lsd1 exons targeted by two gRNAs in corresponding D4m clones and in alignment with reference sequences. From top to bottom: D4m CRISPR-LSD1, clone gRNA5-B37 (SEQ ID NO: 150), reference (SEQ ID NO: 151); D4m CRISPR-LSD1, clone gRNA3-8 (SEQ ID NO: 152), reference (SEQ ID NO: 153) and D4m CRISPR-LSD1, clone gRNA3-8 (SEQ ID NO: 154), reference (SEQ ID NO: 155).

FIG. 7D is a picture of immunoblots of LSD1 in CRISPR/Cas9-modified D4m clones.

FIG. 7E is a picture of immunoblots of LSD1 with two antibodies in CRISPR/Cas9-modified B16 clones transfected with different gRNAs targeting Lsd1.

FIG. 7F is a picture of immunoblots of LSD1 in CRISPR/Cas9-modified B16 clones transfected with different gRNAs targeting Lsd1.

FIG. 10D is bar graphs showing the clonality and entropy of CD8+ TILs in transplanted B16 tumors (n=5 for scamble, n=3 for LSD1 KO) as determined by TCRseq.

FIG. 10E is volcano and M-A plots showing differentially expressed genes in GFP-labeled B16 tumor cells (n=3 for scramble and LSD1 KO) isolated from tumor-beating immunocompetent mice (referred to as ex vivo cells hereafter), as determined by RNA-seq. Dots in grey represent significantly increased or decreased genes (FDR<0.05) in LSD1 KO versus scramble cells.

FIG. 10F is volcano and M-A plots showing differentially expressed genes in GFP-labeled B16 tumor cells (n=3 for scramble and LSD1/MDA5 DKO) isolated from tumor-beating immunocompetent mice (referred to as ex vivo cells hereafter), as determined by RNA-seq. Dots in grey represent significantly increased or decreased genes (FDR<0.05) in LSD1/MDA5 DKO versus scramble cells.

FIG. 10G is a heatmap showing differential expression (FDR<0.05) of ERVs between scramble and LSD1 KO cells (n=3).

FIG. 10H is plots showing LSD1 and H3K4me2 ChIP-seq signals at genomic loci of 74 ERV subfamilies in control and LSD1 KD cells in ex vivo scramble and LSD1 KO B16 cells.

FIG. 10I is plots showing LSD1 and H3K4me2 ChIP-seq signals at genomic loci of a representative ERVK10C subfamily in control and LSD1 KD cells in ex vivo scramble and LSD1 KO B16 cells.

FIG. 10J is a representative dotmap showing the top 10 terms of a GO analysis of upregulated genes (log 2(FC)>1 and FDR<0.05) in LSD1 KO versus control scramble B16 cells. Dot size represents odds ratio.

FIG. 10K is GSEA analysis for inflammatory response in ex vivo LSD1 KO versus scramble B16 cells.

FIG. 10L is a representative box and whisker plot showing log 2(FC) of upregulated genes in the top 10 terms (170 in total) in LSD1 KO and LSD1.MDA5 DKO versus scramble B16 cells.

FIG. 10M is GSEA analysis for positive regulation of cell proliferation in ex vivo LSD1 KO versus scramble B16 cells.

FIG. 10N is a heatmap showing all genes categorized in GO term "MHC protein complex".

Figure 10A:
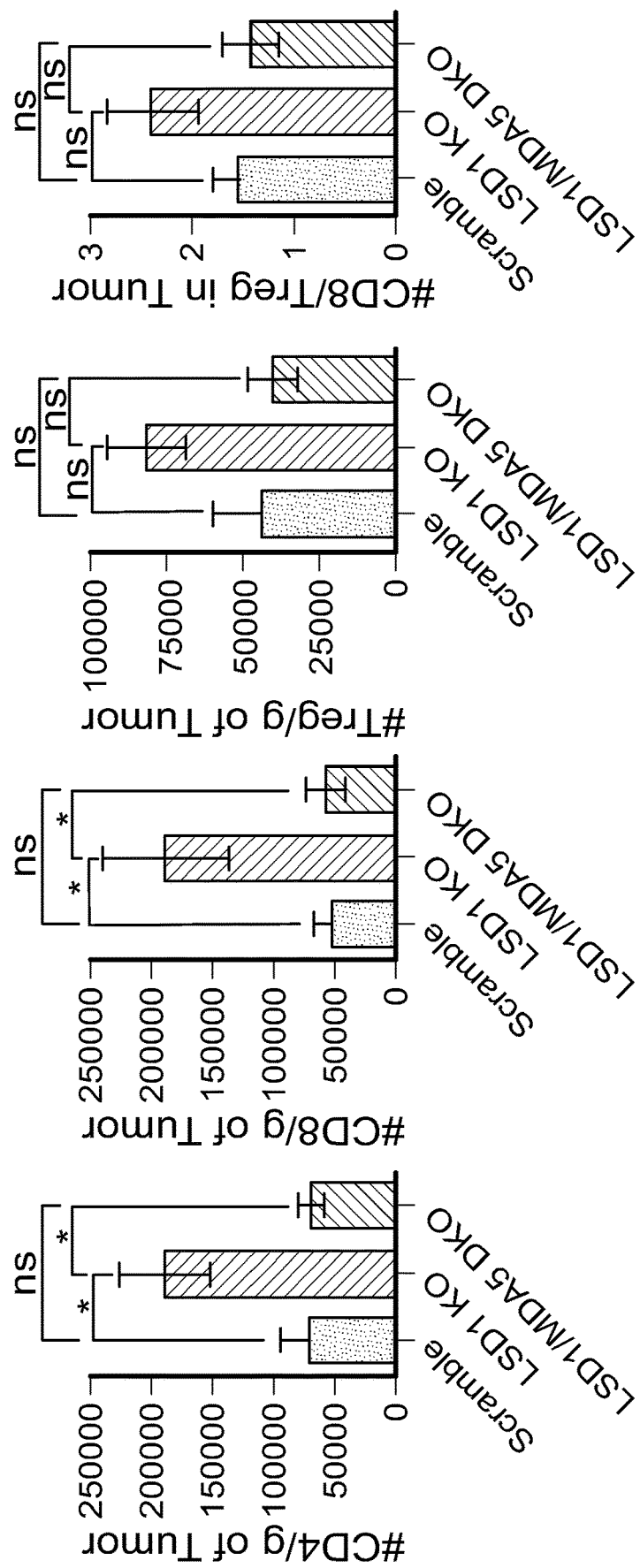
FIG. 10A is bar graphs showing the number of tumor infiltrating lymphocytes (TILs) per gram of B16 tumor in immunocompetent mice (n=5 for scramble, n=5 for LSD1 KO and n=6 for LSD1/MDA5 DKO) as determined by flow cytometry at day 14 when tumor sizes were comparable among the tested groups. Data represents two independent experiments. Error bars represent SEM of individual mice in one experiment. *p<0.05, *p<0.001, **p<0.0001, ns, not significant, as determined by unpaired t-test.
Figure 10B:
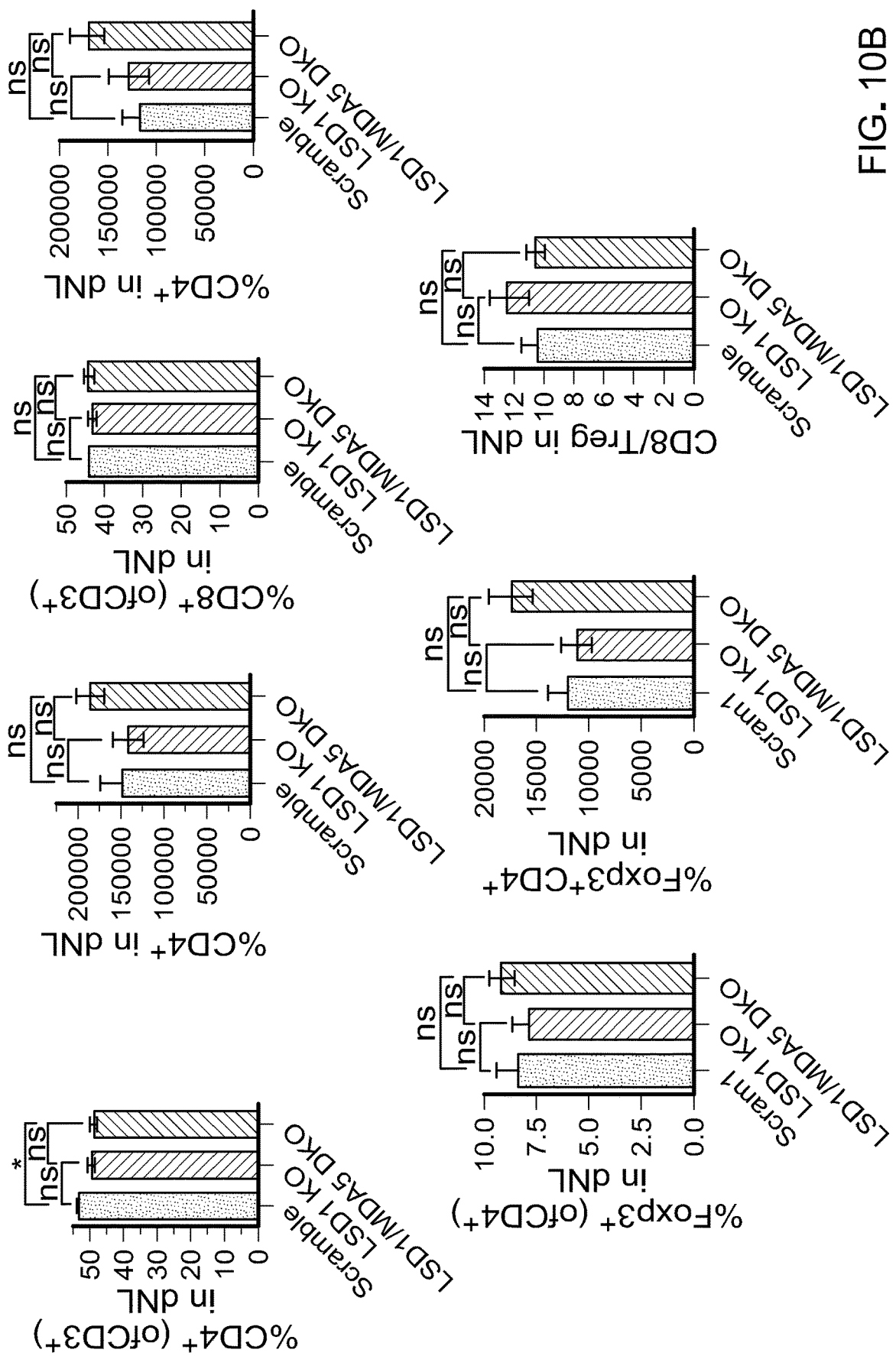
FIG. 10B is bar graphs showing T cells in draining lymph nodes (dNLs) of B16 tumor-bearing immunocompetent mice (n=5 for scramble, n=5 for LSD1 KO and n=6 for LSD1/MDA5 DKO).
Figure 10C:
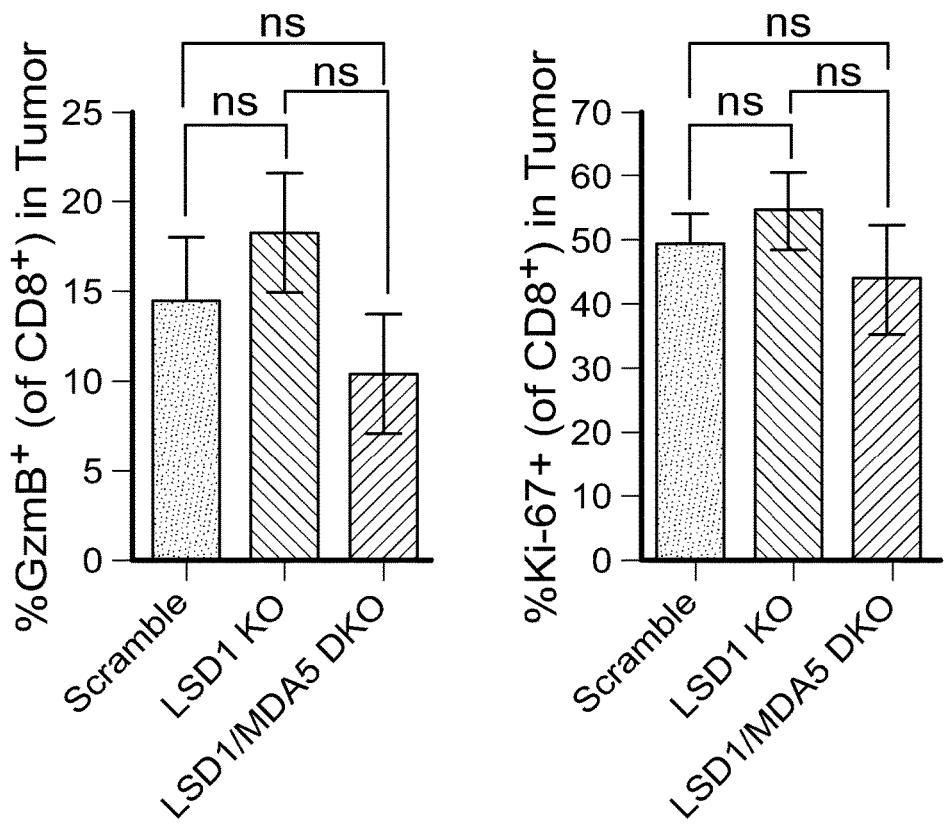
FIG. 10C is bar graphs showing the percentage of granzyme B positive (GzmB+) or Ki-67+CD8+ TILs as in 10A. Error bars represent SEM of individual mice in one experiment. *p<0.05, *p<0.001, **p<0.0001, ns, not significant, as determined by unpaired t-test.
Figure 10D:
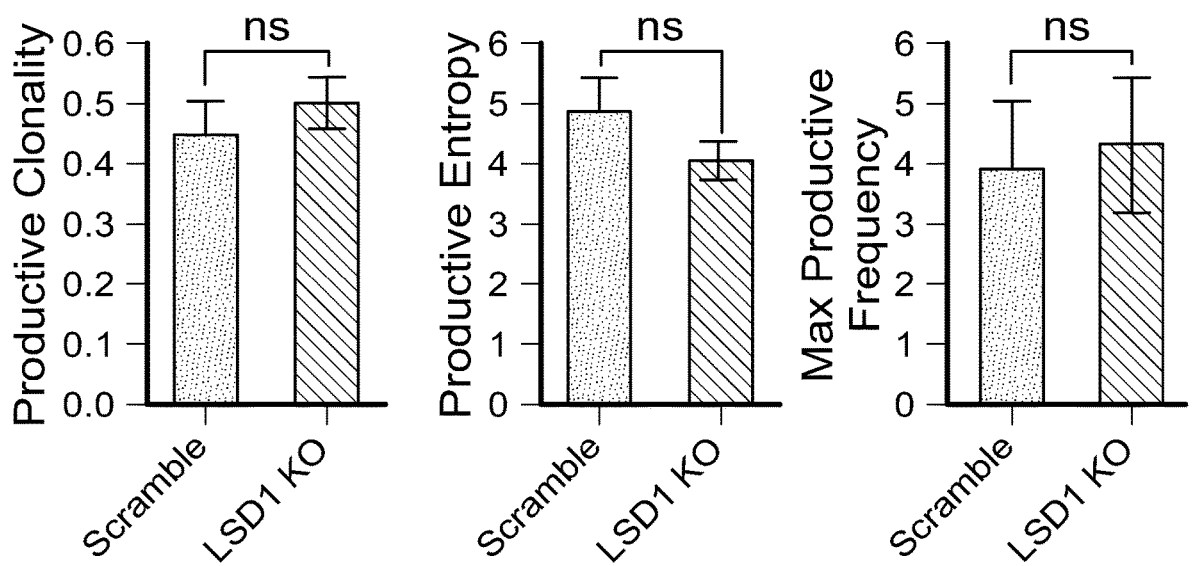
Figure 10E:
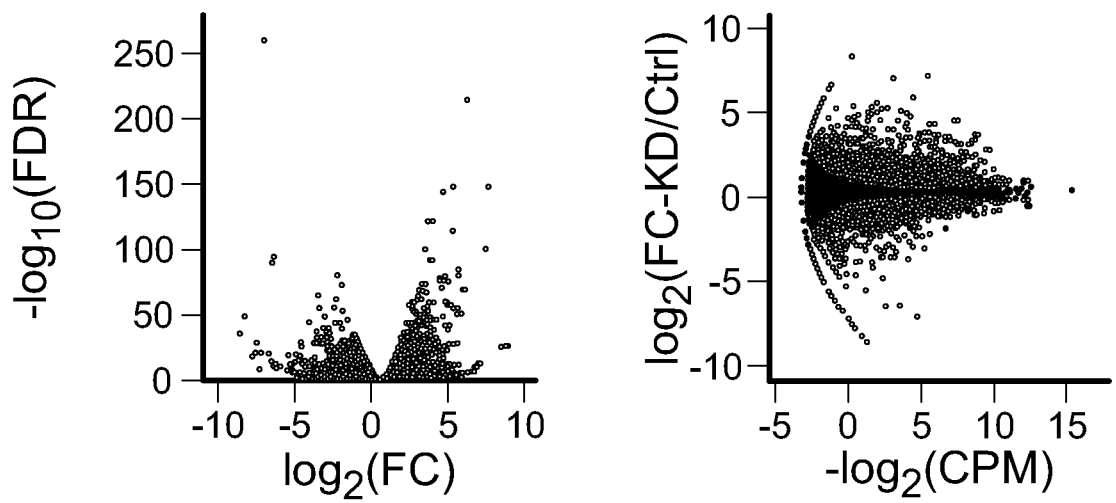
Figure 10F:
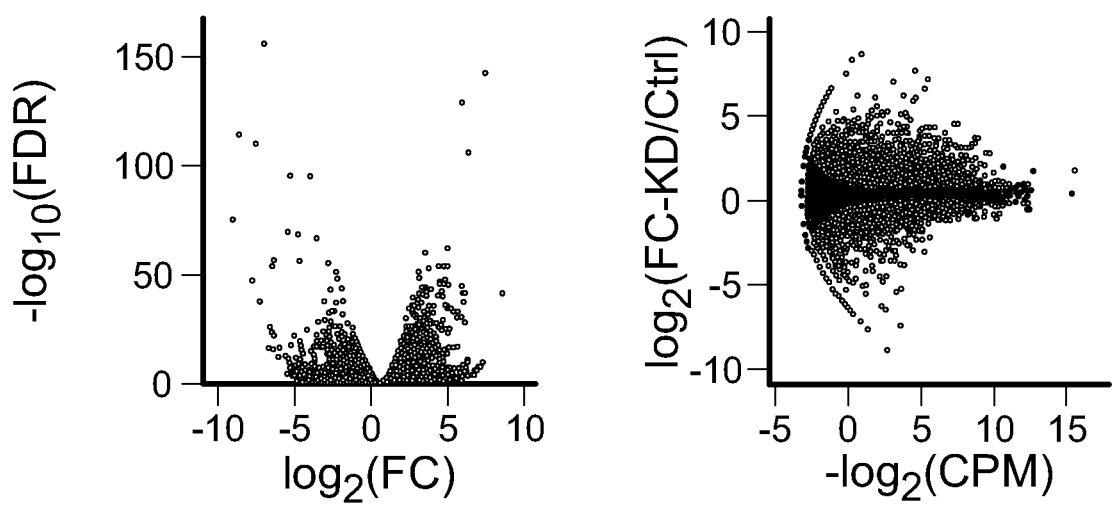
Figure 10G:
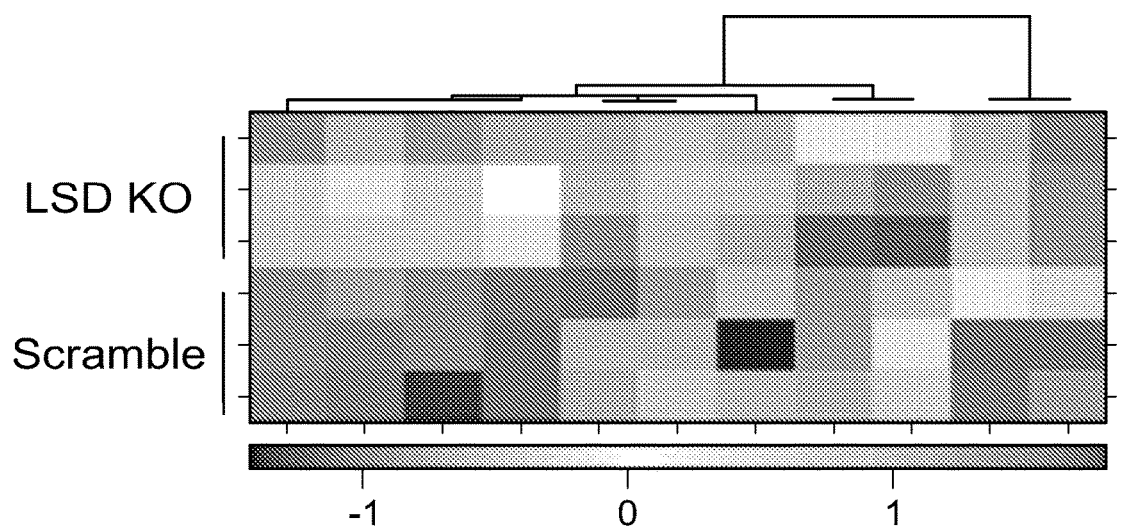
Figure 10H:
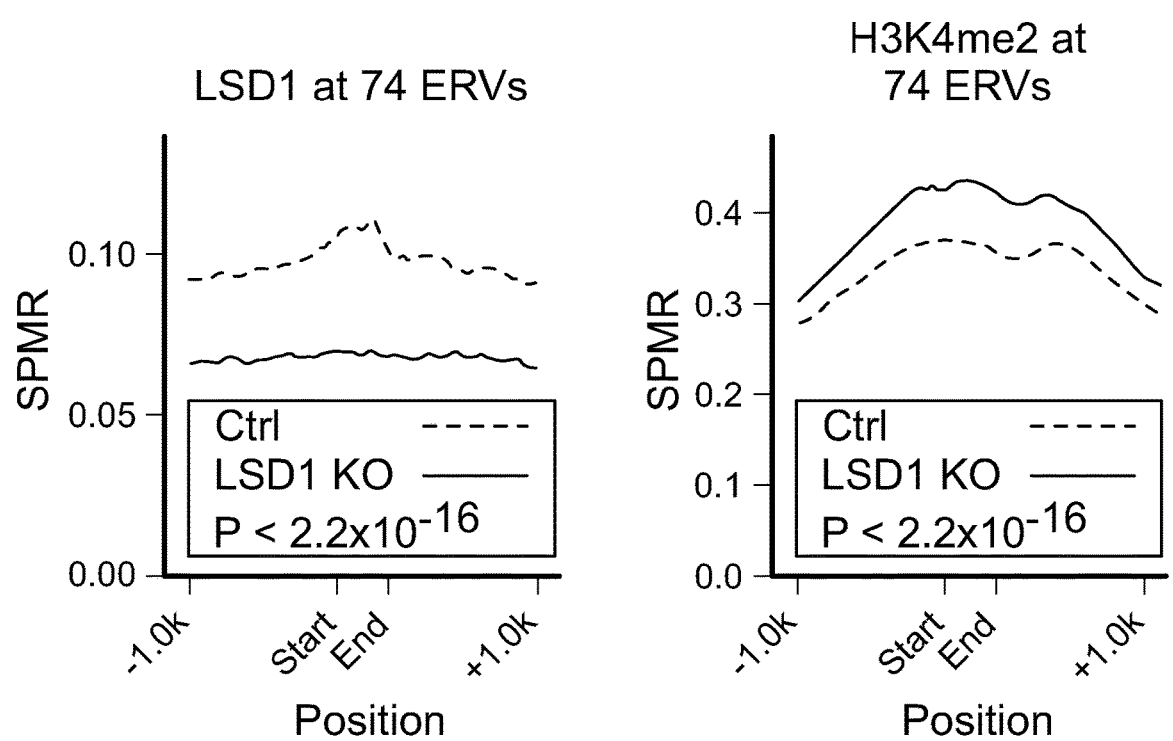
Figure 10I:
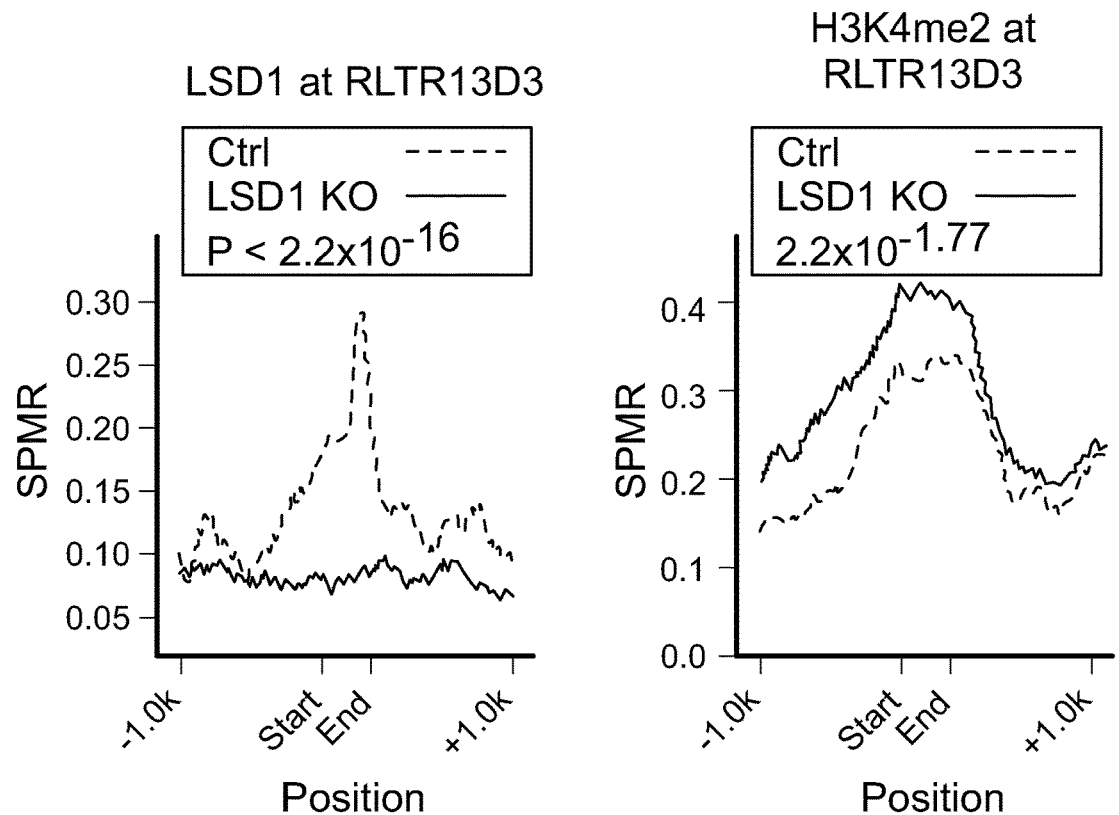
Figure 10J:
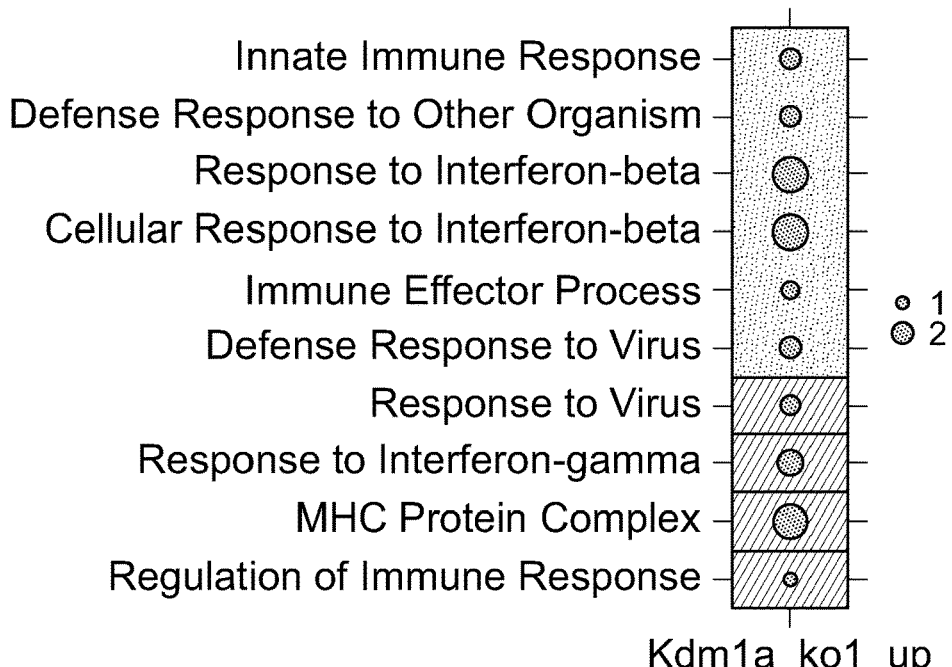
Figure 10N:
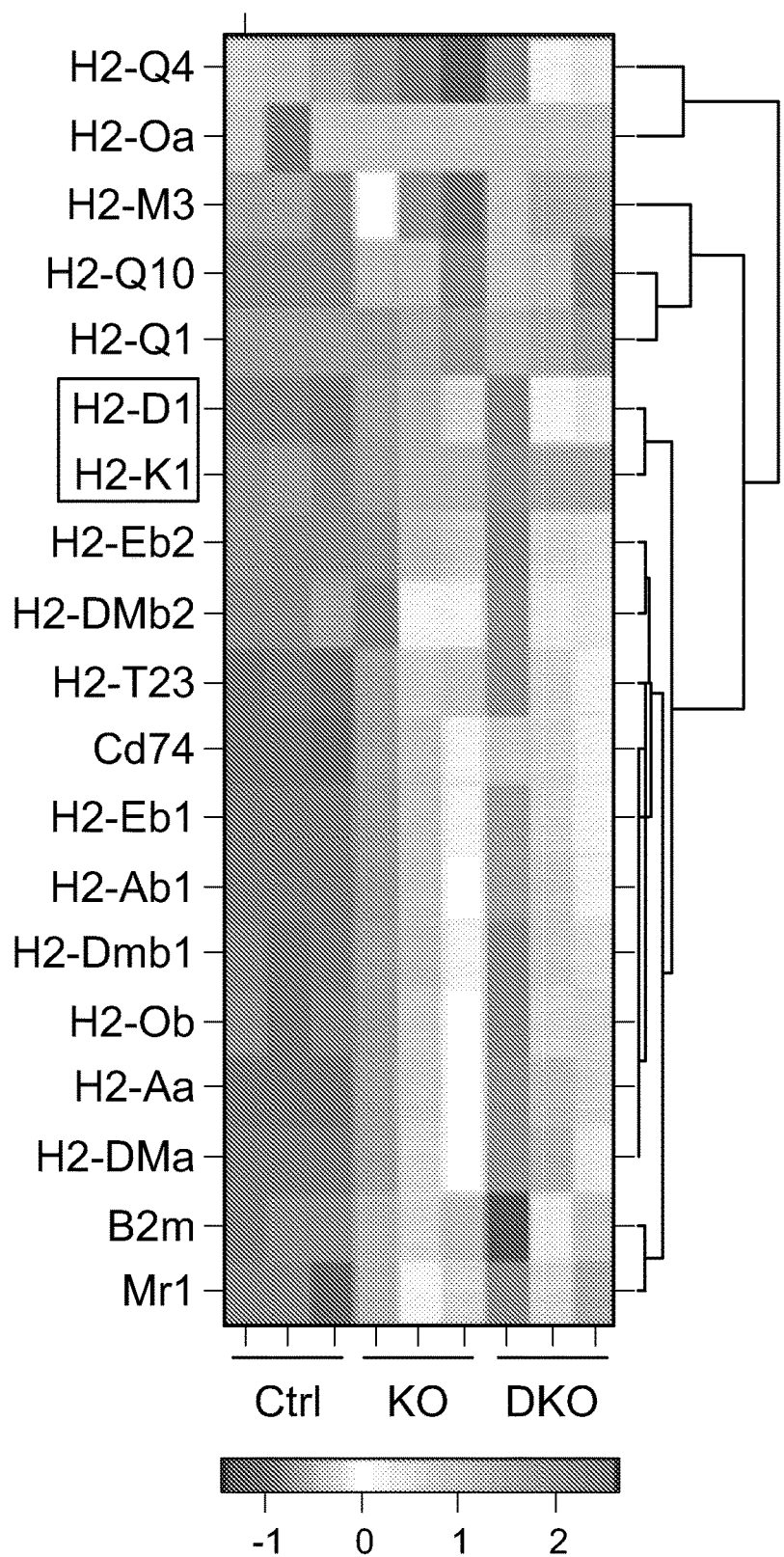
Figure 10O:
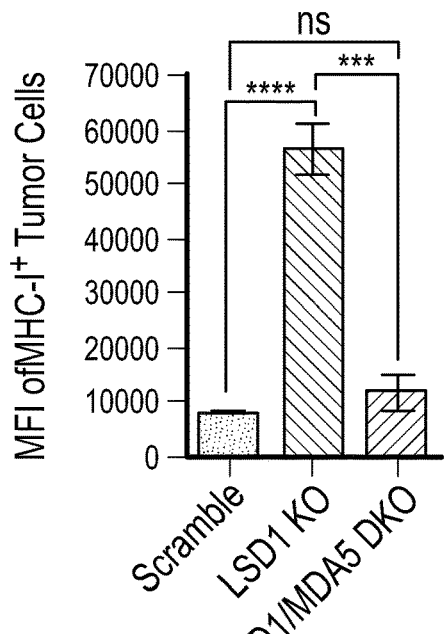

FIG. 10O is a bar graph showing mean fluorescent intensity (MFI) of MHC-1$^+$ B16 cells isolated from scramble, LSD1 KO and LSD1/MDA5 DKO B16 tumors from immunocompetent mice. Data represents two independent experiments. Error bars represent SEM of individual mice in one experiment. *p<0.05, *p<0.001, **p<0.0001, ns, not significant, as determined by unpaired t-test.

Figure 10P:
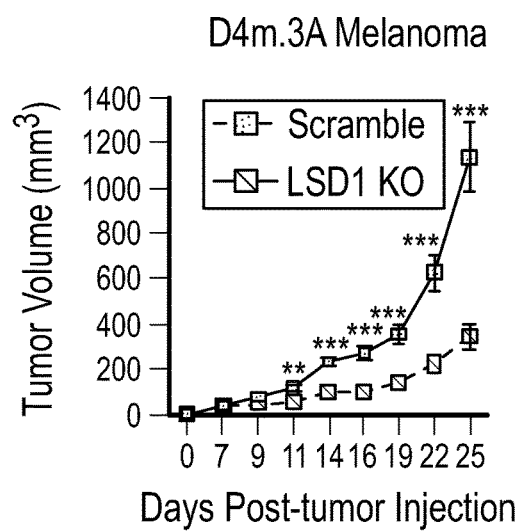

FIG. 10P is a line graph showing tumor growth of immunocompetent mice inoculated with 250 k scramble D4m cells or LSD1 KO D4m cells. Error bars represent SEM of individual mice in one experiment. Data represents two independent experiments. *p<0.05, p<0.01, *p<0.001, ****p<0.0001, ns, not significant, as determined by ANOVA.

Figure 10Q:
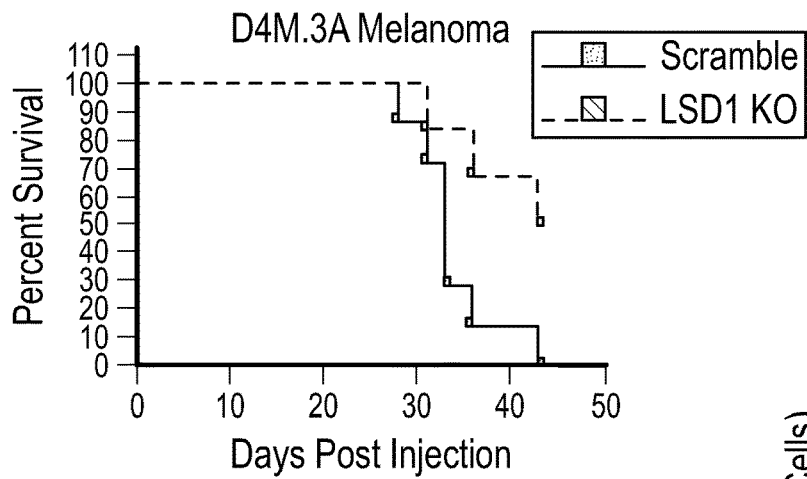

FIG. 10Q is a line graph showing survival of immunocompetent mice inoculated with 250 k scramble D4m cells or LSD1 KO D4m cells. Error bars represent SEM of individual mice in one experiment. **p<0.001, **p<0.0001, ns, not significant, as determined by log-rank test.

Figure 10R:
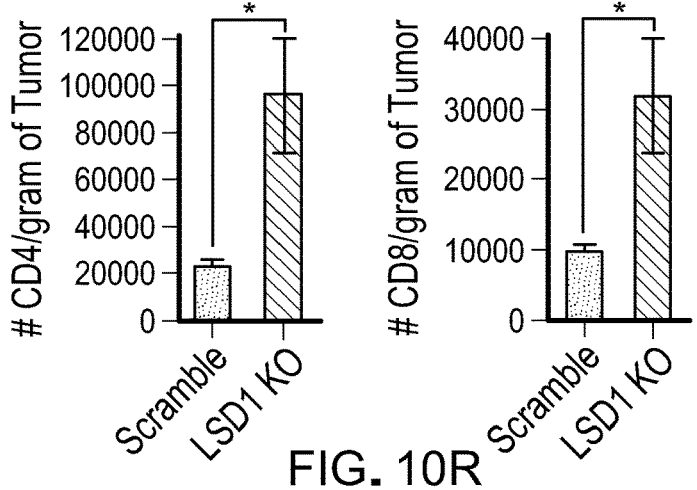

FIG. 10R is bar graphs showing the number of CD4$^+$ and CD8$^+$ TILs per gram of D4m tumor in immunocompetent mice (n=3 in each group) as determined by flow cytometry. Data represents two independent experiments. Error bars represent SEM of individual mice in one experiment. *p<0.05, *p<0.001, **p<0.0001, ns, not significant, as determined by unpaired t-test.

Figure 10S:
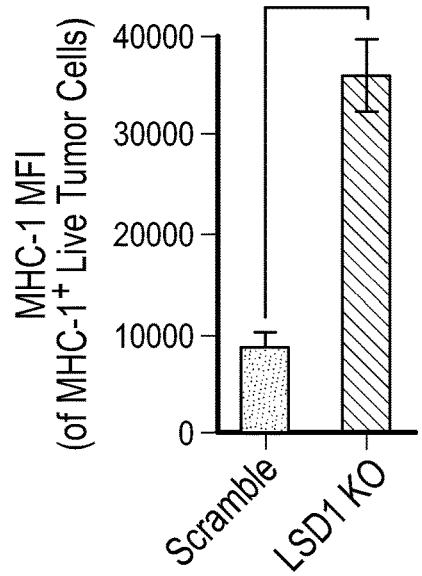

FIG. 10S is a bar graph showing mean fluorescent intensity (MFI) of MHC-1$^+$ ex vivo D4m cells (n=3). Data represents two independent experiments. Error bars represent SEM of individual mice in one experiment. *p<0.05, *p<0.001, **p<0.0001, ns, not significant, as determined by unpaired t-test.

Figure 10T:
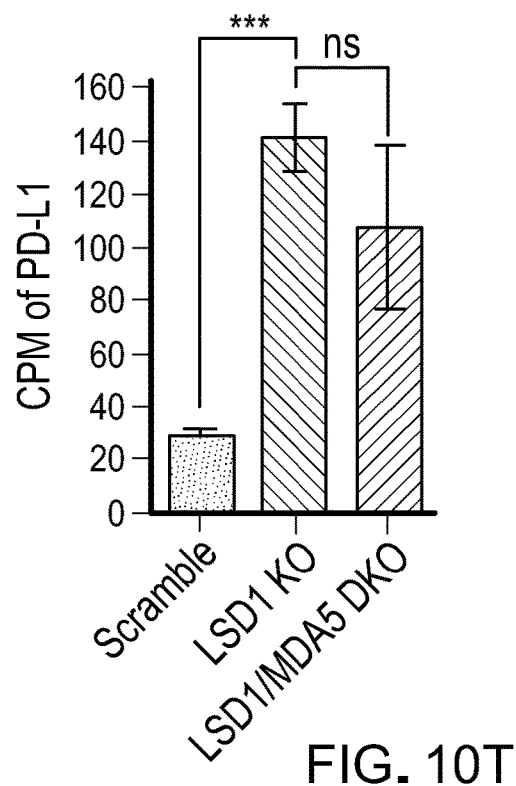

FIG. 10T is a bar graph showing counts per million (CPM) of PD-L1 of tumor-extracted B16 cells (ex vivo; n=3) as determined by RNA-seq. Data represents two independent experiments. Error bars represent SEM of individual mice in one experiment. *p<0.05, *p<0.001, **p<0.0001, ns, not significant, as determined by unpaired t-test.

Figure 10U:
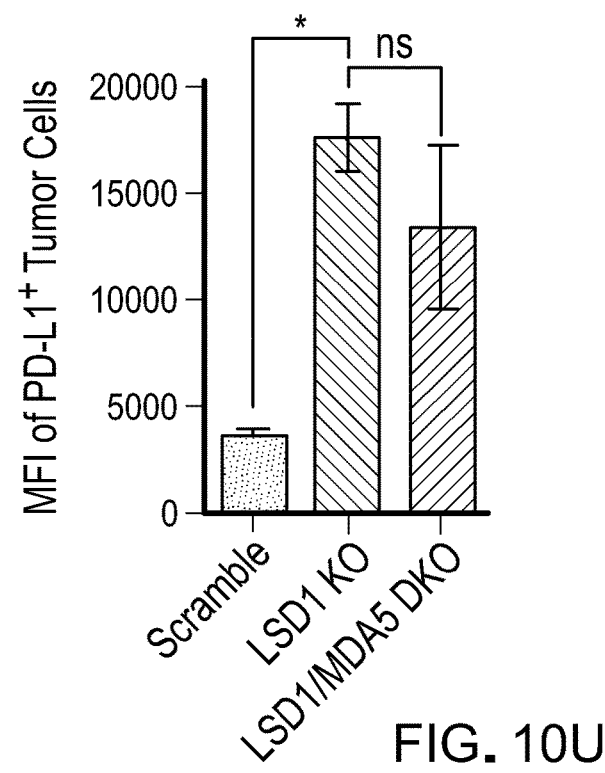

FIG. 10U is a bar graph showing MFI of PD-L1+ B16 cells isolated from scramble, LSD1 KO and LSD1/MDA5 DKO B16 tumors from immunocompetent mice. Data represents two independent experiments. Error bars represent SEM of individual mice in one experiment. *p<0.05, *p<0.001, **p<0.0001, ns, not significant, as determined by unpaired t-test.

Figure 11A:
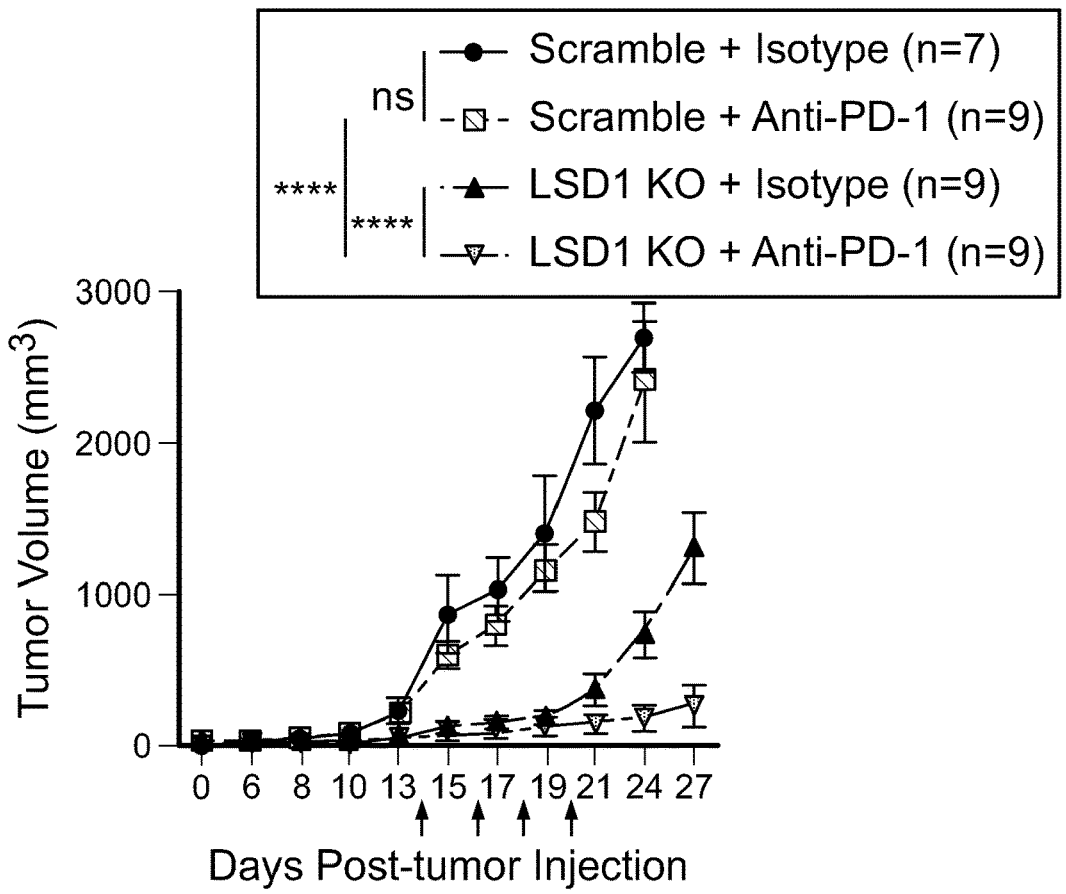

FIG. 11A is a line graph showing tumor growth of immunocompetent mice inoculated with 250 k scramble B16 cells or LSD1 KO B16 cells, and treated with PD-1 blocking antibody or isotype control based on a set time (day 14) for initial treatment. Arrow bars indicate time points of anti-PD-1 injection. Error bars represent SEM of individual mice in one experiment. Data represents two independent experiments. *p<0.05, p<0.01, *p<0.001, ****p<0.0001, ns, not significant, as determined by ANOVA.

Figure 11B:
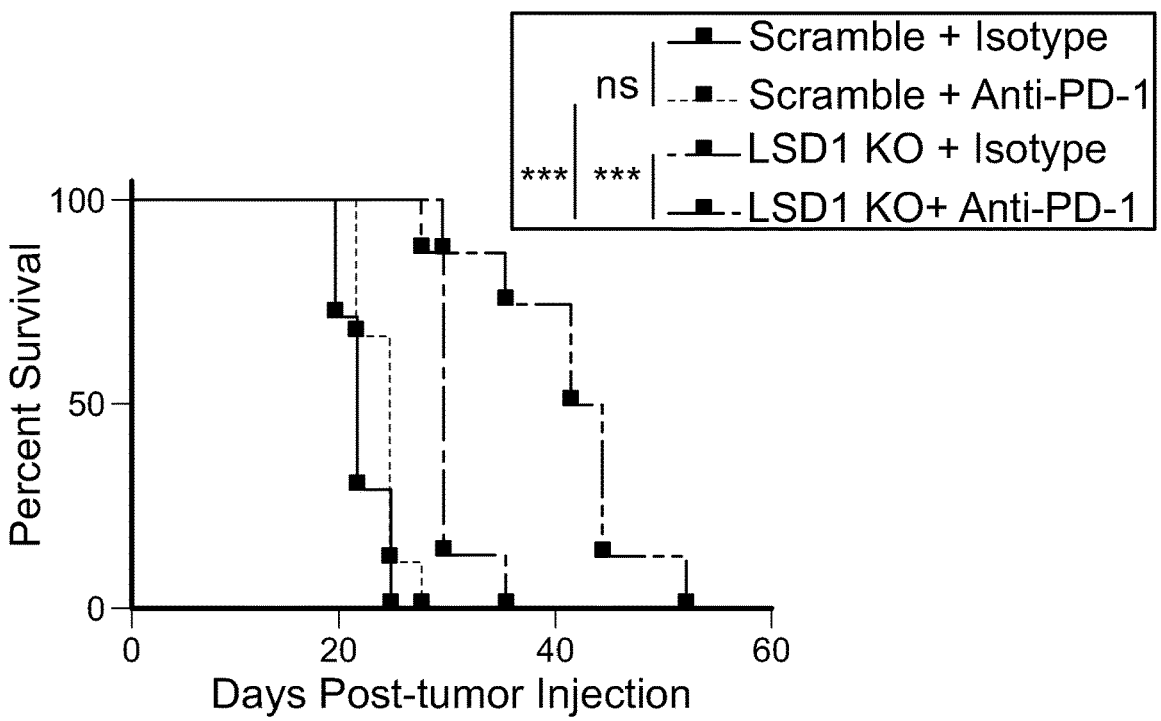

FIG. 11B is a line graph showing survival of immunocompetent mice inoculated with 250 k scramble B16 cells or LSD1 KO B16 cells, and treated with PD-1 blocking antibody or isotype control based on a set time (day 14) for initial treatment. Error bars represent SEM of individual mice in one experiment. **p<0.001, **p<0.0001, ns, not significant, as determined by log-rank test.

Figure 11C:
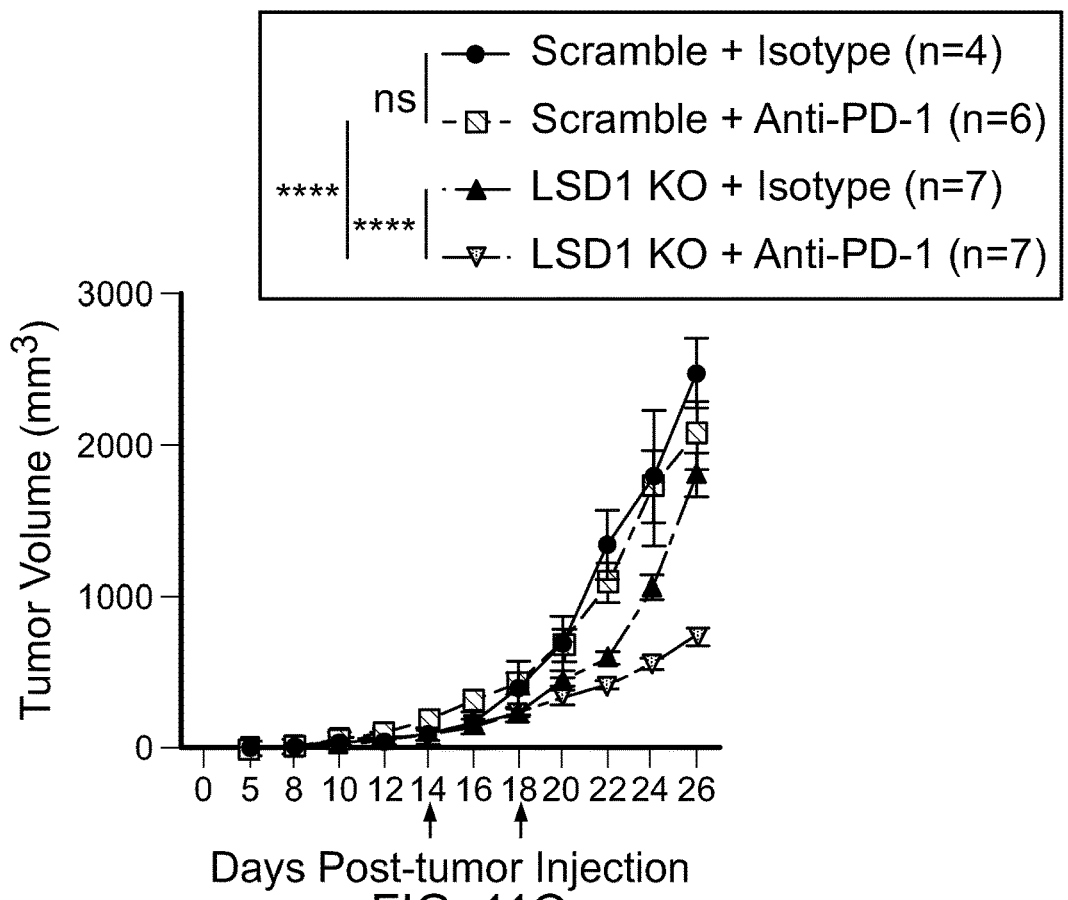

FIG. 11C is a line graph showing tumor growth of immunocompetent mice inoculated with 500 k scramble B16 cells or LSD1 KO B16 cells, and treated with PD-1 blocking antibody or isotype control based on a set tumor size (~200 mm$^3$) for initial treatment. Arrow bars indicate time points of initial anti-PD-1 injection (black arrow (at day 14)—into scramble tumor-bearing mice; grey arrow (at day 18)—into LSD1 KO tumor-bearing mice), followed by continuous injection every other day until the end of experiment. Error bars represent SEM of individual mice in one experiment. Data represents two independent experiments. *p<0.05, p<0.01, *p<0.001, ****p<0.0001, ns, not significant, as determined by ANOVA.

Figure 11D:
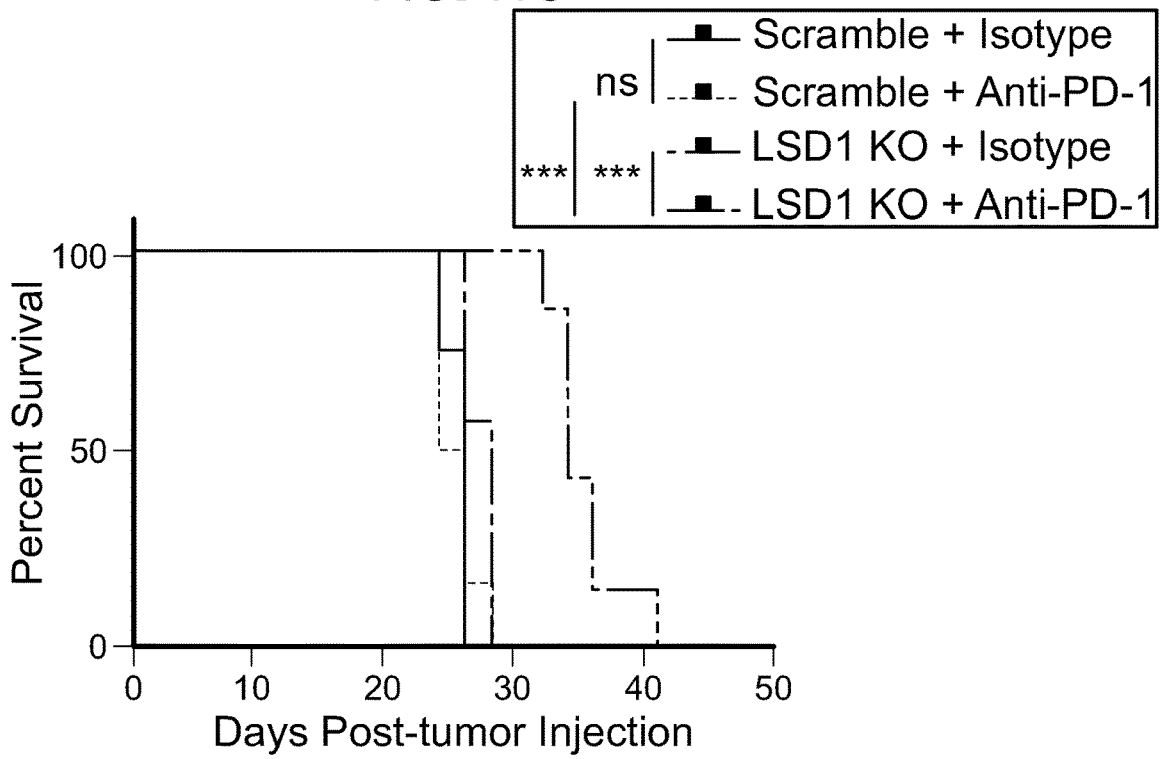

FIG. 11D is a line graph showing survival of immunocompetent mice inoculated with 500 k scramble B16 cells or LSD1 KO B16 cells, and treated with PD-1 blocking antibody or isotype control based on a set tumor size (~200 mm$^3$) for initial treatment. Error bars represent SEM of individual mice in one experiment. **p<0.001, **p<0.0001, ns, not significant, as determined by log-rank test.

Figure 12A:
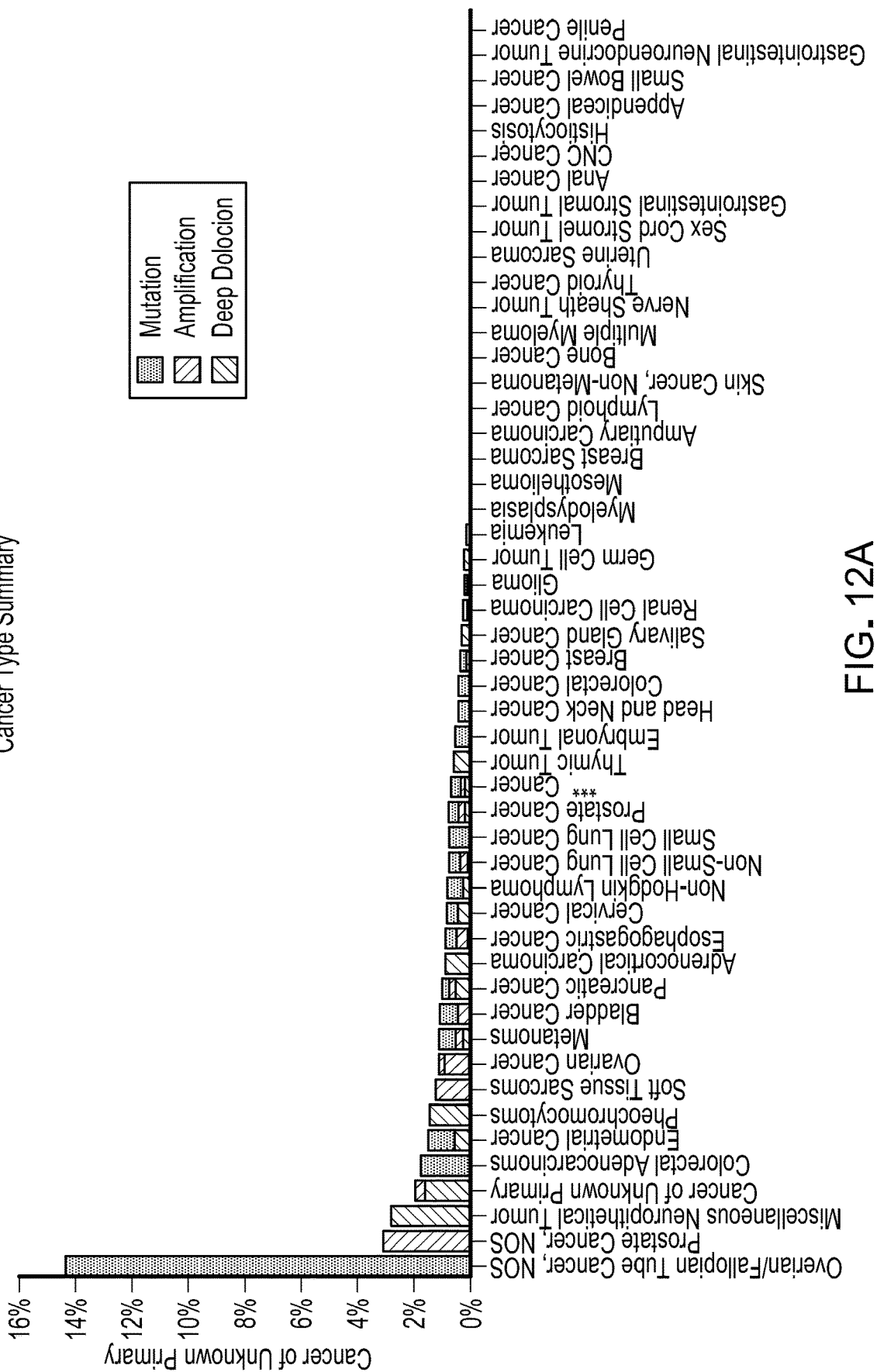

FIG. 12A is bar graph showing the frequencies of mutation, amplification and deletion of LSD1 across a panel of cancer types were analyzed using cBioPortal by selecting all listed studies.

Figure 12B:
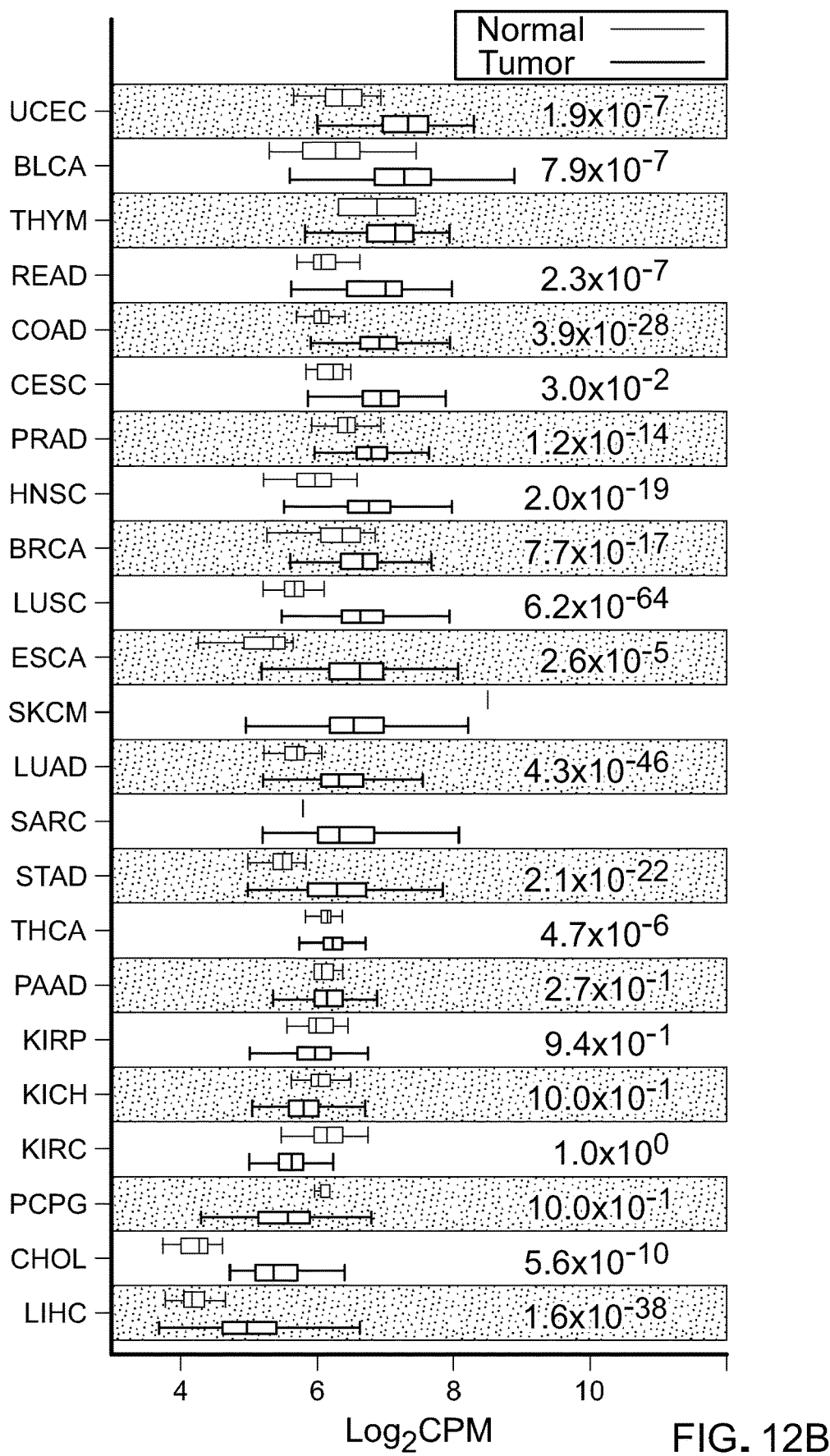

FIG. 12B is a representative plot showing analysis of LSD1 RNA expression in cancerous tissues versus normal tissues from various types of cancer patients in The Cancer Genome Atlas (TCGA) dataset.

FIG. 12C is survival curves of LSD1-low and LSD1-high patient groups dichotomously divided by LSD1 median in two cancer types using TCGA dataset.

Figure 12D:
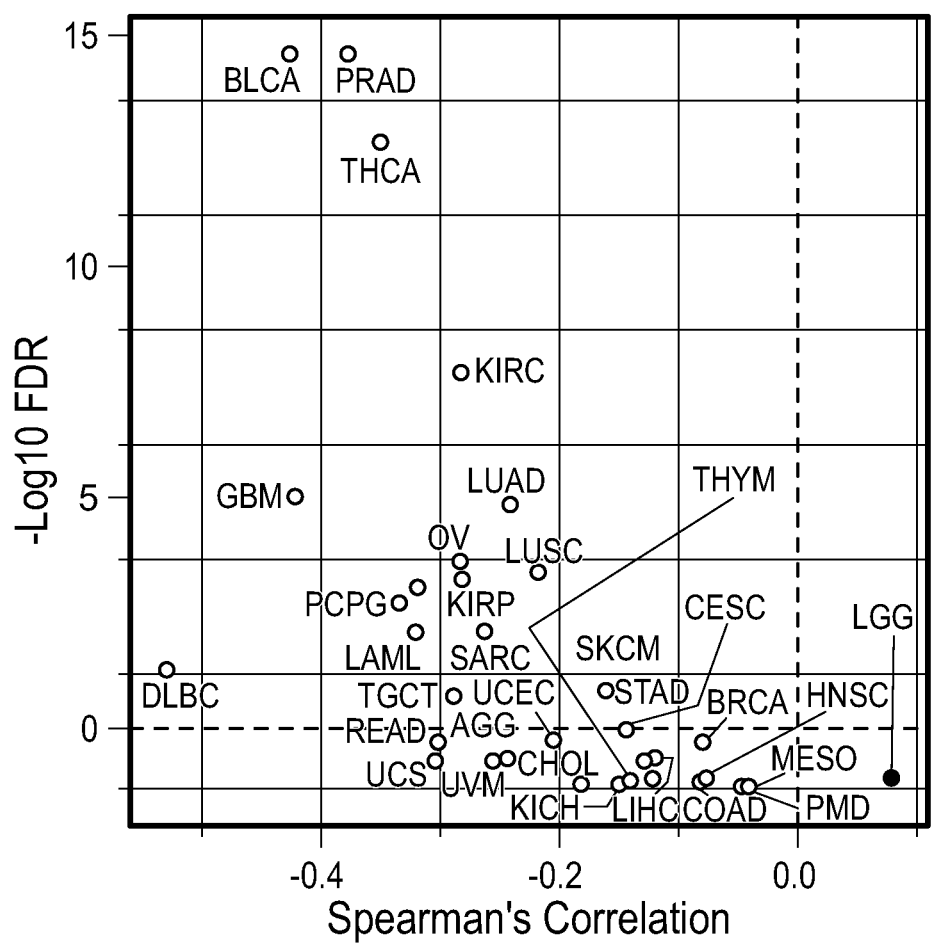

FIG. 12D is a representative correlation analysis for LSD1 expression versus IFN/antiviral response in cancerous tissues from various types of cancer patients in The Cancer Genome Atlas (TCGA) dataset.

Figure 12E:
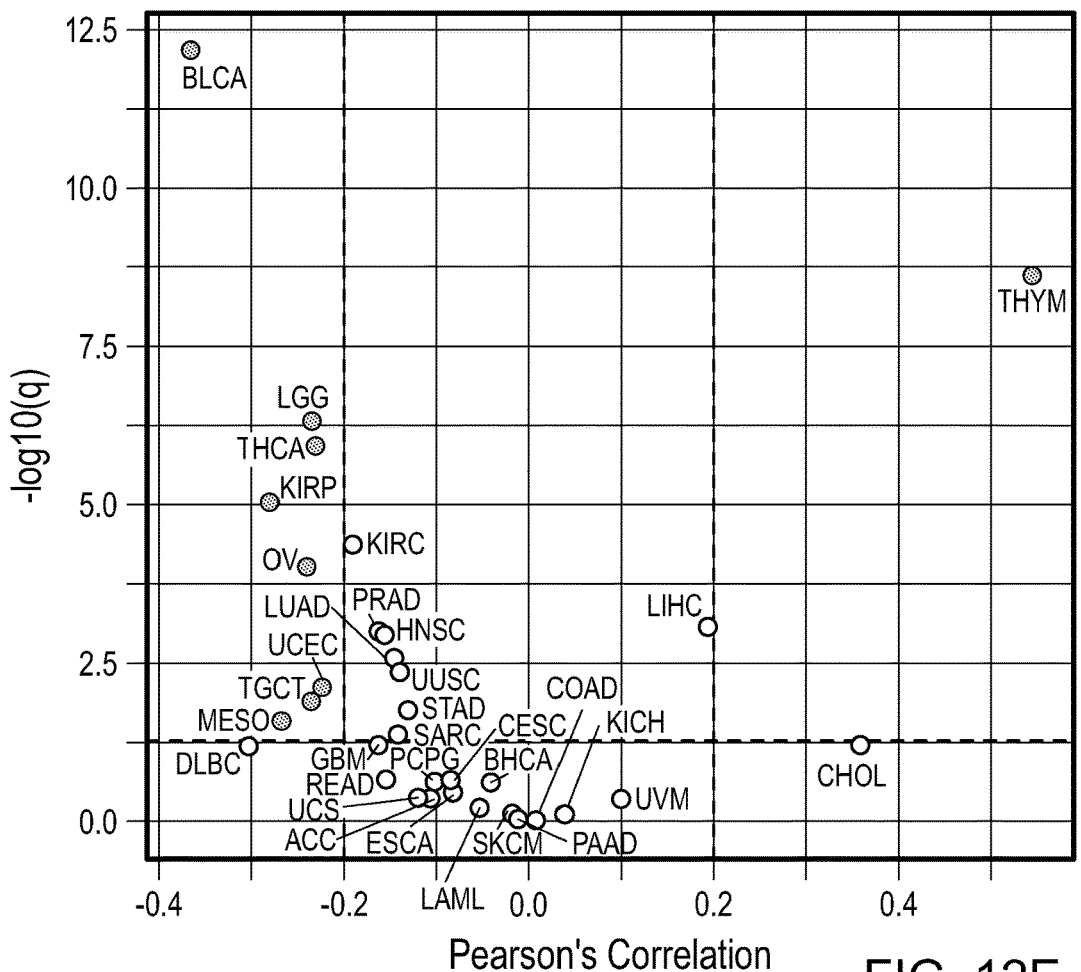

FIG. 12E is a representative correlation analysis for LSD1 expression versus CD8+ T cell infiltration in cancerous tissues from various types of cancer patients in The Cancer Genome Atlas (TCGA) dataset.

Figure 12F:
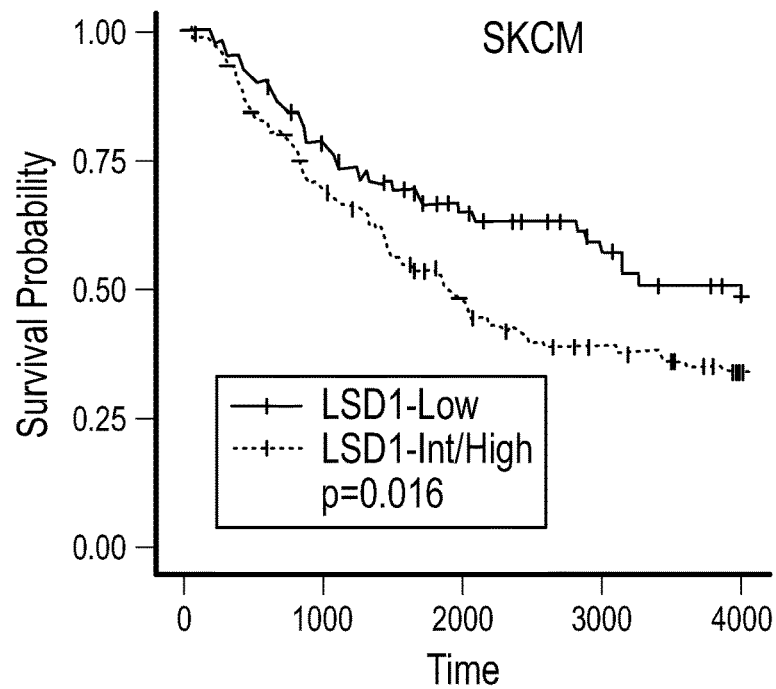

FIG. 12F is survival curves of LSD1-low (first tertile, n=113) and LSD1-int/high (second and third tertiles, n=210) SKCM patient groups divided based on LSD1 expression using TCGA dataset.

Figure 12G:
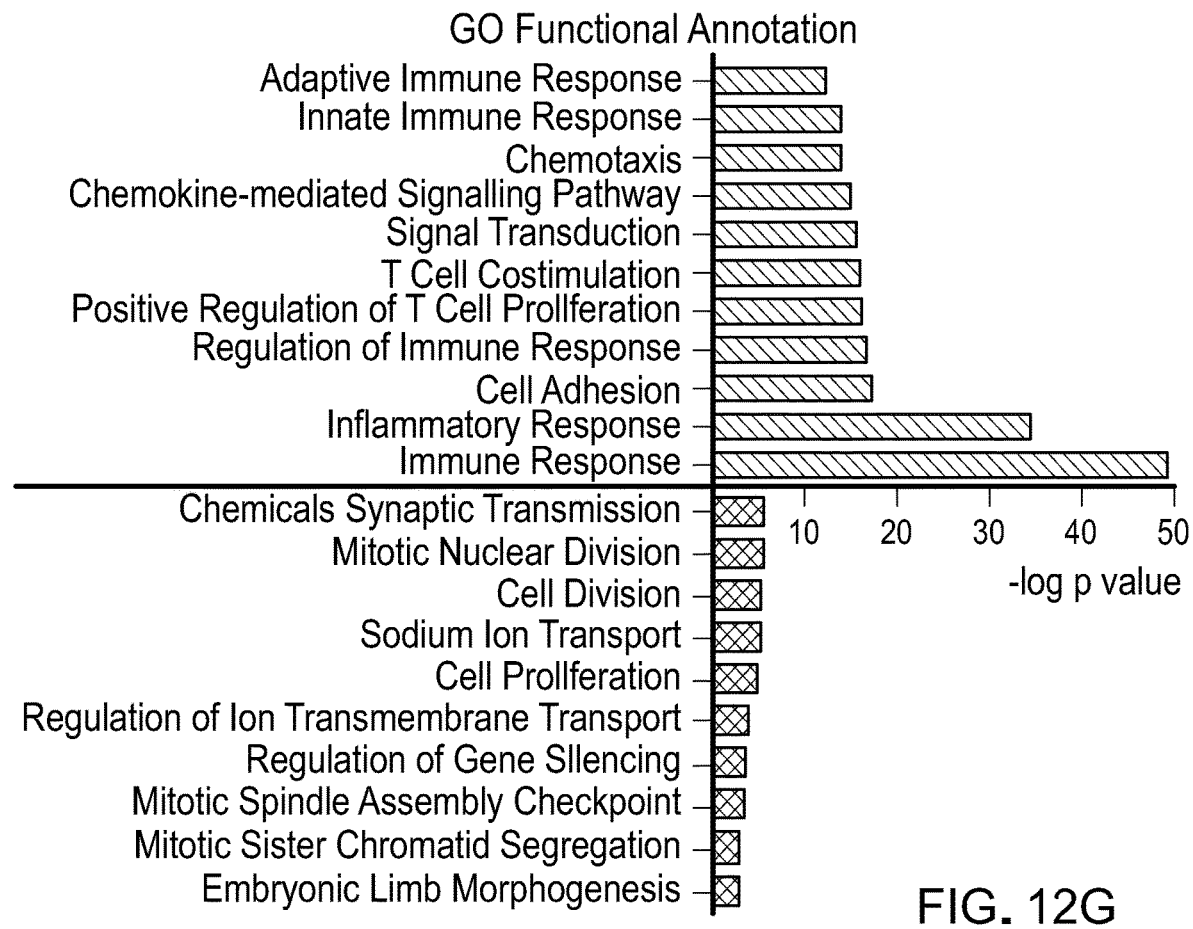

FIG. 12G is a plot of top 10 GO terms based on p value generated by DAVID functional annotation of differentially expressed genes (FC>1.5 or FC<0.67, and FDR<0.05) in LSD1-low group versus LSD1-int/high group of SKCM (increased genes—black(top), decreased genes—grey(bottom)).

Figure 12H:
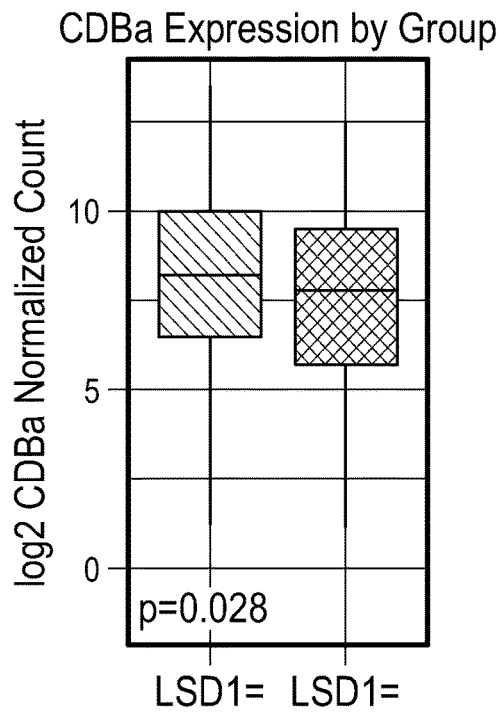

FIG. 12H is a plot comparing CD8a expression between LSD1-low group and LSD1-intermediate (int)/high group of SKCM.

Figure 12I:
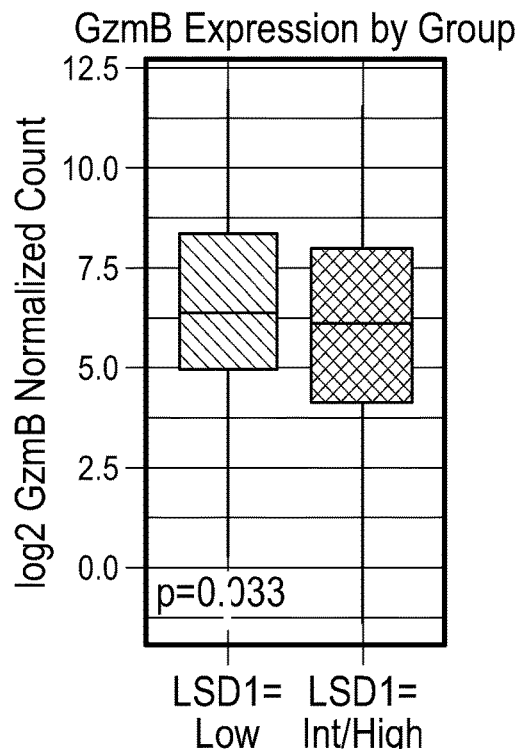

FIG. 12I is a plot comparing GzmB expression between LSD1-low group and LSD1-intermediate (int)/high group of SKCM.

DETAILED DESCRIPTION

Chromatin regulators play a broad role in regulating gene expression. When gene regulation goes awry, this can lead to the development of cancer. Without wishing to be bound by theory, the present disclosure demonstrated that ablation of the histone demethylase lysine-specific demethylase 1A (LSD1) in human and mouse cells leads to double-stranded RNA (dsRNA) stress, through elevating the transcript level of certain repetitive elements and impairing the small RNA machinery, i.e., RNA-induced silencing complex (RISC), which triggers type I interferon activation. Significantly, LSD1 deletion in mouse B16 melanoma cells leads to the activation of potent anti-tumor adaptive immunity, which restrained tumor growth in vivo. Importantly, LSD1 depletion also elicited dramatic responses of checkpoint blockade-refractory B16 tumors to anti-PD-1 therapy. The present disclosure describes the potent impact of LSD1 on tumor responses to host immunity and immunotherapy and describes LSD1 inhibition combined with PD-1 and/or PD-L1 (sometimes collectively referred to herein as "PD-(L)1") blockade as a strategy for cancer treatment.

Cancer immunotherapy, including anti-PD(L)1 therapy, has achieved successful clinical outcomes in controlling tumor progression (Sharma and Allison (2015) Cell 161(2): 205-214). Recent human clinical trial using PD-1 or PD-L1 directed immunotherapy have reported promising results, leading to FDA approval of PD-1 pathway inhibitors for multiple tumor types including melanoma, non-small cell lung cancer (NSCLC), head and neck squamous cell carcinoma (HNSCC), renal cell carcinoma (RCC), Hodgkin's lymphoma, bladder cancer, Merkel cell carcinoma, and microinstability high (MSI$^{hi}$) or mismatch repair deficient adult and pediatric solid tumors (Pauken and Sharpe (2018) Nat Rev Immunol 18(3): 153-167). However, a majority of cancer patients do not respond to anti-PD-(L)-1 therapy, due to multiple mechanisms including dysfunctional T cells and lack of T cell infiltration or recognition by T cells (Sharma et al. (2017) Cell 168: 707-723). The broad roles of chromatin regulators in controlling cancer and T cell functions raise the possibility of their involvement in regulating tumor responses or resistance to immunotherapy. Indeed, a recent study found that inhibition of DNA methylation leads to tumor interferon pathway activation, and increased responses to cancer immunotherapy (Chiappinelli et al. (2015) Cell 162(5): 974-986). On the other hand, blocking de novo DNA methylation in T cells enhances anti-PD-L1-mediated T cells rejuvenation and tumor control (Ghoneim et al. (2017) Cell 170:142-157 e119). However, how the full spectrum of chromatin regulators regulates cancer cells and impacts their responses to the immune system are still poorly understood. Moreover, the therapeutic potential of manipulating these factors to remodel the cancer chromatin landscape for onco-immunotherapy is under-explored.

Naturally occurring dsRNAs derived from a variety of sources including retrotransposons are processed into endo-siRNA by RISC (Watanabe et al. (2008) Nature 453(7194): 539-543). The epigenetic regulation of retrotransposon (such as ERVs) transcription in mammal germ cells and early embryonic development are well documented (Leung and Lorincz (2012) Trends Biochem Sci 37(4): 127-133; Song et al. (2012) Nat Rev Mol Cell Biol 13(5): 283-296), but much less is known in differentiated somatic cells. Without wishing to be bound by theory, the present disclosure shows that LSD1 represses the transcription of a subset of ERVs in human cancer cells, consistent with a previous report showing LSD1 is involved in regulating ERV expression in mESCs (Macfarlan et al. (2011) Genes Dev 25(6): 594-607). Although ERV transcript induction by LSD1 inhibition is not dramatic, their dsRNA forms are much more significantly elevated. Additionally, intracellular dsRNAs can be derived from different categories of transcripts, including ERVs, LINEs, SINes and gene/pseudogene duplexes (Carthew and Sontheimer 2009 Cell 136: 642-655), many of which are also up-regulated in the LSD1 null tumor cells. Importantly, it's the dsRNA forms, rather than the overall transcripts, that are directly recognized by dsRNA sensors to induce IFN activation. LSD1 inhibition also compromises the expression of RISC proteins and subsequently RISC activity, thus blocking dsRNA from entering the RNA interference pathway. By coordinating these two processes, LSD1 inhibition reinforces dsRNA stress and subsequent cellular responses.

Non-limiting aspects of these methods are described below, and can be used in any combination without limitation. Additional aspects of these methods are known in the art.

Methods of Treatment

Provided herein are methods of treating cancer in a patient. Exemplary methods include administering to a patient in need of cancer treatment therapeutically effective amounts of a lysine-specific demethylase 1A (LSD1) inhibitor and a programmed-cell death 1 (PD-1) inhibitor or a programmed-cell death ligand 1 (PD-L1) inhibitor, or both, to thereby treat cancer in the patient.

Also provided herein are methods of treating cancer in a patient that include, e.g. administering to a patient in need of cancer treatment therapeutically effective amounts of a lysine-specific demethylase 1A (LSD1) inhibitor and at least one immunotherapy other than a PD-1 or PD-L1 inhibitor, to thereby treat cancer in the patient.

In methods described herein, the cancer can be, e.g., a primary tumor, a metastatic tumor, or a non-T-cell-infiltrating tumor.

In any of the presently-described methods, the cancer can be, e.g., melanoma, acute myeloid leukemia (AML), squamous cell carcinoma, renal cell carcinoma, non-small cell lung cancer (NSCLC), small cell lung cancer (SCLC), gastric cancer, bladder cancer, kidney cancer, head and neck cancer, Ewing sarcoma, Hodgkin's lymphoma, Merkel cell carcinoma, breast cancer or prostate cancer. Treatment of multiple cancer types at the same time is contemplated by and within the present disclosure.

A cancer described herein can be, e.g., a PD-1 and/or PD-L1 refractory or resistant cancer. In some instances, the patient having the cancer may have previously received cancer treatment (e.g., any of the cancer treatment described herein).

Administering may be performed, e.g., at least once (e.g., at least 2-times, at least 3-times, at least 4-times, at least 5-times, at least 6-times, at least 7-times, at least 8-times, at least 9-times, at least 10-times, at least 11-times, at least 12-times, at least 13-times, or at least 14-times) a week. Also contemplated are monthly treatments, e.g. administering at least once per month for at least 1 month (e.g., at least two, three, four, five, or six or more months, e.g., 12 or more months), and yearly treatments (e.g., administration once a year for one or more years). Administration can be via any art-known means, e.g., intravenous, subcutaneous, intraperitoneal, oral, and/or rectal administration, or any combination of known administration methods.

Administration can include administering compositions in any useful format. For example, skilled practitioners will appreciate that a number of compositions are within the present invention. One useful composition may be a combination composition comprising an LSD1 inhibitor and a PD-1 and/or PD-L1 inhibitor. Such a combined composition can be administered to the patient in any useful dosing regimen. When using separate compositions, e.g., a first composition comprising an LSD1 inhibitor and a second composition comprising a PD-1 and/or PD-L1 inhibitor, the compositions can be administered in any order. For example, the first composition can be administered followed by administration of the second composition, or the second composition can be administered before the first composition, or the first and second compositions can be administered essentially simultaneously.

In one aspect of any of the methods described herein, a first composition comprising an LSD1 inhibitor is administered prior to the administration of a second composition comprising a PD-1 and/or PD-L1 inhibitor. For example, a patient can receive at least one dose (e.g., at least two doses, at least three doses, at least four doses, at least five doses, at least six doses, at least seven doses, at least eight doses, at least nine doses, at least ten doses, at least eleven doses, or at least twelve doses) of first composition comprising an LSD1 inhibitor prior to the administration of a second composition comprising a PD-1 and/or PD-L1 inhibitor.

As used herein, treating includes "prophylactic treatment", which means reducing the incidence of or preventing (or reducing the risk of) a sign or symptom of a cancer in a patient at risk of developing a cancer. The term "therapeutic treatment" refers to reducing signs or symptoms of a cancer, reducing cancer progression, reducing severity of a cancer, and/or re-occurrence in a cancer patient.

The methods described herein may in some instances include administering a composition, e.g., a sterile composition, comprising an inhibitory nucleic acid that is complementary to LSD1 or PD-1 as described herein. A composition may include a LSD1 inhibitory nucleic acid or a PD-1 inhibitory nucleic acid, or both. Inhibitory nucleic acids for use in practicing the methods described herein are described below.

Inhibitory nucleic acids have been employed as therapeutic moieties in the treatment of disease states in subjects, including humans. Inhibitory nucleic acids can be useful therapeutic modalities that can be configured to be useful in treatment regimens for the treatment of cells, tissues and animals, especially humans.

For therapeutics, a subject, e.g., a human, having cancer or suspected of having cancer, or at increased risk of developing a cancer (e.g., by virtue of family history, genetic testing, or presence of other identified risk factor), can be treated by administering an inhibitory nucleic acid in accordance with this disclosure. For example, in one non-limiting embodiment, the methods comprise the step of administering to the subject in need of treatment a therapeutically effective amount of one or more of a LSD1 inhibitory nucleic acid (e.g., a LSD1 antisense molecule, a LSD1 small interfering RNA, a LSD1 small hairpin RNA), a PD-1 inhibitory nucleic acid (e.g., a PD-1 antisense molecule, a PD-1 small interfering RNA, a PD-1 small hairpin RNA) or a PD-L1 inhibitory nucleic acid (e.g., a PD-L1 antisense molecule, a PD-L1 small interfering RNA, a PD-L1 small hairpin RNA) as described herein.

Immunotherapy

An immunotherapy can be administered to the patient in methods described herein. The term "immunotherapy" refers to a therapeutic treatment that involves administering to a patient an agent that modulates the immune system. For example, an immunotherapy can increase the expression and/or activity of a regulator of the immune system. In other instances, an immunotherapy can decrease the expression and/or activity of a regulator of the immune system. In some instances, an immunotherapy can recruit and/or enhance the activity of an immune cell. An example of an immunotherapy is a therapeutic treatment that involves administering at least one, e.g., two or more, immune checkpoint inhibitors. Exemplary immune checkpoint inhibitors useful in the presently-described methods are CTLA-4 inhibitors, PD-1 inhibitors, PD-L1 inhibitors, PD-L2 inhibitors, OX40 inhibitor, TIM3 inhibitors, or LAG3 inhibitors, or combinations thereof.

The immunotherapy can be a cellular immunotherapy (e.g., adoptive T-cell therapy, dendritic cell therapy, natural killer cell therapy). For example, the cellular immunotherapy can be sipuleucel-T (APC8015; Provenge™; Plosker (2011) Drugs 71(1): 101-108). In some instances, the cellular immunotherapy includes cells that express a chimeric antigen receptor (CAR). In some instances, the cellular immunotherapy can be a CAR-T cell therapy, e.g., tisagenlecleucel (Kymriah™).

Immunotherapy can be, e.g., an antibody therapy (e.g., a monoclonal antibody, a conjugated antibody). In some embodiments, the antibody is an anti-CTLA-4 antibody, an anti-PD-1 antibody, an anti-PD-L1 antibody, an anti-PD-L2 antibody, an anti-OX40 antibody, an anti-TIM3 antibody, or an anti-LAG3 antibody. Exemplary antibody therapies are bevacizumab (Mvasti™, Avastin®), trastuzumab (Herceptin®), avelumab (Bavencio®), rituximab (MabThera™, Rituxan®), edrecolomab (Panorex), daratumuab (Darzalex®), olaratumab (Lartruvo™), ofatumumab (Arzerra®), alemtuzumab (Campath®), cetuximab (Erbitux®), oregovomab, pembrolizumab (Keytruda®), dinutiximab (Unituxin®), obinutuzumab (Gazyva®), tremelimumab (CP-675,206), ramucirumab (Cyramza®), ublituximab (TG-1101), panitumumab (Vectibix®), elotuzumab (Empliciti™), avelumab (Bavencio®), necitumumab (Portrazza™), cirmtuzumab (UC-961), ibritumomab (Zevalin®), isatuximab (SAR650984), nimotuzumab, fresolimumab (GC1008), lirilumab (INN), mogamulizumab (Poteligeo®), ficlatuzumab (AV-299), denosumab (Xgeva®), ganitumab, urelumab, pidilizumab or amatuximab.

An immunotherapy described herein can involve administering an antibody-drug conjugate to a patient. The antibody-drug conjugate can be, e.g., gemtuzumab ozogamicin (Mylotarg™), inotuzumab ozogamicin (Besponsa®), brentuximab vedotin (Adcetris®), ado-trastuzumab emtansine (TDM-1; Kadcyla®), mirvetuximab soravtansine (IMGN853) or anetumab ravtansine.

In some instances, the immunotherapy includes blinatumomab (AMG103; Blincyto®) or midostaurin (Rydapt).

An immunotherapy can include administering to the patient a toxin. For example, the immunotherapy can including administering denileukin diftitox (Ontak®).

In some instances, the immunotherapy can be a cytokine therapy. The cytokine therapy can be, e.g., an interleukin 2 (IL-2) therapy, an interferon alpha (IFN-t) therapy, a granulocyte colony stimulating factor (G-CSF) therapy, an interleukin 12 (IL-12) therapy, an interleukin 15 (IL-15) therapy, an interleukin 7 (IL-7) therapy or an erythropoietin-alpha (EPO) therapy. In some embodiments, the IL-2 therapy is aldesleukin (Proleukin®). In some embodiments, the IFN-α therapy is IntronA® (Roferon-A®). In some embodiments, the G-CSF therapy is filgrastim (Neupogen®).

In some instances, the immunotherapy is an immune checkpoint inhibitor. For example, the immunotherapy can include administering one or more immune checkpoint inhibitors. In some embodiments, the immune checkpoint inhibitor is a CTLA-4 inhibitor, a PD-1 inhibitor or a PD-L1 inhibitor. An exemplary CTLA-4 inhibitor would be, e.g., ipilimumab (Yervoy®) or tremelimumab (CP-675,206). In some embodiments, the PD-1 inhibitor is pembrolizumab (Keytruda®) or nivolumab (Opdivo®). In some embodiments, the PD-L1 inhibitor is atezolizumab (Tecentriq®), avelumab (Bavencio®) or durvalumab (Imfinzi™).

In some instances, the immunotherapy is mRNA-based immunotherapy. For example, the mRNA-based immunotherapy can be CV9104 (see, e.g., Rausch et al. (2014) Human Vaccin Immunother 10(11): 3146-52; and Kubler et al. (2015) J. Immunother Cancer 3:26).

In some instances, the immunotherapy can involve *bacillus* Calmette-Guerin (BCG) therapy.

In some instances, the immunotherapy can be an oncolytic virus therapy. For example, the oncolytic virus therapy can involve administering talimogene alherparepvec (T-VEC; Imlygic®).

In some instances, the immunotherapy is a cancer vaccine, e.g., a human papillomavirus (HPV) vaccine. For example, an HPV vaccine can be Gardasil®, Gardasil9® or Cervarix®. In some instances, the cancer vaccine is a hepatitis B virus (HBV) vaccine. In some embodiments, the HBV vaccine is Engerix-B®, Recombivax HB® or GI-13020 (Tarmogen®). In some embodiments, the cancer vaccine is Twinrix® or Pediarix®. In some embodiments, the cancer vaccine is BiovaxID®, Oncophage®, GVAX, ADXS11-001, ALVAC-CEA, PROSTVAC®, Rindopepimut®, CimaVax-EGF, lapuleucel-T (APC8024; Neuvenge™), GRNVAC1, GRNVAC2, GRN-1201, hepcortespenlisimut-L (Hepko-V5), DCVAX®, SCIB1, BMT CTN 1401, PrCa VBIR, PANVAC, ProstAtak®, DPX-Survivac, or viagenpumatucel-L (HS-110).

The immunotherapy can involve, e.g., administering a peptide vaccine. For example, the peptide vaccine can be nelipepimut-S(E75) (NeuVax™), IMA901, or SurVaxM (SVN53-67). In some instances, the cancer vaccine is an immunogenic personal neoantigen vaccine (see, e.g., Ott et al. (2017) Nature 547: 217-221; Sahin et al. (2017) Nature 547: 222-226). In some embodiments, the cancer vaccine is RGSH4K, or NEO-PV-01. In some embodiments, the cancer vaccine is a DNA-based vaccine. In some embodiments, the DNA-based vaccine is a mammaglobin-A DNA vaccine (see, e.g., Kim et al. (2016) OncoImmunology 5(2): e1069940).

Cancer

The methods described herein can be used in cancer treatments. Non-limiting examples of cancer include: acute lymphoblastic leukemia (ALL), acute nmyeloid leukemia (AML), adrenocortical carcinoma, anal cancer, appendix cancer, astrocytoma, basal cell carcinoma, brain tumor, bile duct cancer, bladder cancer, bone cancer, breast cancer, bronchial tumor, Burkitt Lymphoma, carcinoma of unknovni primary origin, cardiac tumor, cervical cancer, chordoma, chronic lymphocytic leukemia (CLL), chronic myelogenous leukemia (CML), chronic miyeloproliferative neoplasm, colon cancer, colorectal cancer, craniopharyngioma, cutaneous T-cell lymphoma, ductal carcinoma, ernybonal tumor, endometrial cancer, ependymoma, esophageal cancer, esthesioneuroblastoma, fibrous histiocytoma, Ewing sarcoma, eye cancer, germ cell tumor, gallbladder cancer, gastric cancer, gastrointestinal carcinoid tumor, gastrointestinal stromal tumor, gestational trophoblastic disease, glioma, head and neck cancer, hairy cell leukemia, hepatocellular cancer, histiocytosis, Hodgkin lymphoma, hypopharyngeal cancer, intraocular melanoma, islet cell tumor, Kaposi sarcoma, kidney cancer, Langerhans cell histiocytosis, laryngeal cancer, leukemia, lip and oral cavity cancer, liver cancer, lobular carcinoma in situ, lung cancer, lymphoma, macroglobulinemia, malignant fibrous histiocytoma, melanoma, Merkel cell carcinoma, mesothelioma, metastatic squamous neck cancer with occult primary, midline tract carcinoma involving NUT gene, mouth cancer, multiple endocrine neoplasia syndrome, multiple myeloma, mycosis fungoides, myelodysplastic syndrome, myelodysplastic/myeloproliferative neoplasm, nasal cavity and para-nasal sinus cancer, nasopharyngeal cancer, neuroblastoma, non-Hodgkin lymphoma, non-small cell lung cancer, oropharyngeal cancer, osteosarcorna, ovarian cancer, pancreatic cancer, papillomatosis, paraganglioma, parathyroid cancer, penile cancer, pharyngeal cancer, pheochromocytomas, pituitary tumor, pleuropulmonary blastoma, primary central nervous system lymphoma, prostate cancer, rectal cancer, renal cell cancer, renal pelvis and ureter cancer, retinoblastoma, rhabdoid tumor, salivary gland cancer. Sezary syndrome, skin cancer, small cell lung cancer, small intestine cancer, soft tissue sarcoma, spinal cord tumor, stomach cancer, T-cell lymphoma, teratoid tumor, testicular cancer, throat cancer, thymoma and thymic carcinoma, thyroid cancer, urethral cancer, uterine cancer, vaginal cancer, vaginal cancer, vulvar cancer, and Wilms' tumor.

For example, any of the methods described herein can be used to treat a cancer selected from the group consisting of: melanoma, acute myeloid leukemia (AML), squamous cell carcinoma, renal cell carcinoma, non-small cell lung cancer (NSCLC), small cell lung cancer (SCLC), gastric cancer, bladder cancer, kidney cancer, head and neck cancer, Ewing sarcoma, Hodgkin's lymphoma, Merkel cell carcinoma, breast cancer and prostate cancer.

LSD1

As used herein, the term "LSD1 inhibitor" refers to a therapeutic agent that reduces, decreases, blocks or inhibits the expression or activity of LSD1. For example, the LSD1 inhibitor can block or disrupt the catalytic active site of LSD1. The LSD1 inhibitor can be, e.g., a selective LSD1 inhibitor or a non-selective LSD1 inhibitor.

The LSD1 inhibitor can be a small molecule, an antibody, or an inhibitory nucleic acid. A non-exhaustive list of small molecule LSD1 inhibitors is provided in Table 1.

TABLE 1

Exemplary list of small molecule LSD1 inhibitors

| Chemical name | Generic name or name as used in clinical trials | CAS# |
|---|---|---|
| trans-2-Phenylcyclopropylamine hemisulfate salt | Tranylcypromine | 13492-01-8 |
| 1-(4-methylpiperazin-1-yl)-2-[[2-(4-phenylmethoxyphenyl)cyclopropyl]amino]ethanone | RN 1 dihydrochloride | 1781835-13-9 |
| rel-N-[(1R,2S)-2-Phenylcyclopropyl]-4-Piperidinamine hydrochloride (1:2) | GSK-LSD1 | 1431368-48-7 |
| 4-[[4-[[[(1R,2S)-2-phenylcyclopropyl]amino]methyl]-1-piperidinyl]methyl]-benzoic acid | GSK2879552 | 1401966-69-5 |
| rel-N1-[(1R,2S)-2-phenylcyclopropyl]-1,4-cyclohexanediamine, dihydrochloride | ORY1001 | 1431326-61-2 |
| (R)-4-[5-(Pyrrolidin-3-ylmethoxy)-2-p-tolyl-pyridin-3-yl]-benzonitrile Bis-TFA Salt | GSK690 | 2101305-84-2 |
| 3-Chloro-6-nitro-2-(trifluoromethyl)-4H-1-benzopyran-4-one | Namoline | 342795-11-3 |
| 1,15-bis{N5-[3,3-(diphenyl)propyl]-N1-biguanido}-4,12-diazapentadecane | Cpd 2d | |
| (1R,2S)-rel-2-[3,5-Difluoro-2-(phenylmethoxy)phenyl]cyclo-prpanamine hydrochloride | S2101 | 1239262-36-2 |
| 4'-[(1R,2S)-2-aminocyclopropyl]-[1,1'-biphenyl]-3-ol | OG-L002 | 1357302-64-7 |
| 3-(4-morpholinylsulfonyl)-benzoic acid (2E)-2-[1-(5-chloro-2-hydroxyphenyl)ethylidene]hydrazide | SP2509 | 1423715-09-6 |
| Methyl-3-(4-(4-carbamimidoylbenzoyl)piperazine-1-carbonyl)-5-((4-carbamimidoyl-piperazin-1-yl)methyl)benzoate | CBB1007 | 1379573-92-8 |
| N-[(2S)-5-{[(1R,2S)-2-(4-fluorophenyl)cyclopropyl]amino}-1-(4-methylpiperazin-1-yl)-1-oxopentan-2-yl]-4-(1H-1,2,3-triazol-1-yl)benzamide, bis-tosylate salt | IMG-7289 | |

In some instances, the LSD1 inhibitor is an inhibitory nucleic acid. SEQ ID NO: 1 is an exemplary human sequence of LSD1:

```
                              (SEQ ID NO: 1; Accession Number: NM_001009999.2)
    a tgttatctgg gaagaaggcg gcagccgcgg 181 cggcggcggc tgcagcggca gcaaccggga cggaggctgg ccctgggaca gcaggcggct 241 ccgagaacgg gtctgaggtg gccgcgcagc ccgcgggcct gtcgggccca gccgaggtcg 301 ggccgggggc ggtgggggag cgcacacccc gcaagaaaga gcctccgcgg gcctcgcccc 361 ccggggccct ggcggaaccg ccggggtccg cagggcctca ggccggccct actgtcgtgc 421 ctggtctgc gaccccatg gaaactggaa tagcagagac tccggagggg cgtcggacca 481 gccggcgcaa gcgggcgaag gtagagtaca gagagatgga tgaaagcttg gccaacctct
```

-continued

```
 541 cagaagatga gtattattca gaagaagaga gaaatgccaa agcagagaag gaaaagaagc 601 ttcccccacc acccccctcaa gccccacctg aggaagaaaa tgaaagtgag cctgaagaac 661 catcggggca agcaggagga cttcaagacg acagttctgg agggtatgga gacggccaag 721 catcaggtgt ggagggcgca gctttccaga gccgacttcc tcatgaccgg atgacttctc 781 aagaagcagc ctgttttcca gatattatca gtggaccaca acagacccag aaggtttttc 841 ttttcattag aaaccgcaca ctgcagttgt ggttggataa tccaaagatt cagctgacat 901 ttgaggctac tctccaacaa ttagaagcac cttataacag tgatactgtg cttgtccacc 961 gagttcacag ttatttagag cgtcatggtc ttatcaactt cggcatctat aagaggataa 1021 aaccccctacc aactaaaaag acaggaaagg taattattat aggctctggg gtctcaggct 1081 tggcagcagc tcgacagtta caaagttttg aatggatgt cacacttttg gaagccaggg 1141 atcgtgtggg tggacgagtt gccacatttc gcaaaggaaa ctatgtagct gatcttggag 1201 ccatggtggt aacaggtctt ggagggaatc ctatggctgt ggtcagcaaa caagtaaata 1261 tggaactggc caagatcaag caaaaatgcc cactttatga agccaacgga caagctgaca 1321 ctgtcaaggt tcctaaagag aaagatgaaa tggtagagca agagtttaac cggttgctag 1381 aagctacatc ttaccttagt catcaactag acttcaatgt cctcaataat aagcctgtgt 1441 cccttggcca ggcattggaa gttgtcattc agttacaaga gaagcatgtc aaagatgagc 1501 agattgaaca ttggaagaag atagtgaaaa ctcaggaaga attgaaagaa cttcttaata 1561 agatggtaaa tttgaaagag aaaattaaag aactccatca gcaatacaaa gaagcatctg 1621 aagtaaagcc acccagagat attactgccg agttcttagt gaaaagcaaa cacagggatc 1681 tgaccgccct atgcaaggaa tatgatgaat tagctgaaac acaaggaaag ctagaagaaa 1741 aacttcagga gttggaagcg aatcccccaa gtgatgtata tctctcatca agagacagac 1801 aaatacttga ttggcatttt gcaaatcttg aatttgctaa tgccacacct ctctcaactc 1861 tctcccttaa gcactgggat caggatgatg actttgagtt cactggcagc cacctgacag 1921 taaggaatgg ctactcgtgt gtgcctgtgg ctttagcaga aggcctagac attaaactga 1981 atacagcagt gcgacaggtt cgctacacgg cttcaggatg tgaagtgata gctgtgaata 2041 cccgctccac gagtcaaacc tttatttata atgcgacgc agttctctgt acccttcccc 2101 tgggtgtgct gaagcagcag ccaccagccg ttcagtttgt gccacctctc cctgagtgga 2161 aaacatctgc agtccaaagg atgggatttg caaccttaa caaggtggtg ttgtgttttg 2221 atcgggtgtt ctgggatcca agtgtcaatt tgttcgggca tgttggcagt acgactgcca 2281 gcagggtga gctcttcctc ttctggaacc tctataaagc tccaatactg ttggcactag 2341 tggcaggaga agctgctggt atcatggaaa acataagtga cgatgtgatt gttggccgat 2401 gcctggccat tctcaaaggg attttttggta gcagtgcagt acctcagccc aaagaaactg 2461 tggtgtctcg ttggcgtgct gatccctggg ctcggggctc ttattcctat gttgctgcag 2521 gatcatctgg aaatgactat gatttaatgg ctcagccaat cactcctggc ccctcgattc 2581 caggtgcccc acagccgatt ccacgactct tctttgcggg agaacatacg atccgtaact 2641 acccagccac agtgcatggt gctctgctga gtgggctgcg agaagcggga agaattgcag 2701 accagttttt gggggccatg tatacgctgc ctcgccaggc cacaccaggt gttcctgcac 2761 agcagtcccc aagcatgtga
```

Inhibitory nucleic acids useful in the present methods and compositions include those that are designed to inhibit LSD1. SEQ ID NO: 2 is an exemplary shRNA sequence that targets human LSD1:

(SEQ ID NO: 2)
5'-CCGG-GCCTAGACATTAAACTGAATA-CTCGAG-

TATTCAGTTTAATGTCTAGGC-TTTTTG-3'.

Bold and underlined portions are targeting/matching sequences in human LSD1 mRNA.

The LSD1 inhibitory nucleic acid can, e.g., comprise SEQ ID NO: 2. For example, the LSD1 inhibitory nucleic acid can be a nucleic acid comprising a sequence that is complementary to a contiguous sequence of at least 5 (e.g., at least 6, at least 7, at least 8, at least 9, at least 10, at least 11, at least 12, at least, 13, at least 14, at least 15, at least 16, at least 17, at least 18, at least 19, at least 20, at least 21, 5, 6, 7, 8, 9, 10, 11, 12, 13, 14, 15, 16, 17, 18, 19, 20, 21, or 22) nucleotides present in SEQ ID NO: 2.

The LSD1 inhibitory nucleic acid can be any LSD1 inhibitory nucleic acid that decreases, reduces or silences the expression and/or activity of LSD1. As shown herein, loss of LSD1 increased the expression of HERV-E, HERV-K, HML-2, ERVL, IFN-α, IFN-β, IL-28, ISG15, OASL, RIG-I, TLR3, and MDA-5. In some embodiments, the LSD1 inhibitory nucleic acid is any LSD1 inhibitory nucleic acid that increases or upregulates the expression and/or activity of HERV-E, HERV-K, HML-2, ERVL, IFN-α, IFN-β, IL-28, ISG15, OASL, RIG-I, TLR3, and/or MDA-5.

In some embodiments, the LSD1 inhibitor can be a compound having the structure of Formula I, or Formula II, or a pharmaceutically acceptable salt thereof:

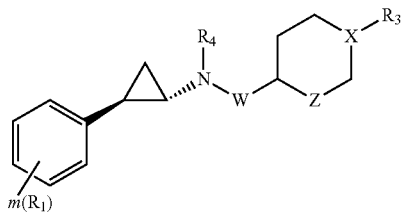

(Formula I)

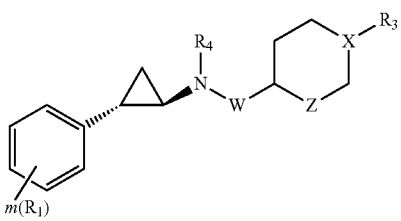

(Formula II)

Wherein $R_1$ is selected from the group consisting of $C_1$-$C_6$ alkyl, —$NHSO_2Me$, —$NHSO_2Ph$, arylalkoxy, $C_3$-$C_7$ cycloalkyl, —$NHC(O)R_a$, 1-methyl-1H-pyrazol-4-yl, hydroxyl, $C_1$-$C_4$alkoxy, halogen, amino, substituted amino, and —$C(O)OR_a$;

$R_3$ is selected from the group consisting of aryl, heteroaryl —$SO_2R_a$, —$NHC(O)R_a$, —$CH_2C(O)OR_a$, —$C(O)OR_a$, —$C(O)R_a$, —$C(O)NR_aR_b$, amino, substituted amino, arylalkyl, and heteroarylalkyl;

each $R_a$ is independently hydrogen, phenyl, phenylmethyl, 3,5-dimethylisoxazol-4-yl, 1,2-dimethyl-1H-imidazol-4-yl, $C_3$-$C_7$cycloalkyl, or $C_1$-$C_6$alkyl;

$R_b$ is hydrogen or $C_1$-$C_3$alkyl; or $R_a$ and $R_b$ together form a 5- or 6-membered heterocycloalkyl ring;

$R_4$ is H;

W is —$(CH_2)_{1-4}$ or —$CH(R_c)(CH_2)_{0-3}$, in which $R_c$ is —CN or $C_1$-$C_4$alkyl;

X is N;

Z is $(CH_2)_q$, wherein q is 0-2, and wherein when q is 0, Z represents a bond; and m is 0-3; or a pharmaceutically acceptable salt thereof. A detailed description regarding these LSD1 inhibitors can be found, e.g., in U.S. Pat. No. 9,346,840, which is incorporated herein by reference in its entirety.

In some embodiments, the LSD1 inhibitor is an LSD1 inhibitor know in the art, e.g., in US 20150225401, US 20170129857, US20170281567, US20170281566, US20170183308, US20170283397, US20170209432, US20170044101, U.S. Pat. Nos. 9,493,442, 9,346,840, WO/2016/007736, WO/2016/161282, US 20160009711, and Fu et al., Advances toward LSD1 inhibitors for cancer therapy, Future Medicinal Chemistry, vol. 9, no. 11 (2017)|; each of which is incorporated herein by reference in its entirety.

PD-1

In some instances, the PD-1 inhibitor is a small molecule, an antibody or an inhibitory nucleic acid. In some embodiments, the PD-1 antibody can, e.g., be selected from the group consisting of: nivolumab (Opdivo®) and pembrolizumab (Keytruda®). Numerous anti-PD-1 antibodies are known in the art, and are described, e.g., in U.S. Pat. No. 9,771,425, US20170240635, US20180030137, U.S. Pat. No. 9,914,783, US20160362489, U.S. Pat. Nos. 9,084,776, 9,102,727, 9,492,540; each of which is incorporated herein by reference in its entirety.

In some instances, the PD-1 inhibitor is an inhibitory nucleic acid. SEQ ID NO: 3 is an exemplary human sequence of PD-1:

(SEQ ID NO: 3; Accession Number NM_005018.2)
at gcagatccca caggcgccct ggccagtcgt ctgggcggtg ctacaactgg 121 gctggcggcc aggatggttc ttagactccc cagacaggcc ctggaacccc cccaccttct 181 ccccagccct gctcgtggtg accgaagggg acaacgccac cttcacctgc agcttctcca 241 acacatcgga gagcttcgtg ctaaactggt accgcatgag cccagcaac cagacggaca 301 agctggccgc cttccccgag gaccgcagcc agcccggcca ggactgccgc ttccgtgtca

```
361 cacaactgcc caacgggcgt gacttccaca tgagcgtggt cagggcccgg cgcaatgaca 421 gcggcaccta cctctgtggg gccatctccc tggccccaa ggcgcagatc aaagagagcc 481 tgcgggcaga gctcagggtg acagagagaa gggcagaagt gcccacagcc caccccagcc 541 cctcacccag gccagccggc cagttccaaa ccctggtggt tggtgtcgtg ggcggcctgc 601 tgggcagcct ggtgctgcta gtctgggtcc tggccgtcat ctgctcccgg gccgcacgag 661 ggacaatagg agccaggcgc accggccagc ccctgaagga ggacccctca gccgtgcctg 721 tgttctctgt ggactatggg gagctggatt ccagtggcg agagaagacc ccggagcccc 781 ccgtgccctg tgtccctgag cagacggagt atgccaccat tgtctttcct agcggaatgg 841 gcacctcatc ccccgcccgc aggggctcag ctgacggccc tcggagtgcc cagccactga 901 ggcctgagga tggacactgc tcttggcccc tctga
```

Inhibitory nucleic acids useful in the present methods and compositions include those that are designed to inhibit PD-1. SEQ ID NO: 4 is an exemplary shRNA sequence that targets human PD-1:

```
                                          (SEQ ID NO: 4)
5'-CCGG-CATTGTCTTTCCTAGCGGAAT-CTCGAG-
ATTCCGCTAGGAAAGACAATG-TTTTTG-3'.
```

Bold and underlined portions are targeting/matching sequences in human PD-1 mRNA.

The PD-1 inhibitory nucleic acid can, e.g., comprise SEQ ID NO: 4. For example, the PD-1 inhibitory nucleic acid can be a nucleic acid comprising a sequence that is complementary to a contiguous sequence of at least 5 (e.g., at least 6, at least 7, at least 8, at least 9, at least 10, at least 11, at least 12, at least, 13, at least 14, at least 15, at least 16, at least 17, at least 18, at least 19, at least 20, at least 21, 5, 6, 7, 8, 9, 10, 11, 12, 13, 14, 15, 16, 17, 18, 19, 20, 21, or 22)nucleotides present in SEQ ID NO: 4.

PD-L1

The PD-L1 inhibitor can be, e.g., a small molecule, an antibody or an inhibitory nucleic acid.

For example, PD-L1 antibodies useful in the presently described methods include durvalumab (Imfinzi™), atezolizumab (Tecentriq®) and avelumab (Bavencio®). Numerous anti-PD-L1 antibodies are known in the art, and are described, e.g., in U.S. Pat. No. 9,789,183, US20170319690, U.S. Pat. No. 9,624,298, US20100086550, U.S. Pat. No. 8,617,546, US20180079814; each of which is incorporated herein by reference in its entirety.

In some instances, the PD-L1 inhibitor is an inhibitory nucleic acid. SEQ ID NO: 5 is an exemplary human sequence of PD-L1:

```
                              (SEQ ID NO: 5; Accession Number NM_014143.3)
     at gaggatattt 121 gctgtcttta tattcatgac ctactggcat ttgctgaacg catttactgt cacggttccc 181 aaggacctat atgtggtaga gtatggtagc aatatgacaa ttgaatgcaa attcccagta 241 gaaaaacaat tagacctggc tgcactaatt gtctattggg aaatggagga taagaacatt 301 attcaatttg tgcatggaga ggaagacctg aaggttcagc atagtagcta cagacagagg 361 gcccggctgt tgaaggacca gctctccctg ggaaatgctg cacttcagat cacagatgtg 421 aaattgcagg atgcaggggt gtaccgctgc atgatcagct atggtggtgc cgactacaag 481 cgaattactg tgaaagtcaa tgcccatac aacaaaatca accaaagaat tttggttgtg 541 gatccagtca cctctgaaca tgaactgaca tgtcaggctg agggctaccc caaggccgaa 601 gtcatctgga caagcagtga ccatcaagtc ctgagtggta agaccaccac caccaattcc 661 aagagagagg agaagctttt caatgtgacc agcacactga gaatcaacac aacaactaat 721 gagatttct actgcacttt taggagatta gatcctgagg aaaaccatac agctgaattg 781 gtcatcccag aactacctct ggcacatcct ccaaatgaaa ggactcactt ggtaattctg 841 ggagccatct tattatgcct tggtgtagca ctgacattca tcttccgttt aagaaaaggg 901 agaatgatgg atgtgaaaaa atgtggcatc caagatacaa actcaaagaa gcaaagtgat 961 acacatttgg aggagacgta a
```

Inhibitory nucleic acids useful in the present methods and compositions include those that are designed to inhibit PD-L1.

SEQ ID NO: 6 is an exemplary shRNA sequence that targets human PD-L1:

(SEQ ID NO: 6)
5'-CCGG-CTGACATTCATCTTCCGTTTA-CTCGAG-

TAAACGGAAGATGAATGTCAG-TTTTTG-3'.

Bold and underlined portions are targeting/matching sequences in human PD-L1 mRNA.

In some embodiments, the PD-L1 inhibitory nucleic acid comprises SEQ ID NO: 6. In some embodiments, the PD-L1 inhibitory nucleic acid is a nucleic acid comprising a sequence that is complementary to a contiguous sequence of at least 5 (e.g., at least 6, at least 7, at least 8, at least 9, at least 10, at least 11, at least 12, at least, 13, at least 14, at least 15, at least 16, at least 17, at least 18, at least 19, at least 20, at least 21, 5, 6, 7, 8, 9, 10, 11, 12, 13, 14, 15, 16, 17, 18, 19, 20, 21, or 22) nucleotides present in SEQ ID NO: 6.

The PD-L1 inhibitory nucleic acid can be any PD-L1 inhibitory nucleic acid that decreases, reduces or silences the expression and/or activity of PD-L1. For example, the PD-L-1 inhibitory nucleic acid can be any PD-L1 inhibitory nucleic acid that decreases, reduces or silences the expression and/or activity of PD-L1.

Inhibitory Nucleic Acids

Inhibitory nucleic acids useful in the present methods and compositions include antisense oligonucleotides, ribozymes, external guide sequence (EGS) oligonucleotides, siRNA compounds, single- or double-stranded RNA interference (RNAi) compounds such as siRNA compounds, modified bases/locked nucleic acids (LNAs), peptide nucleic acids (PNAs), and other oligomeric compounds or oligonucleotide mimetics which hybridize to at least a portion of the target nucleic acid and modulate its function. In some embodiments, the inhibitory nucleic acids include antisense RNA, antisense DNA, chimeric antisense oligonucleotides, antisense oligonucleotides comprising modified linkages, interference RNA (RNAi), short interfering RNA (siRNA); a micro, interfering RNA (miRNA); a small, temporal RNA (stRNA); or a short, hairpin RNA (shRNA); small RNA-induced gene activation (RNAa); small activating RNAs (saRNAs), or combinations thereof. See, e.g., WO 2010040112.

In some embodiments, the inhibitory nucleic acids are 10 to 50, 10 to 20, 10 to 25, 13 to 50, or 13 to 30 nucleotides in length. One having ordinary skill in the art will appreciate that this embodies inhibitory nucleic acids having complementary portions of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length, or any range therewithin. In some embodiments, the inhibitory nucleic acids are 15 nucleotides in length. In some embodiments, the inhibitory nucleic acids are 12 or 13 to 20, 25, or 30 nucleotides in length. One having ordinary skill in the art will appreciate that this embodies inhibitory nucleic acids having complementary portions of 12, 13, 14, 15, 16, 17, 18, 19, 20, 21, 22, 23, 24, 25, 26, 27, 28, 29 or 30 nucleotides in length, or any range therewithin (complementary portions refers to those portions of the inhibitory nucleic acids that are complementary to the target sequence).

The inhibitory nucleic acids useful in the present methods are sufficiently complementary to the target RNA, i.e., hybridize sufficiently well and with sufficient specificity, to give the desired effect. "Complementary" refers to the capacity for pairing, through hydrogen bonding, between two sequences comprising naturally or non-naturally occurring bases or analogs thereof. For example, if a base at one position of an inhibitory nucleic acid is capable of hydrogen bonding with a base at the corresponding position of a RNA, then the bases are considered to be complementary to each other at that position. 100% complementarity is not required.

Routine methods can be used to design an inhibitory nucleic acid that binds to the target sequence (e.g., LSD1, PD-1, PD-L1, PD-L2, OX40, TIM3, LAG3) with sufficient specificity. In some embodiments, the methods include using bioinformatics methods known in the art to identify regions of secondary structure, e.g., one, two, or more stem-loop structures, or pseudoknots, and selecting those regions to target with an inhibitory nucleic acid. For example, "gene walk" methods can be used to optimize the inhibitory activity of the nucleic acid; for example, a series of oligonucleotides of 10-30 nucleotides spanning the length of a target RNA can be prepared, followed by testing for activity. Optionally, gaps, e.g., of 5-10 nucleotides or more, can be left between the target sequences to reduce the number of oligonucleotides synthesized and tested. GC content is preferably between about 30-60%. Contiguous runs of three or more Gs or Cs should be avoided where possible (for example, it may not be possible with very short (e.g., about 9-10 nt) oligonucleotides).

In some embodiments, the inhibitory nucleic acid molecules can be designed to target a specific region of the RNA sequence. For example, a specific functional region can be targeted, e.g., a region comprising a known RNA localization motif (i.e., a region complementary to the target nucleic acid on which the RNA acts). Alternatively or in addition, highly conserved regions can be targeted, e.g., regions identified by aligning sequences from disparate species such as primate (e.g., human) and rodent (e.g., mouse) and looking for regions with high degrees of identity. Percent identity can be determined routinely using basic local alignment search tools (BLAST programs) (Altschul et al., J. Mol. Biol., 1990, 215, 403-410; Zhang and Madden, Genome Res., 1997, 7, 649-656), e.g., using the default parameters.

Pharmaceutical Compositions and Kits

Also provided herein are pharmaceutical compositions that include at least one of any of the LSD1 inhibitors described and at least one of any of the immunotherapies (e.g., at least one PD-1 and/or PD-L1 inhibitor) described herein.

The pharmaceutical compositions can be formulated in any matter known in the art. The pharmaceutical compositions are formulated to be compatible with their intended route of administration (e.g., intravenous, subcutaneous, intraperitoneal, rectal or oral). In some embodiments, the pharmaceutical compositions can include a pharmaceutically acceptable carrier (e.g., phosphate buffered saline). Single or multiple administrations of formulations can be given depending on for example: the dosage and frequency as required and tolerated by the patient. The dosage, frequency and timing required to effectively treat a subject may be influenced by the age of the subject, the general health of the subject, the severity of the disease, previous treatments, and the presence of comorbidities (e.g., diabetes). The formulation should provide a sufficient quantity of active agent to effectively treat, prevent or ameliorate conditions, diseases or symptoms. Toxicity and therapeutic efficacy of compositions can be determined using conventional procedures in cell cultures, pre-clinical models (e.g., mice, rats or monkeys), and humans. Data obtained from in vitro assays and pre-clinical studies can be used to formulate the appropriate dosage of any composition described herein (e.g., any of the pharmaceutical compositions described herein).

Efficacy of any of the compositions described herein can be determined using methods known in the art, such as by the observation of the clinical signs of a cancer (e.g., tumor size, presence of metastasis).

Also provided herein are kits that include at least one of any of the LSD1 inhibitors described and at least one of any of the immunotherapies, e.g., at least one PD-1 and/or PD-L1 inhibitor, described herein. In some instances, the kits can include instructions for performing any of the methods described herein. In some embodiments, the kits can include at least one dose of any of the pharmaceutical compositions described herein.

The disclosure is further described in the following examples, which do not limit the scope of the disclosure described in the claims.

EXAMPLES

Example 1. Materials and Methods

Cell Lines

MCF-7, T47D, B16, LLC and D4m cells were cultured in normal DMEM supplemented with 10% FBS and 1% penicillin/streptomycin in 5% $CO_2$ incubator at 37° C. All cell lines were cultured in 5% $CO_2$ incubator at 37° C., and passaged every 2-3 days. One day before compound treatment, cells were seeded in 6-well or 12-well plates, and then were treated with 1, 2, or 5 µM GSK-LSD1, or DMSO as mock, in duplicates or triplicates for 5-6 days, during which cells were passaged once and replenished with fresh compound.

Mice 6-10-wk-old female mice were used for all experiments. WT C57BL/6 mice were purchased from The Jackson Laboratory. Prior to all experiments, purchased mice were allowed one week to acclimate to housing conditions at the Harvard Medical School Animal Facility. For studies using immunodeficient mice, an in-house strain of WT mice was compared to an in-house strain of TCRα$^{-/-}$ mice. The in-house strains of WT and TCRα$^{-/-}$ were originally purchased from The Jackson Laboratory. Colonies for each strain of mice were maintained in the same animal facility at Harvard Medical School. All experimental mice were housed in specific pathogen-free conditions and used in accordance with animal care guidelines from the Harvard Medical School Standing Committee on Animals and the National Institutes of Health. Animal protocols were approved by the Harvard Medical School Standing Committee on Animals.

Gene Knockdown by shRNA and Rescue Assay

The shRNA oligos, with sequences for their respective target genes listed in Table 2, were annealed and cloned into pLKO. 1-Puromycin$^+$ (Puro) or pLKO. 1-Blasticidin$^+$ (Bsd) lentiviral vector. Lentivirus carrying pLKO.1 plasmid was produced by co-transfecting HEK293T cells with four helper plasmids (pHDM-VSV-G, pHDM-tatlb, pHDM-HgPM2, and pRC-CMVRaII), and by harvesting viral supernatant after 72 h by passing through a 0.45 µm filter. Collected lentivirus was used directly by infecting cells with the addition of 8 µg/ml polybrene (Sigma-Aldrich, cat #H9268), or frozen at −80° C. for later use. Infected cells were selected and expanded with puromycin (Gold Biotechnology, cat #P-600-500) at 1 µg/ml or blasticidin (Sigma-Aldrich, cat #15205) at 5 µg/ml for 5 days before being used for subsequent assays.

For double KD, MCF-7 cells were first transduced with lentiviral pLKO-sh-Scramble-Bsd or pLKO-sh-LSD1-Bsd, and selected with blasticidin for 3 days. Those cells were then transduced again with lentiviral pLKO-sh-GFP-Puro as control or pLKO-sh-Target-Puro, and selected with both blasticidin and puromycin for 3-5 days to achieve double KD. In this context, pLKO-sh-Scramble-Bsd plus pLKO-sh-GFP-Puro was referred as sh-C, and pLKO-sh-LSD1-Bsd plus pLKO-sh-GFP-Puro was referred as sh-LSD1.

For LSD1 rescue assay, MCF-7 cells were first transduced with lentiviral pLKO-sh-Scramble-Bsd or pLKO-sh-LSD1-Bsd, and selected with blasticidin for 3 days. Those cells were then transduced again with lentiviral pHAGE-CMV-Flag-HA-EV/LSD1/LSD1-K661A (puromycin and sh-LSD1 resistant), and selected with both blasticidin and puromycin for 5 days before subsequent analysis. In this context, pLKO-sh-Scramble-Bsd plus pHAGE-CMV-Flag-HA-EV was referred as sh-C, and pLKO-sh-LSD1-Bsd plus pHAGE-CMV-Flag-HA-EV was referred as sh-LSD1. For alternative rescue method, MCF-7 cells were first transduced with lentiviral pLKO-sh-Scramble-Bsd or pLKO-sh-LSD1-Bsd followed by blasticidin selection for 5 days before subsequent analysis.

TABLE 2

DNA oligonucleotide sequences

| shRNA Target | Sequences | SEQ ID NO: |
|---|---|---|
| GFP | GCAAGCTGACCCTGAAGTTCAT | SEQ ID NO: 7 |
| Scramble | CCTAAGGTTAAGTCGCCCTCG | SEQ ID NO: 8 |
| Human LSD1 | GCCTAGACATTAAACTGAATA | SEQ ID NO: 9 |
| Human TLR3 | CCTTACACATACTCAACCT | SEQ ID NO: 10 |
| Human MDA5 | CCAACAAAGAAGCAGTGTATA | SEQ ID NO: 11 |
| Human RIG-I | AATTCATCAGAGATAGTCA | SEQ ID NO: 12 |
| Human MAVS #1 | GCATCTCTTCAATACCCTT | SEQ ID NO: 13 |

TABLE 2 -continued

DNA oligonucleotide sequences

| | Sequences | SEQ ID NO: |
|---|---|---|
| Human MAVS #2 | GGAGAGAATTCAGAGCAAG | SEQ ID NO: 14 |
| Human cGAS | ATCTATTCTCTAGCAACTTAA | SEQ ID NO: 15 |
| Human STING | GCATGGTCATATTACATCG | SEQ ID NO: 16 |
| Human AGO2 | GCACAGCCAGTAATCGAGTTT | SEQ ID NO: 17 |
| Human DICER #1 | AAGAATCAGCCTCGCAACAAA | SEQ ID NO: 18 |
| Human DICER #4 | TCTATTAGCACCTTGATGT | SEQ ID NO: 19 |
| Human TRBP2 #1 | GCTGCCTAGTATAGAGCAA | SEQ ID NO: 20 |
| Human TRBP2 #2 | TCTACGAAATTCAGTAGGA | SEQ ID NO: 21 |
| Human TRBP2 #4 | GGATTCTCTACGAAATTCA | SEQ ID NO: 22 |
| Mouse LSD1 #1 | CACAAGGAAAGCTAGAAGA | SEQ ID NO: 23 |
| Mouse LSD1 #2 | GGATGGGATTTGGCAACCTTA | SEQ ID NO: 24 |
| Mouse LSD1 #3 | AACTCCATGTCATCAGCTACT | SEQ ID NO: 25 |
| Mouse LSD1 #4 | CGGCATCTACAAGAGGATAAA | SEQ ID NO: 26 |
| CRISPR gRNA target Mouse LSD1 #3 (target location exon 2) | ATATTCATCTTCTGAGAGGT | SEQ ID NO: 27 |
| Mouse LSD1 #4 (target location exon 2) | TCTTCCTCAGGTGGGGCTTG | SEQ ID NO: 28 |
| Mouse LSD1 #4 (target location exon 3) | CCTGAGAGGTCATTCGGTCA | SEQ ID NO: 29 |
| Mouse LSD1 #6 (target location exon 3) | CCATGACCGAATGACCTCTC | SEQ ID NO: 30 |
| Mouse MDA5 #4 (target location exon 4) | GGCAGGGATTCAGGCACCAT | SEQ ID NO: 31 |
| RT-qPCR primer target | | |
| Human GAPDH forward | AACGGGAAGCTTGTCATCAA | SEQ ID NO: 32 |
| Human GAPDH reverse | TGGACTCCACGACGTACTCA | SEQ ID NO: 33 |
| Human LSD1 forward | GTGGACGAGTTGCCACATTTC | SEQ ID NO: 34 |
| Human LSD1 reverse | TGACCACAGCCATAGGATTCC | SEQ ID NO: 35 |
| Human HERV-E forward | GGTGTCACTACTCAATACAC | SEQ ID NO: 36 |
| Human HERV-E reverse | GCAGCCTAGGTCTCTGG | SEQ ID NO: 37 |
| Human HERV-F forward | CCTCCAGTCACAACAACTC | SEQ ID NO: 38 |
| Human HERV-F reverse | TATTGAAGAAGGCGGCTGG | SEQ ID NO: 39 |
| Human HERV-K forward | ATTGGCAACACCGTATTCTGCT | SEQ ID NO: 40 |
| Human HERV-K reverse | CAGTCAAAATATGGACGGATGGT | SEQ ID NO: 41 |
| Human HML-2 forward | AAAGAACCAGCCACCAGG | SEQ ID NO: 42 |
| Human HML-2 reverse | CAGTCTGAAAACTTTTCTCTA | SEQ ID NO: 43 |
| Human ERVL forward | ATATCCTGCCTGGATGGGGT | SEQ ID NO: 44 |

TABLE 2 -continued

DNA oligonucleotide sequences

| | Sequences | SEQ ID NO: |
|---|---|---|
| Human ERVL reverse | GAGCTTCTTAGTCCTCCTGTGT | SEQ ID NO: 45 |
| Human Line1 forward | GCCAAGATGGCCGAATAGG | SEQ ID NO: 46 |
| Human Line1 reverse | TGGCACTCCCTAGTGAGATGAA | SEQ ID NO: 47 |
| Human AluYA5 forward | ACCATCCCGGCTAAAACGGTG A | SEQ ID NO: 48 |
| Human AluYA5 reverse | GCGATCTCGGCTCACTG | SEQ ID NO: 49 |
| Human IFN-α forward | AATGACAGAATTCATGAAAGCGT | SEQ ID NO: 50 |
| Human IFN-α reverse | GGAGGTTGTCAGAGCAGA | SEQ ID NO: 51 |
| Human IFN-β forward | GCCATCAGTCACTTAAACAGC | SEQ ID NO: 52 |
| Human IFN-β reverse | GAAACTGAAGATCTCCTAGCCT | SEQ ID NO: 53 |
| Human IL-28a/b forward | TCCAGTCACGGTCAGCA | SEQ ID NO: 54 |
| Human IL-28 a/b reverse | CAGCCTCAGAGTGTTTCTTCT | SEQ ID NO: 55 |
| Human OASL forward | GCAGAAATTTCCAGGACCAC | SEQ ID NO: 56 |
| Human OASL reverse | CCCATCACGGTCACCATTG | SEQ ID NO: 57 |
| Human ISG15 forward | CCTTCAGCTCTGACACC | SEQ ID NO: 58 |
| Human ISG15 reverse | CGAACTCATCTTTGCCAGTACA | SEQ ID NO: 59 |
| Human TLR3 forward | TGGTTGGGCCACCTAGAAGTA | SEQ ID NO: 60 |
| Human TLR3 reverse | TCTCCATTCCTGGCCTGTG | SEQ ID NO: 61 |
| Human MDA5 forward | CACTTCCTTCTGCCAAACTTG | SEQ ID NO: 62 |
| Human MDA5 reverse | GAGCAACTTCTTTCAACCACAG | SEQ ID NO: 63 |
| Human RIG-I forward | CCAGCATTACTAGTCAGAAGGAA | SEQ ID NO: 64 |
| Human RIG-I reverse | CACAGTGCAATCTTGTCATCC | SEQ ID NO: 65 |
| Human MAVS forward | AGGAGACAGATGGAGACACA | SEQ ID NO: 66 |
| Human MAVS reverse | CAGAACTGGGCAGTACCC | SEQ ID NO: 67 |
| Human cGAS forward | TAACCCTGGCTTTGGAATCAAAA | SEQ ID NO: 68 |
| Human cGAS reverse | TGGGTACAAGGTAAAATGGCTTT | SEQ ID NO: 69 |
| Human STING forward | AGCATTACAACAACCTGCTACG | SEQ ID NO: 70 |
| Human STING reverse | GTTGGGGTCAGCCATACTCAG | SEQ ID NO: 71 |
| Human AGO2 forward | CCGGCCTTCTCTCTGGAAAA | SEQ ID NO: 72 |
| Human AGO2 reverse | GCCTTGTAAAACGCTGTTGCT | SEQ ID NO: 73 |
| Mouse LSD1 forward | GTGGTGTTATGCTTTGACCGT | SEQ ID NO: 74 |
| Mouse LSD1 reverse | GCTGCCAAAAATCCCTTTGAGA | SEQ ID NO: 75 |
| MuERV-L forward | TTTCTCAAGGCCCACCAATAGT | SEQ ID NO: 76 |
| MuERV-L reverse | GACACCTTTTTAAC-TATGCGAGCT | SEQ ID NO: 77 |
| Mouse MusD forward | GATTGGTGGAAGTTTAGCTAGCAT | SEQ ID NO: 78 |
| Mouse MusD reverse | TAGCATTCTCATAAGCCAATTG-CAT | SEQ ID NO: 79 |
| Mouse IAP Pol forward | CTTGCCCTTAAAGGTCTAAAAGCA | SEQ ID NO: 80 |
| Mouse IAP Pol reverse | GCGGTATAAGGTACAATTAAAAGATATGG | SEQ ID NO: 81 |

TABLE 2-continued

DNA oligonucleotide sequences

| | Sequences | SEQ ID NO: |
|---|---|---|
| Mouse Line1 forward | TTTGGGACACAATGAAAGCA | SEQ ID NO: 82 |
| Mouse Line1 reverse | CTGCCGTCTACTCCTCTTGG | SEQ ID NO: 83 |
| Mouse IFN-a1 forward | CGGTGCTGAGCTACTGGC | SEQ ID NO: 84 |
| Mouse IFN-a reverse | TTTGTACCAGGAGTGTCAAGG | SEQ ID NO: 85 |
| Mouse IFN-b forward | GGTGGAATGAGACTATTGTTG | SEQ ID NO: 86 |
| Mouse IFN-b reverse | AGGACATCTCCCACGTC | SEQ ID NO: 87 |
| Mouse IL-28b forward | AGCTGCAGGTCCAAGAGCG | SEQ ID NO: 88 |
| Mouse IL-28b reverse | GGTGGTCAGGGCTGAGTCATT | SEQ ID NO: 89 |
| Mouse ISG15 forward | GGTGTCCGTGACTAACTCCAT | SEQ ID NO: 90 |
| Mouse ISG15 reverse | TGGAAAGGGTAAGACCGTCCT | SEQ ID NO: 91 |
| Mouse OASL forward | CAGGAGCTGTACGGCTTCC | SEQ ID NO: 92 |
| Mouse OASL reverse | CCTACCTTGAGTACCTTGAGCAC | SEQ ID NO: 93 |
| Mouse TLR3 forward | GTGAGATACAACGTAGCTGACTG | SEQ ID NO: 94 |
| Mouse TLR3 reverse | TCCTGCATCCAAGATAGCAAGT | SEQ ID NO: 95 |
| Mouse RIG-I forward | AAGAGCCAGAGTGTCAGAATCT | SEQ ID NO: 96 |
| Mouse RIG-I reverse | AGCTCCAGTTGGTAATTTCTTGG | SEQ ID NO: 97 |
| Mouse beta-actin forward | GGCTGTATTCCCCTCCATCG | SEQ ID NO: 98 |
| Mouse beta-actin reverse | CCAGTTGGTAACAATGCCATGT | SEQ ID NO: 99 |
| Mouse GAPDH forward | TGACCTCAACTACATGGTCTACA | SEQ ID NO: 100 |
| Mouse GAPDH reverse | CTTCCCATTCTCGGCCTTG | SEQ ID NO: 101 |
| GFP-com forward | GAACGGCATCAAGGTGAACTT | SEQ ID NO: 102 |
| GFPL reverse | TAGCGTAATCTGGAACATCGTATGGGT | SEQ ID NO: 103 |
| GFP-let7 reverse | GACGACCTCGAGTGAGGTAGTAGGTTGTATA | SEQ ID NO: 104 |
| Gene/Strand-specific PCR primer target | | |
| Non-human Tag | GCACACGACGACAGACGACGCAC | SEQ ID NO: 105 |
| HERV-E tag-TF | GCACACGACGACAGACGACGCACCCAGAGTCAGGTGTCACTACTCAATACAC | SEQ ID NO: 106 |
| HERV-E tag-BR | GCACACGACGACAGACGACGCACTACTGGAGCAACACGCAGCCTAGGTCTCTGG | SEQ ID NO: 107 |
| HERV-E TF | GGTGTCACTACTCAATACAC | SEQ ID NO: 108 |
| HERV-E BR | GCAGCCTAGGTCTCTGG | SEQ ID NO: 109 |
| HERV-K tag-RF(3) | GCACACGACGACAGACGACGCACGGGAAGAATGTGTGGCCAATAGTGCGGT | SEQ ID NO: 110 |
| HERV-K tag-BR(3) | GCACACGACGACAGACGACGCACGGTAGAGATTCCTTTTTCTCCCCATTCCCAG | SEQ ID NO: 111 |

TABLE 2 -continued

DNA oligonucleotide sequences

| | Sequences | SEQ ID NO: |
|---|---|---|
| HERV-K RF(3) | GTGTGGCCAATAGTGCGGT | SEQ ID NO: 112 |
| HERV-K BR(3) | ATTCCTTTTTCTCCCCATTCCCAG | SEQ ID NO: 113 |
| Syn1-tag-TF | GCACACGACGACAGACGACG CACATGGAGCCCAAGATGCAG TCCAAGA | SEQ ID NO: 114 |
| Syn1-tag-BR | GCACACGACGACAGACGACG CACCTAACTGCTTCCTGCTGA ATTGGGGCGTA | SEQ ID NO: 115 |
| Syn1-TF | ATGGAGCCCAAGATGCAG | SEQ ID NO: 116 |
| Syn1-BR | CTAACTGCTTCCTGCTGAATT GGGGCGTAG | SEQ ID NO: 117 |
| Human beta-Actin-tag-TF | GCACACGACGACAGACGACG CACGCTCGTCGTCGACAACGG CTCCGGCAT | SEQ ID NO: 118 |
| Human beta-Actin-tag-BR | GCACACGACGACAGACGACG CACCAAACATGATCTGGGTCA TCTTCTC | SEQ ID NO: 119 |
| Human beta-Actin-TF | GCTCGTCGTCGACAACGGCTC CGGCA | SEQ ID NO: 120 |
| Human beta-Actin-BR | CAAACATGATCTGGGTCATCT TCTC | SEQ ID NO: 121 |

Gene Deletion by CRISPR/Cas9

The gRNA oligos, with sequences for their respective target genes listed in Table 2, were annealed and cloned into Lenti-CRISPR-v2-Puromycin$^+$ vector. To delete target genes, B16 cells were transiently transfected with Lenti-CRISPR-v2 plasmid carrying respective gRNA, and selected with 1 μg/ml puromycin for 2 days. Cells were then transferred into fresh medium without puromycin and seeded at super-low density to allow colony formation from single cell. Colonies were then picked up and expanded for KO validation by immunoblot and by sequencing of target genomic region. For double KO, LSD1 KO B16 cells (clone g5-4) were used for deleting the second target gene as described above.

Generation of ERV Expression Construct and Transduction

Primers with sequences listed in table S1 were used to get 2 kb fragment of HERV-K and 2 kb fragment of HERV-E through PCR amplification with insertion of stop codons at 5' ends and additional 30 bp elongation primers at 3' ends. HERV-K and HERV-E fragments with reverse complementary elongation primers at their 3' ends were mixed, denatured, annealed and elongated, followed by PCR amplification to generate 4 kb HERV-(K+E) fusion fragment, which was further cloned into pHAGE-CMV-Flag-HA lentiviral vector thus expressing sense transcript of HERV-K and antisense transcript of HERV-E. Viral package and transduction were performed at described above. MCF-7 cells transduced with HERV-(K+E) were cultured for 48 hours without drug selection before subsequent analysis.

RNA Extraction and RT-qPCR

All reagents, buffers and containers used for RNA work were RNase-free grade or treated with 0.1% v/v DEPC (Sigma-Aldrich cat #D5758) if applicable, to eliminate RNase contaminants in this section and other relevant sections. For total RNA extraction, cells in culture were directly lysed in TRIzol (Life Technologies, cat #15596018) after medium removal. RNA extraction was performed according to the manufacture's instructions. The extracted RNA was reversely transcribed into cDNA using PrimeScript™ RT Reagent Kit (Clontech cat #RR037B) according to the manufacturer's instructions, with following modifications: 2 μg of RNA samples with the addition of primers were first denatured at 70° C. for 5 min and cooled down on ice before the addition of buffer and reverse transcriptase; incubation time (at 37° C.) was increased up to 30 min. The obtained cDNA samples were diluted and used for real-time quantitative PCR (RT-qPCR). SYBR green (Roche, cat #06649416001) and gene specific primers with sequences listed in Table 2 were used for PCR amplification and detection on a LightCycler 480 system (Roche).

Strand-Specific PCR for Detection of Sense and Antisense ERV Transcripts

The strand-specific PCR method was adapted from (Chiappinelli et al., 2015) and performed with Prime-Script™ RT Reagent Kit (Clontech cat #RR037B) with modifications. In brief, gene- and strand-specific primers (GSP) were synthesized with an extra Tag sequence (listed in Table 2, which does not exist in human genome) at 5'-end to generate Tag-GSP (for example, HERV-E Tag-BR for sense strand, Tag-TF for antisense strand), and were used for reverse transcription, following these steps: 1 μg total RNA in 6 μl H$_2$O was mixed with 1 μl Tag-GSP (10 μM stock), pre-heated at 65° C. for 5 min and cooled down on ice; then added 2 μl buffer (5×), 0.5 μl reverse-transcriptase and 120 ng actinomycin D (Sigma-Aldrich, cat #A9415) in 0.5 μl H$_2$O to a total volume of 10 μl; incubated at 50° C. for 50 min for only first strand cDNA synthesis and deactivated at 85° C. for 5 min; finally added 1 U RNase H (New England Biolabs, cat #M0297S) and incubated at 37° C. for 20 min, followed by ethanol precipitation for cDNA purification.

The obtained cDNA was then used for PCR amplification with paired primers: Tag-primer in pair with TF-primer for amplifying sense strand and Tag-primer in pair with BR-primer for amplifying antisense strand. The amplicons were visualized on 1.5% agarose gels.

DsRNA Analysis by RNase Digestion and RT-qPCR

For dsRNA analysis by RNase A digestion, 5 μg total RNA extracted from MCF-7 or B16 cells was dissolved in 46 μl H$_2$O and mixed well with 3.5 μl NaCl (5 M stock). Then 0.5 μl RNase A (10 mg/ml stock, Thermo Fisher Scientific, cat #EN0531) or H$_2$O as mock was added to a total volume of 50 μl and mixed well, followed by incubation at room temperature for 10 min. Afterwards, 1 ml TRIzol was directly added to the mixture to terminate digestion, followed by RNA extraction. The RNA transcripts of selected retrotransposons were measured by RT-qPCR with GAPDH (Actb for B16 cells) as an internal control. The ratios of (retrotransposon/GAPDH)$_{RNase-A}$/(retrotransposon/GAPDH)$_{mock}$ were calculated as enrichment fold.

For dsRNA analysis by RNase Ti digestion, 2 μg total RNA extracted from MCF-7 was dissolved in 16 μl H$_2$O and mixed well with 2 μl buffer (10×). Then 2 μl RNase T1 (1U/μl stock, Thermo Fisher Scientific, cat #AM2283) or H$_2$O as mock was added to a total volume of 20 μl and mixed well, followed by incubation at 37° C. for 30 min. Afterwards, 1 ml TRIzol was directly added to the mixture to terminate digestion, followed by RNA extraction and analysis as described above.

DsRNA Analysis by J2 Pulldown

Purified total RNA from control or LSD1 KD MCF-7 cells was used for J2 pulldown assay. J2 antibody (Scicons, cat #10010200) and mouse IgG control (Santa Cruz Biotechnology, cat #sc-2025) were first conjugated (1 μg per pulldown) to Protein G dynabeads (Life Technologies, cat #10008D), respectively. For each pulldown, 30 μg RNA was mixed with 500 μl immunoprecipitation (IP) buffer (350 mM NaCl, 25 mM Tris pH7.4, 5 mM DTT and 0.5% NP-40), followed by the addition of 0.5 μl RNase A (10 mg/ml stock, Thermo Fisher Scientific, cat #EN0531) and thorough mixing. The addition of RNase A was to reduce the overwhelming single-stranded RNA (ssRNA) and enrich dsRNA for J2 capture. Then, the whole mixture was mixed with washed beads and rotated at 4° C. for 2 h. Afterwards, the beads were washed with IP buffer and incubated in 50 μl Proteinase K digestion solution (1×TE, 100 mM NaCl, 1% SDS, and 1 μl Proteinase K (20 mg/ml stock, Thermo Fisher Scientific, cat #AM2546)) at 45° C. for 20 min. The elutes were directly added to 1 ml TRIzol for RNA purification and RT-qPCR analysis as described above.

DsRNA Analysis by J2 Immunoblot

Purified total RNA from B16 cells was subjected to digestion with mock, RNase T1 (Thermo Fisher Scientific, cat #AM2283) and RNase III (Thermo Fisher Scientific, cat #AM2290) in their respective buffers and according to the manufacturer's instructions, or RNase A (Thermo Fisher Scientific, cat #EN0531) under high salt condition (350 mM NaCl). The digestion was deactivated by the addition of TRIzol and RNA was subsequently purified. Equal volume (2.5 μl) of purified RNA was dotted on Hybond N+ membrane (GE Healthcare, cat #RPN119B), dried and autocrosslinked in a UV stratalinker 2400 (Stratagene) two times. The membrane was then blocked in 5% milk in PBS-T (0.1% Tween-20) for 30 min and probed with J2 antibody at 4° C. overnight. On the next day, the membrane was washed with PBS-T three times and probed with secondary goat-anti-mouse HRP antibody (Millipore cat #AP124P) in 5% milk at room temperature for 1 h. The membrane was washed again with PBS-T three times and ECL was applied for film development. Afterwards, the membrane was stained with methylene blue solution (0.3% w/v methylene blue+30% v/v ethanol+70% v/v H$_2$O) to visualize RNA presence.

Protein Extraction and Immunoblot Analysis

Cells in culture were washed with ice-cold PBS twice to completely remove residual medium. RIPA lysis buffer (150 mM NaCl, 1% NP-40, 0.5% sodium deoxycholate, 0.1% SDS and 50 mM Tris pH8) supplemented with protease inhibitor (Roche, cat #0469313001) and phosphatase inhibitor (Roche, cat #04906837001) was directly added to cell layers and scraped on ice. Cell lysates were transferred to small tubes and lysed on ice for 10 min before being cleared by top-speed centrifugation at 4° C. Protein concentrations in lysates were measured by Bio-Rad protein assay (Bio-Rad, #5000006) and adjusted equally between samples, followed by the addition of SDS loading dye (5×) and boiled at 95° C. for 5 min. Equal volume and equal quantity of protein samples were subjected to SDS-PAGE and transferred to nitrocellulose membrane (Bio-Rad, cat #162-0097). The membrane was blocked in 5% milk at room temperature for 1 h and incubated with appropriate antibodies at 4° C. overnight. On the next day, the membrane was washed with PBS-T three times and incubated with appropriate secondary HRP antibodies in 5% milk at room temperature for 1 h. The membrane was washed again with PBS-T three times and ECL was applied for film development.

ELISA

The ELISA assay was performed with a Human IFN Beta ELISA Kit (pbl assay science, cat #41415-1) according to the manufacturer's instructions.

LSD1 Demethylase Assay

LSD1 demethylase assays were carried out with proteins immunoprecipitated by anti-HA magnetic beads from MCF-7 cells stably expressing FH-LSD1, FH-LSD1-K661A, FH-AGO2 and FH-AGO2-K726R. In order to increase basal methylation level on purified AGO2, MCF-7 cells stably expressing FH-AGO2 and FH-AGO2-K726R were treated with 2 μM GSK-LSD1 for 24 hours before being used for IP purification. In a reaction of 50 μl volume, immunoprecipitated LSD1 (~2 μg, estimated by SDS-PAGE and coomassie blue staining) and AGO2 (~1 μg) were incubated in demethylation buffer (50 mM Tris pH 8.5, 50 mM KCl, 5 mM MgCl$_2$, 0.5% BSA, 5% glycerol, and complete EDTA-free protease inhibitors) on a thermoshaker at 37° C. for 4 hours. The reaction was terminated by adding SDS loading dye (5×) and boiling at 95° C. for 5 min, followed by SDS-PAGE and immunoblot analysis. In each experiment, calf thymus histones were used as LSD1 demethylase substrate in parallel to check the activity of immunoprecipitated LSD1 by immunoblot analysis of H3K4me2.

GFPL/GFP-Let-7 Dual Reporter Assay

The reporter assay for miRISC activity was performed as previously described (Qi et al., 2008). In brief, U2OS cell line stably expressing dual reporters, GFPL and GFP-let-7, was transduced with lentiviral shRNA against scramble, LSD1 or AGO2. Cells were selected with puromycin at 1 μg/ml and G-418 (Research Products International, cat #G64500) at 200 μg/ml for 4 days before subsequent analysis. The expression of GFPL and GFP was measured by immunoblot and RT-qPCR as described in the above sections. Protein signals in immunoblot were quantified by ImageJ software according to the user manual. The ratios of GFPL over GFP protein signals in different samples were calculated and the ratio in control shRNA sample was considered as 100% miRISC activity.

Cell Colony Formation Assay

B16 cells growing at 80% confluence were trypsinized and transferred into fresh medium in single cell suspension. Cell numbers were counted and diluted appropriately for seeding to 6-well plates (500 cells per well) or 12-well plates (200 cells per well). Cells were allowed to grow for 6 days, with fresh medium addition at day 3 without absorbing old medium, before staining with crystal violet solution (0.5% w/v crystal violet powder, 80% v/v $H_2O$ and 20% v/v methanol).

Mouse Tumor Models

Mice were anesthetized with Avertin (2.5%), shaved at the injection site, and then injected in the flank subcutaneously with 250,000-500,000 B16-F10 tumor cells. Tumors were measured every 2-3 days once palpable (long diameter and short diameter) with a caliper. Tumor volume was determined using the volume formula for an ellipsoid: $½×D×d^2$ where D is the longer diameter and d is the shorter diameter. Mice were sacrificed when tumors reached 2 $cm^3$ or upon ulceration/bleeding.

For antibody treatments, mice were given 100 μg antibody i.p. at days 14, 16, 18, and 20 post tumor injection using the following antibodies: anti-PD-1 (clone 29F. 1A12) kindly provided by G. Freeman (Dana Farber Cancer Institute, Boston, Mass.). Rat IgG2a isotype control antibody was purchased from BioXCell (cat #BE0089). Prior to treatments mice were randomized such that treatment groups had similar average tumor volumes prior to treatment initiation.

B16 Metastasis Assay

200K B16.F10 (scramble or LSD1 KO) were transferred intravenously via tail vein injection. Lungs were removed 14 days post injection and fixed overnight in Fekete's solution. Visible metastases were counted in blinded fashion by two investigators.

Tumor Infiltrating Leukocyte Flow Cytometry

Tumors were excised day 14 post injection and cut into 2 mm sized pieces in collagenase and DNase. Samples were dissociated with a Gentle MACS, incubated for 20 minutes at 37° C., dissociated with a Gentle MACS again, and passed through a 70 m filter. To enrich for leukocytes samples were spun through a Percoll gradient. Leukocytes were isolated from the interface of the 40 and 70% Percoll gradient, stained, and analyzed for fluorescent markers. For intracellular staining the Ebioscience Foxp3 Fixation Permeabilization Kit was used. All antibodies were purchased from Biolegend (CD45.2, CD1 b, CD3, CD4, CD8b, Foxp3, Granzyme-B, Ki67, CD44, PD-L1, MHC-1).

Tumor Infiltrating Lymphocyte TCR Sequencing

T cells were enriched from tumors as above followed by sorting for $CD8b^+$ T cells. Genomic DNA was extracted using a DNeasy Blood & Tissue kit (Qiagen, cat #69506) and submitted to Adaptive Biotechnologies for mouse TCRB CDR3 survey sequencing. Data was analyzed using Adaptive Biotechnologies' online analysis platform.

Directional RNA-Seq of MCF-7 Cells

Purified total RNA was quantified by Qubit (Invitrogen) and analyzed by Agilent Bioanalyzer to assess RNA integrity. 1 μg RNA (RIN>9) was used to generate rRNA-depleted RNA with NEBNext® rRNA Depletion Kit (New England Biolabs, cat #E6310OS) according to the manufacturer's instructions. The rRNA-depleted RNA was subjected to Agilent Bioanalyzer to ensure the complete removal of rRNA, and then used to generate directional RNA library with NEBNext® Ultra™ II Directional RNA Library Prep Kit for Illumina® (New England Biolabs, cat # E7760L) and NEBNext® Multiplex Oligos for Illumina® (New England Biolabs, cat #E7335L) according to the manufacturer's instructions. Library concentrations were quantified by Qubit (Invitrogen) and mixed equally for sequencing at HiSeq 2500 (Illumina) to generate 50 bp reads from paired-ends. The raw data are deposited at the Gene Expression Omnibus (GEO) under the subseries entry GSE105001.

ChIP-Seq of MCF-7 Cells

Cell nuclei were obtained by lysing whole cells in hypotonic buffer (10 mM HEPES pH 7.9, 10 mM KCl, 1.5 mM $MgCl_2$, 0.34 M sucrose, 10% v/v glycerol, 1 mM DTT, and 0.1% v/v Triton X-100) supplemented with protease inhibitor. After washing with PBS, nuclei were fixed in 1% formaldehyde for 10 min at room temperature, followed by quenching in 125 mM glycine. Nuclei were then washed twice with ice-cold PBS, lysed in ChIP sonication buffer (50 mM HEPES pH7.9, 140 mM NaCl, 1 mM EDTA, 1% Triton X-100, 0.1% sodium deoxycholate, 0.2% SDS) supplemented with protease inhibitor, and were subjected to sonication to obtain DNA fragments of 300-800 bp. Subsequent procedures were carried out by following the Epigenesys protocol (www.epigenesys.eu). The following antibodies were used to ChIP: anti-LSD1 (Abcam, cat #ab17721), anti-H3K4me1 (Abcam, cat #ab8895), anti-H3K4me2 (EMDMillipore, cat #07-030), and mouse IgG (Santa Cruz Biotechnology, cat #sc-2025).

ChIP-Seq libraries were prepared using NEBNext® Ultra™ DNA Library Prep Kit for Illumina® (New England Biolabs, cat #E7370L) and NEBNext® Multiplex Oligos for Illumina® (New England Biolabs, cat #E7335L) according to the manufacture's instructions. Library concentrations were quantified by Qubit (Invitrogen) and mixed equally for sequencing at HiSeq 2500 (Illumina) to generate 50 bp reads from single-end. The raw data are deposited at the Gene Expression Omnibus (GEO) under the subseries entry GSE105001.

Statistic Analysis

Statistical analyses were performed using GraphPad Prism 6 software. For RT-qPCR and protein quantification, data were shown as mean±s.d., and considered statistically significant with p values <0.05 by unpaired Student's t test. For tumor growth, data were presented as mean±s.e.m., and considered statistically significant with p values <0.05 by unpaired Student's t test for comparing two groups or by two-way ANOVA for multiple comparisons. For comparing mouse survival curves, Log-rank (Mantel-Cox) test was used.

ChIP-Seq & RNA-Seq Analysis

For ChIP-seq and RNA-seq data, all statistical analysis and visualization was performed with R (version 3.4.0) unless otherwise specified. Student's t-test was used to determine whether significant shift in mean occurs for all comparisons unless otherwise specified.

ChIP-Seq Analysis

Raw reads were aligned to hg19 or mm9 using bwa (version 0.7.2-r351) (PMID: 22569178). The resulted sam files were converted to bam with samtools (version 0.1.18 (r982:295) (PMID: 21245279). MACS2 (version 2.0.10.20131216) (PMID: 18798982) was used to call peak on the bam files. BedGraph files containing signal per million reads produced from MACS2 were converted to bigwig files with ucsctool kit (315). ChIP-seq signals were first extracted with bwtool (version 1.0) (PMID: 24489365) from bigwig files and then visualized in R.

Repeat annotation was downloaded from UCSC for hg19 and mm9, only ERVs were used for downstream analysis. To select ERVs, ERV families originated in Homo Sapien or *Mus Musculus* were downloaded from Repbase (http:// www.girinst.org/repbase/). A peak catalogue consisting all possible peak intervals in ChIP-seq (histones and LSD1) was produced and ERVs were filtered with this catalogue. ChIP-seq signals were extracted with bwtool (version 1.0) (PMID: 24489365) from bigwig files and then visualized in R.

RNA-Seq Analysis

Raw reads were aligned to hg19 or mm9 using STAR (v2.4.2a) with the parameter "quantMode" set as "GeneCounts" to produce count table for each gene. Differential gene analysis was performed on gene raw counts in R with edgeR package (v3.18.1) (PMID: 22287627) from bioconductor. Read count table was filtered so that genes with at least one count across conditions were kept. The negative binomial generalized log-linear model was used in differential analysis. A FDR cut-off of 0.05 was used to determine significantly differentially expressed genes. The R package gProfileR (v0.6.4, PMID: 27098042) was used to perform gene enrichment analysis on differential genes. Geneset enrichment analysis (GSEA) was performed with R package clusterProfiler (v3.4.4, PMID: 22455463).

The function analyzeRepeats.pl from Homer (PMID: 20513432) software was used to get raw counts for repeats from RNA-seq data. Differential expression for repeats was performed with edgeR the same way as for genes.

TCGA Data Analysis

For the association of LSD1 expression with survival, patient vital status (dead and alive) was used as surrogate end-point and patient dichotomized by LSD1 expression. The proportional hazards (PH) assumption was tested using the cox.zph function in the R Survival package (v2.41-3) with 0.1 as cutoff. A log-rank test was used instead if the PH assumption failed.

For analyzing LSD1 expression versus T cell infiltration in each tumor, the total expression of CD8A (log 2 counts per million) was used to assess the infiltration of cytotoxic T-lymphocytes, and correlations were computed versus LSD1 expression.

For human SKCM data, patients were divided into tertiles based on LSD1 expression, and then the second and third tertiles were combined into one group (named LSD1-int/high) due to a lack of observable difference in survival curves between them.

For gene ontology, the online DAVID (david.ncifcrf.gov) was used to analyze the differentially expressed genes (>2 fold) between LSD 1 KD and WT control under the category of GOTERM_BP_DIRECT. For identification of enriched gene sets, the two expression data sets were further utilized and Gene Set Enrichment Analysis (GSEA) was performed based on these normalized data using GSEA tool (www-.broad.mit.edu) with C2. The raw and processed data of ChIP-Seq and RNA-Seq are deposited at the Gene Expression Omnibus (GEO) under the subseries entry GSE105001.

Example 2. Lysine-Specific Demethylase 1A (LSD1) Represses ERV Expression and Antivirus Mimicry in Human Cancer Cells To identify chromatin regulators that control tumor responses to host immunity, a curated screening with compounds targeting chromatin factors was initiated. The screen was designed with two readouts: up-regulation of ERV transcripts and interferon activation, based on the following rationale: (1) ERVs are known to be transcriptionally silenced by epigenetic mechanisms; (2) interferons regulate tumor responses to host immunity (Parker et al. (2016) Nature Reviews Cancer 16:131-144); (3) a potential correlation between ERV activity and tumor immunity has been suggested (Rooney et al. (2015) Cell 160:48-61; Kassiotis and Stoye (2016) Nat Rev Immunology 16(4):207-219) and these two events may be linked by interferon activation (Chiappinelli et al. (2015) Cell 162(5):974-986).

Figure 1A:
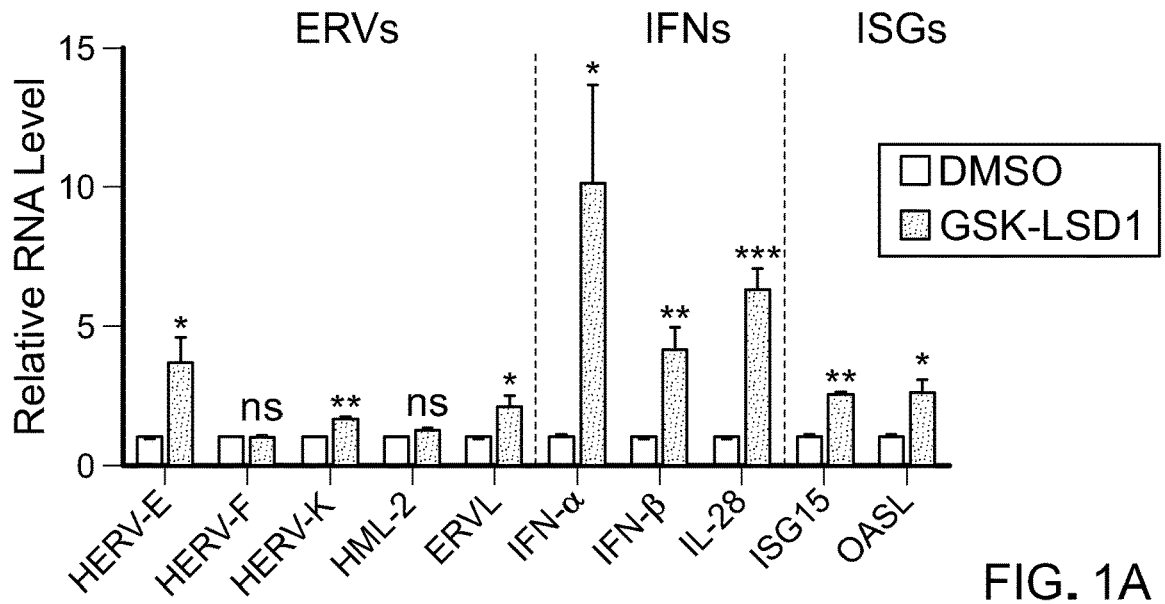
FIG. 1A is a bar graph showing quantitative reverse transcription polymerase chain reaction (RT-qPCR) analysis of selected endogenous retroviruses (ERVs) (HERV-E, HERV-F, HERV-K, HML-2, and ERVL), IFNs (IFN-α, IFN-β and IL-28) and ISGs (ISG15 and OASL) in human MCF-7 breast cancer cells treated with or without GSK-LSD1 for 6 days. The RT-qPCR data were normalized to GAPDH and then relative to DMSO. RT-qPCR was performed in duplicates and repeated two to three times. Error bars represent the standard error of mean (SEM). $*p<0.05$, $p<0.01$, $*p<0.001$, ns, not significant, as determined by unpaired t-test.
Figure 1B:
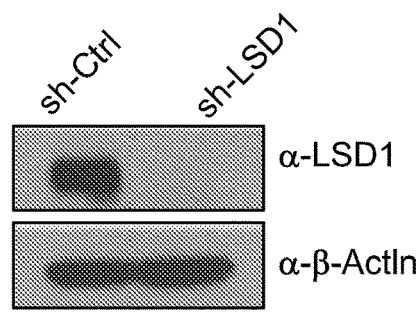
FIG. 1B is a picture of immunoblots showing shRNA-mediated knockdown of LSD1 (sh-LSD1) in MCF-7 cells. Actin was used as a control for protein level.
Figure 1C:
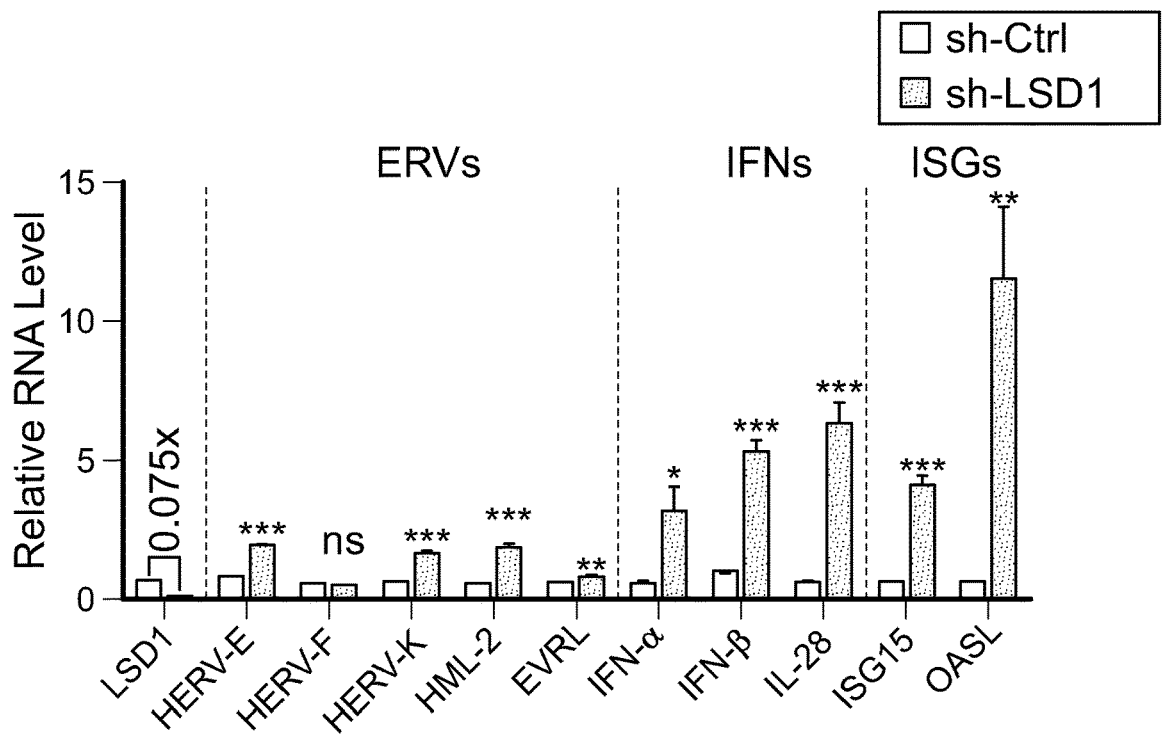
FIG. 1C is a bar graph showing shRNA-mediated knockdown of LSD1 in MCF-7 cells (sh-LSD1) and shRNA against scramble (sh-Ctrl) in MCF-7 cells by RT-qPCR. The RT-qPCR data were normalized to GAPDH and then relative to sh-Ctrl. Error bars represent SEM from three experiments. $*p<0.05$, $p<0.01$, $*p<0.001$, ns, not significant, as determined by unpaired t-test.
Figure 1G:
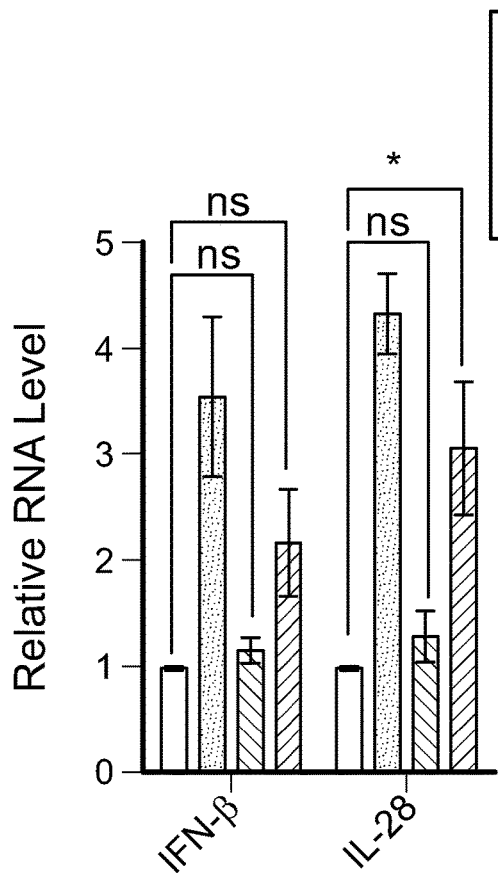
FIG. 1G is a bar graph showing RT-qPCR analysis of IFN-α and IFN-β in MCF-7 cells transduced with shRNA against scramble (sh-C) or LSD1 (sh-LSD1). RT-qPCR was performed in duplicates and repeated two to three times. Error bars represent the SEM from three experiments. $*p<0.05$, $**p<0.01$, ns, not significant, as determined by unpaired t-test.
Figure 1H:
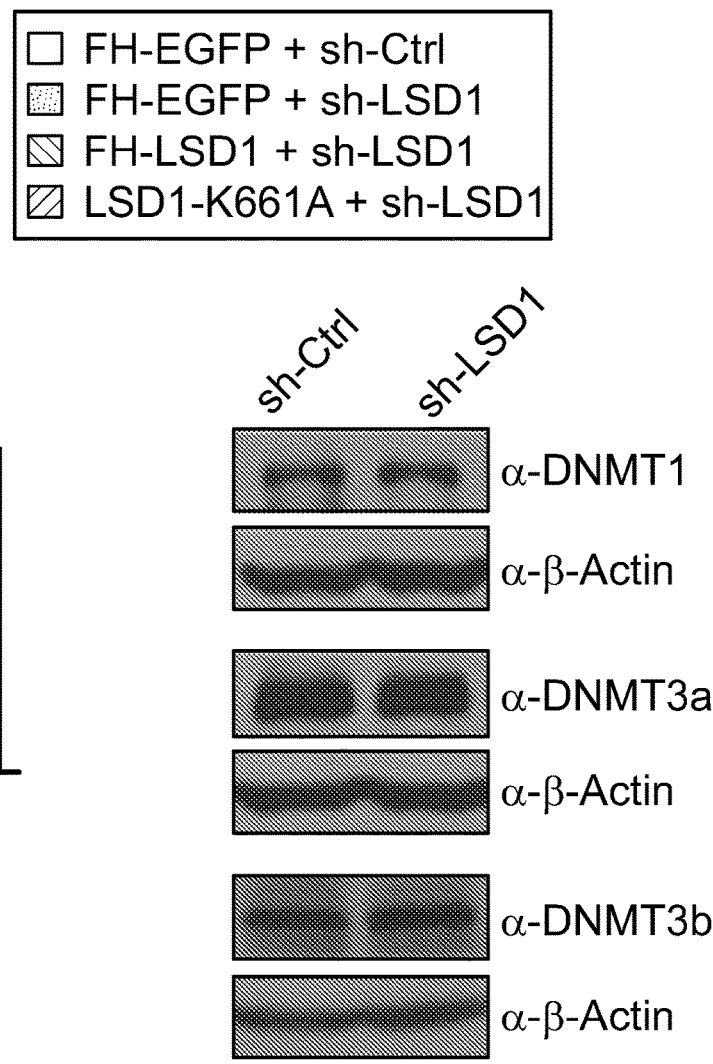
FIG. 1H is a picture of immunoblots showing the protein expression of DNMT proteins in MCF-7 cells with control shRNA or LSD1 KD.
Figure 1I:
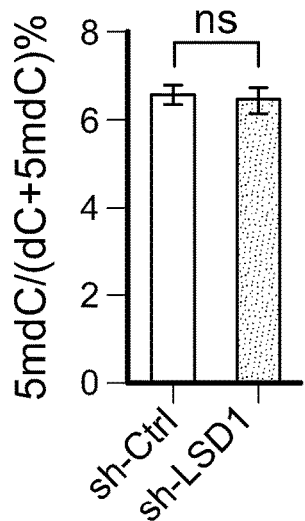
FIG. 1I is bar graph showing 5-methylalcytosine content in genomic DNA of control and LSD1 KD MCF-7 cells as determined by HPLC-MS analysis.
Figure 1J:
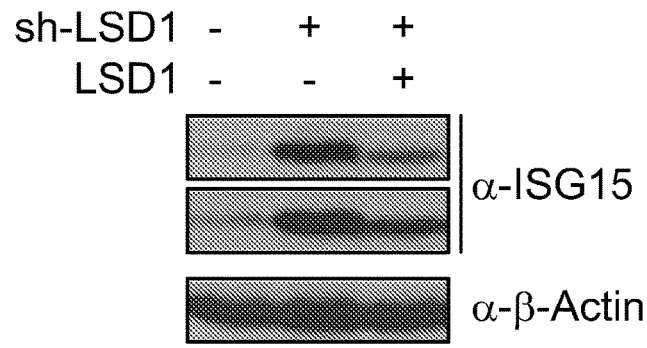
FIG. 1J is a picture of immunoblots showing the protein expression of ISG15 in MCF-7 cells with control shRNA, LSD1 KD, or LSD1 KD rescued with LSD1.
Figure 1K:
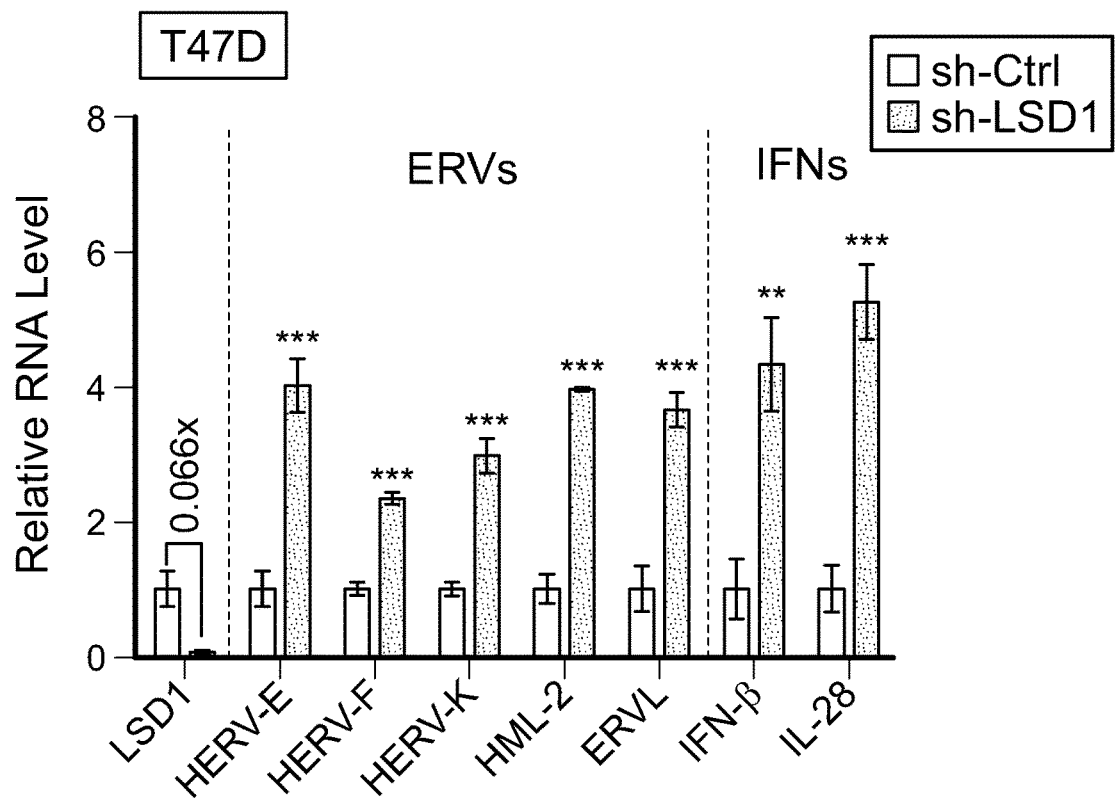
FIG. 1K is a bar graph showing RT-qPCR analysis of selected ERVs (HERV-E, HERV-K, HML-2, and ERVL) and IFNs (IFN-β and IL-28) in human T47D breast cancer cells transduced with shRNA against scramble or LSD1. The RT-qPCR data were normalized to GAPDH and then relative to sh-Ctrl. Error bars represent the standard deviation between triplicates. $*p<0.05$, $p<0.01$, $*p<0.001$, ns, not significant, as determined by unpaired t-test.
Figure 1L:
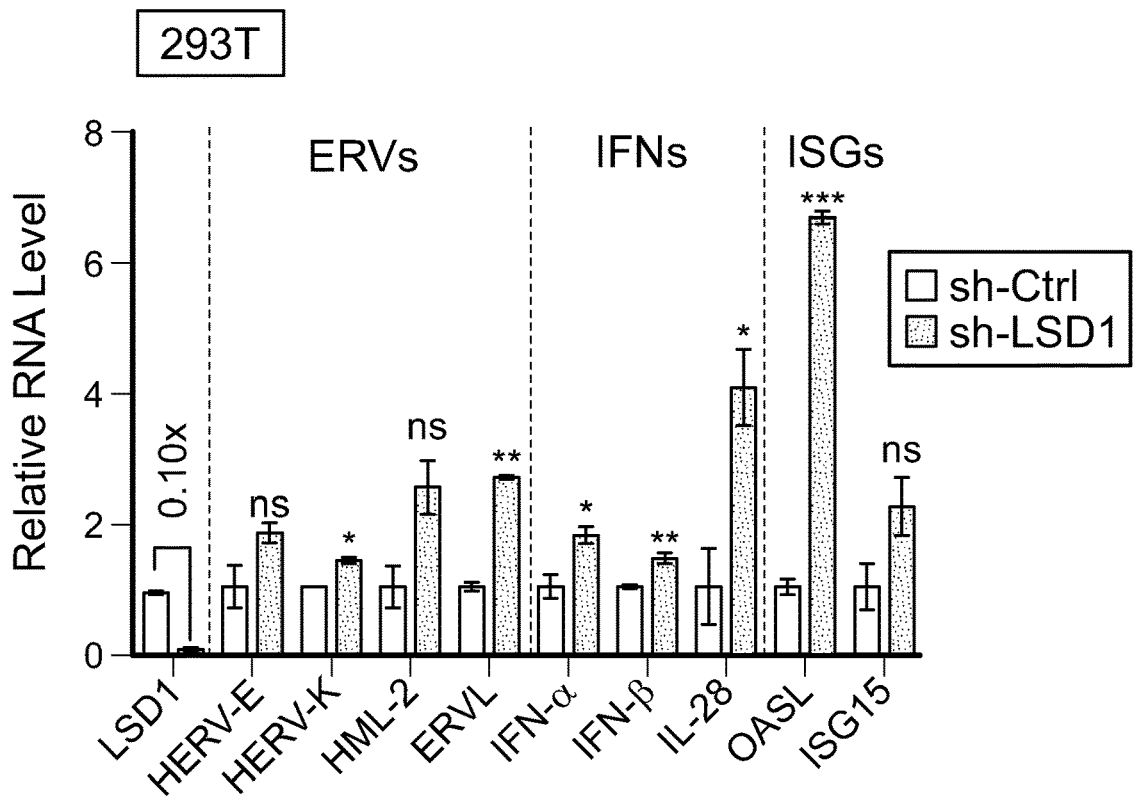
FIG. 1L is a bar graph showing RT-qPCR analysis of selected ERVs (HERV-E, HERV-K, HML-2, and ERVL) and IFNs (IFN-β and IL-28) in human embryonic 293T kidney cells transduced with shRNA against scramble or LSD1. The RT-qPCR data were normalized to GAPDH and then relative to sh-Ctrl. Error bars represent the standard deviation between duplicates. $*p<0.05$, $p<0.01$, $*p<0.001$, ns, not significant, as determined by unpaired t-test.

In this screen, an LSD1 catalytic inhibitor, GSK-LSD1, was shown to significantly induce the up-regulation of a few randomly selected ERVs, type I and type III interferons, as well as interferon-stimulated genes (ISGs) in MCF-7 cells (FIG. 1A). Of note, the PCR primers detected overall transcript levels of the corresponding ERV subfamilies, which may be transcribed from multiple genomic loc. To ascertain that this was caused by a GSK-LSD1 on-target effect, shRNA-mediated LSD1 knockdown (KD) was performed (FIG. 1B), which yielded essentially the same results (FIGS. 1C-D). Furthermore, re-introduction of wild type (WT) LSD1 but not catalytic inactive LSD1 (LSD1-K661A) back into LSD1 KD cells fully restored repression of four tested ERVs, as well as IFN-β and IL-28 activation (FIGS. 1E-G). These results demonstrated that demethylase activity of LSD1 is necessary for ERV repression, which is consistent with the LSD1 inhibitor result (FIG. 1A). Neither DNMT protein expression nor global DNA methylation was affected by LSD1 inhibition (FIGS. 1H and 1I), suggesting a DNA methylation-independent pathway. In addition, the induction of ISGs such as ISG15 was also suppressed by LSD1 rescue (FIG. 1J). These observations were recapitulated in T47D, another breast cancer cell line (FIG. 1K), and 293T cells, a kidney cell line (FIG. 1L) suggesting that these effects were not limited to MCF-7 cells and may be of broad significance in human cancer cells. Together, these results suggest that LSD1 may repress the expression of a group of ERVs and regulate interferon activation in human cancer cells.

Figure 1M:
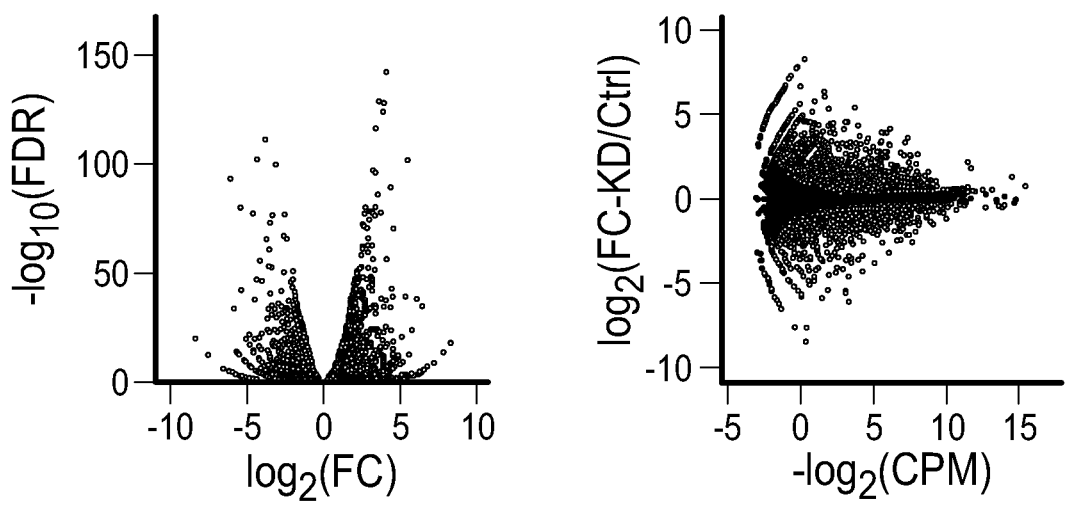
FIG. 1M is volcano and M-A plots showing differentially expressed genes in LSD1 KD versus control MCF-7 cells as determined by RNA-seq. Dots in grey represent significantly increased or decreased genes (FDR<0.05).
Figure 1N:
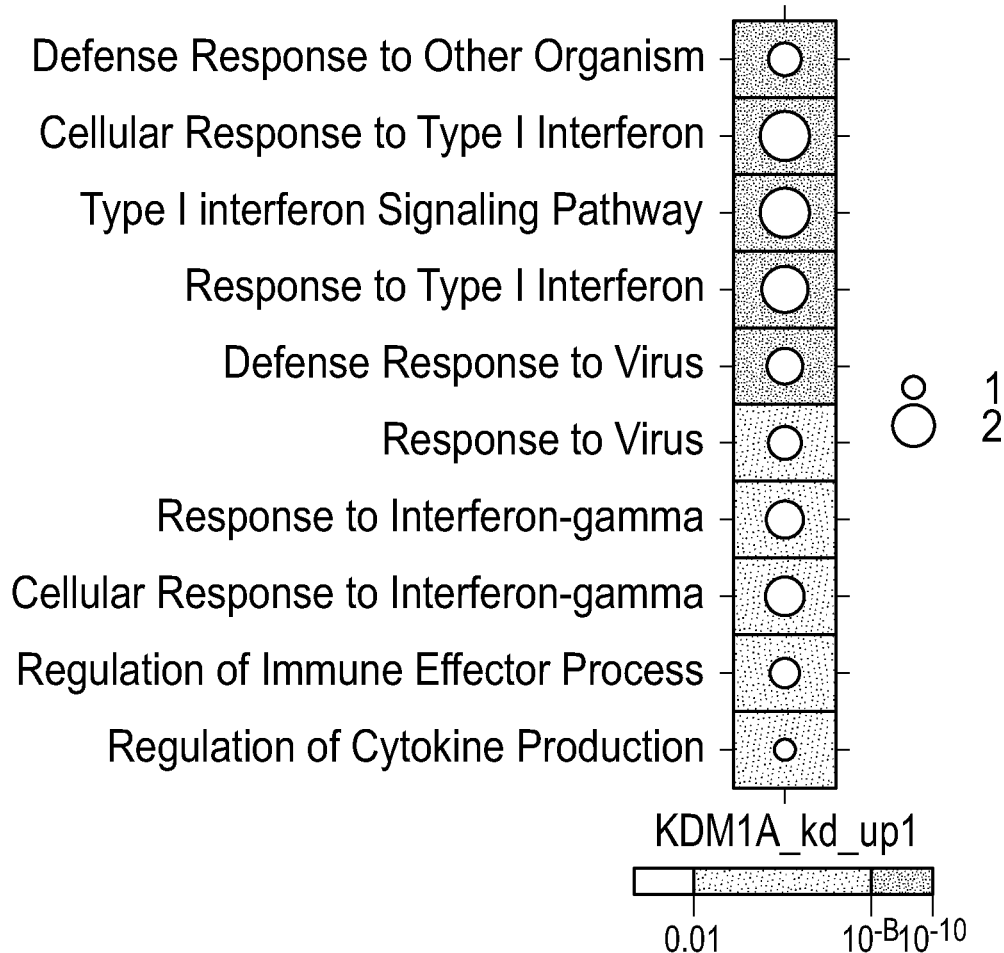
FIG. 1N is a representative dotmap showing the top 10 terms of a gene ontology (GO) analysis of upregulated genes (log 2(FC)>1 and FDR<0.05) in LSD1 KD versus control MCF-7 cells. Dot size represents odds ratio.
Figure 1O:
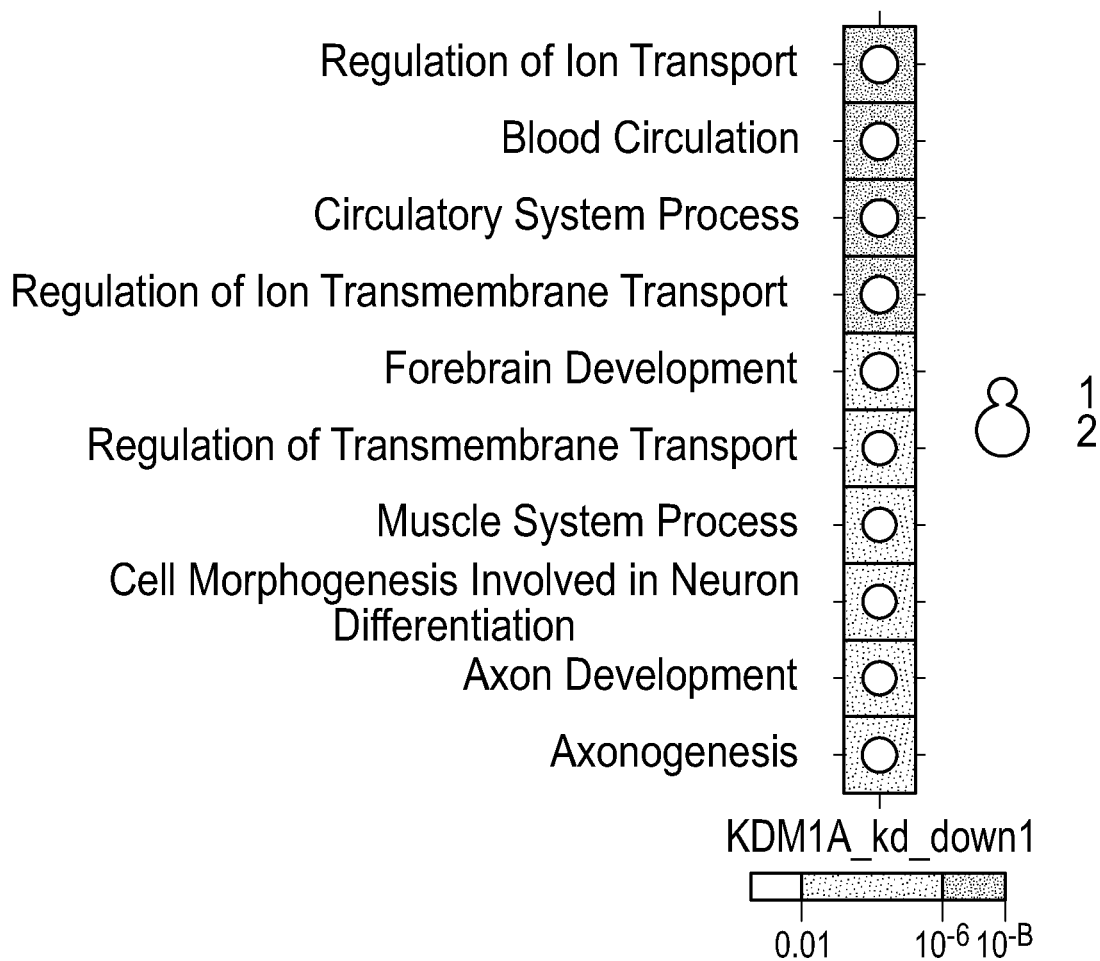
FIG. 1O is representative dotmap showing the top 10 terms of a gene ontology (GO) analysis of downregulated genes (log 2(FC)<−1 and FDR<0.05) in LSD1 KD versus control MCF-7 cells. Dot size represents odds ratio.
Figure 2A:
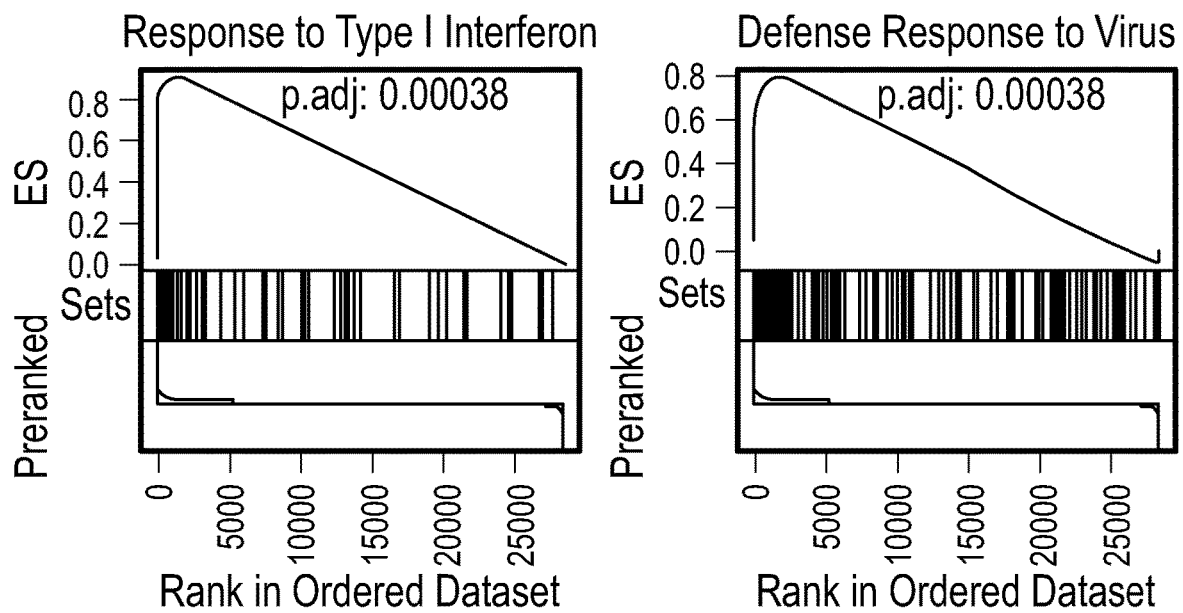
FIG. 2A is a Gene Set Enrichment Analysis (GSEA) analysis for response to type 1 interferon (IFN) and antiviral response pathway in LSD1 KD versus WT control MCF-7 cells.

Next, transcriptomic analysis was carried out to comprehensively explore how LSD1 regulates ERV expression and interferon activation. A significant impact of LSD1 inhibition on gene expression in MCF-7 cells (FIG. 1M). Gene ontology (GO) enrichment analysis of these differentially expressed genes revealed that the up-regulated genes were significantly enriched in GO terms related to type I interferon response and antiviral response (FIG. 1N), whereas the down-regulated genes seemed to be enriched in GO terms related to neuronal development (FIG. 1O). GSEA analysis confirmed the remarkable enrichment in type I interferon and antiviral responsive pathways in LSD1 KD cells compared to WT control (FIG. 2A). However, almost none of the up-regulated interferon/antiviral responsive genes (FDR<0.05 and log 2(FC)>0, 125 in total) appeared to be direct targets of LSD1, as ChIP-seq analysis failed to identify LSD1 at their promoters (Table 3 and FIG. 2B) An example of such genes indirectly regulated by LSD1 at their promoters and an example of LSD1 direct target genes were shown in FIGS. 2C and 2D.

TABLE 3

List of up-regulated interferon/antiviral responsive genes in LSD1 KD cells compared to WT control, related to FIG. 2.

| No LSD1-bound | LSD1-bound |
|---|---|
| CD274, IFIT3, IFI6, HERC5, XAF1, OASL, IFIH1, IFI35, DHX58, GBP4, TMEM106A, IFI44, RSAD2, APOBEC3G, APOL1, PARP12, SAMD9L, MB21D1, TRIM22, IRF7, CXCL10, CXCL11, IFI27, PSMB9, IFIT2, TLR3, BST2, | DDX60, IFIT1, OAS2, OAS3, IFI44L, EPSTI1, APOL6, IFIT5, MX1, EIF2AK2, TNFSF10, LAMP3, TDRD7, RARRES3, STAT1, |

TABLE 3-continued

List of up-regulated interferon/antiviral responsive genes
in LSD1 KD cells compared to WT control, related to FIG. 2.

| No LSD1-bound | LSD1-bound |
|---|---|
| SP110, STX11, UBE2L6, GBP2, GBP1, OAS1, GMPR, TRIM21, MX2, SP100, PSMB8, NMI, ISG15, HLA-F, TAP1, TYMP | KIF5C, SAMHD1, PLSCR1, PDZD2, ISG20, IL15 |

Figure 2B:
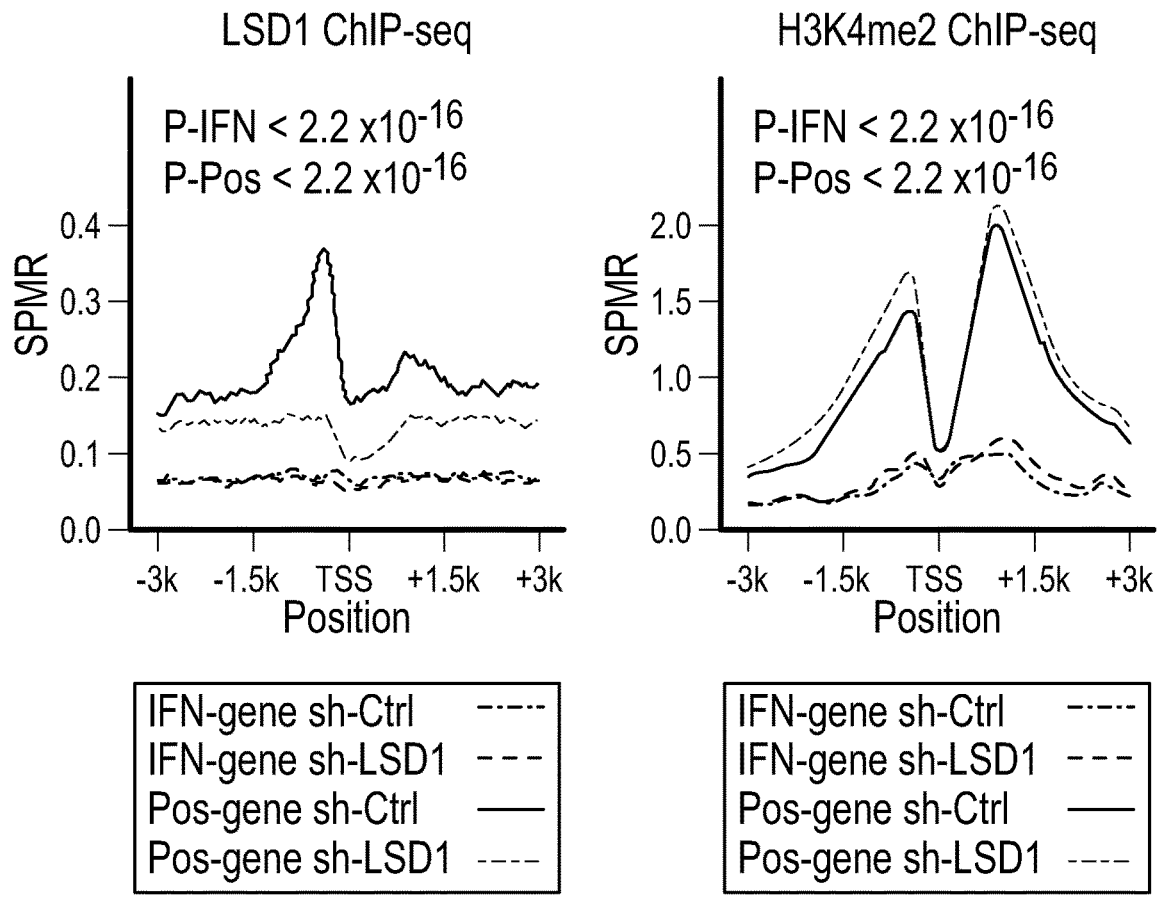
FIG. 2B is a plot showing LSD1 and H3K4me2 ChIP-seq signals at promoter regions of 125 induced interferon/antiviral responsive genes (IFN-gene, log 2(FC)>0 and FDR<0.05) or 537 selected genes with LSD1 peaks as positive control (Pos-gene) in control (sh-Ctrl) and LSD1 KD (sh-LSD1) cells.
Figure 2C:
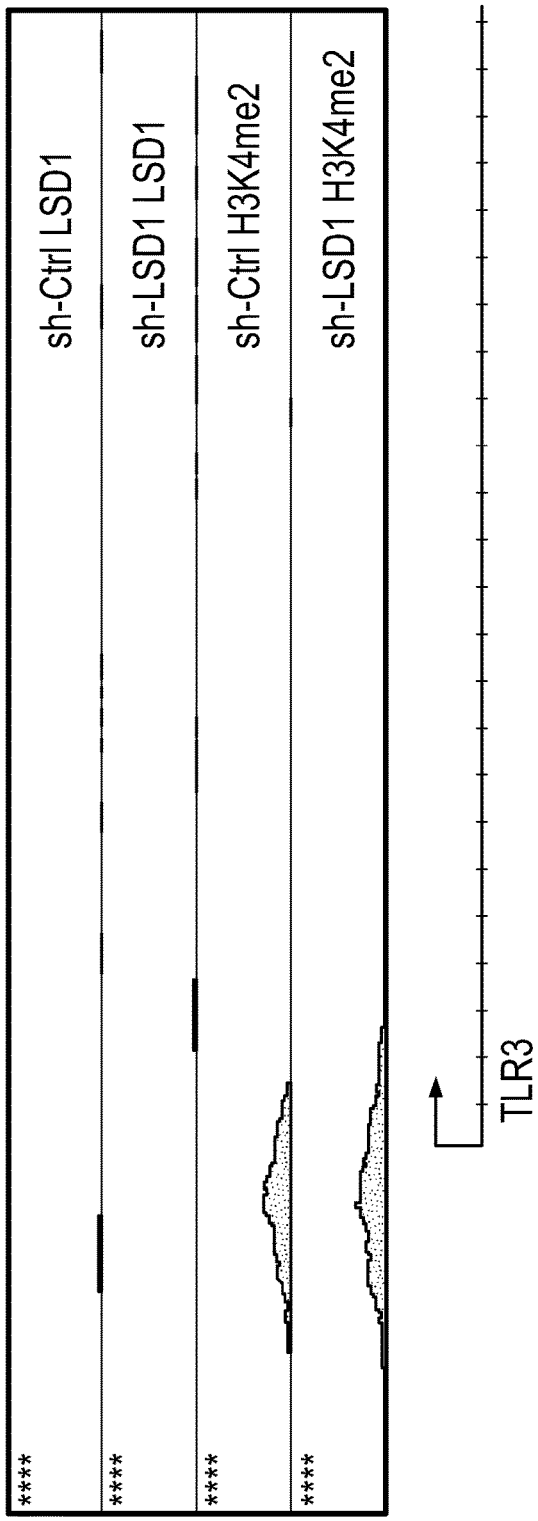
FIG. 2C is IGV images of TLR3 loci showing LSD1 and H3K4me2 levels in LSD1 KD and control MCF-7 cells.
Figure 2D:
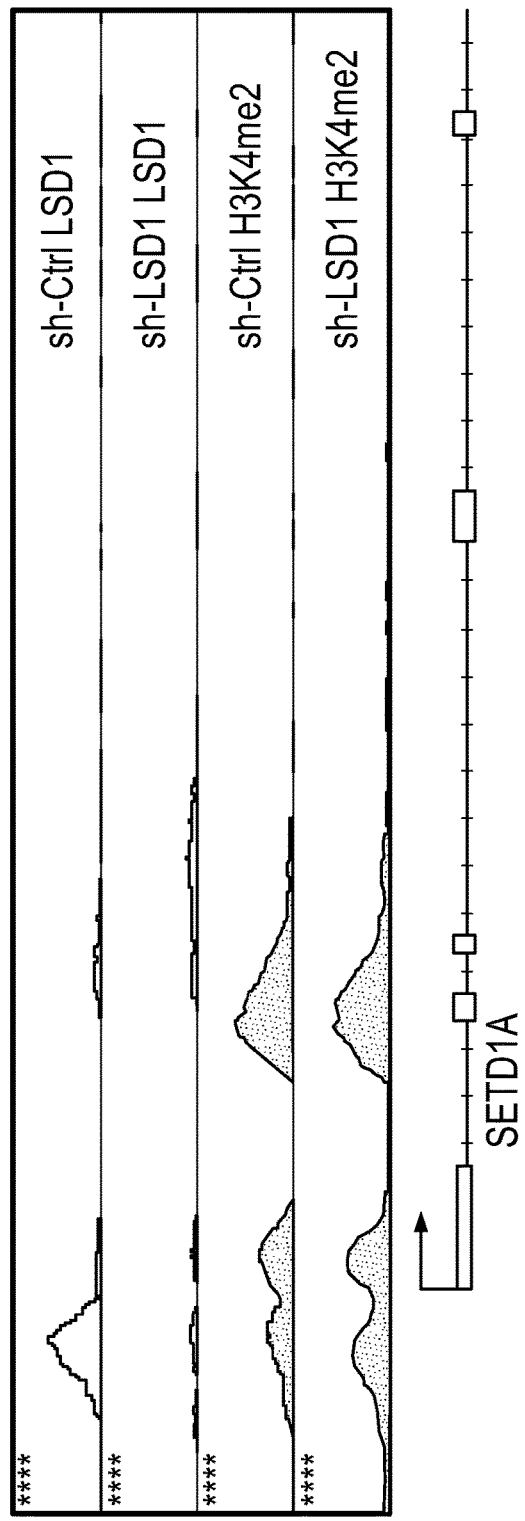
FIG. 2D are IGV images of SEDIA loci showing LSD1 and H3K4me2 levels in LSD1 KD and control MCF-7 cells.
Figure 2G:
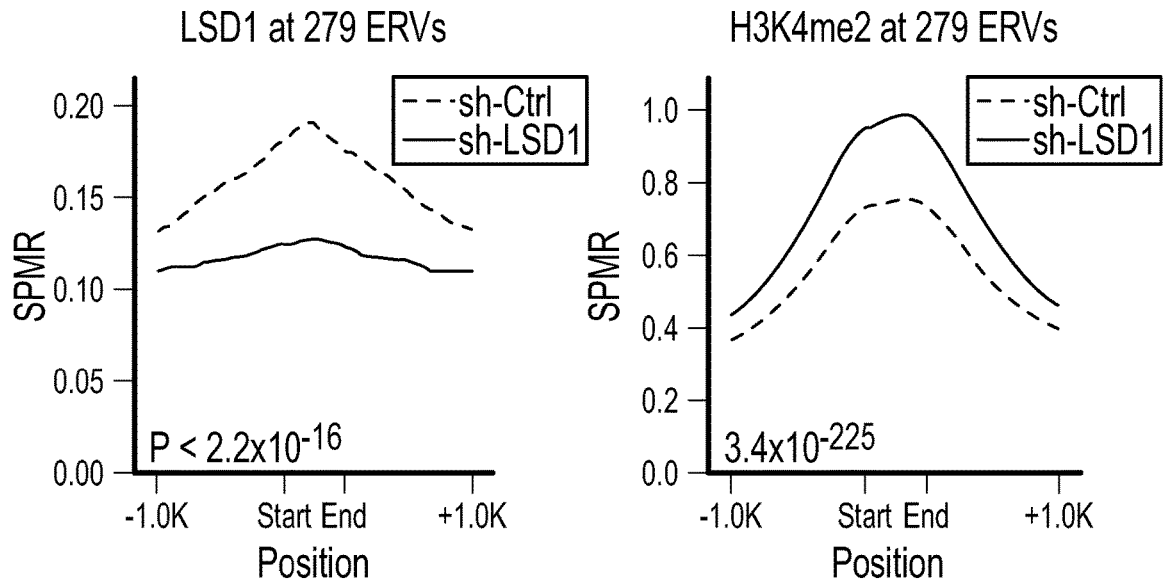
FIG. 2G is plots showing LSD1 and H3K4me2 ChIP-seq signals at genomic loci of 8593 individual ERVs from 279 ERV subfamilies in control and LSD1 KD cells.
Figure 2H:
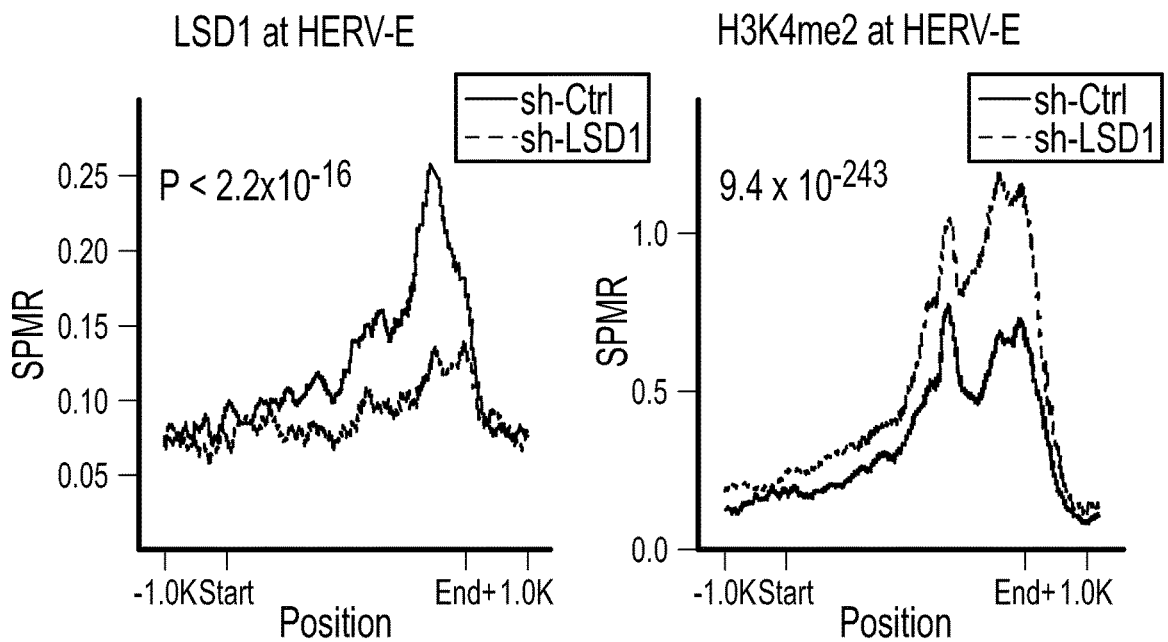
FIG. 2H is plots of LSD1 and H3K4me2 ChIP-seq signals at genomic loc of HERV-E subfamily in control and LSD1 KD cells.
Figure 2I:
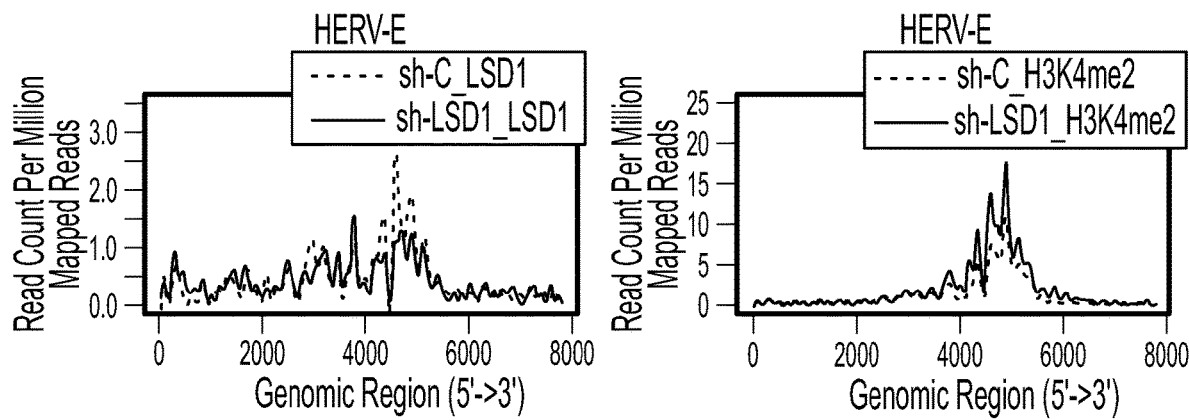
FIG. 2I is histogram plots of normalized ChIP-Seq tag intensities of LSD1 and H3K4me2 at HERV-E loci of 7813 bp in length.
Figure 2J:
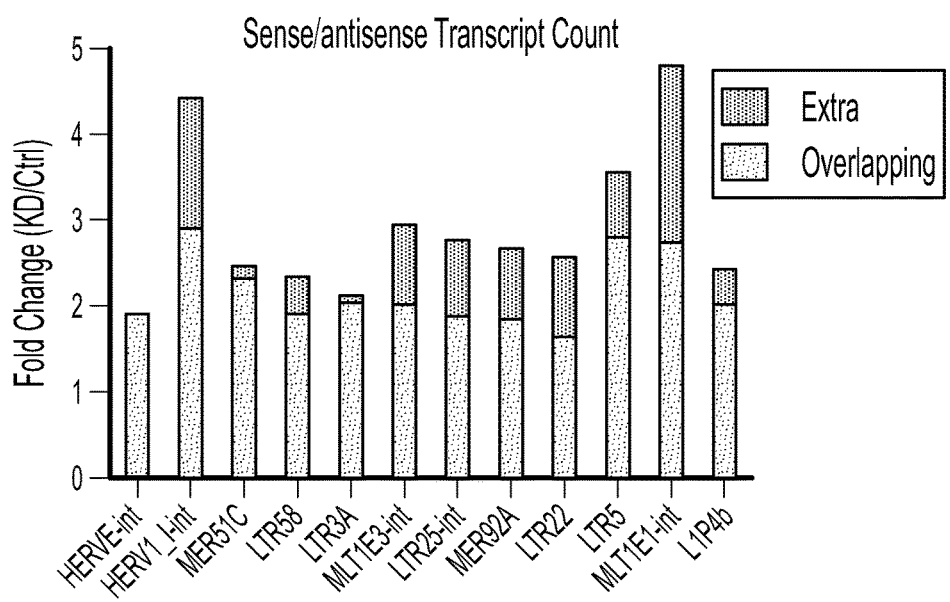
FIG. 2J is a bar graph showing fold changes of reverse complementary sense-/antisense transcripts (overlapping) and extra sense or antisense transcripts (extra) of a number of retrotransposons between LSD1 KD and control cells determined by directional RNA-Seq
Figure 2K:
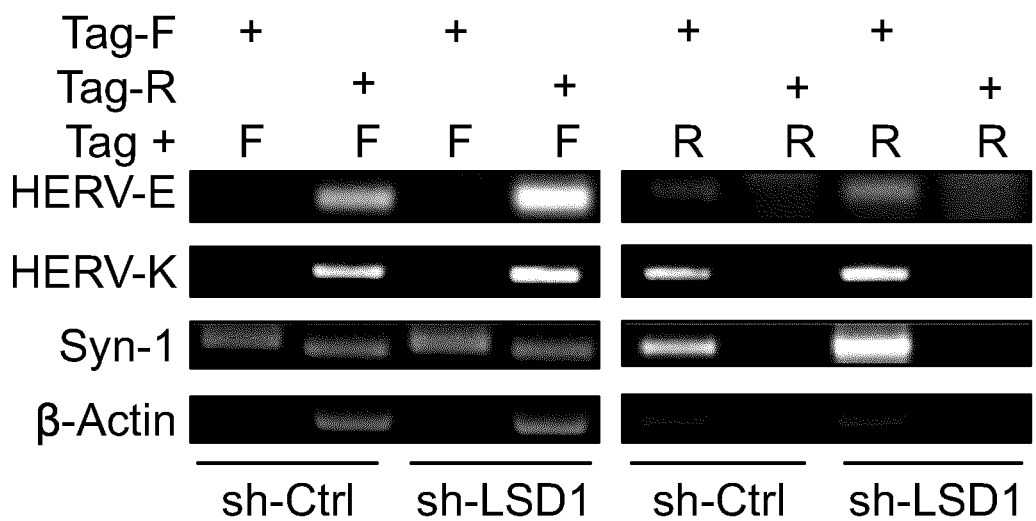
FIG. 2K is a picture of a PCR gel showing PCR amplification of selected ERVs using strand specific primers in MCF-7 cells with sh-C or sh-LSD1. An asterisk indicates non-specific bands.
Figure 2L:
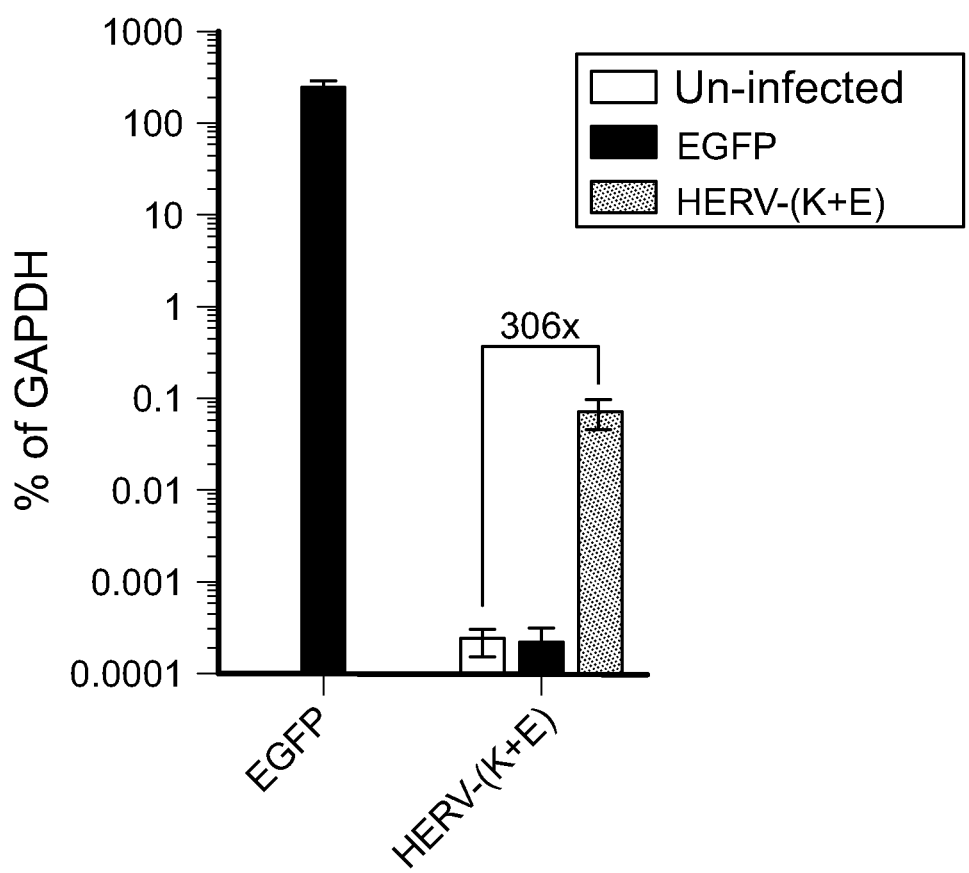
FIG. 2L is a bar graph showing RT-qPCR analysis of EGFP, engineered HERV-(K+E) in MCF-7 cells transduced with pHAGE-EGFP or pHAGE-HERV-(K+E). The RT-qPCR data were normalized to GAPDH and then relative to untransduced cells. Error bars represent SEM from three experiments two experiments. $*p<0.05$, $p<0.01$, $*p<0.001$, ns, not significant, as determined by unpaired t-test.
Figure 2M:
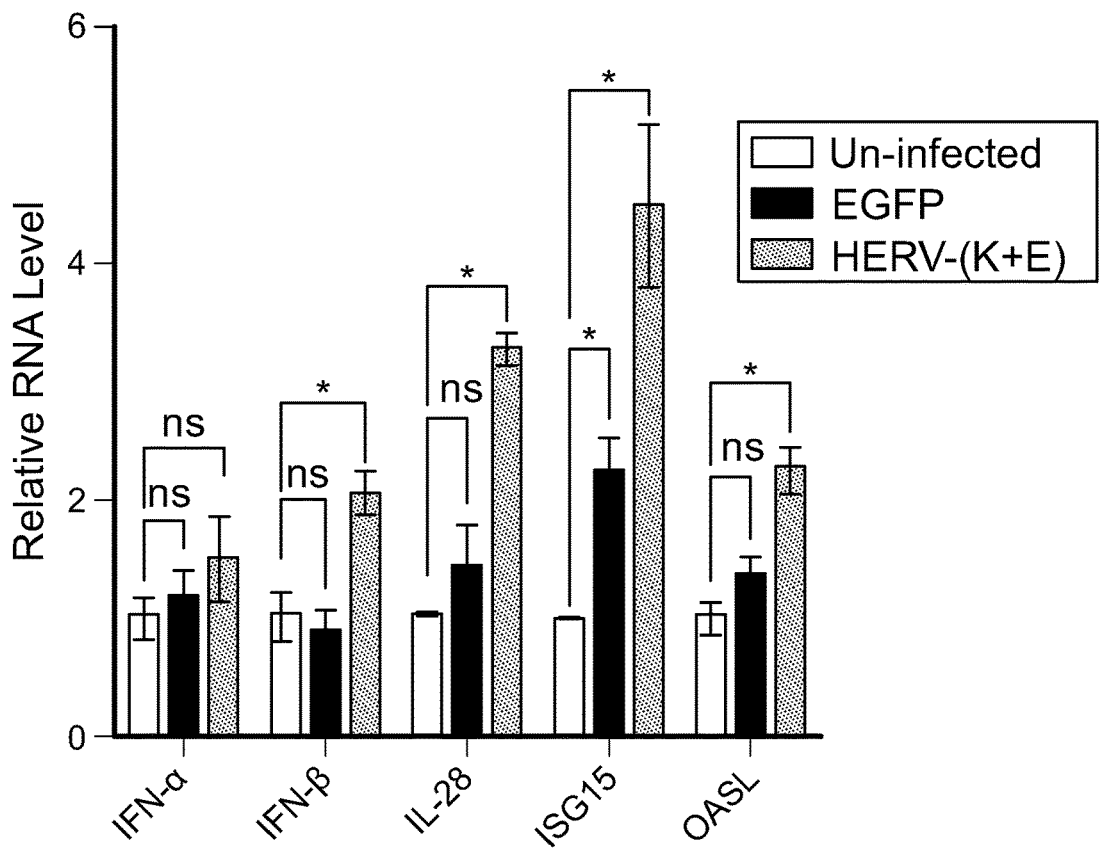
FIG. 2M is a bar graph showing RT-qPCR analysis of IFNα, IFNβ, IL-28, ISG15 and OASL in MCF-7 cells transduced with pHAGE-EGFP or pHAGE-HERV-(K+E). The RT-qPCR data were normalized to GAPDH and then relative to untransduced cells. Error bars represent SEM from three experiments two experiments. $*p<0.05$, $p<0.01$, $*p<0.001$, ns, not significant, as determined by unpaired t-test.

Nevertheless, those genes are, by and large, downstream ISGs and therefore are unlikely to be directly responsible for the up-regulation of no-LSD1-bound genes and interferon pathway activation. A main mode of interferon/antiviral responses by LSD1 inhibition is speculated to be through activation of an upstream event, such as ERV transcript expression. The expression of repetitive elements in RNA-seq data was then analyzed. Many of the repetitive elements were up-regulated by LSD1 inhibition (FIG. 2E), including a number of ERVs (either sense or anti-sense transcripts) were significantly increased in LSD1 KD cells (FIG. 2F). Furthermore, many ERVs appeared to be direct targets of LSD1 as they were bound by LSD1 and showed elevated H3K4me2 levels upon LSD1 KD (FIGS. 2G and 2H). (HERV-E is shown as an example in FIG. 2I). Importantly, a number of up-regulated retrotransposons, including ERVs, LTRs and LINEs, were expressed in both sense and anti-sense directions with overlapping sequences potentially allowing for the formation of double stranded RNAs (FIG. 2J). This observation was confirmed by analyzing a number of selected ERVs using strand-specific PCR (FIG. 2K). Thus, these findings demonstrated that LSD1 is important for transcriptionally silencing ERVs, consistent with a previous report suggesting that LSD1 regulates the expression of repetitive elements in mouse embryonic stem cells (mESCs) (Macfarlan et al. (2011) Genes Dev 25(6): 94-607).

To determine whether ERV transcript up-regulated caused by LSD1 inhibition was a causal factor for the induction of IFN/antiviral responsive genes, an engineered 4 kb ERV fragment was ectopically expressed without protein coding capacity, derived from HERV-K and HERV-E. Its RNA overexpression readily caused the induction of IFNs and ISGs in MCF7 cells (FIGS. 2L and 2M), which demonstrated the sufficiency of ERV up-regulation in triggering IFN activation.

Figure 2N:
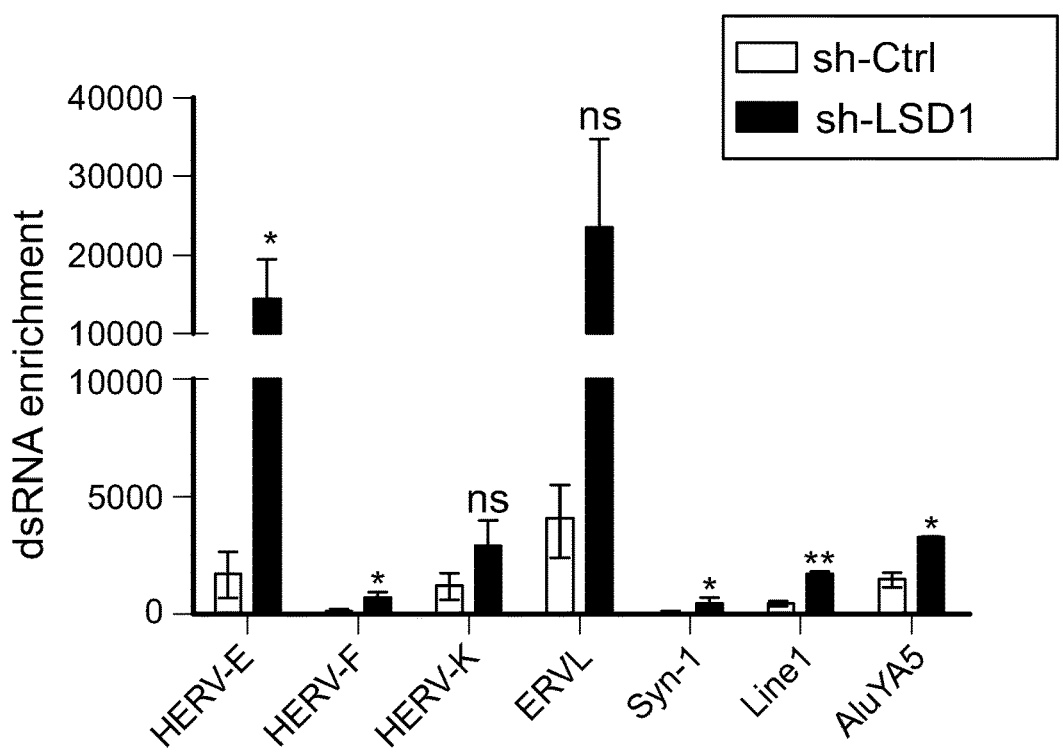
FIG. 2N is a bar graph showing double-stranded RNA (dsRNA) enrichment of selected retrotransposons (HERV-E, HERV-F, HERV-K, ERVL, Syn-1, Line1 and AluYA5) in control (sh-C) and LSD1 KD (sh-LSD1) MCF-7 cells by RT-qPCR. Total RNA extract from control or LSD1 KD MCF-7 cells was digested with RNase A versus mock under high salt condition (350 mM NaCl), followed by a second round of RNA extraction with TRIzol. The ratios of (retrotransposon/GAPDH)RNase/(retrotransposon/GAPDH) mock were calculated as enrichment fold. GAPDH was used as an internal control. Error bars represent SEM from three experiments. $p<0.05$, $p<0.01$, $*p<0.001$, ns, not significant, as determined by unpaired t-test.
Figure 3A:
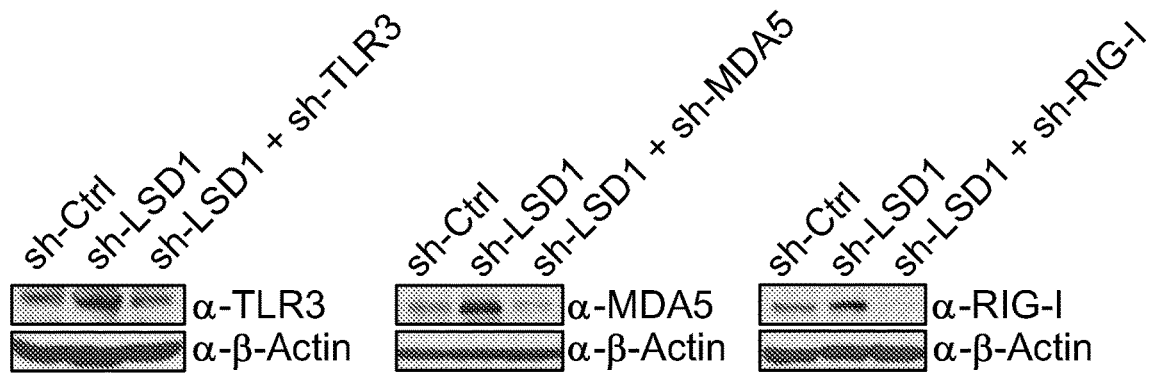
FIG. 3A is a picture of immunoblots showing TLR3, MDA5 and RIG-I expression in control (sh-C), LSD1 KD (sh-LSD1), LSD1/TLR3 DKO (sh-LSD1+sh-TLR3), LSD1/MDA5 DKO (sh-LSD1+sh-MDA5), or LSD1/RIG-I DKO (sh-LSD1+sh-RIG-I) MCF-7 cells.
Figure 3B:
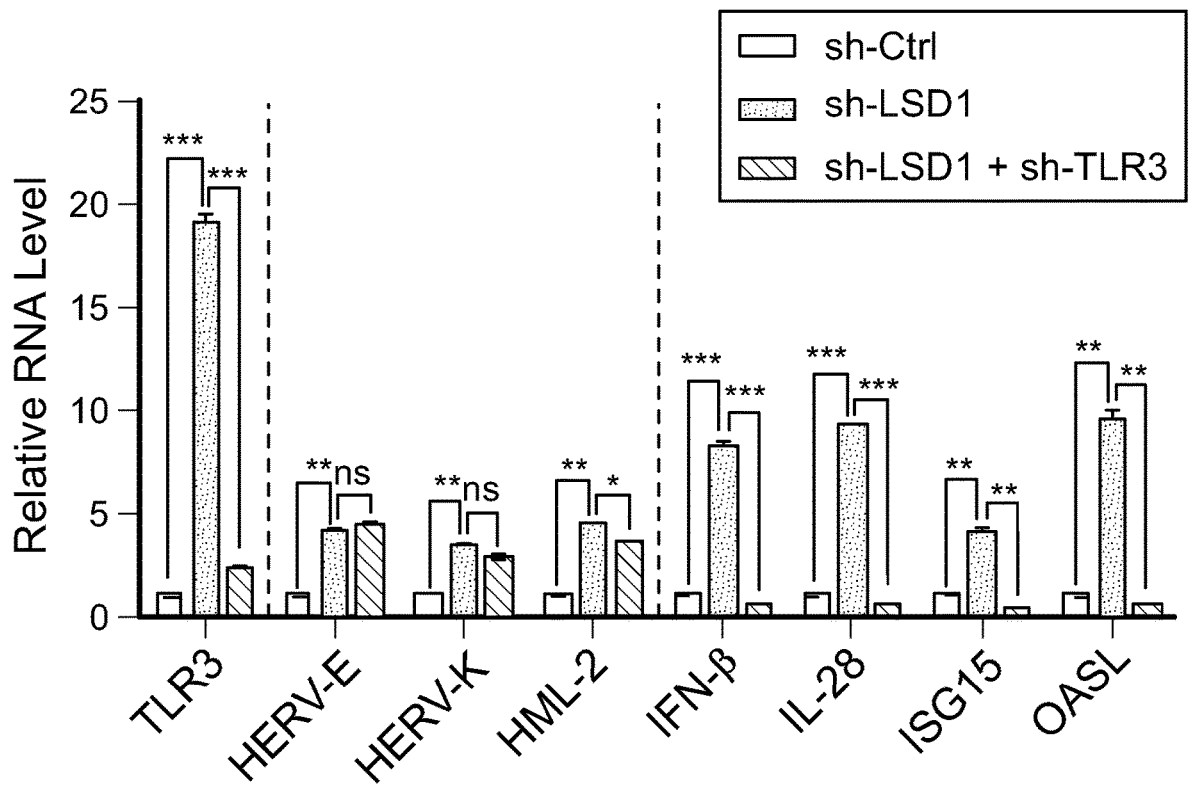
FIG. 3B is a bar graph showing RT-qpCR analysis of TLR3, selected ERVs (HERV-E, HERV-K and HML-2), IFNs (IFN-β and IL-28) and ISGs (ISG15 and OASL) in MCF-7 cells transduced with shRNA against scramble, LSD1 or LSD1 and TLR3. RT-qPCR was performed in duplicates and repeated two to three times. Error bars represent standard deviation (SD). $p<0.05$, $p<0.01$, $*p<0.001$, ns, not significant as determined by unpaired t-test.
Figure 3C:
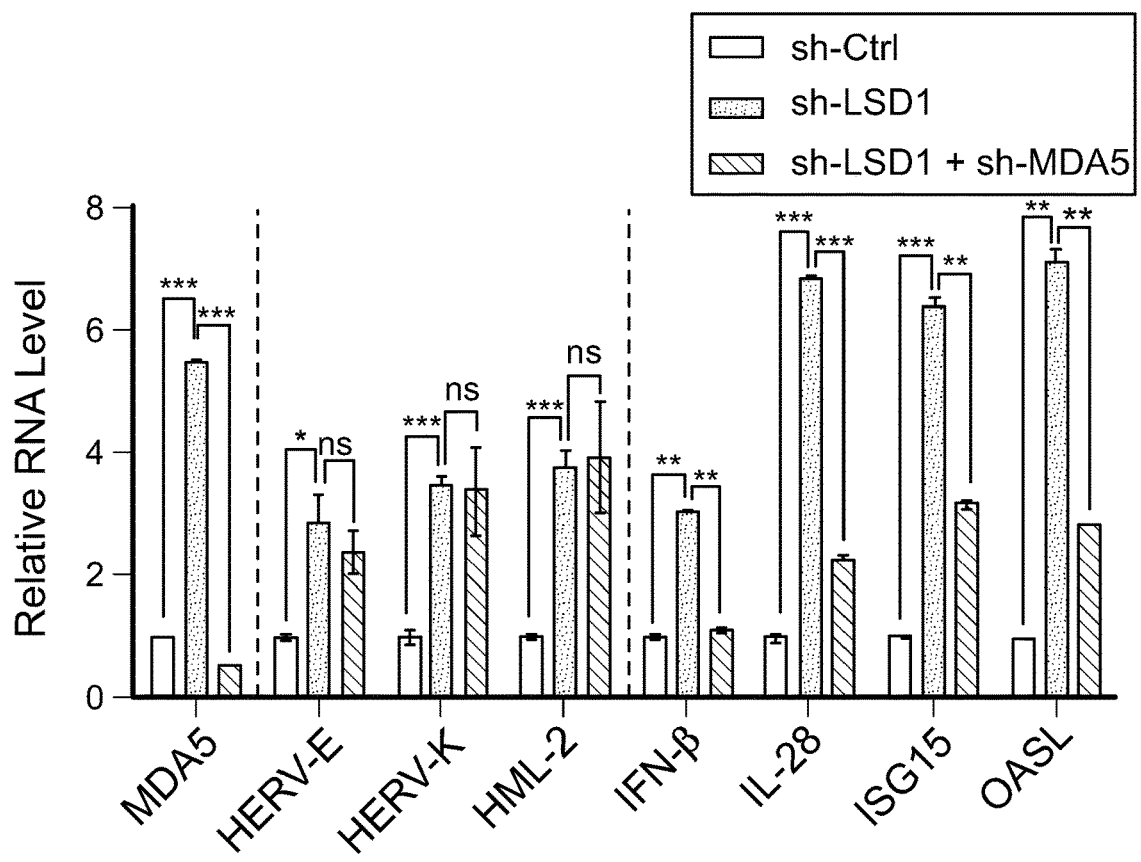
FIG. 3C is a bar graph showing RT-qPCR analysis of MDA5, selected ERVs (HERV-E, HERV-K and HML-2), IFNs (IFN-β and IL-28) and ISGs (ISG15 and OASL) in MCF-7 cells transduced with shRNA against scramble, LSD1 or LSD1 and MDA5. RT-qPCR was performed in duplicates and repeated two to three times. Error bars represent standard deviation (SD). $*p<0.05$, $p<0.01$, $*p<0.001$, ns, not significant as determined by unpaired t-test.
Figure 3D:
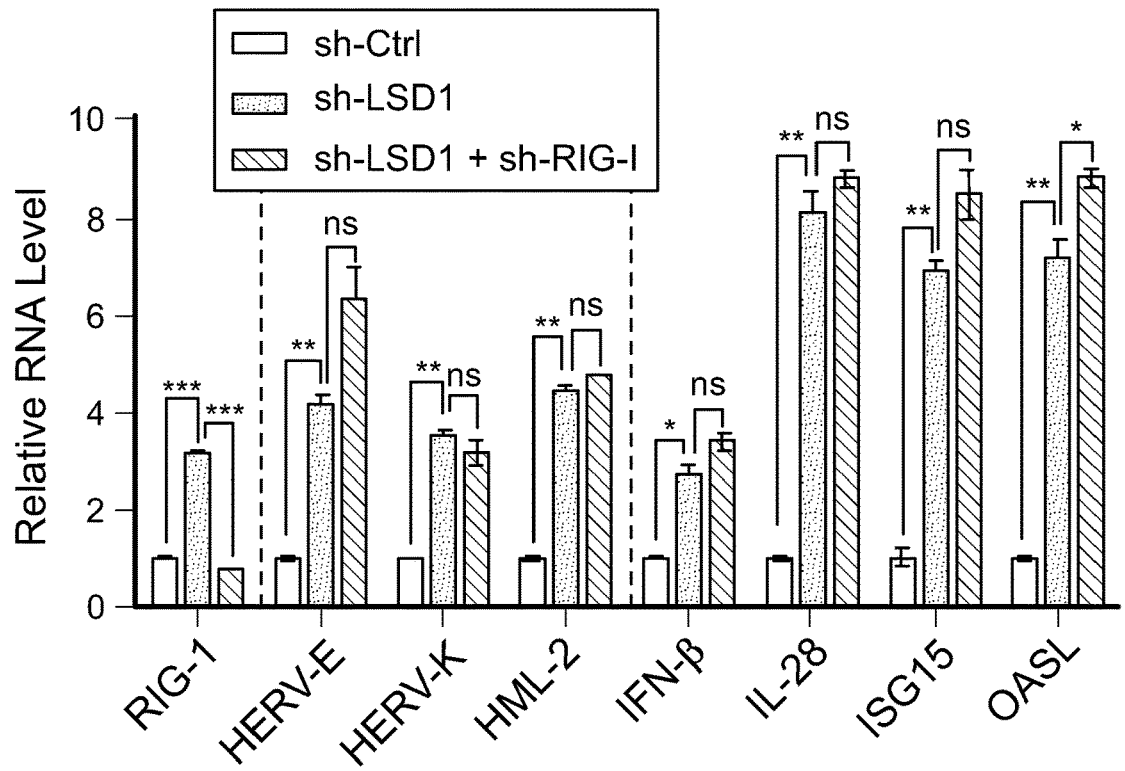
FIG. 3D is a bar graph showing RT-qPCR analysis of RIG-I, selected ERVs (HERV-E, HERV-K and HML-2), IFNs (IFN-β and IL-28) and ISGs (ISG15 and OASL) in MCF-7 cells transduced with shRNA against scramble, LSD1 or LSD1 and RIG-I. RT-qPCR was performed in duplicates and repeated two to three times. Error bars represent standard deviation (SD). $*p<0.05$, $p<0.01$, $*p<0.001$, ns, not significant as determined by unpaired t-test.
Figure 3E:
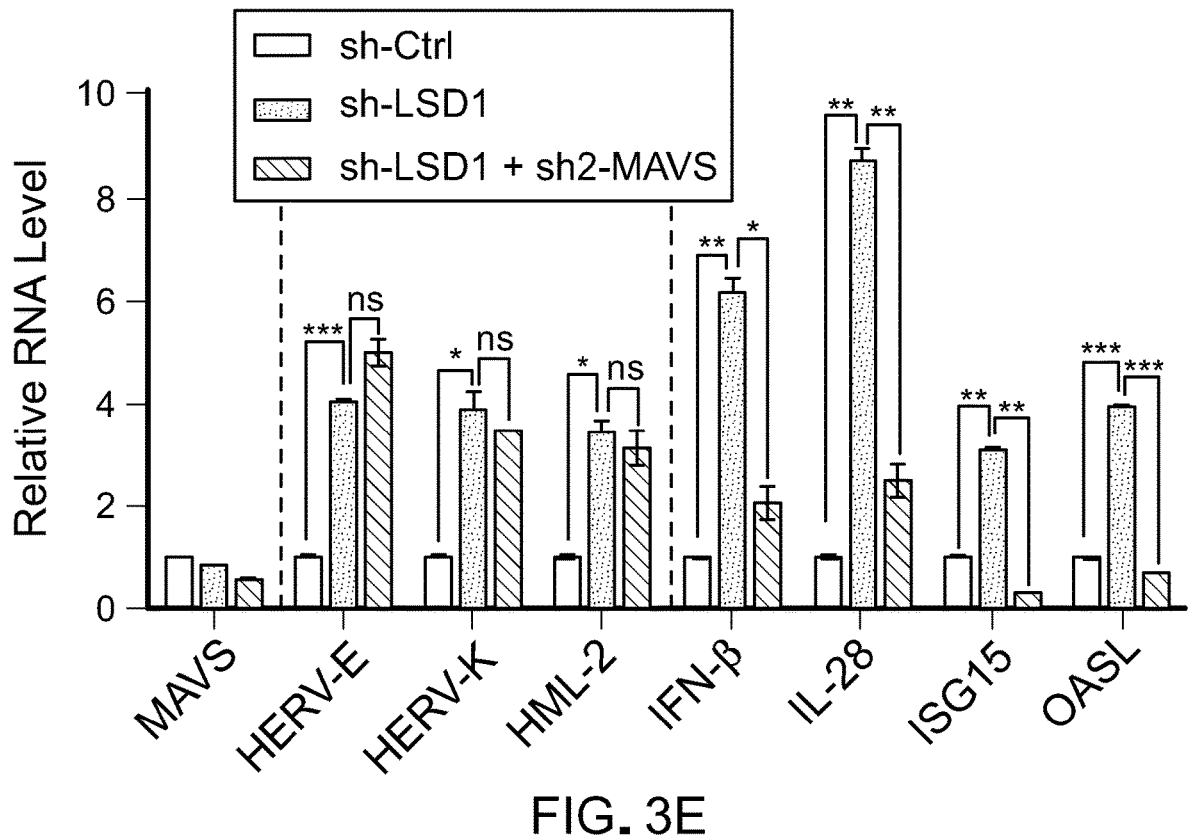
FIG. 3E is a bar graph showing RT-qPCR analysis of MAVS, selected ERVs (HERV-E, HERV-K and HML-2), IFNs (IFN-β and IL-28) and ISGs (ISG15 and OASL) in MCF-7 cells transduced with shRNA against scramble, LSD1 or LSD1 and MAVS. Error bars represent standard deviation between duplicates. $*p<0.05$, $p<0.01$, $*p<0.001$, ns, not significant as determined by unpaired t-test.
Figure 3F:
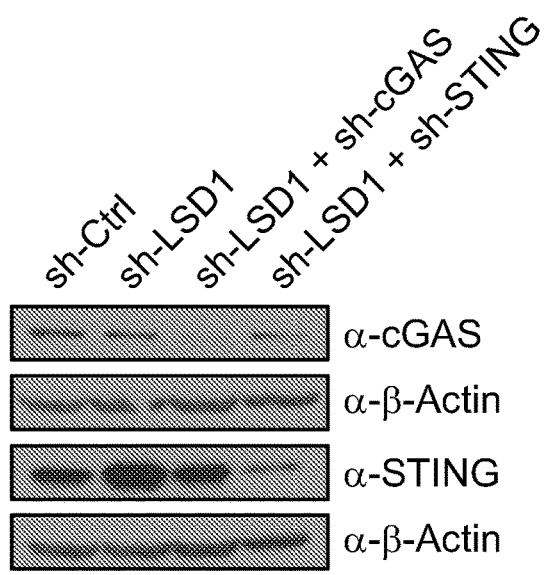
FIG. 3F is a picture of immunoblots showing cGAS and STING proteins in MCF-7+sh-Ctrl, sh-LSD1, sh-LSD1+shcGAS and sh-LSD1+shSTING cells.
Figure 3G:
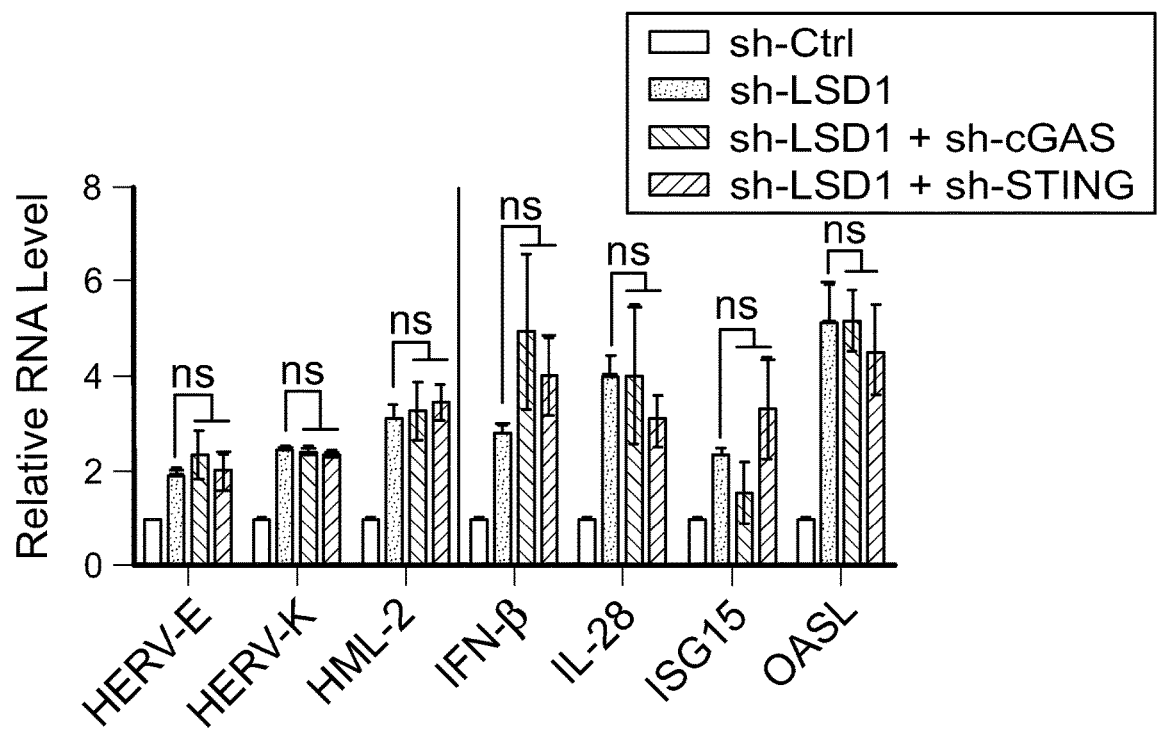
FIG. 3G is a bar graph showing RT-qPCR analysis of HERV-E, HERV-K, HML-2, IFN-β, IL-28, ISG15 and OASL in MCF-7+sh-Ctrl cells, MCF-7+sh-LSD1 cells, MCF-7+sh-LSD1+sh-cGAS cells, and MCF-7+sh-LSD1+sh-STING cells. The RT-qPCR data were normalized to GAPDH and then relative to sh-Ctrl. Error bars represent SEM from three experiments. $*p<0.05$, $p<0.01$, $*p<0.001$, ns, not significant, as determined by unpaired t-test.
Figure 3H:
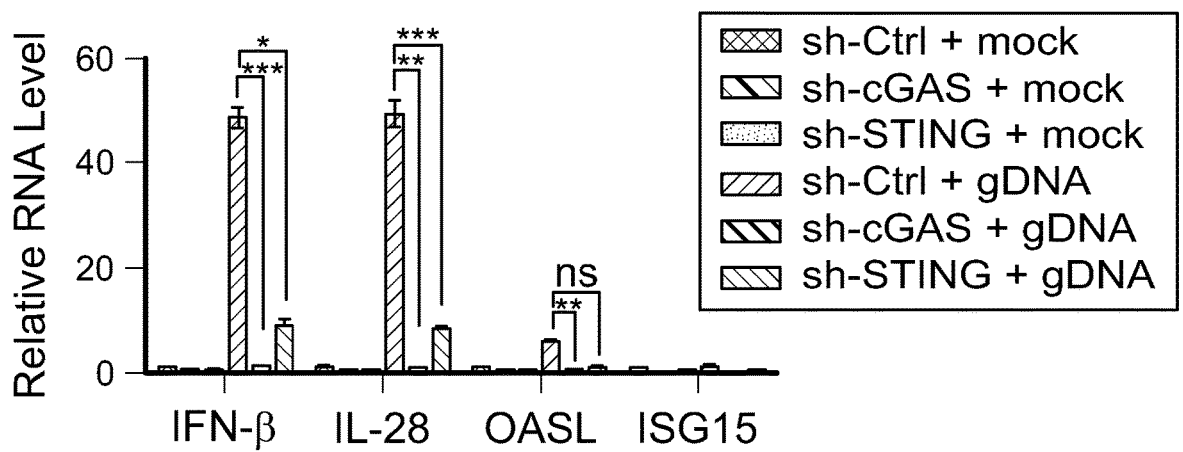
FIG. 3H is a bar graph showing RT-qPCR analysis of IFN-β, IL-28, OASL and ISG15 in control, cGAS KD and STING KD MCF-7 transfected with fragmented genomic DNA from mammalian cells or mock transfected. The RT-qPCR data were normalized to GAPDH and then relative to sh-Ctrl. Error bars represent SD between duplicates in one of two experiments. $*p<0.05$, $p<0.01$, $*p<0.001$, ns, not significant, as determined by unpaired t-test.
Figure 4E:
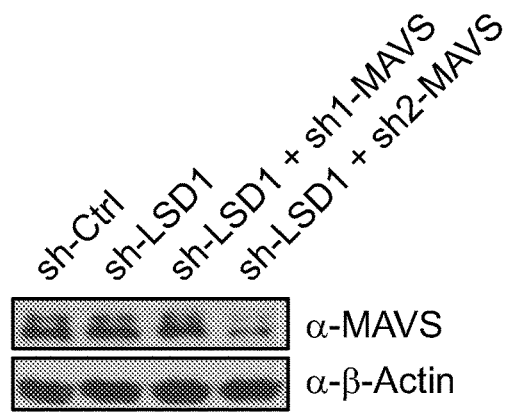
FIG. 4E is a picture of immunoblots showing MAVS protein expression in MCF-7+sh-C cells, MCF-7+sh-LSD1 cells, MCF-7+sh-LSD1+sh1-MAVS cells, and MCF-7+sh-LSD1+sh2-MAVS cells. Actin was used as a control for protein level.

Example 3. TLR3 and MDA5 Sense dsRNA Accumulation Caused by LSD1 Abrogation, which Triggers Interferon Activation To determine whether ERV up-regulation as well as other retrotransposons in both sense and antisense directions in LSD1 KD cells contribute to the generation of dsRNAs, which may then trigger interferon activation, RNases and a dsRNA-specific antibody (J2) were used (White et al. (2014) Nat Struct Mol Biol 21(6): 552-559) to measure the presence of dsRNA. RNase A (under high salt condition) or RNase Ti cleaves single stranded (ss) RNA and preserves dsRNA (Roulois (2015) Cell 162: 961-973). By digesting total RNA isolated from control and LSD1 KD cells, and by normalizing to undigested RNA, the relative dsRNA enrichment was calculated in the presence and absence of LSD1. dsRNA enrichment for a number of ERVs as well as a few other retrotransposons was much higher in LSD1 KD samples as compared to control samples (FIGS. 2N and 2O). Using the dsRNA-specific J2 antibody, more transcripts of selected retrotransposons were captured in LSD1 KD samples (FIG. 2O). These results provide evidence for the elevation of intracellular dsRNA levels, which are elevated as a result of LSD1 inhibition. Intracellular dsRNAs are recognized by pattern recognition receptors, TLR3, MDA5 and RIG-I, which are involved in subsequent activation of the interferon pathways (Takeuchi and Akira (201) Cell 140:805-820). In LSD1 KD cells, all three dsRNA sensors were among the up-regulated genes identified by RNA-seq (FIG. 2P). Furthermore, all three sensors were induced considerably at the protein level in LSD1 KD cells as well (FIG. 2Q), implying that those sensors might be responsible for detecting intracellular dsRNA accumulation in the absence of LSD1. To identify which sensor was essential for recognizing dsRNAs to elicit cellular responses, expression of individual sensors were inhibited by shRNA-mediated knockdown in LSD1 KD cells, and the impact of knockdown on interferon activation was assessed. Each shRNA efficiently knocked down the expression of its target sensor (FIG. 3A). Importantly, abrogation of TLR3 and MDA5, but not RIG-I, significantly diminished the induction of interferon-β, IL-28 as well as ISGs without altering ERV expression level (FIGS. 3B-D and FIG. 4D). In addition, the abrogation of MAVS, which is a downstream adaptor of the MDA5 pathway, also blocked interferon activation in LSD1 KD cells (FIGS. 3E and 4E). As a further control, two key molecules, cGAS and STING, were knocked down in the cytoplasmic DNA sensing pathway (Chen et al. (2016) Nat Immunol 17(10): 1142-1149) and showed that cytoplasmic DNA is unlikely the trigger of interferon responses in LSD1 KD cells (FIGS. 3G and 3H). Therefore, dsRNA recognition by TLR3 and MDA5 was essential for IFN activation upon LSD1 inhibition, consistent with the observation that the up-regulated IFN/antiviral responsive genes were indirect targets of LSD1 (FIG. 2B).

Previous studies of these sensors (Takeuchi and Akira (201) Cell 140:805-820) suggest that TLR3 and MDA5 recognize dsRNAs that are at least 40 bp in length or longer, respectively (see, e.g., Liu et al. (2008) Science 320(5874): 379-381; Kato et al. (2006) Nature 441(7089):101-105, and Kato et al. (2008) J Exp Med 205(7): 1601-1610), whereas RIG-I prefers ssRNA or short dsRNA with 5' triphosphate ends (see, e.g., Pichlmair et al. (2006) Science 314(5801): 997-1001, Hornung et al. (2006) Science 314: 994-997; and Kato et al. (2008) J Exp Med 205(7): 1601-1610). The involvement of TLR3 and MDA5 in response to dsRNA stress is consistent with the directional RNA-seq analysis suggesting that those enriched dsRNAs are sufficiently long to be recognized by the dsRNA sensors TLR3 and MDA5.

Figure 4F:
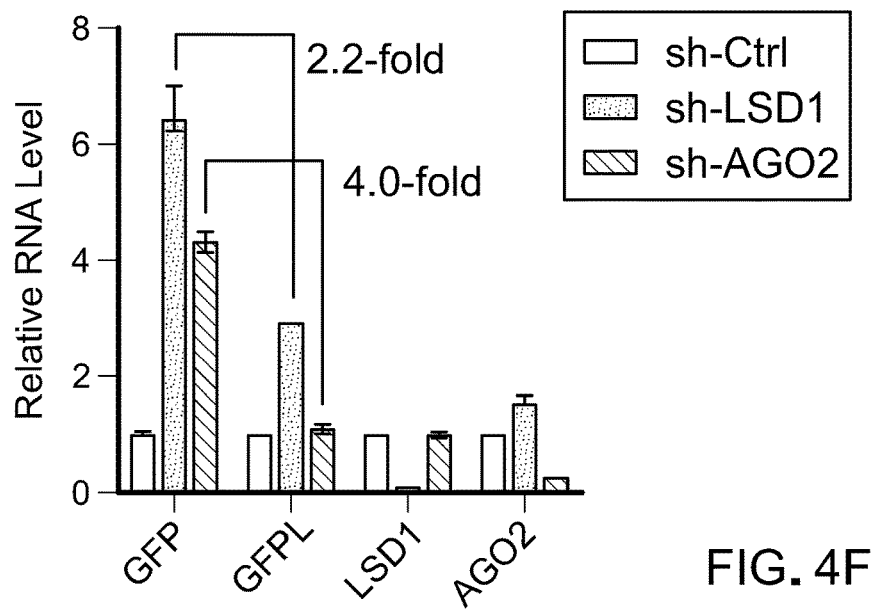
FIG. 4F is a bar graph showing relative let-7 miRISC activity by quantifying GFP and GFPL protein signals in U2OS cells expressing dual reporters GFPL/GFP-let-7 and transduced with shRNA against scramble, LSD1 or AGO2. Error bars represent SD between duplicates. $p<0.05$, $p<0.01$, $*p<0.001$, ns, not significant, as determined by unpaired t-test.
Figure 4G:
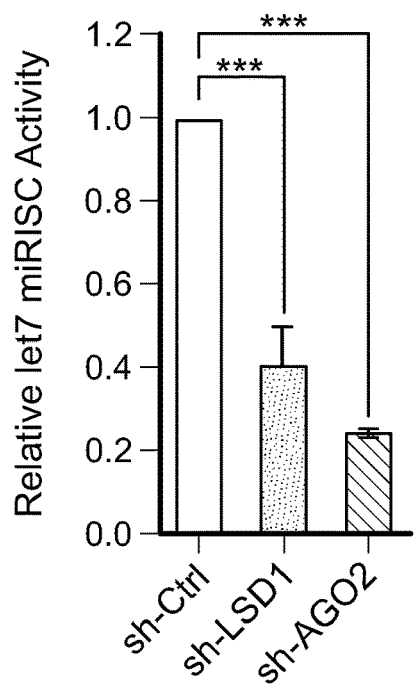
FIG. 4G is a bar graph showing the ratios of GFPL over GFP protein in different samples from five repeats for sh-LSD1 and two repeats for sh-AGO2. The ratio in control shRNA sample was considered as 100% miRISC activity.
Figure 4H:
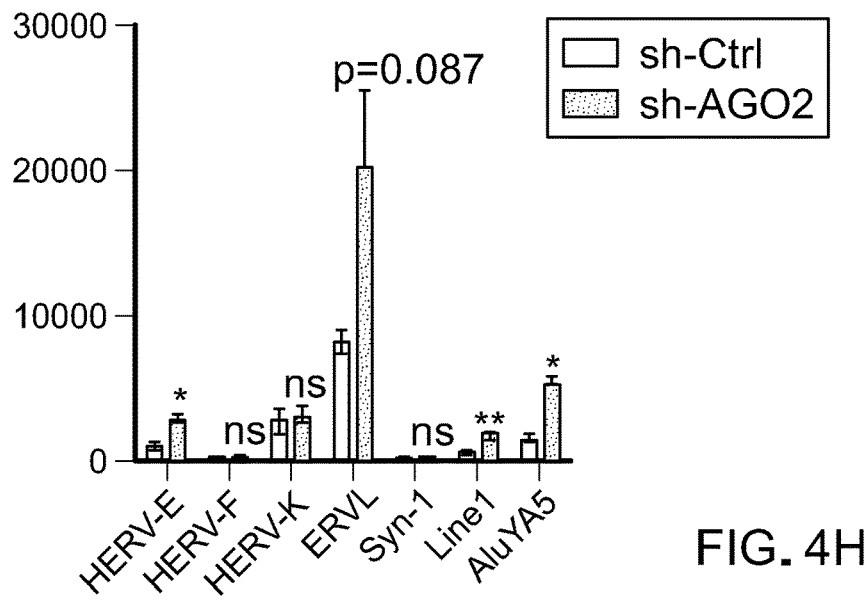
FIG. 4H is a bar graph showing double-stranded RNA (dsRNA) enrichment of selected retrotransposons (HERV-E, HERV-F, HERV-K, ERVL, Syn-1, Line1 and AluYA5) in control (sh-C) and AGO2 KD (sh-AGO2) MCF-7 cells by RT-qPCR. Total RNA extract from control or LSD1 KD MCF-7 cells was digested with RNase A versus mock under high salt condition (350 mM NaCl), followed by a second round of RNA extraction with TRIzol. The ratios of (retrotransposon/GAPDH)RNase/(retrotransposon/GAPDH) mock were calculated as enrichment fold. GAPDH was used as an internal control. RT-qPCR was performed in duplicates and repeated two to three times. Error bars represent SD between duplicates. $p<0.05$, $p<0.01$, $*p<0.001$, ns, not significant, as determined by unpaired t-test.
Figure 4I:
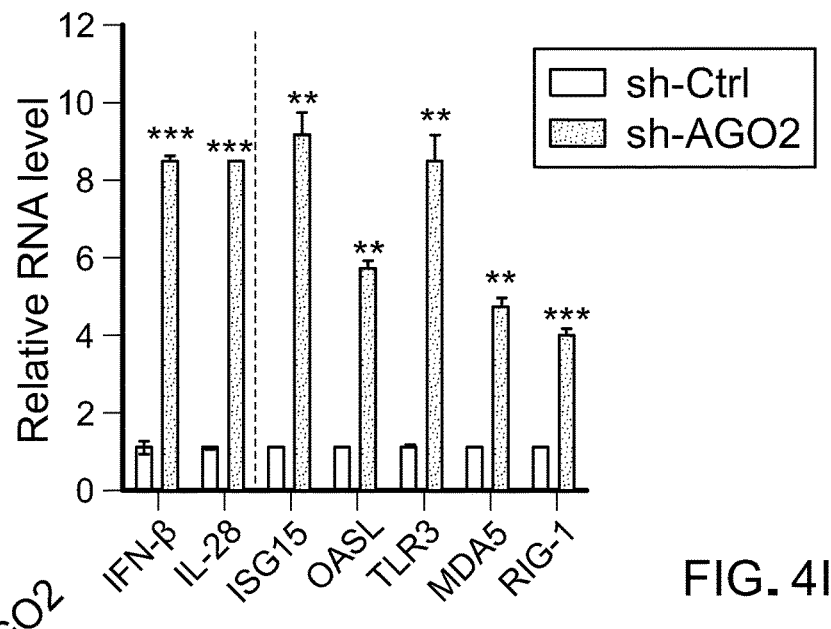
FIG. 4I is a bar graph showing RT-qPCR analysis of selected IFNs (IFN-$\beta$ and IL-28), ISGs (OASL and ISG15), TLR3, MDA5 and RIG-I in MCF-7 cells transduced with shRNA against scramble or AGO2. RT-qPCR was performed in duplicates and repeated twice. Error bars represent standard deviation. $p<0.05$, $p<0.01$, $*p<0.001$, ns, not significant, as determined by unpaired t-test.
Figure 4J:
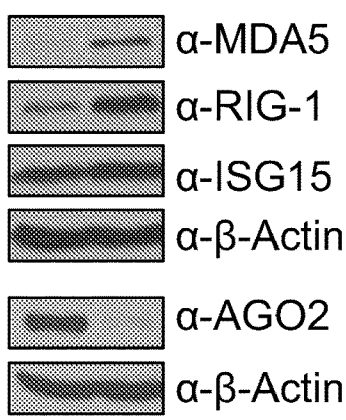
FIG. 4J is a picture of immunoblots showing protein expression of MDA5, RIG-I and ISG15 in the same cells used in FIG. 4I. Actin was used as a control for protein level.
Figure 4K:
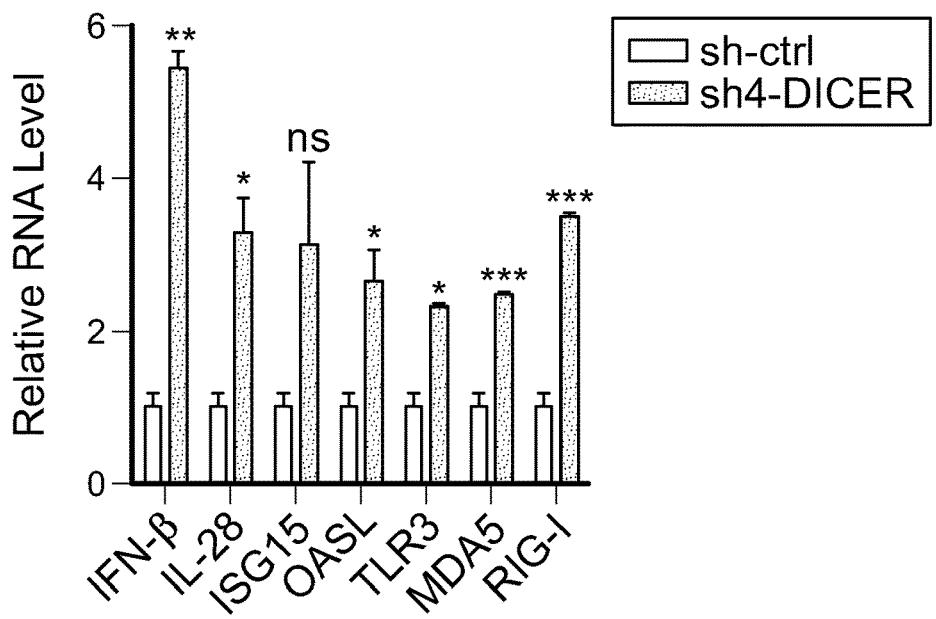
FIG. 4K is bar graph showing RT-qPCR analysis of IFN-$\beta$, IL-28, ISG15, OASL, TLR3, MDA5 and RIG-I in MCF-7 cells transduced with shRNA against scramble (sh-Ctrl) or DICER (sh-DICER). The RT-qPCR data were normalized to GAPDH and then relative to sh-Ctrl. Error bars represent SD between duplicates in one experiment. $*p<0.05$, $p<0.01$, $*p<0.001$, ns, not significant, as determined by unpaired t-test.
Figure 4L:
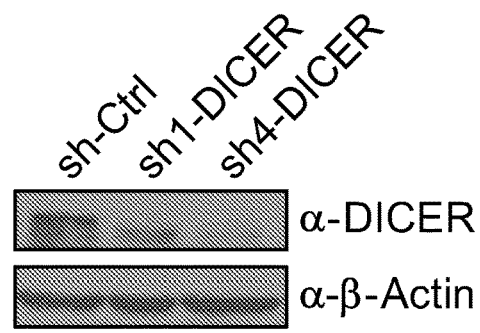
FIG. 4L is a picture of immunoblots showing protein expression of DICER in MCF-7+sh-Ctrl, MCF-7+sh1-DICER, MCF-7+sh4-DICER cells. Actin was used as a control for protein level.
Figure 4M:
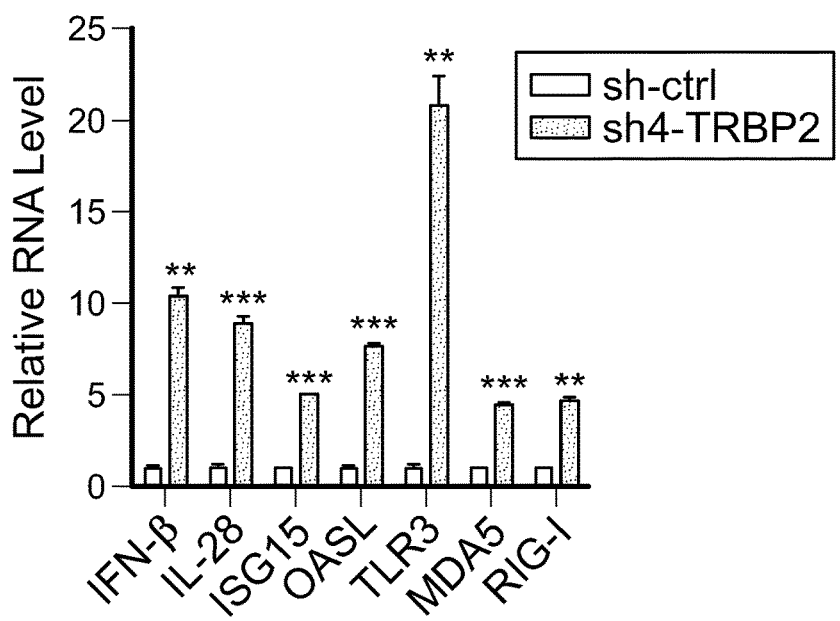
FIG. 4M is bar graph showing RT-qPCR analysis of IFN-$\beta$, IL-28, ISG15, OASL, TLR3, MDA5 and RIG-I in MCF-7 cells transduced with shRNA against scramble (sh-Ctrl) or TRBP2 (sh4-TRBP2). The RT-qPCR data were normalized to GAPDH and then relative to sh-Ctrl. Error bars represent SD between duplicates in one experiment. $*p<0.05$, $p<0.01$, $*p<0.001$, ns, not significant, as determined by unpaired t-test.
Figure 4N:
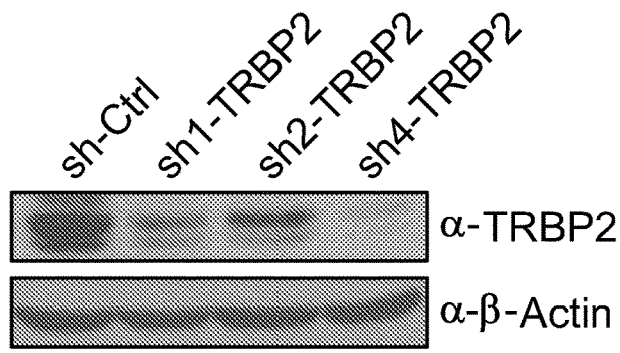
FIG. 4N is a picture of immunoblots showing protein expression of TRBP2 in MCF-7+sh-Ctrl, MCF-7+sh1-TRBP2, MCF-7+sh4-TRBP2 cells. Actin was used as a control for protein level.
Figure 4O:
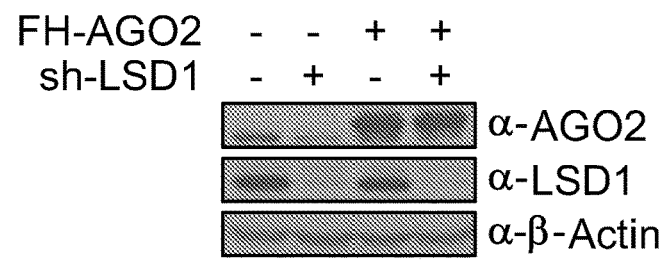
FIG. 4O is a picture of immunoblots showing protein expression of AGO2 and LSD1 in MCF-7+sh-LSD1 cells and MCF-7+FH-AGO2 cells. Actin was used as a control for protein level.
Figure 4P:
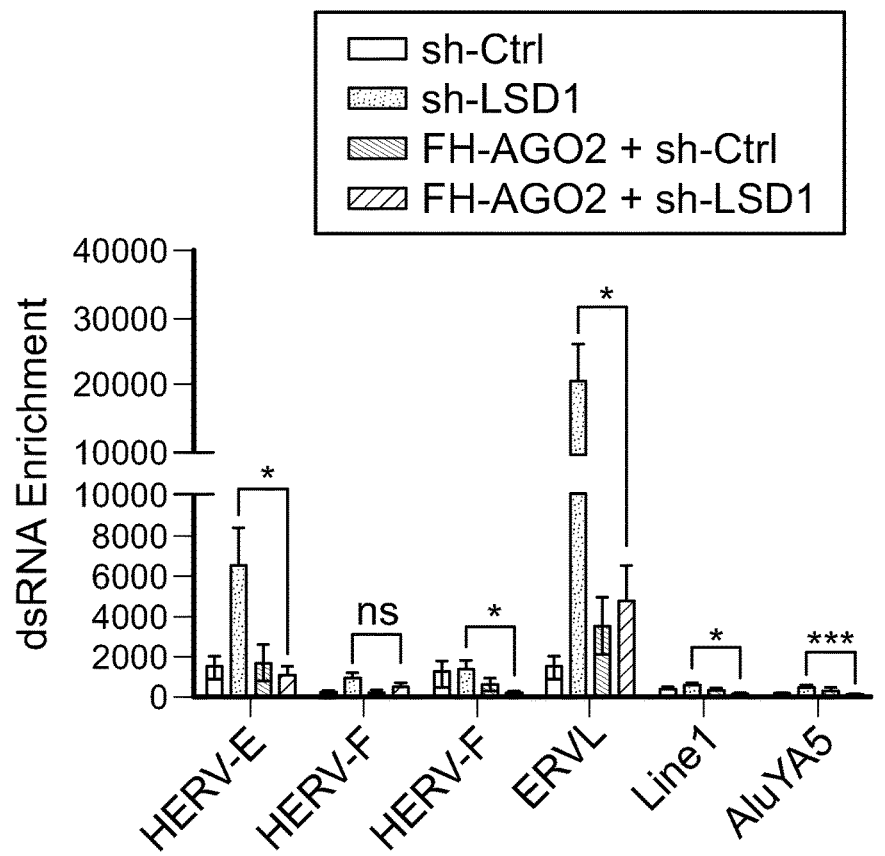
FIG. 4P is a bar graph showing dsRNA enrichment of retrotransposons (HERV-E, HERV-F, HERV-K, ERVL, Line1 and AluYA5) in MCF-7+sh-control cells, MCF-7+sh-LSD1 cells, MCF-7+FH-AGO2+sh-control cells, and MCF-7+FH-AGO2+sh-LSD1 cells. Error bars represent standard error of the mean (SEM) from five experiments. $*p<0.05$, $p<0.01$, $*p<0.001$, ns, not significant, as determined by unpaired t-test.
Figure 4Q:
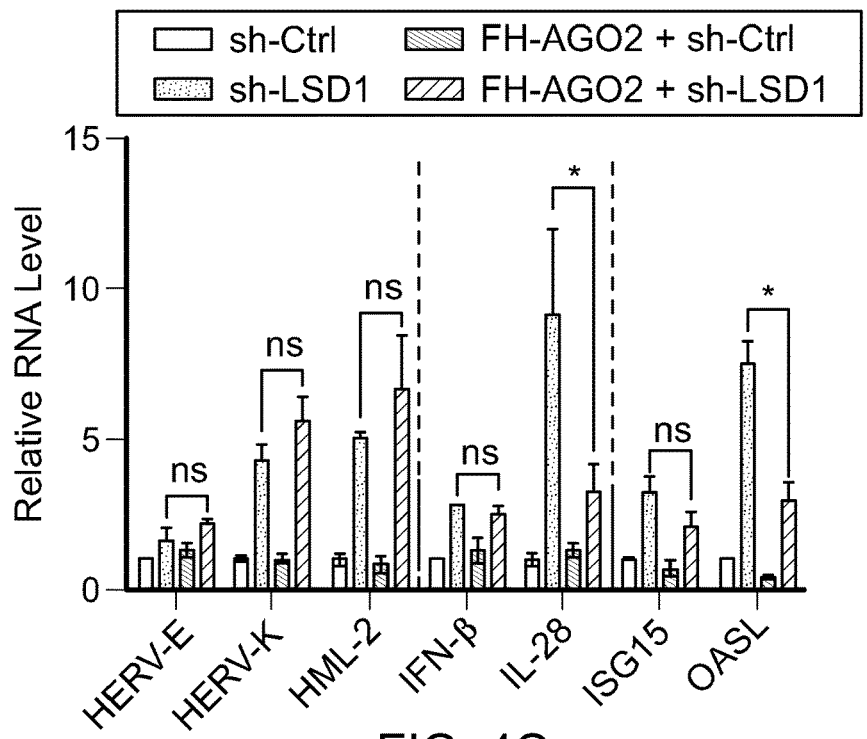
FIG. 4Q is a bar graph showing RNA levels of HERV-E, HERV-K, HML-2, IFN$\beta$, IL-28, ISG15 and OASL in MCF-7+sh-control cells, MCF-7+sh-LSD1 cells, MCF-7+FH-AGO2+sh-control cells, and MCF-7+FH-AGO2+sh-LSD1 cells. Error bars represent SD between triplicates. $p<0.05$, $p<0.01$, $*p<0.001$, ns, not significant, as determined by unpaired t-test.

Example 4. Decreased RISC Activity Due to Loss of LSD1 Reinforces Intracellular dsRNA Stress and Promotes IFN Activation Double stranded RNAs derived from ERV transcripts can go on to trigger interferon responses or be processed by the RISC complex to generate endogenous small interfering RNA (endo-siRNA) and RNA interference (see, e.g., Watanabe et al. (2008) Nature 453(7194): 539-543; Tam et al. (2008) Nature 453(7194): 534-538; and Okamura and Lai (2008) Nat Rev Mol Cell Biol 9(9): 673-678). Thus the steady state of dsRNA pool is determined not only by ERV transcription but also the action of the RISC complex. Next, it was determined whether LSD1 might also regulate the RISC complex to influence the steady state of dsRNA pool. LSD1 KD led to reduced protein expression of key components (DICER, AGO2 and TRBP2) of RISC (FIG. 4A). The regulation of RISC is dependent on LSD1 catalytic activity, as re-introduction of WT LSD1 but not LSD1-K661A back into LSD1 KD cells restored the protein expression of DICER, AGO2 and TRBP2 (FIG. 4A). In contrast, an obvious impact of LSD1 on the expression of Drosha, a crucial enzyme for miRNA biogenesis was not observed (FIG. 4B). Consistent with the above expression analysis, LSD1 KD also resulted in an elevated expression of a GFP reporter (FIGS. 4C, 4F and 4G), whose expression was under the control of let-7 miRISC activity (Qi et al. (2008) Nature 455(7211): 421-424). This finding suggests that RISC may also be involved in dsRNA stress and interferon responses. Indeed, when AGO2 expression was inhibited by shRNA, an increase was observed in dsRNA abundance derived from a few retrotransposons tested (FIG. 4H), leading to the induction of interferon-β and IL-28 as well as ISGs (FIGS. 4I and 4J). Similarly, inhibition of either DICER or TRBP2 also activated the interferon pathway (FIGS. 4K-4N). Therefore, disruption of the RISC complex, which perturbs intracellular dsRNA homeostasis, is sufficient to elicit IFN activation. To confirm that RISC complex is necessary for LSD1 inhibition-stimulated IFN activation, the reduction of RISC was compensated for by overexpressing AGO2 in LSD1 KD cells. AGO2 overexpression significantly diminished dsRNA accumulation caused by LSD1 inhibition, leading to a reduction in IFN activation (FIGS. 4O-4Q). Collectively, these findings suggest that, in addition to regulating ERV transcription, LSD1 also regulates the expression of RISC components and consequently RISC activity. Both actions of LSD1 contribute to its suppression of dsRNA accumulation.

Example 5. LSD1 Regulates AGO2 Protein Demethylation and Stability

Figure 5A:
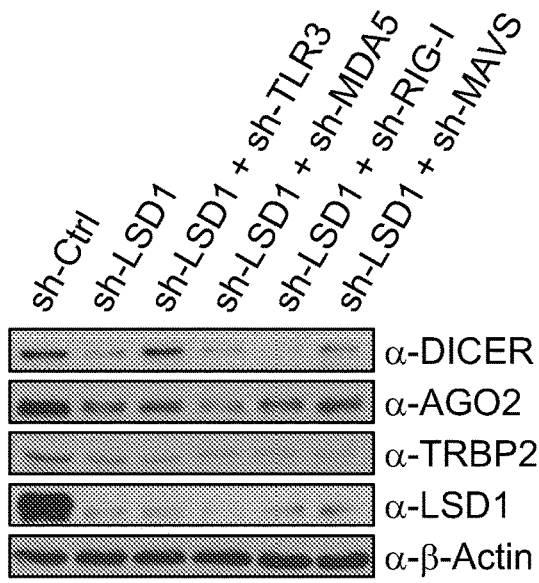
FIG. 5A is a picture of immunoblots showing the protein expression of core components of the RISC complex (DICER, AGO2 and TRBP2) in MCF-7+sh-C cells, MCF-7+sh-LSD1 cells, MCF-7+sh-LSD1+LSD1 cells, and MCF-7+sh-LSD1+LSD1-K661A cells. Actin was used as a control for protein level.
Figure 5B:
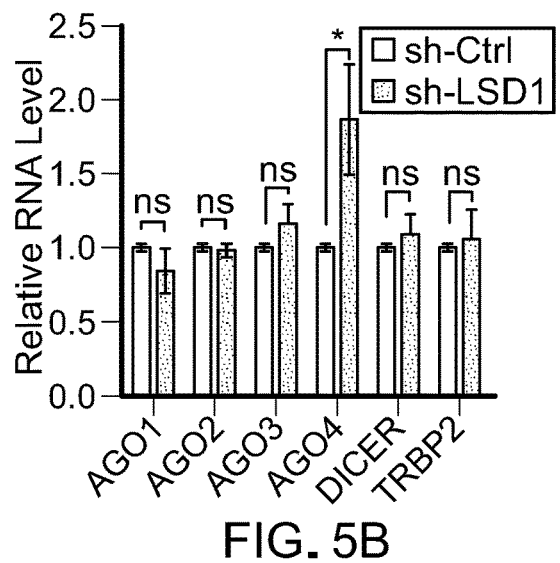
FIG. 5B is a bar graph showing RT qPCR analysis of AGO1-4, DICER and TRBP2 in control and LSD1 KD MCF-7 cells. Data was normalized to GAPDH and relative to sh-Ctrl. Error bars represent SEM from two experiments. $*p<0.05$, $**p<0.01$, ns, not significant, as determined by unpaired t-test.
Figure 5C:
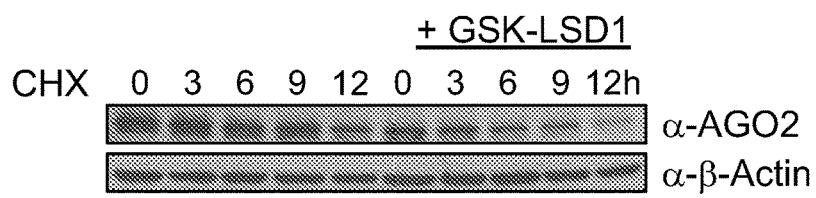
FIG. 5C is a picture of immunoblots showing the protein expression of AGO2 in MCF-7 cells treated with 50 µg/ml cycloheximide (CHX) in the presence of absence of 2 µM GSK-LSD1 at 0, 3, 6, 9, 12, hours. Actin was used as a control for protein level.
Figure 5D:
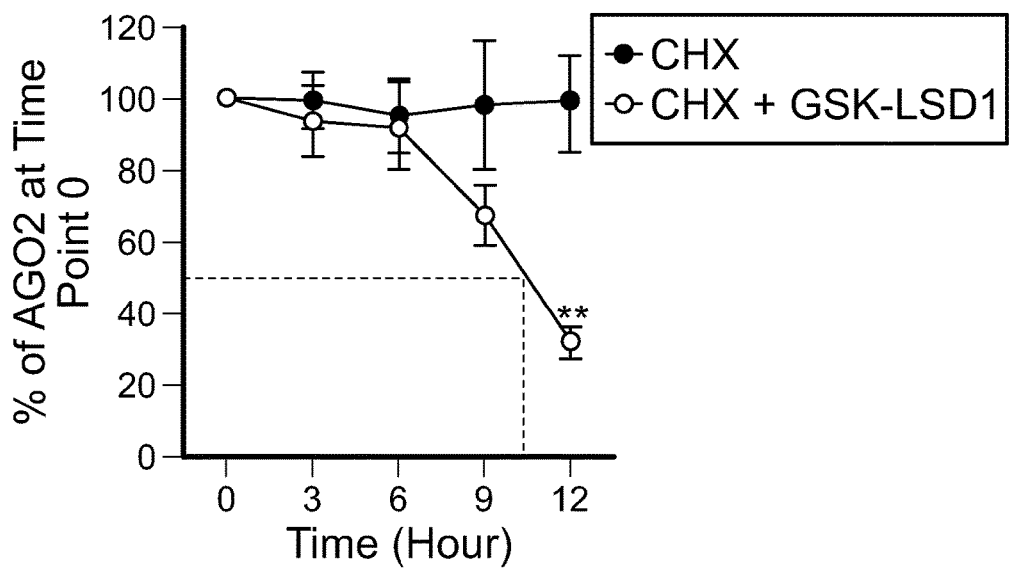
FIG. 5D is a graph showing the quantification of AGO2 signal from five experiments of MCF-7 cells treated with 50 µg/ml cycloheximide (CHX) in the presence of absence of 2 µM GSK-LSD1 at 0, 3, 6, 9, 12, hours. Error bars represent SEM from five experiments. $*p<0.05$, $**p<0.01$, ns, not significant, as determined by unpaired t-test.
Figure 5E:
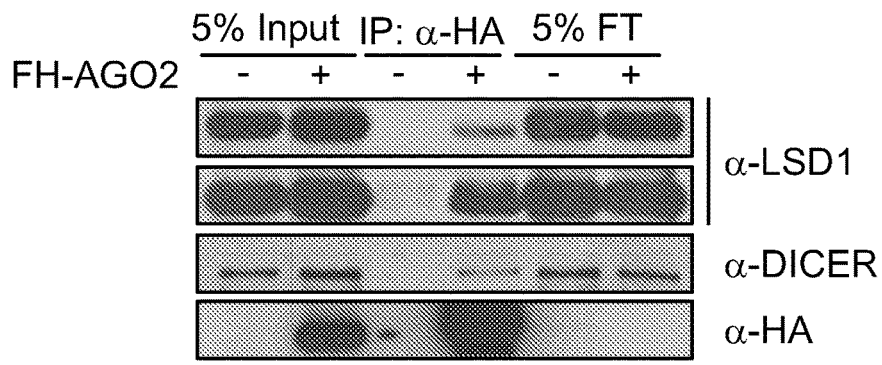
FIG. 5E is a picture of immunoblots showing the physical interaction between LSD1 and AGO2 by co-immunoprecipitation assay using whole cell lysate (WCL) of MCF-7 cells stably expressing FH-AGO2.
Figure 5F:
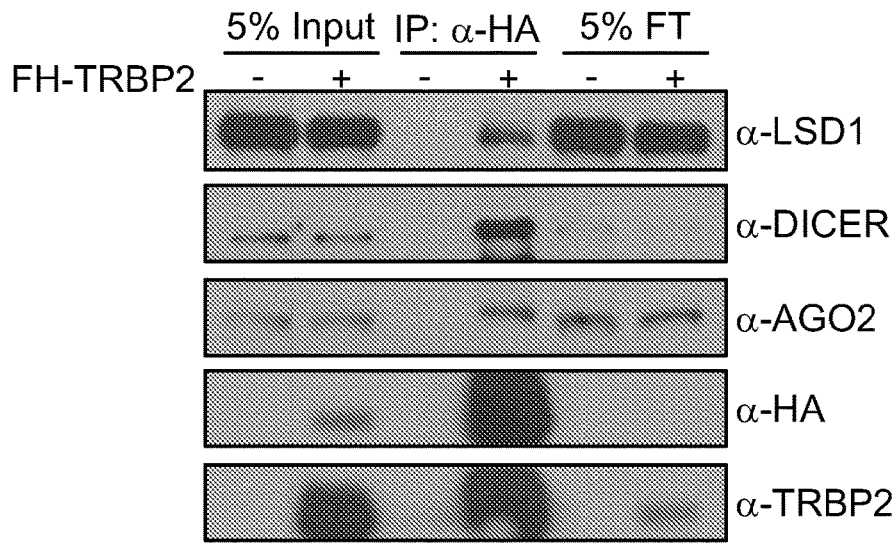
FIG. 5F is a picture of immunoblots showing the physical interaction between LSD1 and TRBMP2 by co-immunoprecipitation assay using whole cell lysate (WCL) of MCF-7 cells stably expressing FH-TRBP2.
Figure 5G:
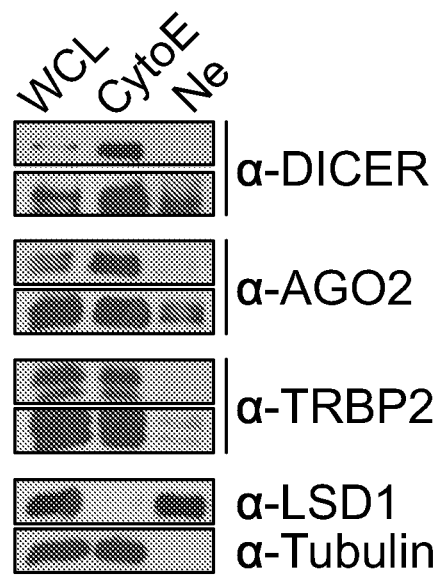
FIG. 5G is a picture of immunoblots showing protein expression of DICER, AGO2, TRBP2 and LSD1 in whole cell lysate (WCL), cytoplasm (CytoE) and nuclear lysate (NE).
Figure 5H:
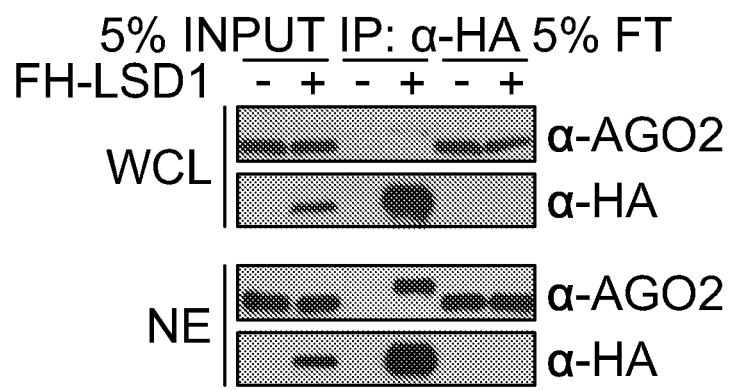
FIG. 5H is a picture of immunoblots showing the physical interaction between LSD1 and AGO2 by co-immunoprecipitation assay using nuclear lysate (NE) of MCF-7 cells stably expressing FH-LSD1.

In order to understand the mechanism by which LSD1 regulates the expression of RISC components, it was determined whether LSD1 inhibition-induced dsRNA stress, which was previously reported to decreases DICER protein expression (Wiesen and Tomasi, 2009), was involved. To this end, dsRNA stress was released by blocking its recognition by dsRNA sensors; TLR3 KD fully restored the protein level of DICER but not AGO2 or TRBP2 in LSD1 KD cells (FIG. 5A). This result confirmed that the regulation of DICER expression by LSD1 was indirect, through dsRNA stress, while it also suggested that the regulation of AGO2 and TRBP2 expression was likely independent of dsRNA stress. Given that AGO2 is the central component responsible for RNA cleavage, the role of AGO2 was investigated in greater detail. No alterations in AGO2 RNA levels were detected upon LSD1 KD (FIG. 5B), suggesting the regulation occurs at post-transcriptional level. Indeed, in a cyclohexamide (CHX) chase assay, a substantial decrease in AGO2 protein half-life was detected when LSD1 was inhibited (FIGS. 5C and 5D), implicating a regulatory role of LSD1 in AGO2 protein stability. Interestingly, LSD1 was found to physically interacted with RISC complex as shown by co-immunoprecipitation assays using whole cell lysate (WCL) of MCF-7 cells stably expressing FH-AGO2 or FH-TRBP2 (FIGS. 5E and 5F). In addition, this physical interaction likely occurred in the nucleus, because a portion of RISC components was detected in the nuclear fraction and LSD1 is exclusively localized in the nucleus (FIG. 5G). As further evidence, reciprocal co-immunoprecipitation with WCL or nuclear extract (NE) of MCF-7 cells stably expressing FH-LSD1 was performed, and a much stronger interaction between LSD1 and AGO2 in NE was detected compared with that in WCL (FIG. 3H).

Figure 5N:
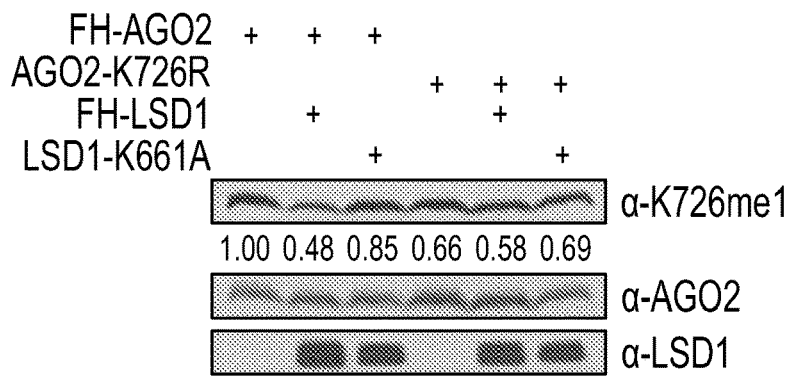
FIG. 5N is a picture of immunoblots showing AGO2 mono-methylation with immunoprecipitated proteins from MCF-7 cells.
Figure 5O:
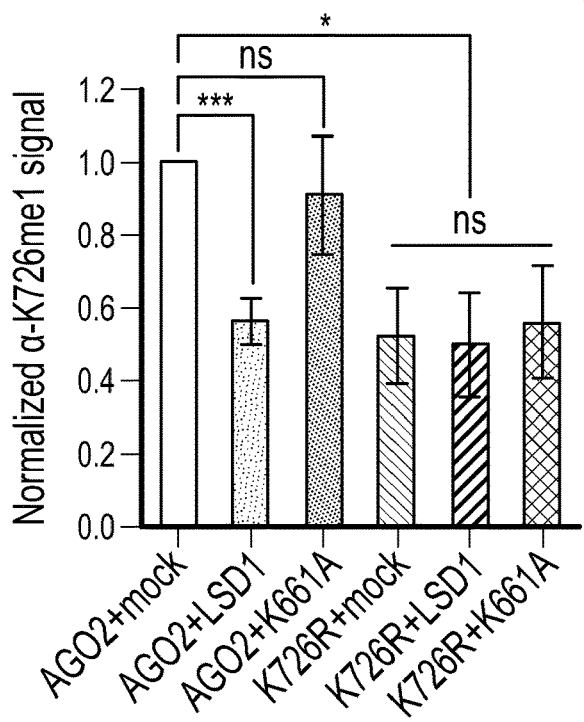
FIG. 5O is a bar graph showing signal intensities of AGO2 mono-methylation status at K726 in in vitro demethylation assay with immunoprecipitated proteins from MCF-7 cells. Error bars represent SD between duplicates in one experiment, or represent SEM from three experiments. *$p<0.05$, $p<0.01$, *$p<0.001$, ns, not significant, as determined by unpaired t-test.

To investigate whether LSD1 regulates AGO2 stability by controlling AGO2 methylation, overexpressed FH-AGO2 from MCF-7 cells with or without LSD1 inhibition were purified and used for mass spectrometry analysis. A lysine residue at position 726 (K726) was consistently mono-methylated when LSD1 was inhibited either by shRNA-mediated KD or by GSK-LSD1 (FIG. 5I). To validate this finding, an antibody was raised that preferentially recognized AGO2 peptides mono-methylated at K726 (K726me1) compared with un-methylated or di-methylated peptides (FIG. 5J). Furthermore, this antibody detected increased K726me1 on ectopically expressed AGO2 when LSD1 was inhibited, which can be abrogated by substituting K726 with arginine (K726R) or alanine (K726A) (FIGS. 5K and 5L). Importantly, this methyl specific antibody also detected more mono-methylation at K726 on endogenous AGO2 upon LSD1 inhibition (FIG. 5M), suggesting that LSD1 regulates AGO2 demethylation in vivo. To gain more insights into this regulation, an in vitro demethylation assay was performed using immunoprecipitated FH-LSD1, FH-LSD1-K661A (catalytically compromised LSD1), FH-AGO2 and FH-AGO2-K726R proteins purified from mammalian cells. FH-LSD1 but not FH-LSD1-K661A decreased K726me1 level on FH-AGO2, but had no observable effects on FH-AGO2-K726R (FIGS. 5N and 5O). Together, these results show that LSD1 regulates AGO2 demethylation at K726 in vivo, most likely through its catalytic activity against AGO2.

Figure 5P:
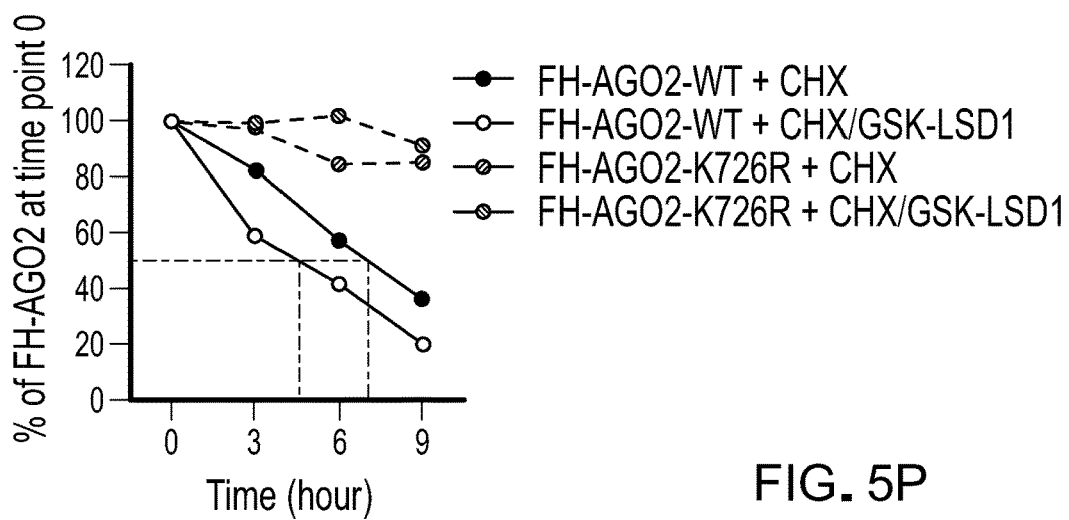
FIG. 5P is a graph showing protein stability of transiently expressed wild type FH-AGO2 and FH-AGO2-K726R in 293T cells measured using CHX chase assay in the presence or absence of 2 μM GSK-LSD1. The averaged AGO2 quantification from two experiments was shown.

To ascertain that K726 demethylation is responsible for sustaining AGO2 stability, its methylation was blocked by a substitution of lysine for arginine, and observed an increased stability for AGO2-K726R compared to wild-type AGO2 under physiological condition as well as in response to LSD1 inhibition (FIG. 5P). Taken together, LSD1 modulates AGO2 stability by regulating AGO2 demethylation at K726, which is required for basal RISC activity that critically controls intracellular dsRNA homeostasis. Inhibition of LSD1 disrupts the above pathway, in addition to causing ERV up-regulation, leading to dsRNA stress and IFN activation in human cancer cells.

Figure 6A:
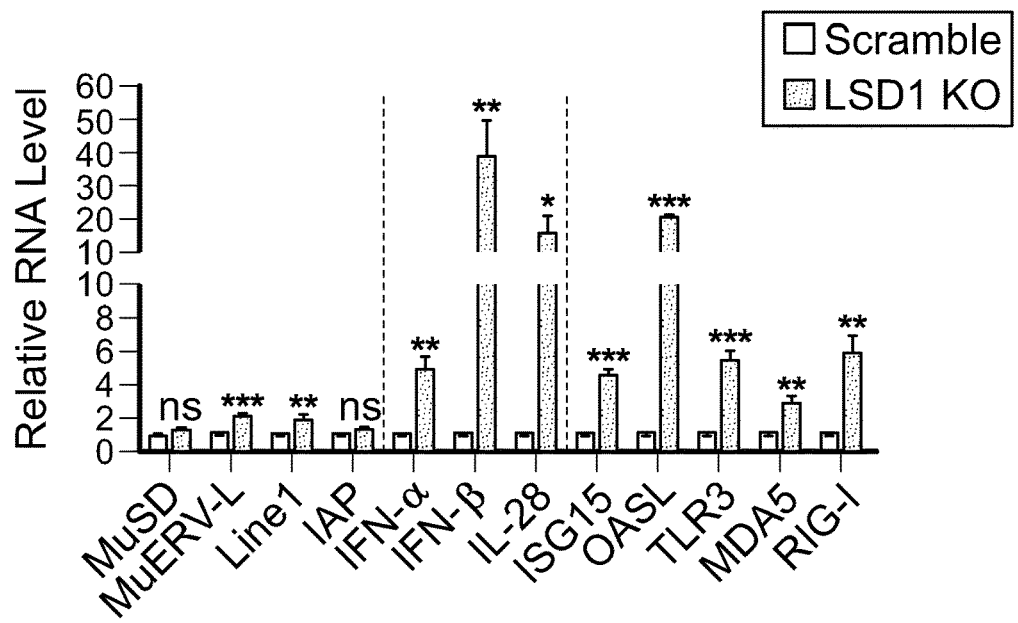
FIG. 6A is bar graph showing RT-qPCR analysis of selected retrotransposons (MuSD, MuERV-L, Line1 and IAP), IFNs (IFN-α, IFN-β and IL-28) and ISG15, OASL, TLR3, MDA5 and RIG-I in murine B16 melanoma cells transduced with gRNA against scramble (scramble) or LSD1 (LSD1 KO, clone g4-7) (n=2). Data was normalized to GAPDH relative to sh-Ctrl. Error bars represent SEM from two experiments. *$p<0.05$, $p<0.01$, *$p<0.001$, ****$p<0.0001$, ns, not significant, as determined by unpaired t-test.
Figure 6B:
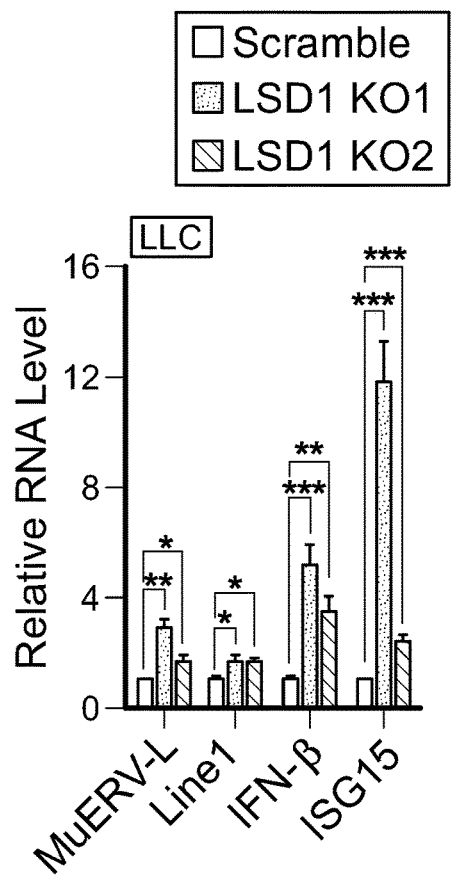
FIG. 6B is bar graph showing RT-qPCR analysis of MuERV-L, Line 1, IFN-β and ISG15 in murine Lewis lung carcinoma (LLC) cells transduced with shRNA against scramble (scramble), LSD1 KO1 and LSD1 KO2. The RT-qPCR data were normalized to GAPDH and then relative to scramble. Error bars represent SEM from three experiments. *$p<0.05$, $p<0.01$, *$p<0.001$, ns, not significant, as determined by unpaired t-test.
Figure 8A:
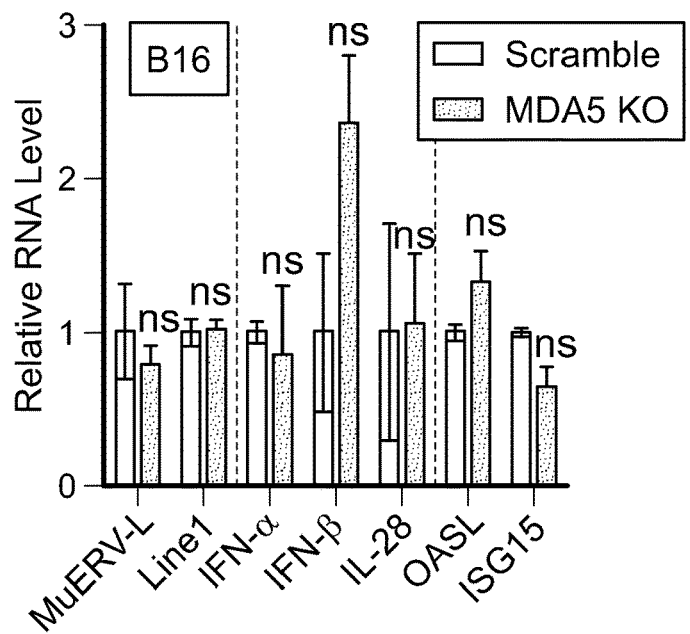
FIG. 8A is a bar graph showing RT-qPCR analysis of MuERV-L, Line1, IFN-α, IFN-β, IL-28, OASL and ISG15 in B16 scramble cells and MDA5 KO B16 cells. The RT-qPCR data were normalized to GAPDH and then relative to scramble. Error bars represent SD between duplicates. $*p<0.05$, $p<0.01$, $*p<0.001$, ns, not significant, as determined by unpaired t-test.
Figure 8B:
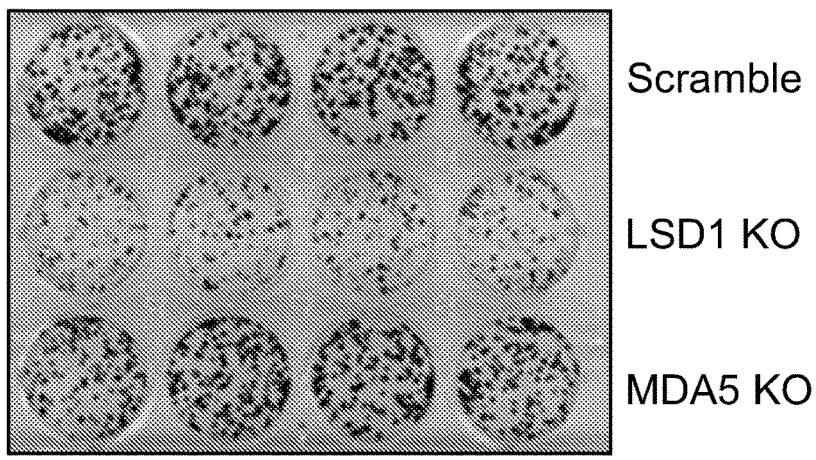
FIG. 8B is a picture of a crystal violet cell proliferation assay of B16 scramble cells, B16 LSD1 KO cells and B16 LSD1/MDA5 KO cells, after 6 days of growth before crystal violet staining.
Figure 8C:
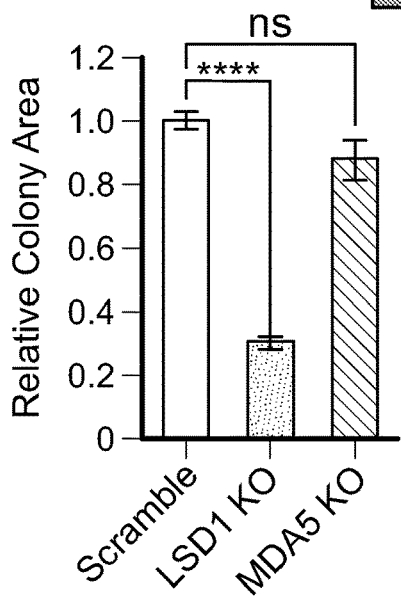
FIG. 8C is a bar graph showing the relative colony area of the proliferation assay of FIG. 8B relative to B16 scramble. Error bars represent SD between quadruplicates in one of two experiments. $*p<0.05$, $p<0.01$, $*p<0.001$, $****p<0.0001$, ns, not significant, as determined by unpaired t-test.
Figure 8D:
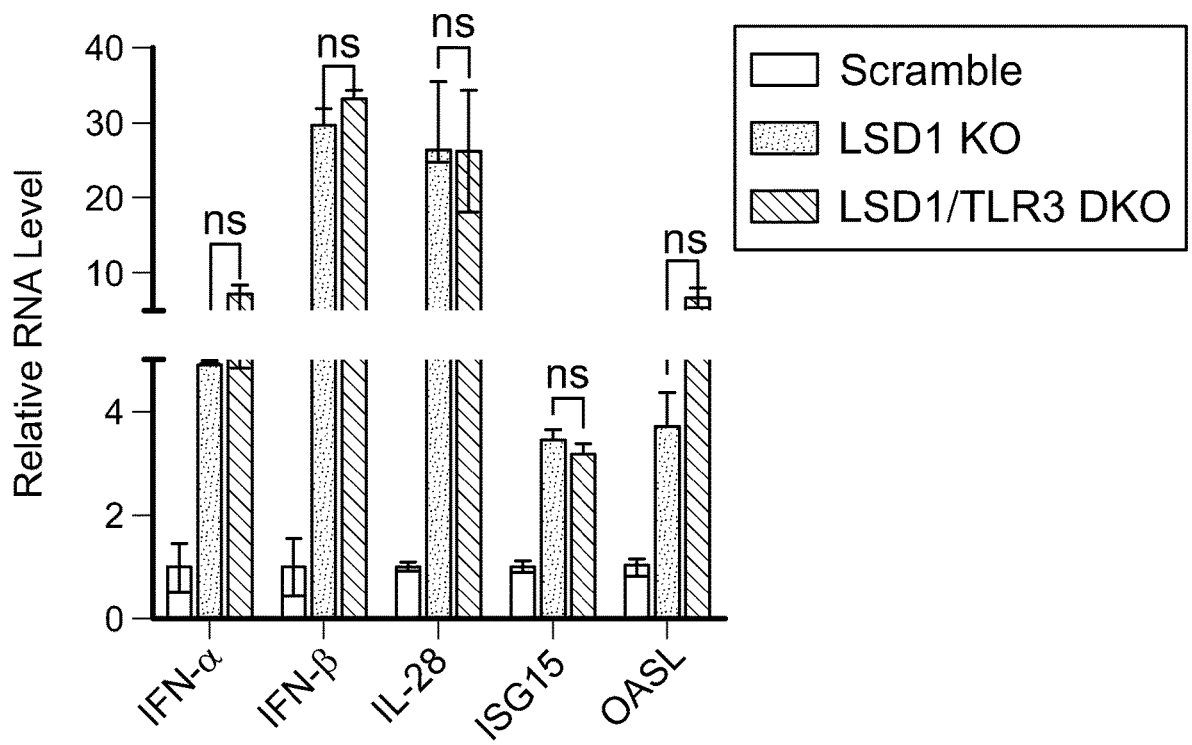
FIG. 8D is a bar graph showing RT-qPCR analysis of IFN-α, IFN-β, IL-28, OASL and ISG15 in B16 scramble cells and TLR3 KO B16 cells. The RT-qPCR data were normalized to GAPDH and then relative to scramble. Error bars represent SD between duplicates. $*p<0.05$, $p<0.01$, $*p<0.001$, ns, not significant, as determined by unpaired t-test.
Figure 8E:
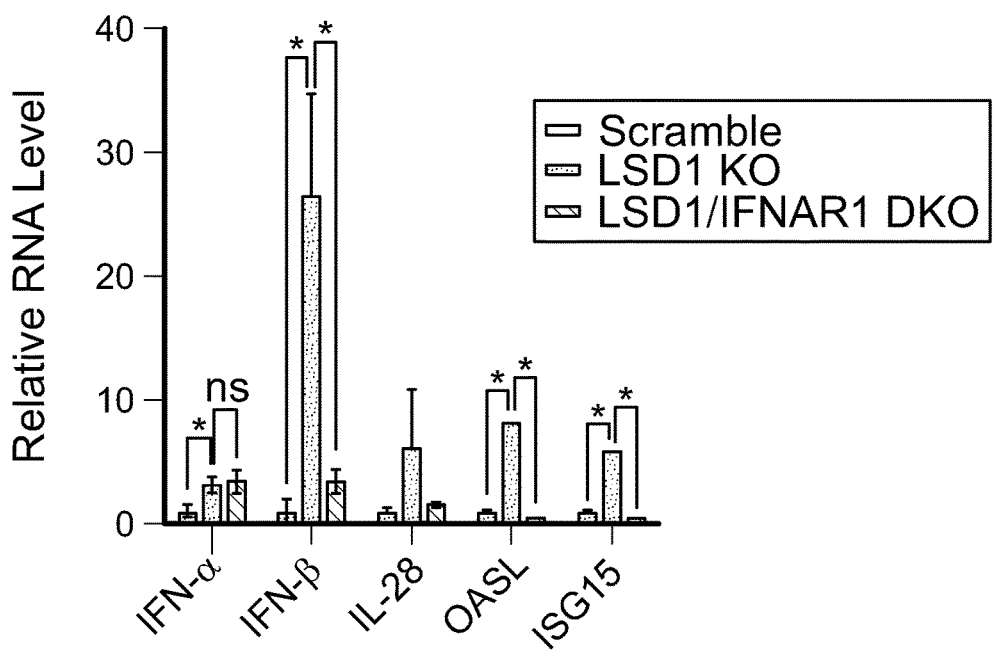
FIG. 8E is a bar graph showing RT-qPCR analysis of IFN-α, IFN-β, IL-28 OASL and ISG15 in B16 scramble cells, B16 LSD1 KO cells and B16 LSD1/IFNAR1 KO cells. Error bars represent SD between duplicates. $*p<0.05$, $p<0.01$, $*p<0.001$, ns, not significant, as determined by unpaired t-test.
Figure 8F:
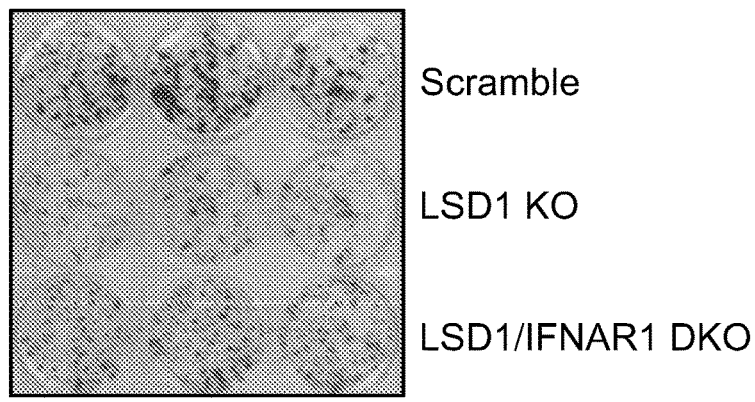
FIG. 8F is a picture of a crystal violet cell proliferation assay of B16 scramble cells, B16 LSD1 KO cells and B16 LSD1/IFNAR1 KO cells, after 6 days of growth before crystal violet staining.
Figure 8G:
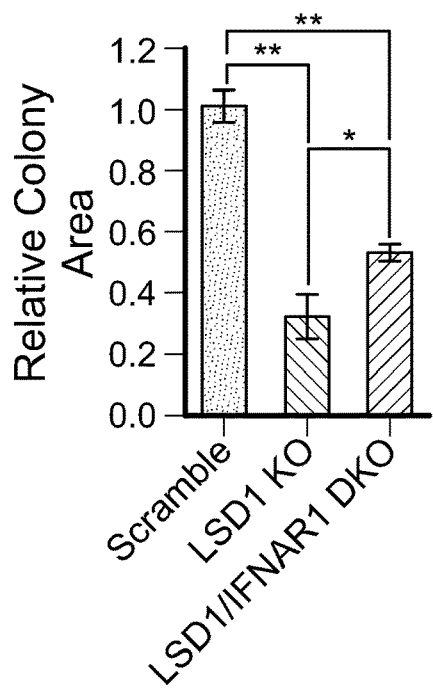
FIG. 8G is a bar graph showing the relative colony area of the proliferation assay of FIG. 8F relative to B16 scramble. Error bars represent SD between triplicates in one of two experiments. $*p<0.05$, $p<0.01$, $*p<0.001$, $****p<0.0001$, ns, not significant, as determined by unpaired t-test.
Figure 8H:
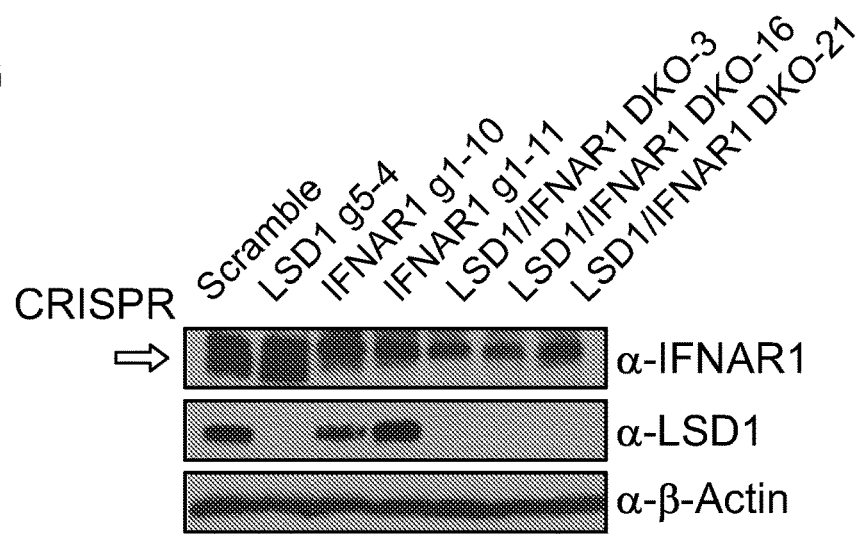
FIG. 8H is a picture of immunoblots showing IFNAR1 expression in CRISPR/Cas9-modified B16 cells as indicated.
Figure 8I:
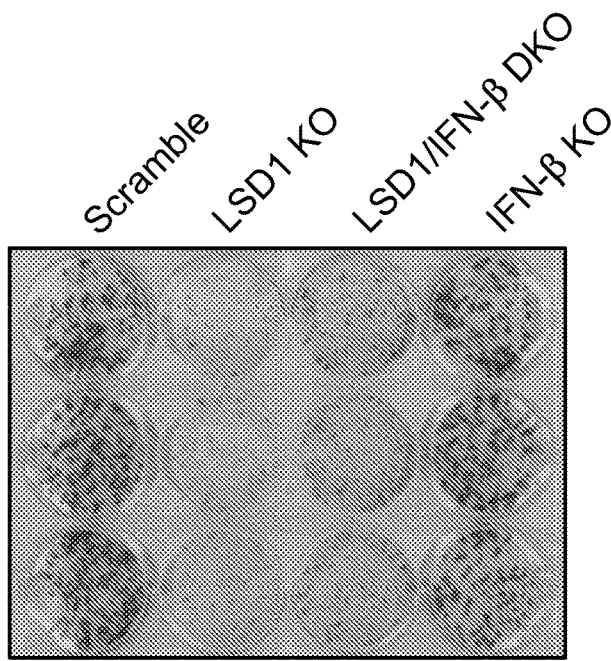
FIG. 8I is a picture of a crystal violet cell proliferation assay of B16 scramble cells, B16 LSD1 KO cells, B16 IFN-β KO cells and B16 LSD1/IFN-β KO cells, after 6 days of growth before crystal violet staining.
Figure 8J:
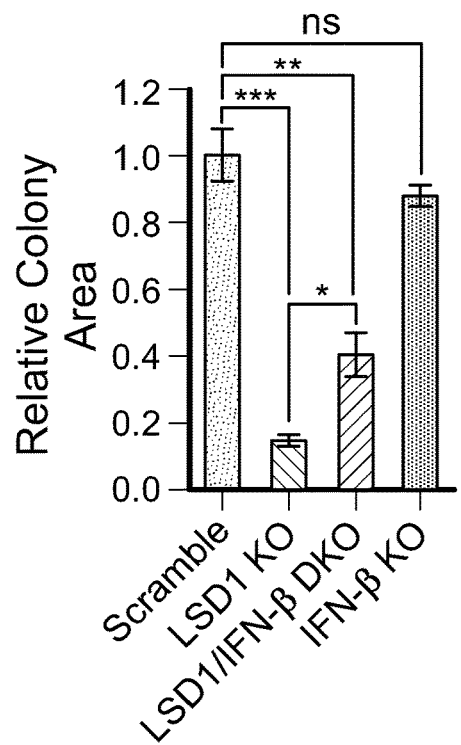
FIG. 8J is a bar graph showing the relative colony area of the proliferation assay of FIG. 8J relative to B16 scramble. Error bars represent SD between triplicates in one of two experiments. $*p<0.05$, $p<0.01$, $*p<0.001$, $****p<0.0001$, ns, not significant, as determined by unpaired t-test.

Example 6. LSD1 Abrogation-Induced dsRNA Stress Suppresses Tumor Cell Growth In Vitro To address the biological consequence of LSD1 inhibition-induced dsRNA stress, and in particular, whether dsRNA stress-triggered cellular responses can be harnessed for anti-tumor immunity, C57BL/6 syngeneic mouse models were used. First, it was determined whether the previous observations made in human cells could be recapitulated in mouse cells. Lewis lung carcinoma (LLC), D4.m3A cells and B16 melanoma cells are all mouse tumor cell lines on the C57BL/6 genetic background with poor immunogenicity (Lechner et al. (2013) J Immunother 36(9): 477-489). LSD1 inhibition by Clustered Regularly Short Palindromic Repeats (CRISPR)/Cas9-mediated gene deletion resulted in upregulation of retrotransposons and activation of IFN pathways in those lines (FIGS. 6A-6D and 7A-7F), which recapitulated the findings in human cells described in Examples 2-5. In addition, dsRNA accumulation was observed in response to LSD1 loss (FIGS. 6E-6G). Taken together, the present results showed that LSD1 restrained intracellular dsRNA stress and interferon activation in both human and mouse cancer cells. LSD1 inhibition either by shRNA-mediated KD or by CRISPR/Cas9-mediated KO resulted in compromised growth of B16 cells in vitro (FIGS. 6H-6K), consistent with what has been reported previously for LSD1 in other cell lines (see, e.g., Zhang et al. (2013) Cell Rep 5(2): 445-457; Harris et al. (2012) Cancer Cell 21(4): 473-487; and Mohammad et al. (2015) Cancer Cell 28(1): 57-69). To determine whether the growth phenotype is due to LSD1 abrogation-induced dsRNA stress, the dsRNA sensor MDA5 or TLR3 was deleted in LSD1 KO B16 cells (FIGS. 6L and 6M). The deletion of MDA5 significantly, albeit partially, rescued the growth defect of LSD1 KO B16 cells (FIGS. 6N and 6O), suggesting that the growth defect was in part due to the dsRNA stress induced by LSD1 deletion. At the molecular level, the induction of interferons and ISGs, but not dsRNA abundance, was significantly diminished in the LSD1/MDA5 double knockout (DKO) cells (FIGS. 6P and 6Q). As a control, deletion of MDA5 alone had minimal effects on B16 cell growth and interferon activation (FIGS. 8A-C). No apparent rescue was observed by TLR3 genetic deletion (FIG. 8D), which could be explained by the observation that TLR3 was not or minimally expressed in B16 cells (data shown). Therefore, similar to human cells, removal of dsRNA sensors blocks downstream interferon activation triggered by dsRNA stress caused by LSD1 loss.

Figure 8K:
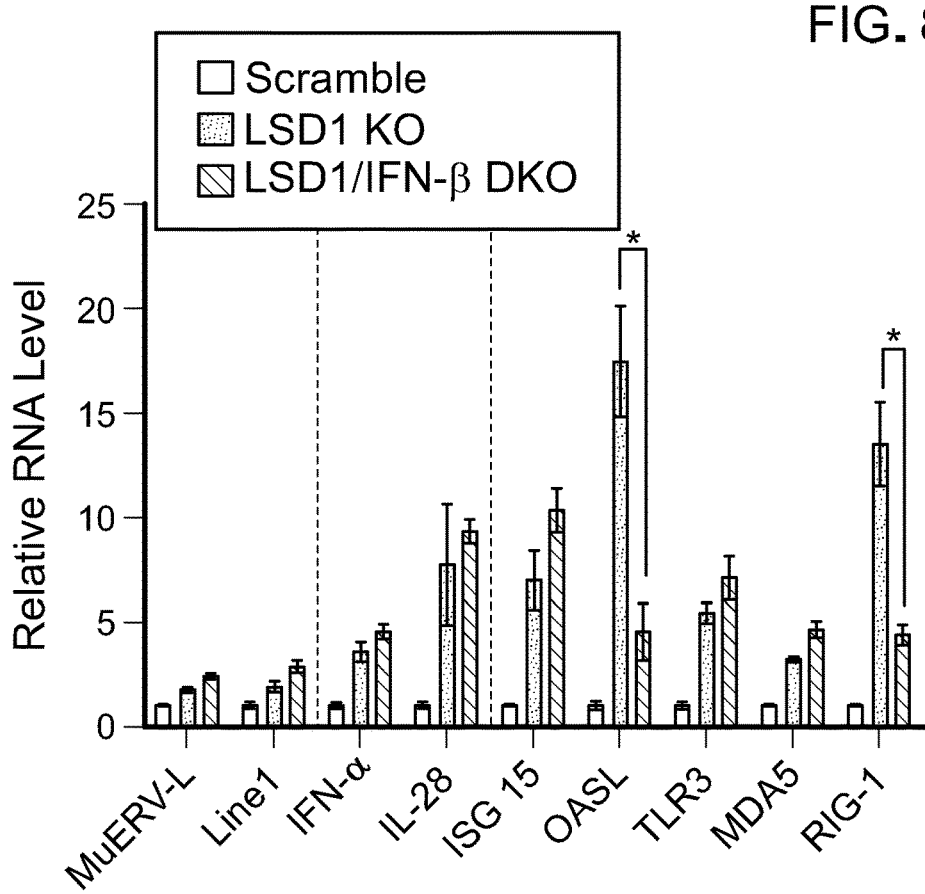
FIG. 8K is a bar graph showing RT-qPCR analysis of MuERV-L, Line1, IFN-α, IL-28, ISG15, OASL, TLR3, MDA5, RIG-I in B16 scramble cells and LSD1/IFN-β KO B16 cells. The RT-qPCR data were normalized to GAPDH and then relative to scramble. Error bars represent SD between duplicates. $*p<0.05$, $p<0.01$, $*p<0.001$, ns, not significant, as determined by unpaired t-test.
Figure 8L:
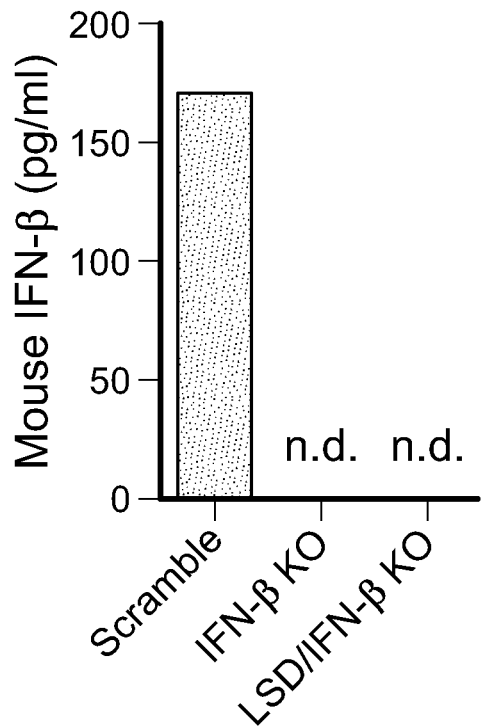
FIG. 8L is bar graph showing mouse IFN-γ levels in scramble, IFN-β KO, LSD1/IFN-β DKO B16 cells challenged by poly(I:C), as determined by enzyme-linked immunosorbent assay (ELISA).

A similar rescue effect on cell growth by blocking IFN pathway in LSD1 KO B16 cells. Indeed, the deletion of IFNAR1, a crucial subunit for type 1 IFN receptor, also diminished IFN activation and partially restored cell growth (FIGS. 8E-J), in line with the suppressive effect of type 1 IFN on cell growth. In addition, IFN-β deletion also displayed a similar, albeit milder, rescue effect (FIGS. 8K-L). LSD1-abrogation in mouse cancer cells causes dsRNA stress and subsequent IFN activation, leading to cell growth inhibition in vitro.

Example 7. LSD1 Abrogation-Induced dsRNA Stress Triggers Anti-Tumor T Cell Immunity In Vivo The role of LSD1 in basic cancer biology has been previously reported, which includes sustaining cancer stem cell self-renewal and suppressing differentiation, promoting cell proliferation, enhancing an epithelial-to-mesenchymal transition (EMT) as well as modulating metastasis (reviewed in Hosseini and Minucci, 2017). However, those studies used either in vitro cell culture systems or transplanted human cancer cells into immuno-deficient, in which the role of LSD1 in regulating tumor response to host immunity was not possibly to be explored.

Figure 9A:
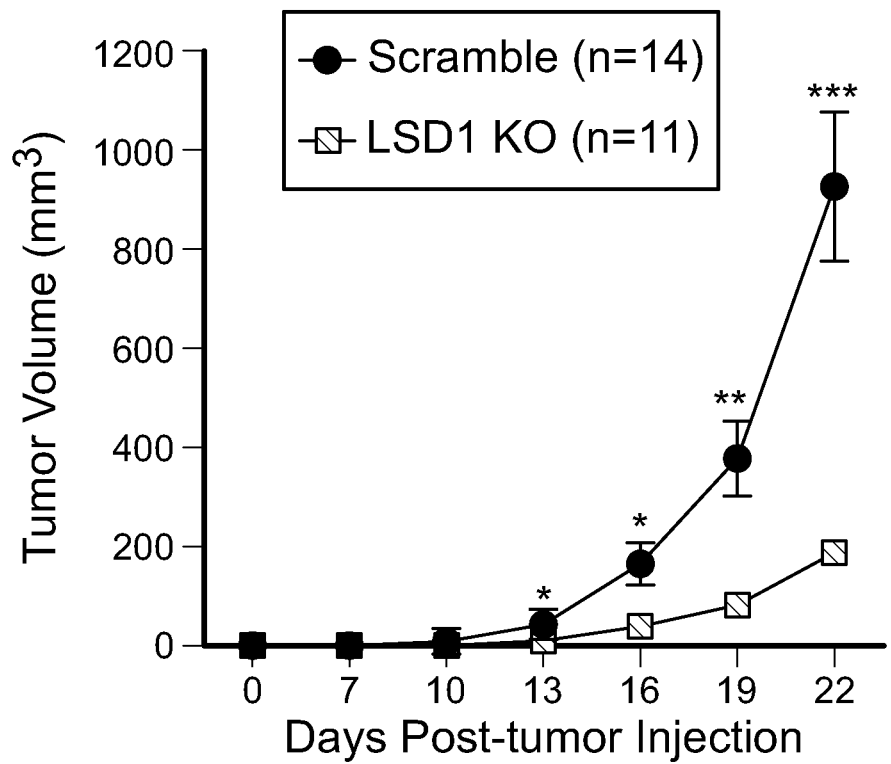
FIG. 9A is a line graph showing tumor growth of immunocompetent mice inoculated with 500 k scramble (n=14) or LSD1 KO B16 cells (n=1). Error bars represent SEM of individual mice in one experiment. Data represents two independent experiments. $*p<0.05$, $p<0.01$, $*p<0.001$, $****p<0.0001$, ns, not significant, as determined by unpaired t-test.
Figure 9B:
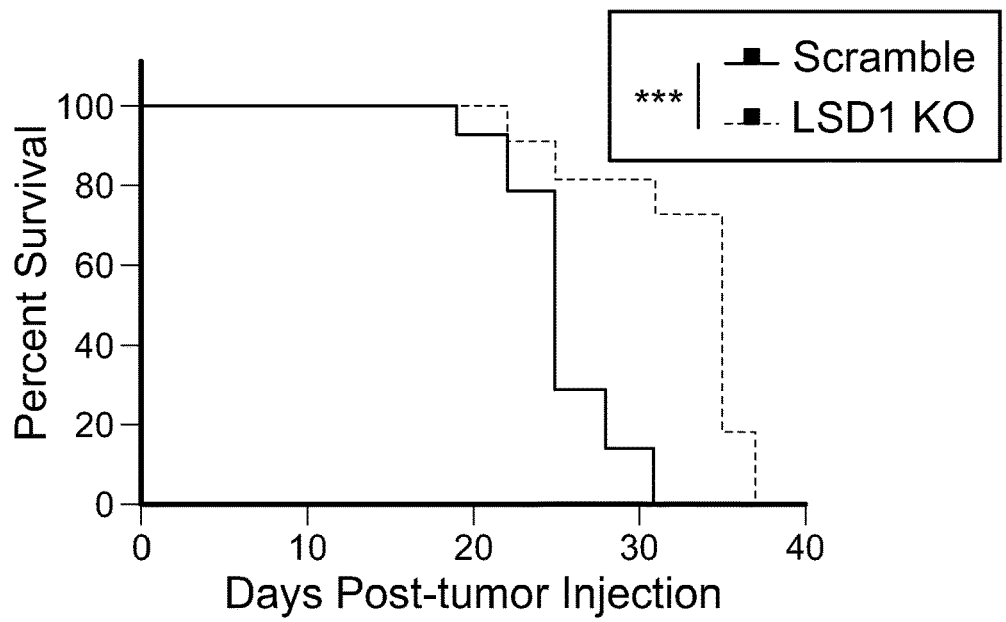
FIG. 9B is a line graph showing survival of immunocompetent mice inoculated with 500 k scramble or LSD1 KO B16 cells. Data represents two independent experiments. Error bars represent SEM of individual mice in one experiment. $*p<0.05$, $p<0.01$, $*p<0.001$, $****p<0.0001$, ns, not significant, as determined by log-rank test.
Figure 9C:
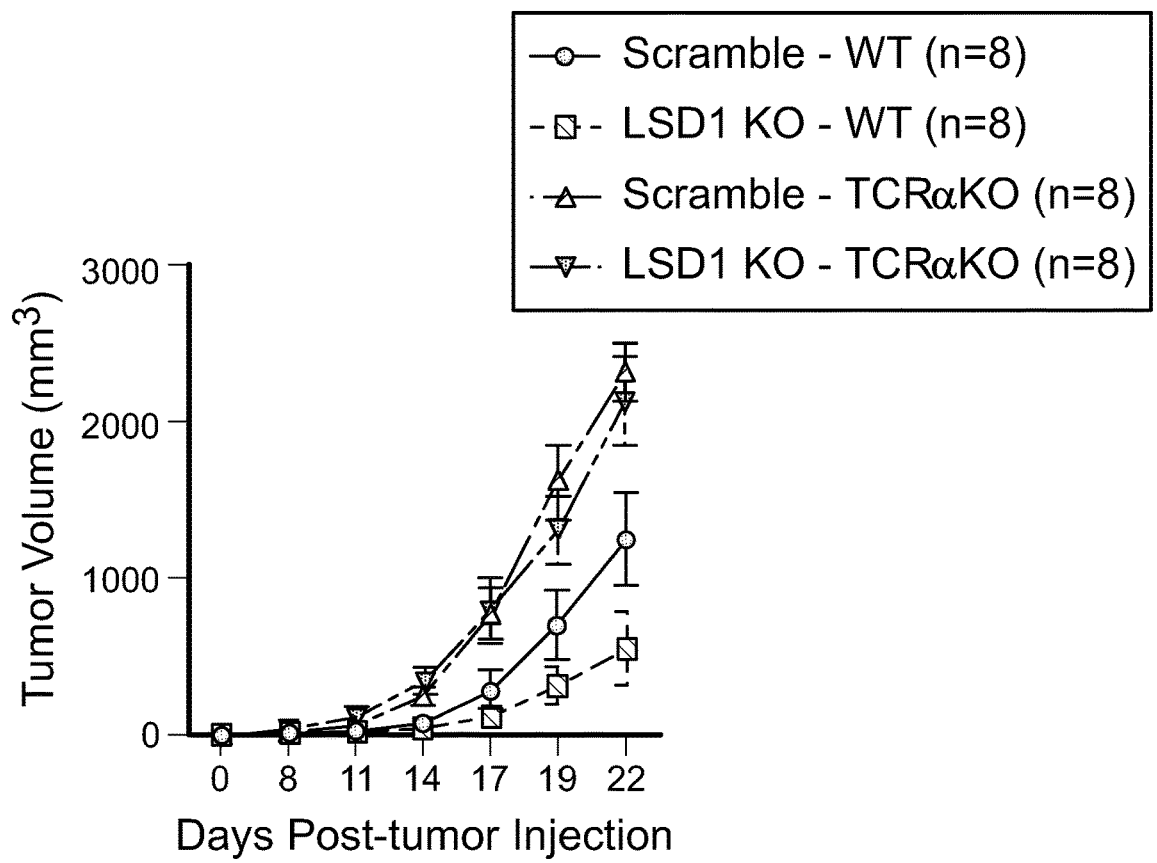
FIG. 9C is a line graph showing tumor growth of immunodeficient mice (TCRα KO) or immunocompetent mice inoculated with 500 k scramble or LSD1 KO B16 cells. Error bars represent SEM of individual mice in one experiment. Data represents two independent experiments. $*p<0.05$, $p<0.01$, $*p<0.001$, $****p<0.0001$, ns, not significant, as determined by ANOVA.
Figure 9D:
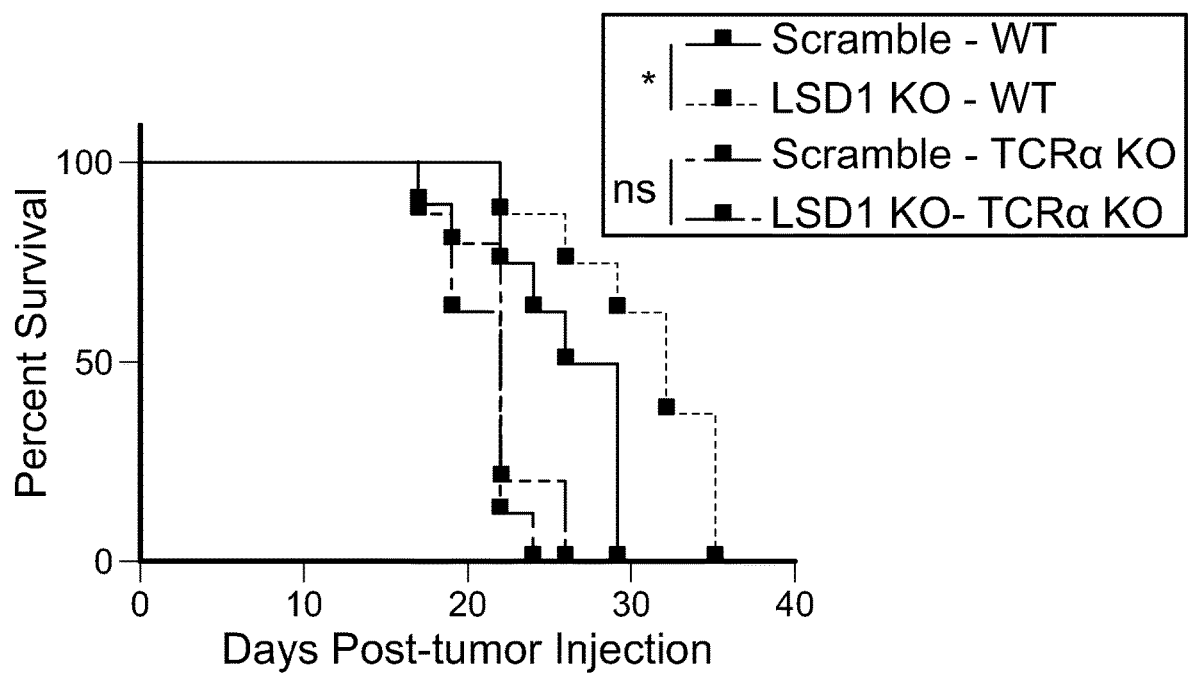
FIG. 9D is a line graph showing survival of immunodeficient mice (TCRα KO) or immunocompetent mice inoculated with 500 k scramble or LSD1 KO B16 cells. Data represents two independent experiments. Error bars represent SEM of individual mice in one experiment. *p<0.05, p<0.01, *p<0.001, ****p<0.0001, ns, not significant, as determined by log-rank test.

To determine whether LSD1 deletion-induced dsRNA stress and interferon activation might trigger anti-tumor immunity in vivo, C57BL/6 WT mice were subcutaneously inoculated with B16 cells. The deletion of LSD1 in B16 cells significantly inhibited tumor growth in vivo (FIGS. 9A and 9B), in agreement with the previous in vitro observations (FIGS. 6H-K). To distinguish the role of LSD1 in regulating tumor autonomous growth versus host anti-tumor immunity, both immunocompetent (WT) and immunodeficient, T-cell receptor α (TCRα) KO, mice were used for subcutaneous tumor growth assays. Although LSD1 deletion inhibited B16 tumor growth in WT mice, there was no growth difference between LSD1 KO and control B16 tumors in the TCRα-deficient mice (FIGS. 9C and 9D). This result indicated that LSD1 inhibition in tumor cells elicits potent anti-tumor T cell immunity in vivo, rather than affecting tumor autonomous growth, to restrain tumor burden. The reason for the loss of autonomous growth defects of LSD1 KO cells in vivo is not known at the present time, however, this could be due to the possibility that host somatic cells, such as stromal cells in the tumor microenvironment, foster cell proliferation and tumor growth by secreting growth-promoting factors that may substitute the need for LSD1 in cell proliferation.

Figure 9E:
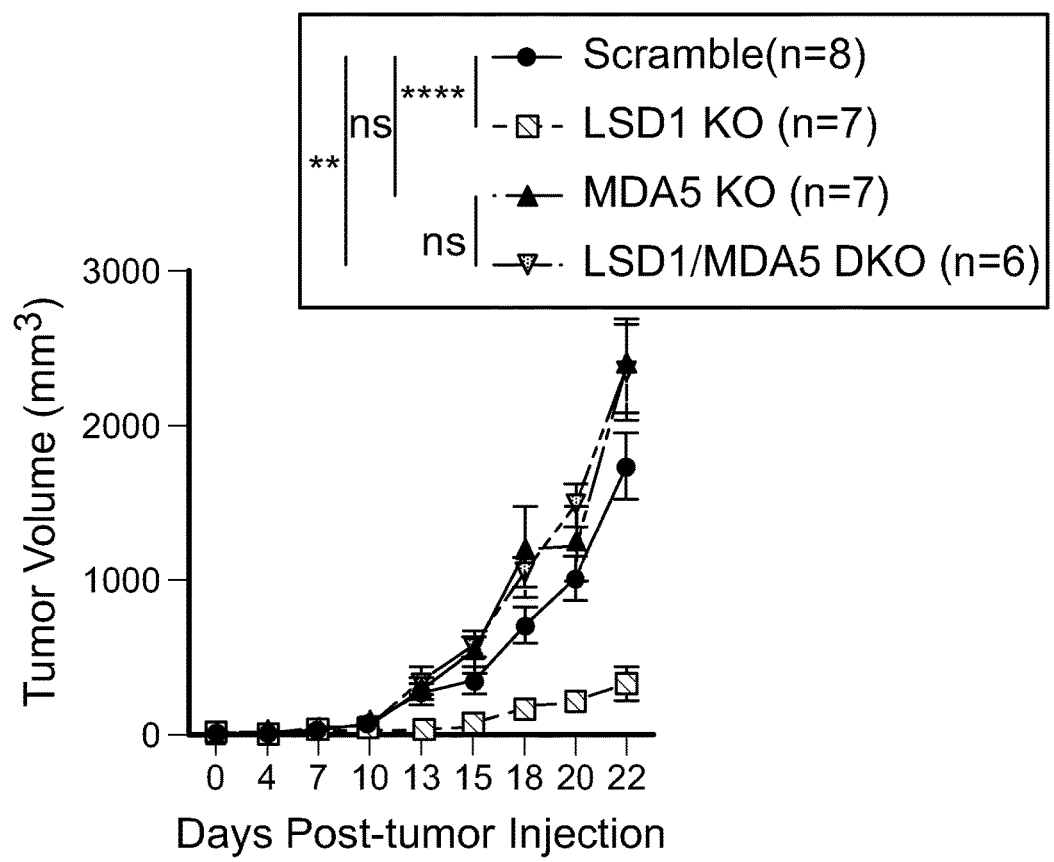
FIG. 9E is a line graph showing tumor growth of immunocompetent mice inoculated with 500 k scramble B16 cells, LSD1 KO B16 cells, MDA5 KO B16 cells, or LSD1/MDA5 DKO B16 cells. Error bars represent SEM of individual mice in one experiment. Data represents two independent experiments. *p<0.05, p<0.01, *p<0.001, ****p<0.0001, ns, not significant, as determined by ANOVA.
Figure 9F:
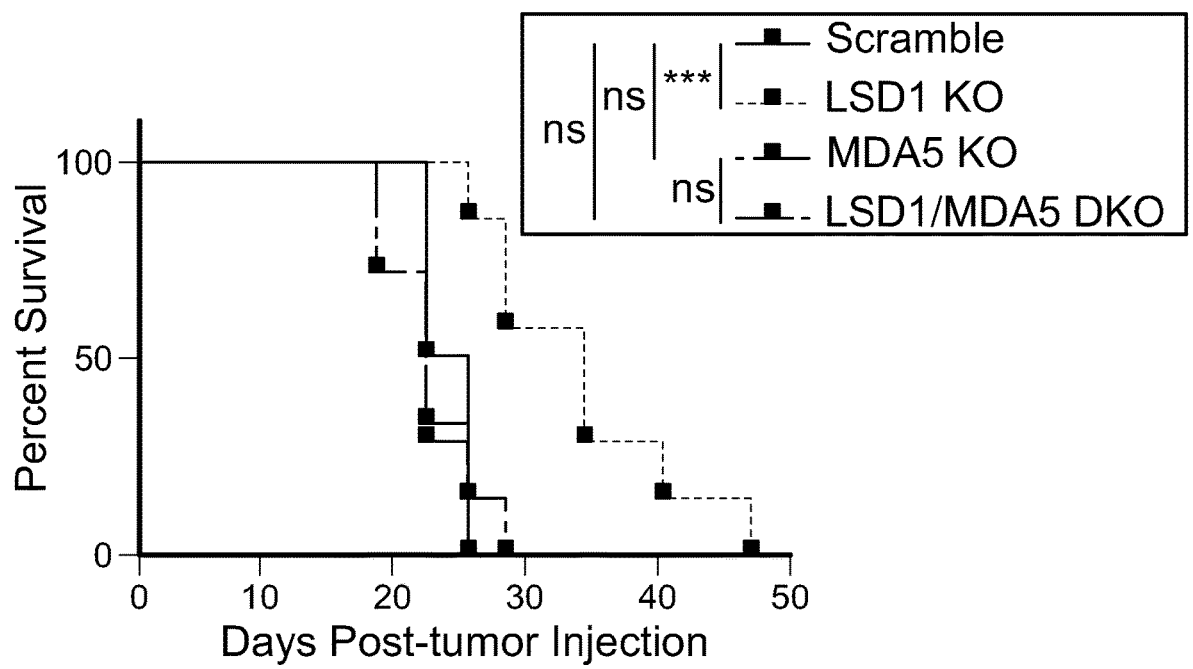
FIG. 9F is a line graph showing survival of immunocompetent mice inoculated with 500 k scramble B16 cells, LSD1 KO B16 cells, MDA5 KO B16 cells, or LSD1/MDA5 DKO B16 cells. Data represents two independent experiments. Error bars represent SEM of individual mice in one experiment. *p<0.05, p<0.01, *p<0.001, ****p<0.0001, ns, not significant, as determined by log-rank test.
Figure 9G:
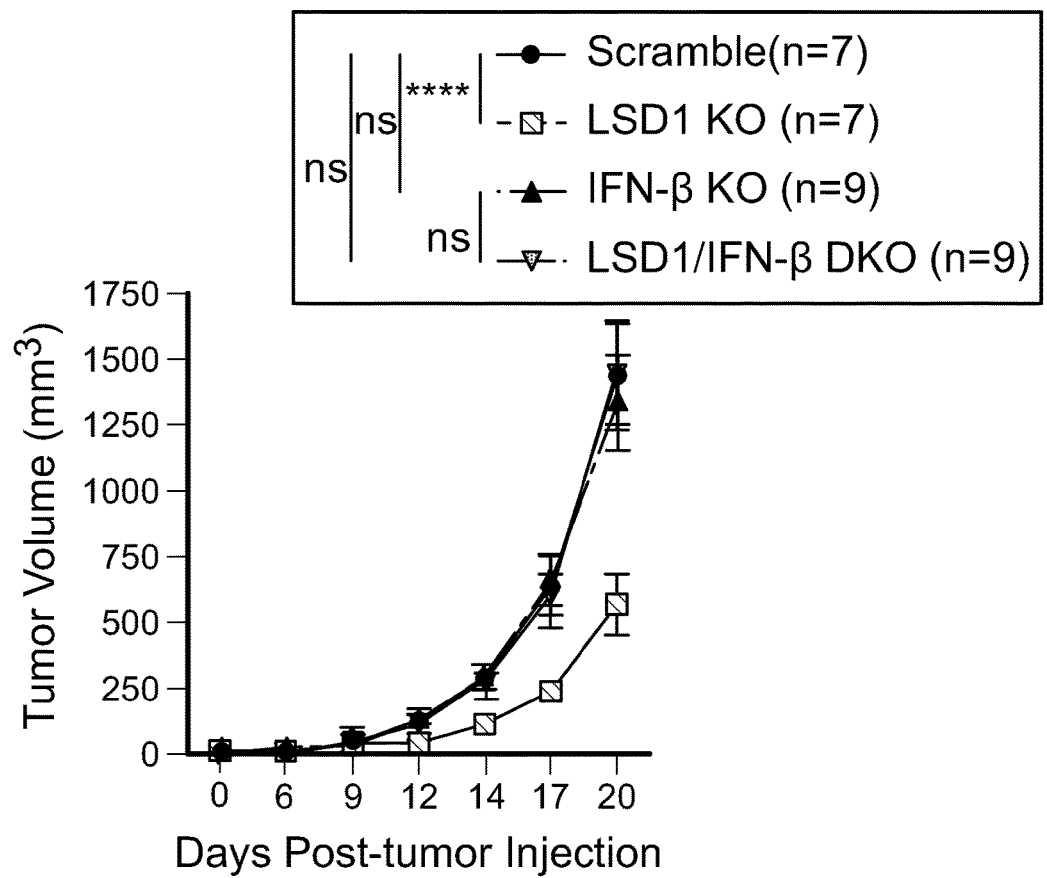
FIG. 9G is a line graph showing tumor growth of immunocompetent mice inoculated with 500 k scramble B16 cells, LSD1 KO B16 cells, IFN-β KO B16 cells, or LSD1/IFN-β DKO B16 cells. Error bars represent SEM of individual mice in one experiment. Data represents two independent experiments. *p<0.05, p<0.01, *p<0.001, ****p<0.0001, ns, not significant, as determined by ANOVA.
Figure 9H:
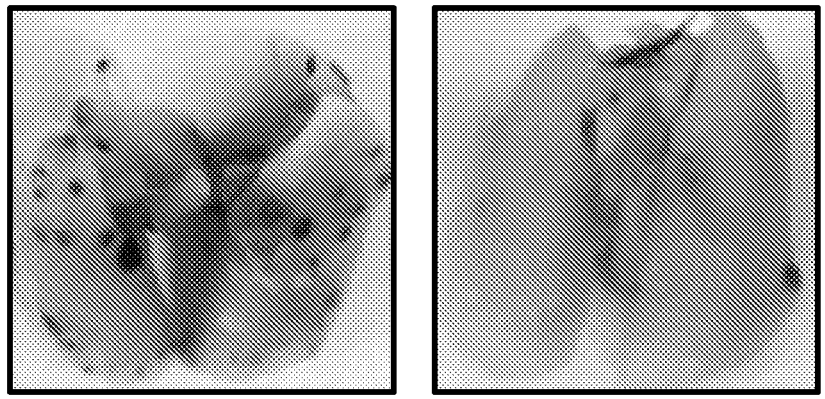
FIG. 9H is representative images of lung metastasis in immunocompetent mice receiving 200 k scramble or LSD1 KO B16 cells intravenously taken 14 days post-injection.
Figure 9I:
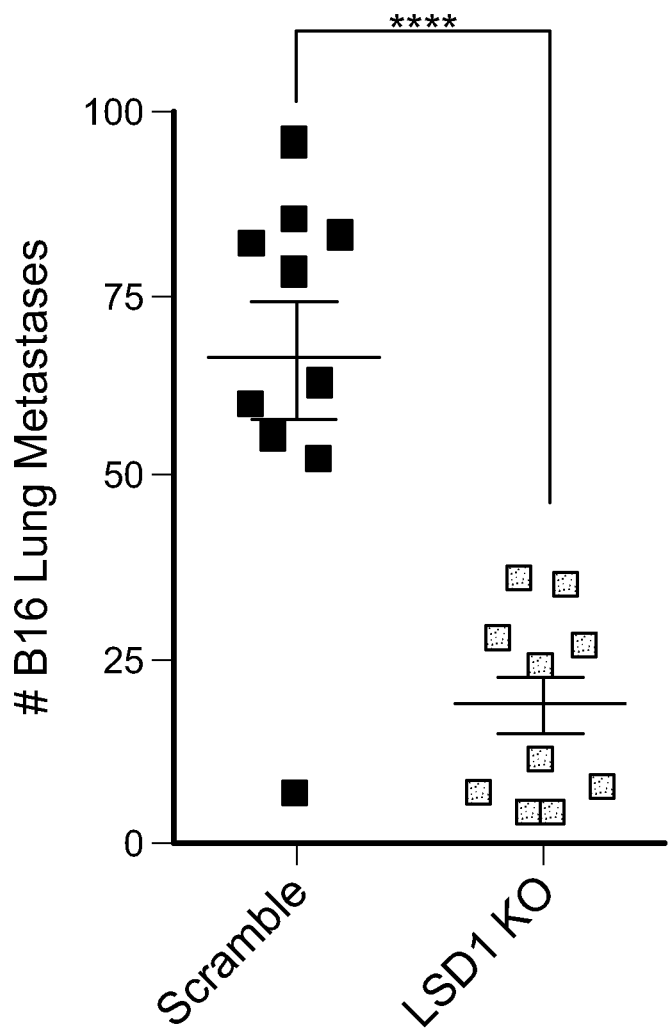
FIG. 9I is a dot plot showing the quantification of lung metastasis immunocompetent mice receiving 200 k scramble or LSD1 KO B16 cells intravenously.

To confirm that host anti-tumor T cell immunity was boosted by tumor-intrinsic dsRNA stress as elucidated above, tumor growth of LSD1 KO and LSD1/MDA5 DKO B16 cells was compared in immunocompetent mice. Deletion of MDA5 was sufficient to diminish LSD1 inhibition-elicited anti-tumor immunity, evidenced by the finding that LSD1/MDA5 DKO tumors displayed similar growth ability as control tumors targeted with scrambled gRNA or MDA5 single KO tumors (FIGS. 9E and 9F). To further examine whether MDA5-associated type 1 IFN response is essential for LSD1 inhibition-elicited anti-tumor immunity, IFN-β production was abrogated in LSD1 KO B16 tumors (FIGS. 6L and 8L), which completely reverse growth inhibition to a level comparable to that of the control of IFN-β single KO tumors in the immunocompetent mice (FIG. 9G). In addition to controlling tumor growth, LSD1 inhibition resulted in a marked reduction in B16 tumor metastasis (FIGS. 9H and 9I). Thus, LSD1 inhibition-caused dsRNA stress and resultant IFN response sensitize tumors to T cell immunity, likely by increasing tumor immunogenicity.

This finding is consistent with previous reports demonstrating that LSD1 promotes cell proliferation in cell culture and in mouse xenograft models (Zhang et al. (2013) Cell Rep 5(2): 445-457; and Mohammad et al. (2015) Cancer Cell 28(1): 57-69). However, since these studies transplanted human tumor cells into immunodeficient mice, the potential impact from tumor microenvironments, in particular immune cells, was not taken into consideration. When syngeneic immunodeficient and immunocompetent mice were used in parallel, LSD1 was found not to be required for B16 tumor autonomous growth in vivo, revealing that LSD1 inhibition mainly elicits a potent anti-tumor adaptive immunity, which drastically reduces tumor growth.

Example 8. LSD1 Inhibition Manifests Tumor Immunogenicity and Increases T Cell Infiltration To further elucidate the mechanism connecting LSD1 inhibition to enhanced anti-tumor T cell immunity, the impact of tumor cell-intrinsic LSD1 on T cell activity in the tumor microenvironment was determined. By analyzing tumor-infiltrating lymphocytes (TILs) in transplanted B16 tumors, LSD1 ablation in tumor cells resulted in a significant increase in CD4$^+$ and CD8$^+$ T cell infiltration, indicating a stronger ability to induce T cell immunity (FIG. 10A). Importantly, the increase in T cell infiltration was diminished when MDA5 was concurrently ablated (FIG. 10A). In contrast, no significant alteration in T cell populations was detected in draining lymph nodes (dLNs) of B16 tumor-bearing mice (FIG. 10B), suggesting the impact on T cells by tumor cell LSD1 ablation is restricted to tumor sites. To assess the functional activity of CD8$^+$ TILs, the expression of a proliferation marker, Ki-67, and a cytotoxic factor, Granzyme-B (GzmB) were detected, but neither showed a noticeable alteration when LSD1 was deleted in B16 tumor cells (FIG. 10C). Thus, in consideration of the aforementioned tumor growth inhibition (FIGS. 9A-I), these results suggest that increased T cell infiltration mediated by dsRNA recognition pathway imparts potent anti-tumor immunity to LSD1-null tumors.

To investigate whether the increased T cell infiltration is associated with increased TCR repertoire diversity of CD8$^+$ TILs in LSD1 KO B16 tumors, the clonality and entropy of these T cells was analyzed by T cell receptor (TCR) sequencing, but no significant changes were found compared to their counterparts in WT tumors (FIG. 10D). Thus, the increased T cell infiltration in LSD1 KO tumors is not due to an unlikely alteration in tumor antigenicity.

To investigate tumor cell characteristics, which are associated with tumor response to T cell immunity and critically regulated by LSD1 inhibition-induced dsRNA stress, GFP-labeled B16 lines were created to facilitate the accurate isolation of tumor cells from in vivo transplanted tumors, and then these ex vivo tumor cells were used for transcriptomic analysis. LSD1 deletion significantly altered gene expression profile in B16 tumor cells in vivo, which appeared to be suppressed when MDA5 was simultaneously deleted (FIGS. 10E and 10F). Consistent with the in vitro results with human cancer cells, LSD1 ablation also led to upregulation of ERVs by regulating their transcription in B16 tumor cells in vivo (FIGS. 10G-I), suggesting the aforementioned mechanism is conserved in vivo.

Genes whose expression was selectively up-regulated (FDR<0.05 and log 2(FC)>1) in LSD1 KO tumor cells compared with control tumor cells were filtered out for GO analysis. This analysis showed that immune response-related biological processes, including innate immune response, response to IFN-β, defense response to virus and MHC protein complex, were ranked among the top 10 GO terms in LSD1 KO tumor cells (FIG. 10J), providing evidence for the increased tumor immunogenicity. The GO term response to IFN-γ was also significantly enriched (FIG. 10J), implying an increased response of LSD1 KO tumor cells to T cell killing. In addition, genes associated with inflammatory response were also enriched in LSD1 KO tumor cells as analyzed by GSEA (FIG. 10K). Importantly, the induced expression of genes associated with the top 10 GO terms was significantly diminished by simultaneous MDA5 deletion in LSD1 KO cells (FIG. 10L), suggesting a critical role of dsRNA recognition pathway in mediating tumor immunogenicity. Of note, there was no apparent alteration by LSD1 deletion of cell proliferation pathways by GSEA (FIG. 10M), which further supported the notion that autonomous growth of B16 tumor cells in syngeneic mice is likely independent of LSD1 status.

In order to validate the findings from RNA-seq, it was determined whether antigen presentation on tumor cell surface restricted by MHC-1, whose alteration enables immune escape and is commonly found in solid tumors, is affected by LSD1. In the RNA-seq analysis, most MHC-1 coding genes were upregulated in LSD1 KO B16 cells, among which the induction of H2-D1 and H2-K1, encoding classical class 1 antigens, was largely dependent on MDA5 pathway (FIG. 10N). Consistently, in flow cytometric analysis of GFP-labeled B16 cells isolated from in vivo transplanted tumors, LSD1 deletion caused a marked induction of MHC-1 expression on tumor cell surface, which was completely abrogated by concurrent deletion of MDA5 (FIG. 10O). Altogether, these results show that LSD1 inhibition through the dsRNA recognition pathway manifests tumor immunogenicity, associated with increased T cell infiltration.

Figure 6C:
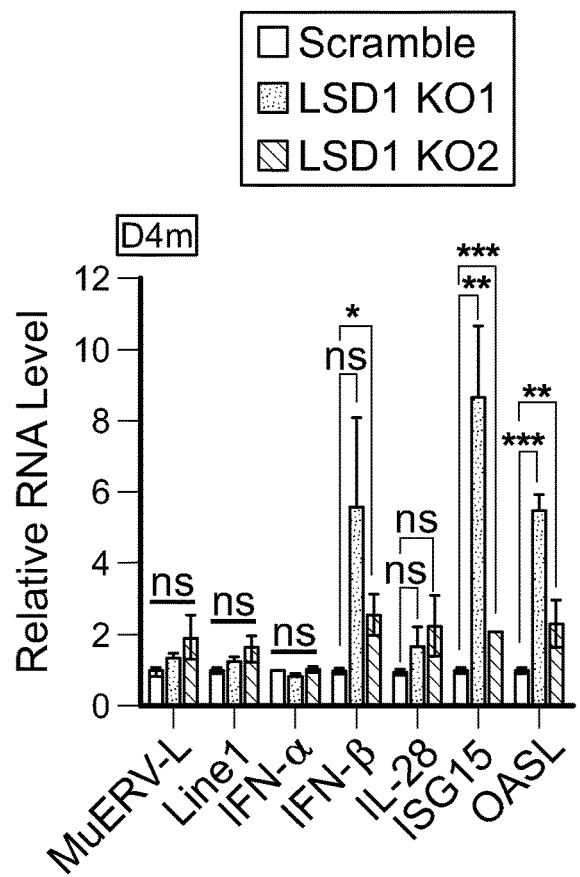
FIG. 6C is bar graph showing RT-qPCR analysis of MuERV-L, Line 1, IFN-α, IFN-β, IL-28, ISG15 and OASL in D4m cells transduced with shRNA against scramble (scramble), LSD1 KO1 and LSD1 KO2. The RT-qPCR data were normalized to GAPDH and then relative to scramble. Error bars represent SEM from three experiments. *$p<0.05$, $p<0.01$, *$p<0.001$, ns, not significant, as determined by unpaired t-test.
Figure 6D:
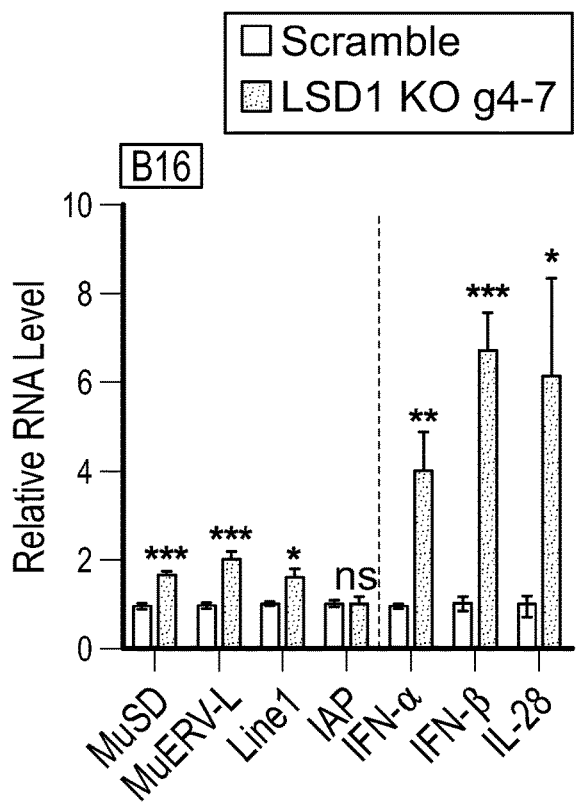
FIG. 6D is bar graph showing RT-qPCR analysis of MuERV-L, Line 1, IFN-α, IFN-β, IL-28, ISG15 and OASL in B16 cells transduced with shRNA against scramble (scramble), LSD1 KO1 and LSD1 KO2. The RT-qPCR data were normalized to GAPDH and then relative to scramble. Error bars represent SEM from three experiments.
Figure 6E:
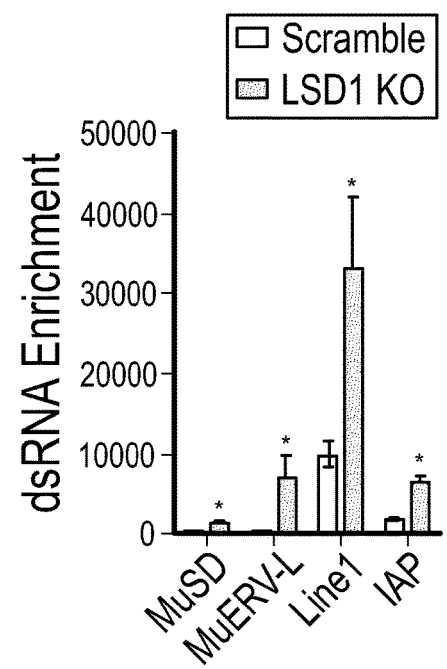
FIG. 6E is a bar graph showing double-stranded RNA (dsRNA) enrichment of selected retrotransposons (MuSD, MuERV-L, Line1 and IAP) in control or LSD1 KO B16 cells. Total RNA extract from control or LSD1 KD MCF-7 cells was digested with RNase A versus mock under high salt condition (350 mM NaCl), followed by a second round of RNA extraction with TRIzol. The ratios of (retrotransposon/Actin)RNase/(retrotransposon/Actin)mock were calculated as enrichment fold. Error bars represent SEM between triplicates. *$p<0.05$, $p<0.01$, *$p<0.001$, ns, not significant, as determined by unpaired t-test.
Figure 6F:
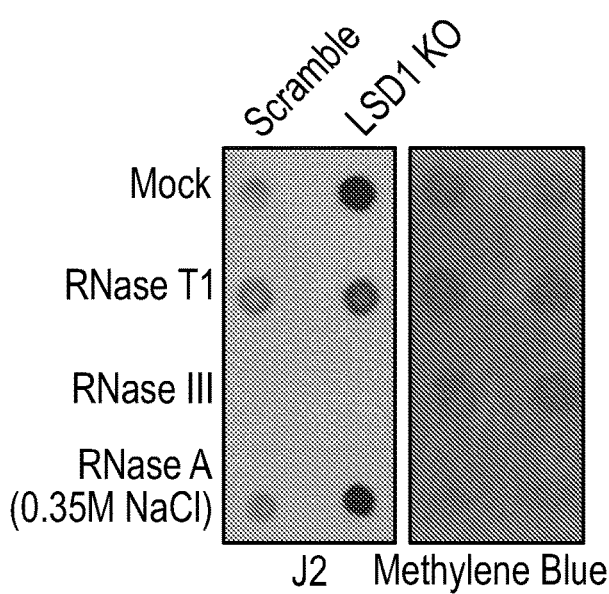
FIG. 6F is a picture of Hybond N+ membranes immunoblotted with a dsRNA-specific antibody (J2) using total RNA extracted from scramble or LSD1 KO B16 cells and treated with mock, RNase Ti, RNase III or RNase A (350 mM NaCl), followed by a second round of RNA extraction with TRIzol.
Figure 6G:
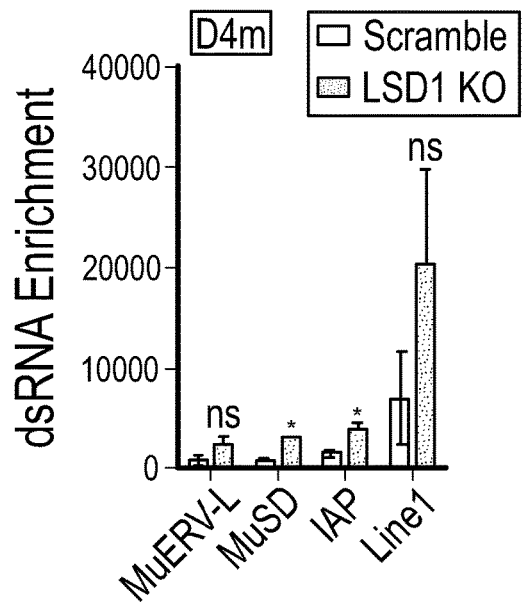
FIG. 6G is a bar graph showing double-stranded RNA (dsRNA) enrichment of MuERV-L, MuSD, IAP and Line1 in control and LSD1 KO D4m cells by RT-qPCR. Total RNA extract from control or LSD1 KO D4m cells was digested with RNase A versus mock under high salt condition (350 mM NaCl), followed by a second round of RNA extraction with TRIzol. The ratios of (retrotransposon/GAPDH)RNase/(retrotransposon/GAPDH)mock were calculated as enrichment fold. GAPDH was used as an internal control. Error bars represent SEM from three experiments. $p<0.05$, $p<0.01$, *$p<0.001$, ns, not significant, as determined by unpaired t-test.
Figure 6H:
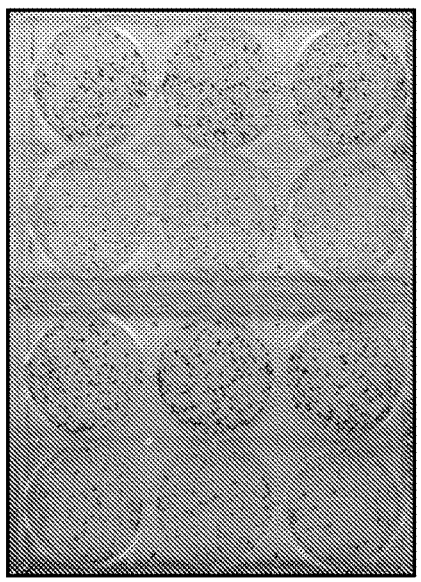
FIG. 6H is a picture of a crystal violet cell proliferation assay of B16+sh-Ctrl cells and B16+sh1-LSD1 cells, after 6 days of growth before crystal violet staining.
Figure 6I:
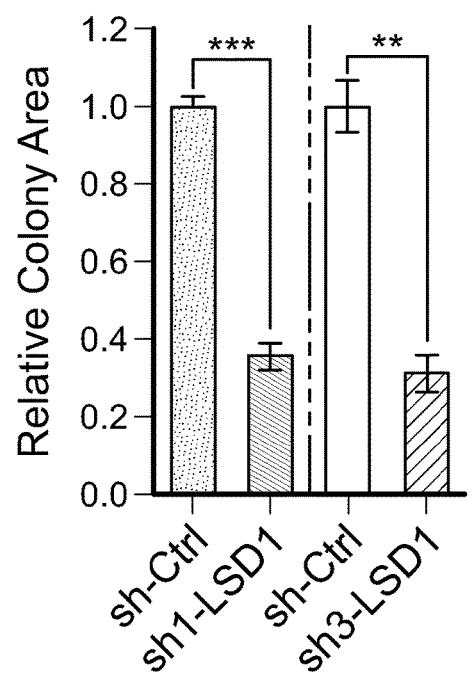
FIG. 6I is a bar graph showing the relative colony area of the proliferation assay of FIG. 6H relative to B16+sh-Ctrl. Error bars represent SD between triplicates in one of two experiments. *$p<0.05$, $p<0.01$, *$p<0.001$, ****$p<0.0001$, ns, not significant, as determined by unpaired t-test.
Figure 6J:
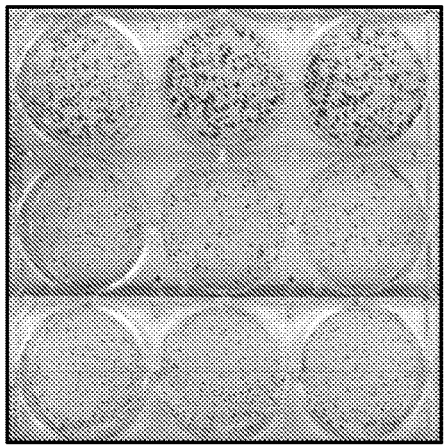
FIG. 6J is a picture of a crystal violet cell proliferation assay of B16 (LSD1 KO, clone g4-7), after 6 days of growth before crystal violet staining.
Figure 6K:
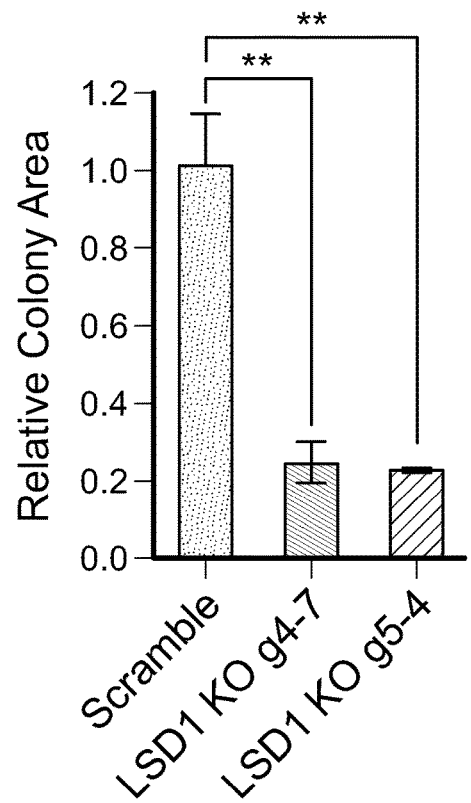
FIG. 6K is a bar graph showing the relative colony area of the proliferation assay of FIG. 6J relative to scramble. Error bars represent SD between triplicates in one of two experiments. *$p<0.05$, $p<0.01$, *$p<0.001$, ****$p<0.0001$, ns, not significant, as determined by unpaired t-test.
Figure 6M:
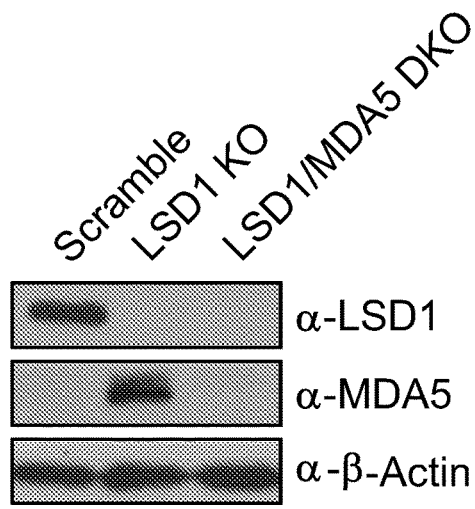
FIG. 6M is a picture of immunoblots showing LSD1 and MDA5 expression in CRISPR/Cas9-modified B16 cells (scramble, LSD1 KO, and LSD1/MDA5 DKO).
Figure 6N:
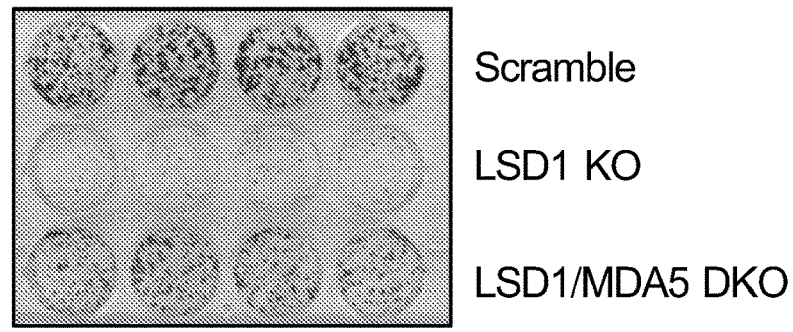
FIG. 6N is a picture of a crystal violet cell proliferation assay of B16 scramble cells, B16 LSD1 KO cells and B16 LSD1/MDA5 KO cells, after 6 days of growth before crystal violet staining.
Figure 6O:
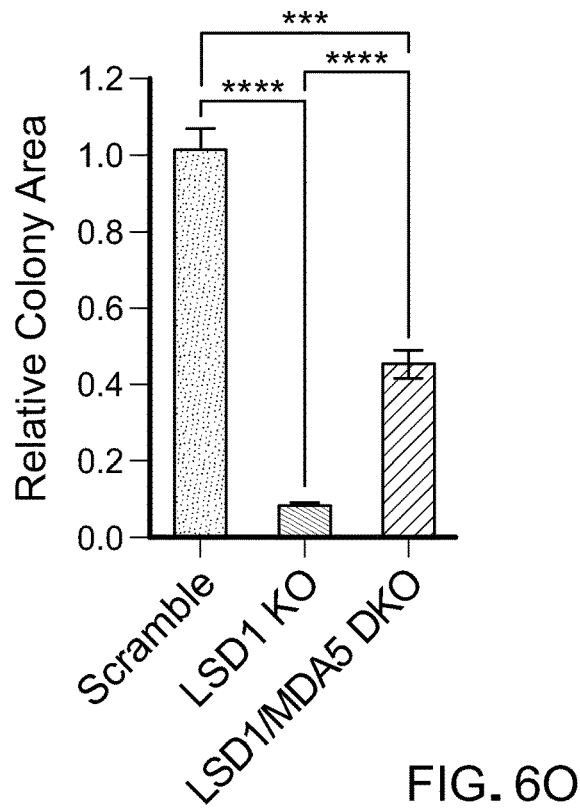
FIG. 6O is a bar graph showing the relative colony area of the proliferation assay of FIG. 6N relative to B16 scramble. Error bars represent SD between quadruplicates in one of two experiments. $*p<0.05$, $p<0.01$, $*p<0.001$, $****p<0.0001$, ns, not significant, as determined by unpaired t-test.
Figure 6P:
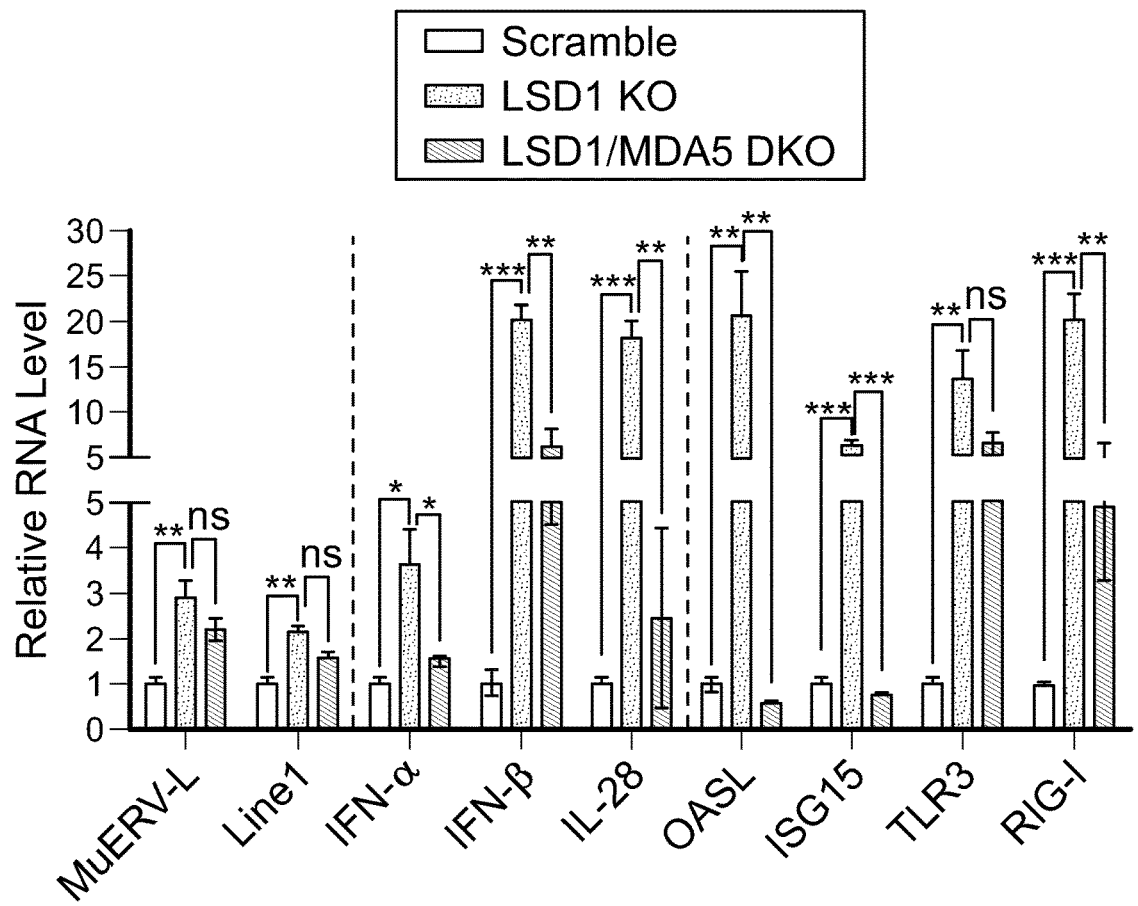
FIG. 6P is a bar graph showing RT-qPCR analysis of selected retrotransposons (MuERV-L and Line1) and IFNs (IFN-α, IFN-j3 and IL-28), OASL, ISG15, TLR3 and RIG-I in B16 scramble cells, B16 LSD1 KO cells and B16 LSD1/MDA5 KO cells. Error bars represent SEM between duplicates. $*p<0.05$, $p<0.01$, $*p<0.001$, ns, not significant, as determined by unpaired t-test.
Figure 6Q:
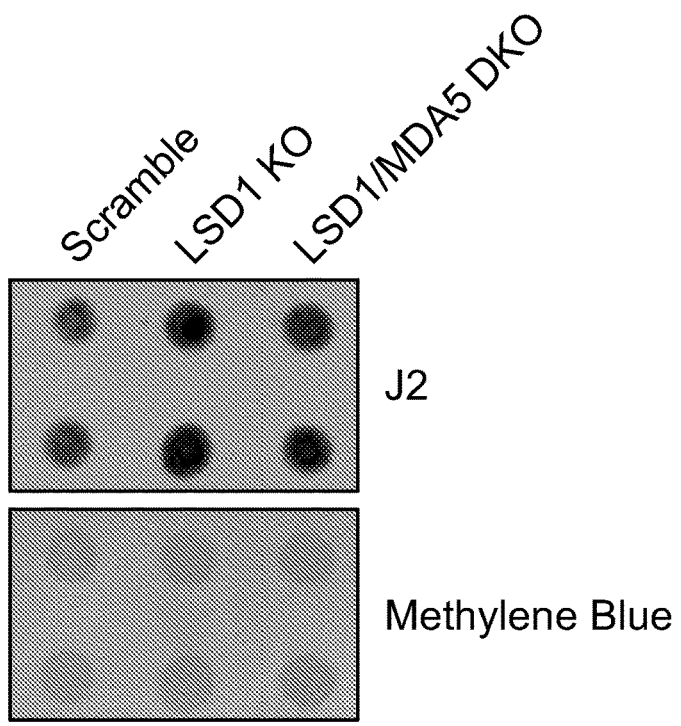
FIG. 6Q is a picture of Hybond N+ membranes immunoblotted with a dsRNA-specific antibody (J2) using total RNA extracted from scramble, LSD1 KO or LSD1/MDA5 DKO B16 cells and treated with mock, RNase Ti, RNase III or RNase A (350 mM NaCl), followed by a second round of RNA extraction with TRIzol.

To examine whether the enhanced tumor immunogenicity by LSD1 inhibition is a generalizable mechanism, another "cold" tumor model, D4m melanoma, in which LSD1 ablation also caused increased dsRNA levels and IFN activation, was used (FIGS. 6C and 6G). In syngeneic immunocompetent mice, LSD1 KO D4m tumors displayed slower growth than wild type control tumors (FIGS. 10P and 10Q). Consistently and critically, increased T cell infiltration in LSD1 KO tumors and elevated MHC-1 expression on the surface of LSD1 KO tumor cells was found compared with control tumors (FIGS. 10R and 10S), indicating enhanced T cell immunity. Thus, these results suggested that the enhanced tumor immunogenicity by LSD1 inhibition was not limited to B16 tumor model and are of broader significance.

Notably, RNA-seq and flow cytometry identified up-regulation of PD-L1 expression in the B16 tumor cells in vivo, which is independent of MDA5 (FIGS. 10T and 10U). It is possible that PD-L1 induction may suppress the functional activity of $CD8^+$ TILs (Juneja et al., 2017), thus compromising the anti-tumor effect of increased TILs caused by LSD1 inhibition. In summary, our results reveal a critical impact of tumor cell-intrinsic LSD1 on modulating tumor response to T cell immunity.

Example 9. LSD1 Inhibition Overcomes Tumor Resistance to PD-1 Blockade

In cancer patients, the presence of $CD8^+$ TILs that are suppressed by PD-L1 predicts the responsiveness to PD-(L)1 blockade (see, e.g., Herbst et al. (2014) Nature 515 (7528): 563-567; and Tumeh et al. (2014) Nature 515(7528): 568-571). B16 tumors have high expression of PD-L1 expression but poor immunogenicity, and are known to be non-responsive to PD-1/PD-L1 blockade in the absence of vaccination (see, e.g., Chen et al. (2015) Cancer Immunol Res 3(2): 149-160; Kleffel et al. (2015) Cell 162(6): 1242-1256; and Juneja et al. (2017) J Exp Med 214(4): 895-904). Given that LSD1 inhibition elicits anti-tumor immunity, it was determined whether LSD1 inhibition would sensitize B16 tumors to PD-1/PD-L1 blockade. Consistent with previous reports (see, e.g., Chen et al. (2015) Cancer Immunol Res 3(2): 149-160; Kleffel et al. (2015) Cell 162(6): 1242-1256; and Juneja et al. (2017) J Exp Med 214(4): 895-904), PD-1 blockade alone had no overt effects on wild type B16 tumor growth (FIGS. 11A and 11B). Strikingly, PD-1 blockade showed a dramatic effect on controlling LSD1 KO B16 tumors (FIGS. 11A and 11B). Furthermore, this responsiveness to PD-1 blockade doesn't rely on tumor size, because re-scheduled anti-PD-1 administration when tumor sizes reached a set volume also had a profound effect on controlling growth of LSD1 KO tumors but not WT tumors (FIGS. 11C and 11D). Moreover, this profound delay in tumor growth was achieved with a late initiation of PD-1 blockade as well as a low dose of blocking antibody. These results demonstrated a strong synergy between LSD1 inhibition and PD-1 blockade in controlling tumor growth and suggest that targeting LSD1 bypasses the need for vaccination to obtain PD-1 blockade responsiveness in the B16 tumor model. Importantly, these results also implicate increased T cell infiltration caused by LSD1 inhibition as a likely mechanism underlying the synergism between LSD1 inhibition and PD-1 blockade. Taken together, the combination of LSD1 inhibition and PD-1 blockade may work through simultaneously eliciting anti-tumor adaptive immunity and reinvigorating dysfunctional T cells to achieve a synergistic effect for tumor treatment. Given the general role of LSD1 in regulating dsRNA and interferon responses, targeting LSD1 in combination with anti-PD-(L)1 may prove to be a broadly applicable new strategy in cancer immunotherapy. Furthermore, LSD1 inhibition may overcome the resistance of B16 tumors to PD-1 blockade by increasing immunogenicity.

Example 10. Anti-PD-1 Treatment of B16 Tumors

To determine whether the synergistic effect between LSD1 inhibition and PD-1 blockade relies on the dsRNA sensor MDA5, immunocompetent C57BL/6 mice are anesthetized with Avertin (2.5%), shaved at the injection site, and then these mice are injected in the flank subcutaneously with 250,000-500,000 B16-F10 tumor cells of scramble, LSD1 KO or LSD1/MDA5 DKO (20 mice per genetically modified tumors, 20×3=60 mice in total). Tumors are measured every 2-3 days once palpable (long diameter and short diameter) with a caliper. Tumor volume is determined using the volume formula for an ellipsoid: ½×D×d$^2$ where D is the longer diameter and d is the shorter diameter. Mice are sacrificed when tumors reached 2 cm$^3$ or upon ulceration/bleeding.

For antibody treatments, mice are given 100 μg antibody intra-peritoneally when tumor size reaches 200 mm$^3$ or at day 8-10. Antibody treatment is repeated every other day for a total of four injections. The following antibodies are used: half mice receiving anti-PD-1 (clone 29F.1A12) are provided by G. Freeman (Dana Farber Cancer Institute, Boston, Mass.) and the other half mice receiving rat IgG2a isotype control antibody are purchased from BioXCell (cat #BE0089). Prior to treatments mice are randomized such that treatment groups have similar average tumor volumes prior to treatment initiation.

Example 11. LSD1 Chemical Inhibitor in Combination with Anti-PD-1 Treatment for B16 Tumors To assess the efficacy of LSD1 chemical inhibition in combination with anti-PD-1 treatment in controlling B16 tumor growth, WT B16 tumor cells are inoculated as described in Example 10 (40 mice in total: 10 mice for vehicle+isotype; 10 mice for GSK2879552+isotype; 10 mice for vehicle+anti-PD-1; 10 mice for GSK2879552+anti-PD-1). For inhibitor treatment, GSK2879552 is orally administrated or intra-peritoneally injected 1.5 mg/kg daily or every other day starting from the second day after tumor inoculation. For antibody treatment, anti-PD-1 or isotype is intra-peritoneally injected very other day starting from day 8 after tumor inoculation for a total for four injections. Tumor volume is recorded and is determined using the volume formula for an ellipsoid: ½×D×d$^2$ where D is the longer diameter and d is the shorter diameter. Mice are sacrificed when tumors reached 2 cm$^3$ or upon ulceration/bleeding.

Example 12. Syngeneic Tumor Models with LLC, D4M and Renca Cells

To determine whether these findings can be generalized to other tumor models, LSD1 is deleted by CRISPR/Cas9 LLC cells, D4M cells and Renca cells. LLC LSD1 KO cells, D4M LSD1 KO cells and Renca LSD1 KO cells (250,000-500,000 per mouse) are injected into their syngeneic immunocompetent mice (LLC to B6 mice, D4M to B6 mice and Renca to Balb/c mice). Tumors are measured every 2-3 days once palpable (long diameter and short diameter) with a caliper. Tumor volume is determined using the volume formula for an ellipsoid: ½×D×d2 where D is the longer diameter and d is the shorter diameter. Mice are sacrificed when tumors reached 2 cm3 or upon ulceration/bleeding.

Example 13. WT Versus LSD1 KO B16 Tumor Growth in B6 Mice for Tumor-Infiltrating Lymphocyte (TIL) Analysis To analyze the tumor immunogenicity ant anti-tumor immunity caused by LSD1 deletion, B16 tumor cells are inoculated into immunocompetent mice as described in Example 10 (5 mice for WT control and 5 mice for LSD1 KO B16 cells). At day 12, mice are sacrificed and tumors are collected. Isolated tumors are then excised into small pieces and are digested by collagenase to obtain single cell suspension. Some of the cells are directly stained with appropriate antibodies for profiling various immune cells, including CD4 T cells, CD8 T cells, macrophages, DCs and NK cells. Some of the cells are fixed, are permeabilized and are stained with anti-TCRβ, anti-CD4, anti-CD25 and anti-Foxp3 for Treg cells, and anti-TCRβ, anti-CD8 and anti-GzmB for effector CD8 T cells. In addition, some of the cells are re-stimulated for intracellular cytokine staining, such as IFN-γ and IL-2. Stained cells are subjected to flow cytometry for analysis. Alternatively, some tumor samples are subjected to IHC analysis.

Example 14. WT Versus LSD1 KO B16 Tumor Growth in B6 Mice for Tumor-Infiltrating Lymphocyte (TIL) Analysis To analyze the tumor immunogenicity and anti-tumor immunity in the setting of LSD1 ablation plus anti-PD-1 treatment, B16 tumor cells are inoculated into immunocompetent mice, which previously would have received anti-PD-1 or isotype antibody injection at day 8 and day 10 (5 mice for scramble B16+isotype; 5 mice for LSD1 KO B16+isotype; 5 mice for scramble B16+anti-PD-1; 5 mice for LSD1 KO B16+anti-PD-1). At day 12, TIL are analyzed as described in Example 13.

Example 15. B16 Tumor Growth in WT or IFNAR1 KO Mice

To determine if B16-derived IFN-β is important for LSD1 deletion-induced anti-tumor immunity and what types of cells are the crucial targets of IFN-β, B16 tumor cells are inoculated into immunocompetent WT or IFNAR1 KO mice, which would receive anti-PD-1 or isotype antibody injection at day 8, 10, 12 and 14 (5 mice for scramble B16+isotype; 5 mice for LSD1 KO B16+isotype; 5 mice for scramble B16+anti-PD-1; 5 mice for LSD1 KO B16+anti-PD-1; 5 mice for LSD1/IFN-β DKO B16+isotype; 5 mice for LSD1/IFN-β DKO B16+anti-PD-1, 5 mice for LSD1/IFNAR1 DKO B16+isotype; 5 mice for LSD1/IFNAR1 DKO B16+anti-PD-1). Tumors are measured every 2-3 days once palpable (long diameter and short diameter) with a caliper. Tumor volume is determined using the volume formula for an ellipsoid: ½×D×d2 where D is the longer diameter and d is the shorter diameter. Mice are sacrificed when tumors reached 2 cm3 or upon ulceration/bleeding.

Example 16. Translational Significance

To demonstrate that these findings have translational significance, the public datasets on human cancer were explored. LSD1 was infrequently mutated, amplified or deleted in a majority of cancer types examined (FIG. 12A), but LSD1 was found to be overexpressed in cancerous tissues compared with normal tissues in a variety of cancer types (FIG. 12B). To determine whether LSD1 expression level in tumors correlated with clinical outcome, patients of each cancer type were divided by LSD1 expression median, and overall survival between the two groups was compared. This analysis showed that LSD-high group had a significantly shorter overall survival time than LSD1-low group for a number of cancer types (FIG. 12C), suggesting LSD1 overexpression is a poor prognostic factor. In line with the finding that LSD1 inhibition caused IFN/antiviral response in in vitro MCF-7 cells and ex vivo B16 cells (FIGS. 1N and 10J), LSD1 expression level was found to be inversely correlated with IFN/antiviral response in a variety of cancer types in TCGA cancer patient dataset (FIG. 12D). LSD1 expression level was also inversely correlated with CD8$^+$ T cell infiltration in most cancer types (FIG. 12E), consistent with the finding of increased T cell infiltration by LSD1 inhibition in mouse models (FIGS. 10A and 10P).

Further analysis on the TCGA skin cutaneous melanoma (SKCM) cohort showed that patient group with low LSD1 expression (LSD1-low) had better survival probability than that with intermediate or high LSD1 expression (LSD1-int/high) (FIG. 12F), and consistently, LSD1-low group was associated with increased expression of genes enriched in immune responses (FIG. 12G). Specifically, both CD8a and GzmB were expressed higher in the LSD1-low group than in the LSD1-int/high group, indicating increased CD8$^+$ T cell infiltration (FIGS. 12H and 12I).

Other Embodiments

It is to be understood that while the disclosure has been described in conjunction with the detailed description thereof, the foregoing description is intended to illustrate and not limit the scope of the disclosure, which is defined by the scope of the appended claims. Other aspects, advantages, and modifications are within the scope of the following claims.

What is claimed is:

1. A method of treating cancer in a patient, the method comprising:
   administering to a patient in need thereof a therapeutically effective amount of a lysine-specific demethylase 1A (LSD1) inhibitor to thereby treat cancer in the patient, wherein the LSD1 inhibitor comprises an inhibitory nucleic acid comprising SEQ ID NO: 2.

2. A method of treating cancer in a patient, the method comprising:
   administering to a patient in need of cancer treatment therapeutically effective amounts of a lysine-specific demethylase 1A (LSD1) inhibitor and at least one immunotherapy, to thereby treat cancer in the patient, wherein the LSD1 inhibitor comprises an inhibitory nucleic acid comprising SEQ ID NO: 2.

3. The method of claim 1, wherein the method further comprises identifying the patient as having cancer prior to administering.

4. The method of claim 1, wherein the method further comprises administering a PD-1 inhibitor.

5. The method of claim 1, wherein the method further comprises administering a PD-1 inhibitor and a PD-L1 inhibitor.

6. The method of claim 1, wherein the method further comprises administering a PD-L1 inhibitor.

7. The method of claim 2, wherein the at least one immunotherapy is selected from the group consisting of: an antibody, an adoptive cellular therapy, an antibody-drug conjugate, a toxin, a cytokine therapy, a cancer vaccine, and a checkpoint inhibitor.

8. The method of claim 4, wherein the PD-1 inhibitor is selected from the group consisting of: a small molecule, an antibody, and an inhibitory nucleic acid.

9. The method of claim 8, wherein the PD-1 inhibitor is an anti-PD-1 antibody.

10. The method of claim 6, wherein the PD-L1 inhibitor is selected from the group consisting of: a small molecule, an antibody, and an inhibitory nucleic acid.

11. The method of claim 10, wherein the PD-L1 inhibitor is an anti-PD-L1 antibody.

12. The method of claim 1, wherein the cancer is selected from the group consisting of: melanoma, acute myeloid leukemia (AML), squamous cell carcinoma, renal cell carcinoma, non-small cell lung cancer (NSCLC), small cell lung cancer (SCLC), gastric cancer, bladder cancer, kidney cancer, head and neck cancer, Ewing sarcoma, Hodgkin's lymphoma, Merkel cell carcinoma, breast cancer and prostate cancer.

13. The method of claim 1, wherein the cancer is a non-T-cell-infiltrating cancer, a PD-1 or PD-L1 refractory cancer, or a PD-1 or PD-L1 resistant cancer.

14. The method of claim 1, wherein administering occurs at least once a week.

15. The method of claim 1, wherein administering is via intravenous, subcutaneous, intraperitoneal, rectal, or oral administration.

16. The method of claim 5, wherein the LSD1 inhibitor the PD-1 inhibitor, and the PD-L1 inhibitor are administered simultaneously to the patient or wherein the LSD1 inhibitor is administered to the patient prior to administration of the PD-1 inhibitor and the PD-L1 inhibitor.

17. The method of claim 1, wherein the method further comprises administering a chemotherapeutic agent.

18. The method of claim 1, wherein treating comprises reducing the volume of primary tumor in the patient delaying cancer progression in the patient, modifying the tumor microenvironment of a cancer in the patient, sensitizing a cancer to a checkpoint inhibitor therapy, decreasing the risk of developing at least one metastatic tumor in the patient, decreasing the rate of tumor growth in the patient, or eliciting tumor-intrinsic double stranded RNA stress in a cancer cell in the patient.

19. The method of claim 2, wherein treating comprises reducing the volume of primary tumor in the patient, delaying cancer progression in the patient, modifying the tumor microenvironment of a cancer in the patient, sensitizing a cancer to a checkpoint inhibitor therapy, decreasing the risk of developing at least one metastatic tumor in the patient, decreasing the rate of tumor growth in the patient, or eliciting tumor-intrinsic double stranded RNA stress in a cancer cell in the patient.

20. The method of claim 6, wherein the PD-L1 inhibitor comprises an inhibitory nucleic acid comprising SEQ ID NO: 6.

21. A method of treating cancer in a patient, the method comprising:
    administering to a patient in need thereof a therapeutically effective amount of a PD-L1 inhibitor to thereby treat cancer in the patient, wherein the PD-L1 inhibitor comprises an inhibitory nucleic acid comprising SEQ ID NO: 6.

* * * * *

UNITED STATES PATENT AND TRADEMARK OFFICE
CERTIFICATE OF CORRECTION

PATENT NO. : 11,685,782 B2
APPLICATION NO. : 16/758474
DATED : June 27, 2023
INVENTOR(S) : Yang Shi et al.

It is certified that error appears in the above-identified patent and that said Letters Patent is hereby corrected as shown below:

In the Claims

Column 112, Line 11, Claim 16, delete "LSD1 inhibitor" and insert -- LSD1 inhibitor, --

Signed and Sealed this
Sixteenth Day of April, 2024

Katherine Kelly Vidal
*Director of the United States Patent and Trademark Office*